(12) United States Patent
Jensen et al.

(10) Patent No.: US 11,958,865 B1
(45) Date of Patent: Apr. 16, 2024

(54) LEUCINE-RICH REPEAT KINASE 2 (LRRK2) INHIBITORS

(71) Applicant: H. Lundbeck A/S, Valby (DK)

(72) Inventors: Thomas Jensen, Valby (DK); Thomas Andersen, Valby (DK); Mikkel Jessing, Valby (DK); Jacob Nielsen, Valby (DK); Henrik Daver, Valby (DK); Christopher Richard Jones, Valby (DK)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 18/467,162

(22) Filed: Sep. 14, 2023

(30) Foreign Application Priority Data

Sep. 15, 2022 (DK) ................................ 22195861.4
Apr. 20, 2023 (DK) ................................ 23168862.3

(51) Int. Cl.
*C07D 498/22* (2006.01)

(52) U.S. Cl.
CPC ........ *C07D 498/22* (2013.01); *C07B 2200/05* (2013.01)

(58) Field of Classification Search
CPC .................................................. C07D 498/22
See application file for complete search history.

(56) References Cited

U.S. PATENT DOCUMENTS

| | | | |
|---|---|---|---|
| 11,780,851 B2 | 10/2023 | Jensen et al. | |
| 2014/0005183 A1 | 1/2014 | Galatsis et al. | |
| 2016/0031905 A1 | 2/2016 | Hoflack et al. | |
| 2017/0240565 A1 | 8/2017 | Hoflack et al. | |
| 2023/0144725 A1 | 5/2023 | Jensen et al. | |

FOREIGN PATENT DOCUMENTS

| | | | |
|---|---|---|---|
| WO | WO 2013/046019 A1 | 4/2013 | |
| WO | WO 2014/134772 A1 | 9/2014 | |
| WO | WO 2014/134774 A1 | 9/2014 | |
| WO | WO 2014/137719 A1 | 9/2014 | |
| WO | WO 2014/137723 A1 | 9/2014 | |
| WO | WO 2014/137725 A1 | 9/2014 | |
| WO | WO 2014/137728 A1 | 9/2014 | |
| WO | WO 2014/140235 A1 | 9/2014 | |
| WO | WO 2015/026683 A1 | 2/2015 | |
| WO | WO 2015/07334 A1 | 5/2015 | |
| WO | WO 2015/092592 A1 | 6/2015 | |
| WO | WO 2015/113451 A1 | 8/2015 | |
| WO | WO 2015/113452 A1 | 8/2015 | |
| WO | WO 2016/036586 A1 | 3/2016 | |
| WO | WO 2016/042089 A1 | 3/2016 | |
| WO | WO 2016/130920 A2 | 8/2016 | |
| WO | WO 2017/012576 A1 | 1/2017 | |
| WO | WO 2017/087905 A1 | 5/2017 | |
| WO | WO 2017/106771 A1 | 6/2017 | |
| WO | WO 2017/156493 A1 | 9/2017 | |
| WO | WO 2017/218843 A1 | 12/2017 | |
| WO | WO 2018/137573 A1 | 8/2018 | |
| WO | WO 2018/137593 A1 | 8/2018 | |
| WO | WO 2018/137607 A1 | 8/2018 | |
| WO | WO 2018/155916 A2 | 8/2018 | |
| WO | WO 2018/217946 A1 | 11/2018 | |
| WO | WO 2019/012093 A1 | 1/2019 | |
| WO | WO 2019/074809 A1 | 4/2019 | |
| WO | WO 2019/074810 A1 | 4/2019 | |
| WO | WO 2019/112269 A1 | 6/2019 | |
| WO | WO 2020/106685 A1 | 5/2020 | |
| WO | WO 2023/222005 A1 | 11/2023 | |
| WO | WO 2023/224894 A1 | 11/2023 | |

OTHER PUBLICATIONS

Jensen et al., U.S. Appl. No. 18/331,289, filed Jun. 8, 2023.*
Deng et al., Leucine-rich repeat kinase 2 inhibitors: a patent review (2006-2011). Expert Opin Ther Pat. Dec. 2012;22(12):1415-26. Epub Nov. 6, 2012.
Ding et al., Discovery of 4-ethoxy-7H-pyrrolo[2,3-d]pyrimidin-2-amines as potent, selective and orally bioavailable LRRK2 inhibitors. Bioorg Med Chem Lett. May 15, 2018;28(9):1615-1620. Epub Mar. 19, 2018.
Ding et al., Leucine-rich repeat kinase 2 inhibitors: a patent review (2014-present). Expert Opin Ther Pat. Apr. 2020;30(4):275-286. Epub Feb. 18, 2020.
Domingos et al., Targeting leucine-rich repeat kinase 2 (LRRK2) for the treatment of Parkinson's disease. Future Med Chem. Aug. 2019;11(15):1953-1977.
Estrada et al., Discovery of highly potent, selective, and brain-penetrable leucine-rich repeat kinase 2 (LRRK2) small molecule inhibitors. J Med Chem. Nov. 26, 2012;55(22):9416-33. Epub Oct. 15, 2012.
Estrada et al., Discovery of highly potent, selective, and brain-penetrant aminopyrazole leucine-rich repeat kinase 2 (LRRK2) small molecule inhibitors. J Med Chem. Feb. 13, 2014;57(3):921-36. Epub Jan. 15, 2014.
Galatsis, P. Leucine-rich repeat kinase 2 inhibitors: a patent review (2014-2016). Expert Opin Ther Pat. Jun. 2017;27(6):667-676. Epub Jan. 31, 2017.

(Continued)

*Primary Examiner* — Susanna Moore
(74) *Attorney, Agent, or Firm* — Wolf, Greenfield & Sacks, P.C.

(57) ABSTRACT

The present invention is directed to compounds of formula IIa

These compounds are considered useful for the treatment of diseases associated with leucine-rich repeat kinase 2 (LRRK2) such as Parkinson's disease. Furthermore, the invention relates to pharmaceutical compositions comprising said compounds.

19 Claims, No Drawings

(56) References Cited

OTHER PUBLICATIONS

Hatcher et al., Discovery of a Pyrrolopyrimidine (JH-II-127), a Highly Potent, Selective, and Brain Penetrant LRRK2 Inhibitor. ACS Med Chem Lett. Apr. 7, 2015;6(5):584-9.

Henderson et al., Discovery and preclinical profiling of 3-[4-(morpholin-4-yl)-7H-pyrrolo[2,3-d]pyrimidin-5-yl]benzonitrile (PF-06447475), a highly potent, selective, brain penetrant, and in vivo active LRRK2 kinase inhibitor. J Med Chem. Jan. 8, 2015;58(1):419-32. Epub Nov. 17, 2014.

Kethiri et al., Leucine-rich repeat kinase 2 inhibitors: a review of recent patents (2011-2013). Expert Opin Ther Pat. Jul. 2014;24(7):745-57. Epub Jun. 11, 2014.

Scott et al., Discovery of a 3-(4-Pyrimidinyl) Indazole (MLi-2), an Orally Available and Selective Leucine-Rich Repeat Kinase 2 (LRRK2) Inhibitor that Reduces Brain Kinase Activity. J Med Chem. Apr. 13, 2017;60(7):2983-2992. Epub Mar. 16, 2017.

\* cited by examiner

LEUCINE-RICH REPEAT KINASE 2 (LRRK2) INHIBITORS

CROSS-REFERENCE TO RELATED APPLICATIONS

This application claims priority to European Application No. EP22195861.4, filed Sep. 15, 2022, and European Application No. EP23168862.3, filed Apr. 20, 2023, the entire contents of the aforementioned applications are hereby incorporated herein by reference.

FIELD OF THE INVENTION

The present invention relates to compounds which are LRRK2 inhibitors and to pharmaceutical composition comprising said compounds. Further the invention relates to methods of treating diseases using said compounds or pharmaceutical compositions.

BACKGROUND OF THE INVENTION

Parkinson's disease (PD) is a neurodegenerative disease. It is the second most common neurodegenerative disease after Alzheimer's disease and affects more than 1% of the general population above the age of 65. Parkinson's disease is clinically characterized by resting tremor, bradykinesia, muscular rigidity, and postural instability. In addition to motor symptoms, other symptoms such as neuropsychiatric symptoms are also present in many patients, and in late stages of the disease, Parkinson's disease dementia commonly develops. Pathologically, the disease is characterized by loss of dopaminergic neurons with consequent decrease in dopamine levels in the brain and by aggregation of the protein α-synuclein in the dopaminergic neurons. These aggregations, called Lewy bodies, are composed of various elements, but insoluble α-synuclein phosphorylated at serine-129 and ubiquitin are both abundantly found in Lewy bodies.

Current Parkinson's disease therapeutic intervention strategies aim at increasing the dopamine levels by administration of levodopa or monoamine oxidase B inhibitors. As an alternative, dopamine agonists are administered to stimulate dopaminergic receptors, an effect similar to that obtained by increasing the dopamine levels. Although these therapies provide significant symptomatic benefit to the patient, they are also associated with adverse side effects and often become ineffective after prolonged treatment and progression of the underlying disease. Importantly, none of the existing therapies addresses the underlying and disease-causing problem, i.e. the progressive loss of dopaminergic neurons.

Leucine-rich repeat kinase 2 (LRRK2) is a 2527 amino acid protein involved in catalyzing protein phosphorylation. Evidence is mounting for a relationship between LRRK2 and the pathogenesis of Parkinson's disease. Single nucleotide polymorphisms that alter amino acids in functional domains of LRRK2 have been shown to cause familiar and sporadic Parkinson's disease. Several such pathogenic variants have been identified including G2019S, I2020T, N1437H, R1441C, R1441G, R1441H and Y1699C (Shu et al., A Comprehensive Analysis of Population Differences in LRRK2 Variant Distribution in Parkinson's Disease, Front Aging Neurosci., 11:13, 2019; Chittoor-Vinod et al., Genetic and Environmental Factors Influence the Pleomorphy of LRRK2 Parkinsonism, Int. J. Mol. Sci., 2021, 22, 1045). The most common pathogenic form of LRRK2-associated Parkinson's disease is the amino acid substitution G2019S in the kinase domain of the LRRK2 protein. G2019S Parkinson's disease is inherited in an autosomal dominant fashion suggesting a gain-of-function mutation of the LRRK2 protein. In support of this notion, biochemical studies have shown that both G2019S and other pathogenic LRRK2 variants lead to an increased kinase activity of LRRK2 (West et al, Parkinson's disease-associated mutations in leucine-rich repeat kinase 2 augment kinase activity, Proc. Nat. Acad. Sci, 102, 16842-16847, 2005; Chittoor-Vinod et al., Genetic and Environmental Factors Influence the Pleomorphy of LRRK2 Parkinsonism, Int. J. Mol. Sci., 2021, 22, 1045). The clinical and pathological features of Parkinson's disease associated with LRRK2 mutations are very similar to those of idiopathic Parkinson's disease (Trinh et al., A comparative study of Parkinson's disease and leucine-rich repeat kinase 2 p.G2019S parkinsonism, Neurobiol. Aging., 35(5), 1125-31, 2014). This strongly suggests a causal involvement of overactive LRRK2 in the pathogenesis of Parkinson's disease in patients with such activating mutations in LRRK2 and that inhibitors of LRRK2 could be used as disease modifying treatment in familiar Parkinson's disease.

In addition to the rare high-penetrance exonic LRRK2 variants mentioned above, there are also common LRRK2 variants with lower but significant association with Parkinson's disease showing that LRRK2 also contributes to idiopathic Parkinson's disease. These include very common single-nucleotide polymorphisms in the LRRK2 gene promotor region, where the Parkinson's disease associated variants appear to be associated with increased LRRK2 expression at least in some cell types (Nalls et al., Identification of novel risk loci, causal insights, and heritable risk for Parkinson's disease: a meta-analysis of genome-wide association studies, Lancet Neurol, 2019, 18, 1091-1102; Sun et al., Genetic Variants Associated With Neurodegenerative Diseases Regulate Gene Expression in Immune Cell CD14+ Monocytes, Front Genet., 2018, 18, 9:666; Langston et al., Association of a Common Genetic Variant with Parkinson's Disease is Propagated through Microglia, bioRxiv, 2021) suggesting that LRRK2 inhibition might be relevant. Further, investigations of common exonic polymorphic variants have highlighted several LRRK2 Parkinson's disease risk variants including the A419V and G2385R that are common in the Asian population (Shu et al., A Comprehensive Analysis of Population Differences in LRRK2 Variant Distribution in Parkinson's Disease, Front Aging Neurosci., 11:13, 2019). There is also a protective variant of LRRK2 with reduced kinase activity such as the LRRK2 N551K R1398H variant (Wang et al., Understanding LRRK2 kinase activity in preclinical models and human subjects through quantitative analysis of LRRK2 and pT73 Rab10, Scientific Reports, 2021, 11:12900), which lends further support to the potential of LRRK2 inhibition in idiopathic Parkinson's disease by showing that wild-type LRRK2 activity is not optimal in a Parkinson's disease context. Functionally, LRRK2 affects trafficking of lysosomes and other vesicles through phosphorylation of RAB GTPases, and PD-associated genes are enriched for genes involved in lysosomal function and autophagy (Chang et al., A meta-analysis of genome-wide association studies identifies 17 new Parkinson's disease risk loci, Nat Genet., 2017, 49(10): 1511-1516). Two genes associated with Parkinson's disease, VPS35 and RAB29, have been shown to directly interact with LRRK2 biology as they increase LRRK2 activity (Taylor et al., Advances in elucidating the function of leucine-rich repeat protein kinase-2 in normal cells and Parkinson's disease, Curr Opin Cell Biol., 2020, 63:102-113), and as mentioned above, LRRK2 associated Parkinson's disease is very similar to idiopathic PD. Together this strongly supports the relevance of LRRK2 inhibition in treatment of idiopathic PD.

Several lines of evidence suggest that LRRK2 activity may impact α-synuclein pathology development after seeding with α-synuclein (O'Hara et al., LRRK2 and α-Synuclein: Distinct or Synergistic Players in Parkinson's Disease?, Front Neurosci., 2020, 17; 14:577).

In addition to strengthening the case for potential of LRRK2 inhibitors for treatment of Parkinson's disease, this indicates potential of LRRK2 inhibitors for treatment of other synucleinopathies including Lewy body dementia and multiple system atrophy.

LRRK2 is highly expressed in white blood cells and spleen suggesting a potential for LRRK2 inhibitors for treatment of aberrant immune responses. This is further supported by genetic association of LRRK2 with such diseases particularly inflammatory bowel diseases including Crohn's disease and leprosy (Liu et al., Association analyses identify 38 susceptibility loci for inflammatory bowel disease and highlight shared genetic risk across populations, Nat Genet., 2015, 47(9):979-986; Rastegar et al., Leucine Rich Repeat Kinase 2 and Innate Immunity, Front Neurosci., 2020, 10; 14:193). Thus, LRRK2 inhibitors may have potential for treatment of these diseases.

Both from the pharmaceutical industry and academic labs there has been a high interest in developing potent selective LRRK2 inhibitors due to their great promise in treating Parkinson's disease and other synucleinopathies.

The historic development of LRRK2 inhibitors is well described in the literature (Delgado et al., N-bridged 5,6-bicyclic pyridines: Recent applications in central nervous system disorders, European Journal of Medicinal Chemistry 97 (2015) 719-731); Xiao Ding & Feng Ren (2020) Leucine-rich repeat kinase 2 inhibitors: a patent review (2014-present), Expert Opinion on Therapeutic Patents, 30:4, 275-286). Even though a lot of focus has been on designing new LRRK2 inhibitors by the pharmaceutical industry and academic labs, the task of designing a brain penetrant, potent, selective LRRK2 inhibitor remains a challenge for the medicinal chemistry community (Delgado et al., N-bridged 5,6-bicyclic pyridines: Recent applications in central nervous system disorders, European Journal of Medicinal Chemistry 97 (2015) 719-731).

Despite the tremendous efforts from pharmaceutical industry and academic labs only two molecules (DNL201 and DNL151) from Denali Therapeutics have reached clinical phase (Xiao Ding & Feng Ren (2020) Leucine-rich repeat kinase 2 inhibitors: a patent review (2014-present), Expert Opinion on Therapeutic Patents, 30:4, 275-286).

Against this background there is still a high unmet need to provide LRRK2 inhibitors with good pharmacokinetic properties, whilst maintaining high potency and good selectivity.

SUMMARY OF THE INVENTION

The present inventors have surprisingly found that certain 2,4,12,13-tetrahydro-11H-5,7-(azenometheno)dipyrazolo[3,4-b:5',1'-g][1]oxa[4,6,8]triazacycloundecine compounds are LRRK2 inhibitors.

In a first aspect, the invention provides a compound of formula IIa, or a pharmaceutically acceptable salt thereof, wherein:

IIa

X is CH, $CR_1$ or N;
Y is CH, $CR_1$ or N;
$R_1$ is independently selected from the group consisting of a $C_1$-$C_3$ alkyl, a $C_1$-$C_3$ haloalkyl, and halogen;
$R_2$ is selected from a $C_1$-$C_3$ alkyl or an isotopically labelled $C_1$-$C_3$ alkyl;
$R_3$ is selected from the group consisting of a halogen, a cyano, and a $C_1$-$C_3$ haloalkyl;
$R_4$ is selected from the group consisting of a $C_1$-$C_3$ alkyl, an isotopically labelled $C_1$-$C_3$ alkyl, a $C_1$-$C_3$ haloalkyl, a O—$C_1$-$C_3$ alkyl, an isotopically labelled O—$C_1$-$C_3$ alkyl, a O—$C_1$-$C_3$ haloalkyl,
and a O—$C_3$-$C_6$ cycloalkyl;
n is 0, 1 or 2.

In an embodiment, the invention provides a compound of formula I, or a pharmaceutically acceptable salt thereof, wherein:

I $R_1$ is independently selected from the group consisting of a $C_1$-$C_3$ alkyl, a $C_1$-$C_3$ haloalkyl, and a halogen;
$R_2$ is selected from a $C_1$-$C_3$ alkyl or an isotopically labelled $C_1$-$C_3$ alkyl;
$R_3$ is selected from the group consisting of a halogen, a cyano, and a $C_1$-$C_3$ haloalkyl;
$R_4$ is selected from the group consisting of a $C_1$-$C_3$ alkyl, a O—$C_1$-$C_3$ haloalkyl, a O—$C_1$-$C_3$ alkyl, and a $C_1$-$C_3$ haloalkyl;
n is 0, 1 or 2.

In a further embodiment, is provided a compound of formula Ia, or a pharmaceutically acceptable salt thereof wherein:

Ia $R_1$ is selected from the group consisting of a $C_1$-$C_3$ alkyl, a $C_1$-$C_3$ haloalkyl, and a halogen;
$R_2$ is selected from a $C_1$-$C_3$ alkyl or an isotopically labelled $C_1$-$C_3$ alkyl;
$R_3$ is halogen;
$R_4$ is selected from the group consisting of a $C_1$-$C_3$ alkyl, a O—$C_1$-$C_3$ haloalkyl, a O—$C_1$-$C_3$ alkyl, and a $C_1$-$C_3$ haloalkyl;
n is 0 or 1.

In an embodiment X is CH or $CR_1$ and Y is CH or $CR_1$.
In an embodiment X is CH and Y is CH.
In an embodiment X is $CR_1$ and Y is $CR_1$.
In an embodiment X is CH and Y is $CR_1$.
In an embodiment X is $CR_1$ and Y is CH.
In an embodiment X is CH or $CR_1$ and Y is N.
In an embodiment X is N and Y is CH or $CR_1$.
In an embodiment X is N and Y is $CR_1$.
In an embodiment X is N and Y is CH.
In an embodiment X is CH and Y is N.
In an embodiment X is $CR_1$ and Y is N.
In an embodiment, $R_1$ is a $C_1$-$C_3$ alkyl.
In an embodiment, $R_1$ is —$CH_3$.
In an embodiment, $R_1$ is —$CH_2CH_3$.
In an embodiment, $R_1$ is a halogen.
In an embodiment, $R_1$ is fluoro.
In an embodiment, $R_2$ is selected from the group consisting of —$CH_3$, —$CH_2CH_3$, and —$CD_3$.
In an embodiment, $R_2$ is —$CH_3$.
In an embodiment, $R_2$ is —$CH_2CH_3$.
In an embodiment, $R_2$ is —$CD_3$.
In an embodiment, $R_3$ is a halogen.
In an embodiment, $R_3$ is chloro.
In an embodiment, $R_4$ is selected from the group consisting of —$CH_3$, —$CH_2CH_3$, —$OCH_3$, —$OCH_2CH_3$, —$CHF_2$, —$CF_3$, —O—$C_3$ cycloalkyl, O-cyclopropane, —$OCH_2F$, —$OCHF_2$, —$OCF_3$, and —$OCD_3$.
In an embodiment, $R_4$ is —$CH_3$.
In an embodiment, $R_4$ is —$CH_2CH_3$.
In an embodiment, $R_4$ is —$OCH_3$.
In an embodiment, $R_4$ is —$OCH_2CH_3$.
In an embodiment, $R_4$ is —$CHF_2$.
In an embodiment, $R_4$ is —$CF_3$.
In an embodiment, $R_4$ is —$CF_2CH_3$.
In an embodiment, $R_4$ is —O—$C_3$ cycloalkyl.
In an embodiment, $R_4$ is O-cyclopropane.
In an embodiment, $R_4$ is —$OCH_2F$.
In an embodiment, $R_4$ is —$OCHF_2$.
In an embodiment, $R_4$ is —$OCF_3$.
In an embodiment, $R_4$ is —$OCD_3$.
In an embodiment, n is 2.
In an embodiment, n is 1.
In an embodiment, n is 0.
In an embodiment, the compound of the invention is selected from the list consisting of:

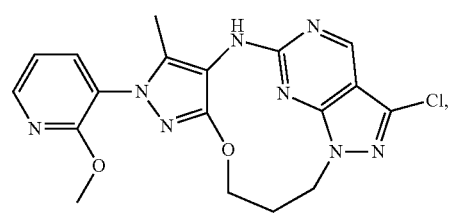

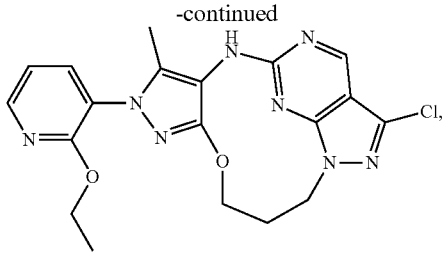

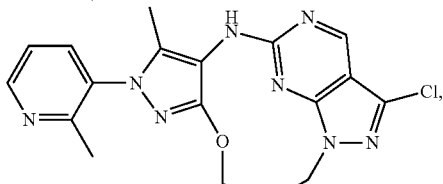

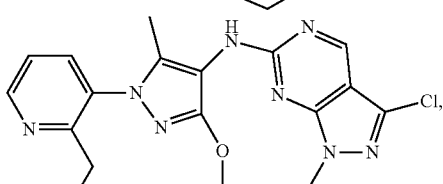

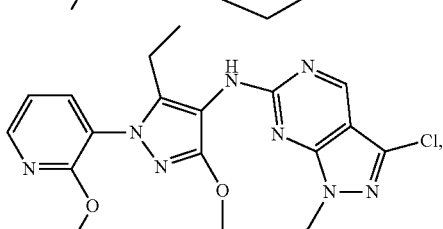

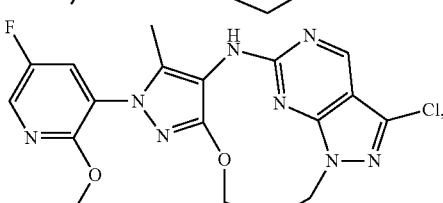

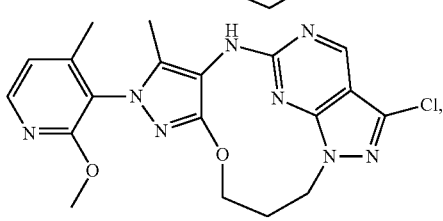

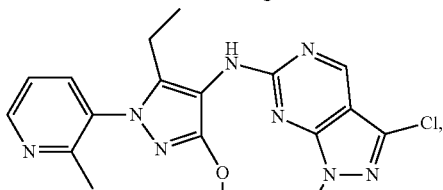

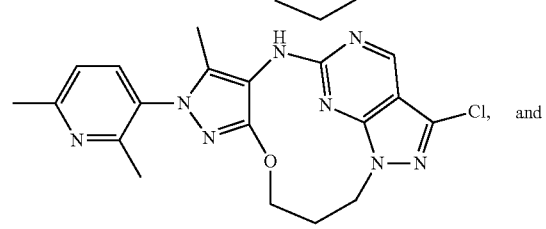

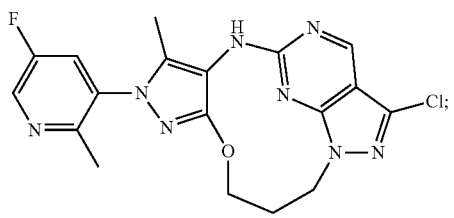
or a pharmaceutically acceptable salt thereof.
In an embodiment, the compound of the invention is selected from the list consisting of:
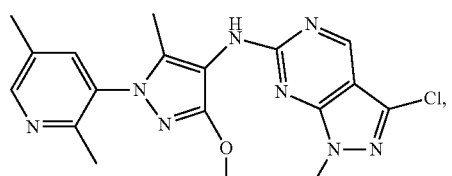
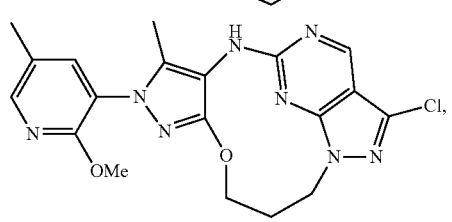
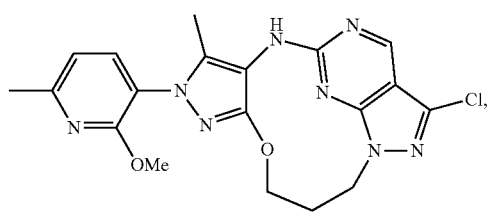
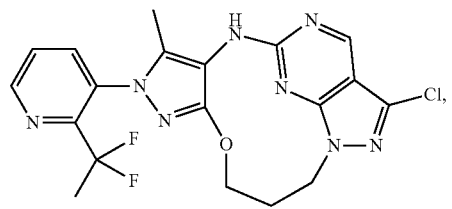
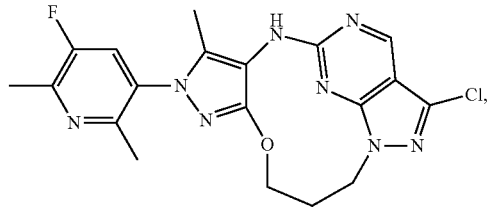
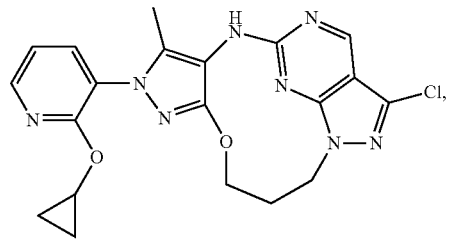
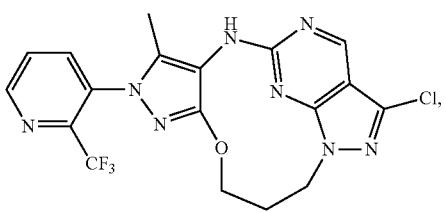
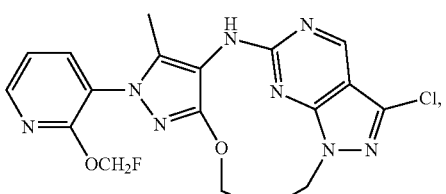
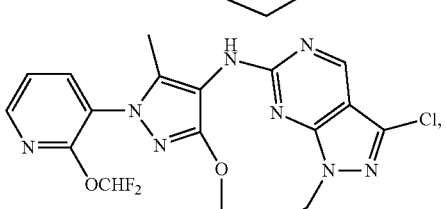
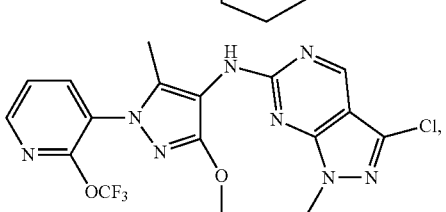
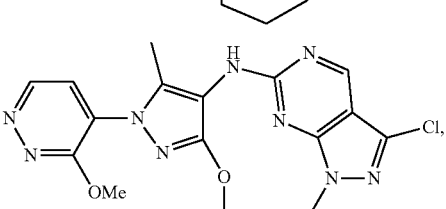
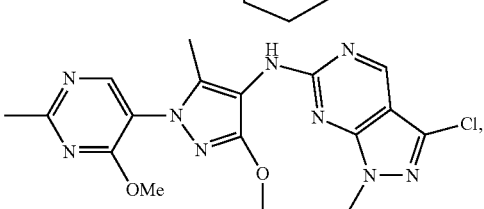
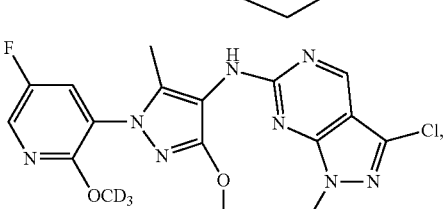
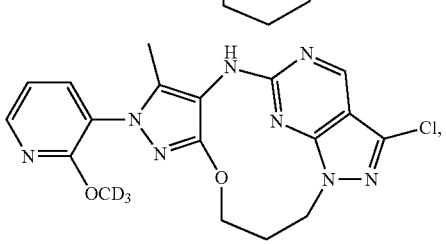

-continued

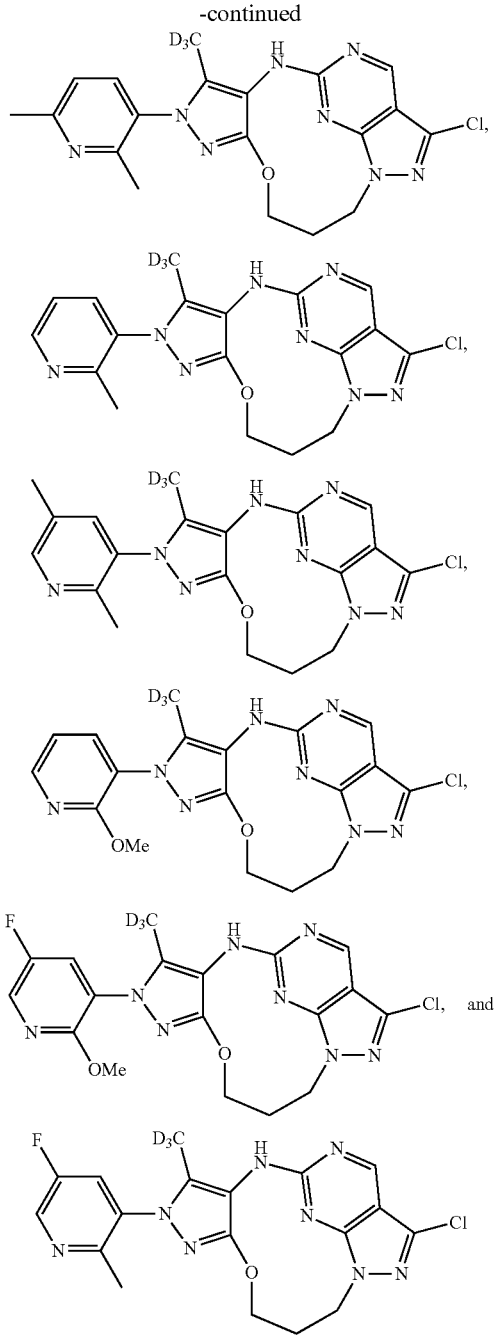

or a pharmaceutically acceptable salt thereof.

In an embodiment, the compound is

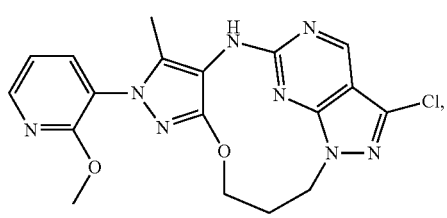

or a pharmaceutically acceptable salt thereof.

In an embodiment, the compound is

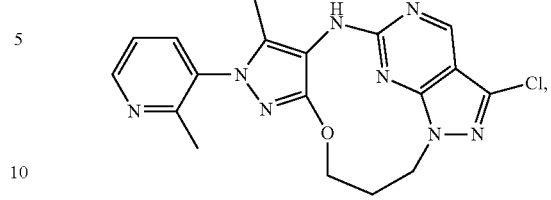

or a pharmaceutically acceptable salt thereof.

In an embodiment, the compound is

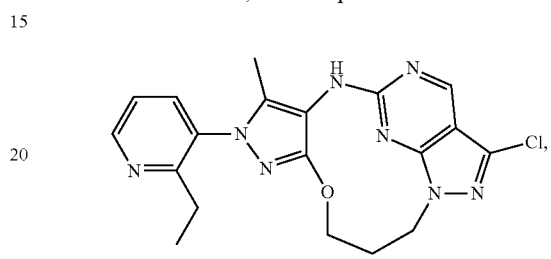

or a pharmaceutically acceptable salt thereof.

In an embodiment, the compound is

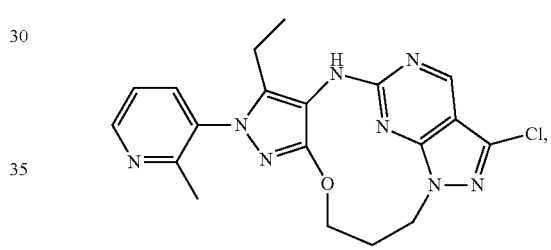

or a pharmaceutically acceptable salt thereof.

In an embodiment, the compound is

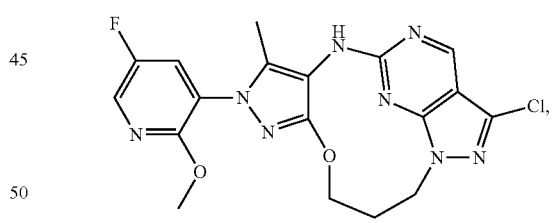

or a pharmaceutically acceptable salt thereof.

In a further aspect, the invention provides a pharmaceutical composition comprising a compound of formula I, formula IIa or formula Ia as disclosed herein or a pharmaceutically acceptable salt thereof and one or more pharmaceutically acceptable carriers.

In a further aspect, the invention provides compounds of formula I, formula Iia or formula Ia as disclosed herein or pharmaceutically acceptable salts thereof for use in therapy.

In a further aspect, the invention provides compounds of formula I, formula Iia or formula Ia as disclosed herein or pharmaceutically acceptable salts thereof for use in the treatment of a synucleinopathy.

In a further aspect, the invention provides use of compounds of formula I, formula Ia or formula Ia as disclosed herein or pharmaceutically acceptable salts thereof in the treatment of a synucleinopathy.

In a further aspect, the invention relates to the use of a compound of formula I, formula IIa or formula Ia as disclosed herein or a pharmaceutically acceptable salt thereof in the manufacture of a medicament for use in the treatment of a synucleinopathy.

In a further aspect, the invention relates to a method for the treatment of a disease associated with LRRK2 such as synucleinopathies, the method comprising the administration of a therapeutically effective amount of a compound of formula I, formula IIa or formula Ia as disclosed herein or a pharmaceutically acceptable salt thereof to a patient in need thereof.

In a further aspect, the invention provides compounds of formula I, formula IIa or formula Ia as disclosed herein or pharmaceutically acceptable salts thereof for use in the treatment of a disease associated with LRRK2, such as Parkinson's disease.

In a further aspect, the invention provides compounds of formula I, formula IIa or formula Ia as disclosed herein or pharmaceutically acceptable salts thereof for use in the treatment of Lewy body dementia, multiple system atrophy, or Parkinson's disease. In a further aspect, the invention relates to the use of a compound of formula I, formula IIa or formula Ia as disclosed herein or a pharmaceutically acceptable salt thereof in the manufacture of a medicament for use in the treatment of a disease associated with LRRK2 such as Parkinson's disease.

In a further aspect, the invention relates to a method for the treatment of a disease associated with LRRK2 such as Parkinson disease, the method comprising the administration of a therapeutically effective amount of a compound of formula I, formula IIa or formula Ia as disclosed herein or a pharmaceutically acceptable salt thereof to a patient in need thereof.

DETAILED DESCRIPTION OF THE INVENTION

The inventors of the present disclosure have identified new compounds that are LRRK2 inhibitors. These compounds are listed in table 1. As can be seen from the examples I-V of the present disclosure, these compounds were demonstrated to possess a both low clearance and a high brain penetrance, while maintaining a high potency and selectivity for LRRK2, as well as displaying a good pharmacokinetic profile. As has been demonstrated in the historic literature of LRRK2 inhibitors, as presented above, the provision of compounds which are LRRK2 inhibitors, and which also display characteristics mentioned above is a highly complex and unpredictable.

TABLE 1

Compounds of the invention

| Compound number | Name | Structure |
|---|---|---|
| 1 | 8-Chloro-2-(2-methoxypyridin-3-yl)-3-methyl-2,4,12,13-tetrahydro-11H-5,7-(azenometheno)dipyrazolo[3,4-b:5',1'-g][1]oxa[4,6,8]triazacycloundecine | 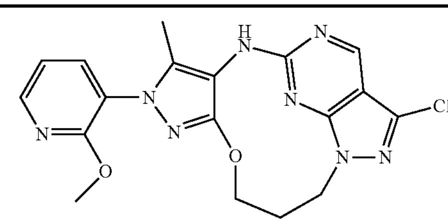 |
| 2 | 8-Chloro-2-(2-ethoxypyridin-3-yl)-3-methyl-2,4,12,13-tetrahydro-11H-5,7-(azenometheno)dipyrazolo[3,4-b:5',1'-g][1]oxa[4,6,8]triazacycloundecine | 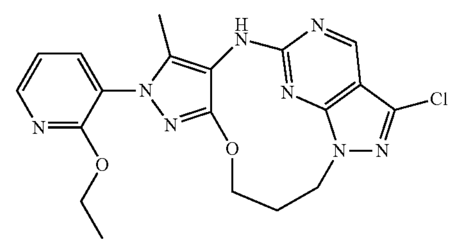 [SMILES: CCOc1ncccc1-n1nc2c(c1C)Nc1ncc3c(Cl)nn(c3n1)CCCO2] |
| 3 | 8-Chloro-3-methyl-2-(2-methylpyridin-3-yl)-2,4,12,13-tetrahydro-11H-5,7-(azenometheno)dipyrazolo[3,4-b:5',1'-g][1]oxa[4,6,8]triazacycloundecine | 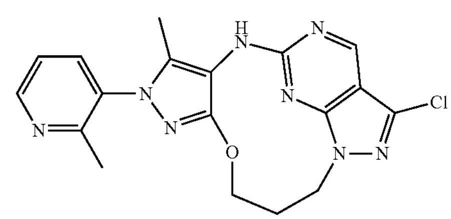 [SMILES: Cc1ncccc1-n1nc2c(c1C)Nc1ncc3c(Cl)nn(c3n1)CCCO2] |

TABLE 1-continued

Compounds of the invention

| Compound number | Name | Structure |
|---|---|---|
| 4 | 8-Chloro-2-(2-ethylpyridin-3-yl)-3-methyl-2,4,12,13-tetrahydro-11H-5,7-(azenometheno)dipyrazolo[3,4-b:5',1'-g][1]oxa[4,6,8]triazacycloundecine | 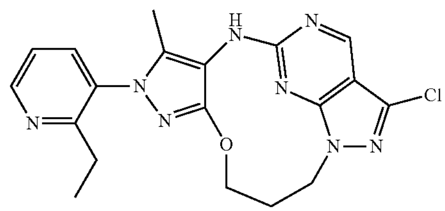 [SMILES: CCc1ncccc1-n1nc2c(c1C)Nc1ncc3c(Cl)nn(c3n1)CCCO2] |
| 5 | 8-Chloro-3-ethyl-2-(2-methoxypyridin-3-yl)-2,4,12,13-tetrahydro-11H-5,7-(azenometheno)dipyrazolo[3,4-b:5',1'-g][1]oxa[4,6,8]triazacycloundecine | 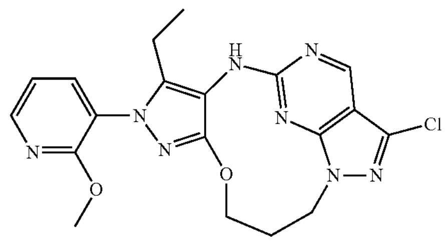 [SMILES: CCc1c2c(nn1-c1cccnc1OC)OCCCn1nc(Cl)c3cnc(nc31)N2] |
| 6 | 8-Chloro-2-(5-fluoro-2-methoxypyridin-3-yl)-3-methyl-2,4,12,13-tetrahydro-11H-5,7-(azenometheno)dipyrazolo[3,4-b:5',1'-g][1]oxa[4,6,8]triazacycloundecine | 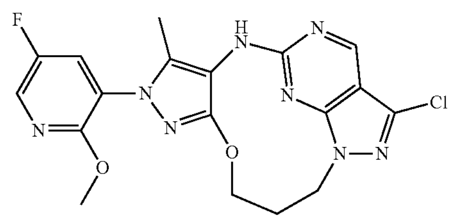 [SMILES: COc1ncc(F)cc1-n1nc2c(c1C)Nc1ncc3c(Cl)nn(c3n1)CCCO2] |
| 7 | 8-Chloro-2-(2-methoxy-4-methylpyridin-3-yl)-3-methyl-2,4,12,13-tetrahydro-11H-5,7-(azenometheno)dipyrazolo[3,4-b:5',1'-g][1]oxa[4,6,8]triazacycloundecine | 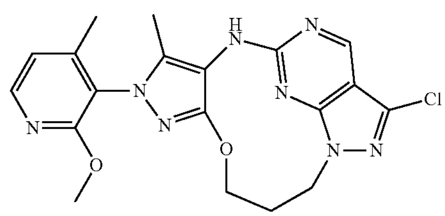 [SMILES: COc1nccc(C)c1-n1nc2c(c1C)Nc1ncc3c(Cl)nn(c3n1)CCCO2] |
| 8 | 8-Chloro-3-ethyl-2-(2-methylpyridin-3-yl)-2,4,12,13-tetrahydro-11H-5,7-(azenometheno)dipyrazolo[3,4-b:5',1'-g][1]oxa[4,6,8]triazacycloundecine | 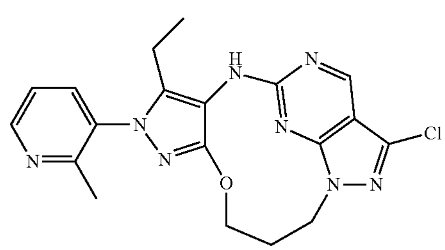 [SMILES: CCc1c2c(nn1-c1cccnc1C)OCCCn1nc(Cl)c3cnc(nc31)N2] |
| 9 | 8-Chloro-2-(2,6-dimethylpyridin-3-yl)-3-methyl-2,4,12,13-tetrahydro-11H-5,7-(azenometheno)dipyrazolo[3,4-b:5',1'-g][1]oxa[4,6,8]triazacycloundecine | 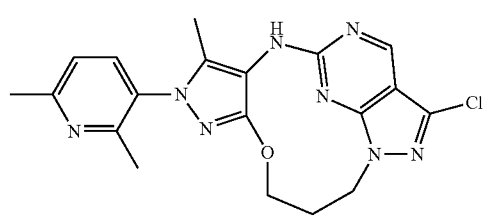 [SMILES: Cc1ccc(-n2nc3c(c2C)Nc2ncc4c(Cl)nn(c4n2)CCCO3)c(C)n1] |

TABLE 1-continued

Compounds of the invention

| Compound number | Name | Structure |
|---|---|---|
| 10 | 8-Chloro-2-(5-fluoro-2-methylpyridin-3-yl)-3-methyl-2,4,12,13-tetrahydro-11H-5,7-(azenometheno)-dipyrazolo[3,4-b:5',1'-g][1]oxa[4,6,8]triazacycloundecine | 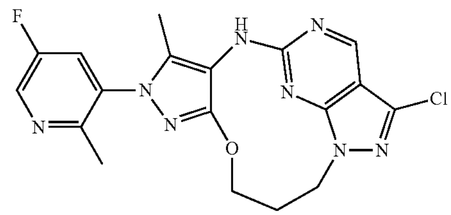 [SMILES: Cc1ncc(F)cc1-n1nc2c(c1C)Nc1ncc3c(Cl)nn(c3n1)CCCO2] |
| 11 | 8-Chloro-2-(2,5-dimethylpyridin-3-yl)-3-methyl-2,4,12,13-tetrahydro-11H-5,7-(azenometheno)dipyrazolo[3,4-b:5',1'-g][1]oxa[4,6,8]triazacycloundecine | 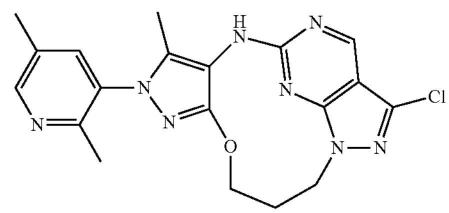 [SMILES: Cc1cnc(C)c(-n2nc3c(c2C)Nc2ncc4c(Cl)nn(c4n2)CCCO3)c1] |
| 12 | 8-Chloro-2-(2-methoxy-5-methylpyridin-3-yl)-3-methyl-2,4,12,13-tetrahydro-11H-5,7-(azenometheno)dipyrazolo[3,4-b:5',1'-g][1]oxa[4,6,8]triazacycloundecine | 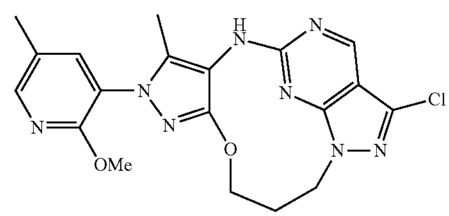 [SMILES: COc1ncc(C)cc1-n1nc2c(c1C)Nc1ncc3c(Cl)nn(c3n1)CCCO2] |
| 13 | 8-Chloro-2-(2-methoxy-6-methylpyridin-3-yl)-3-methyl-2,4,12,13-tetrahydro-11H-5,7-(azenometheno)dipyrazolo[3,4-b:5',1'-g][1]oxa[4,6,8]triazacycloundecine | 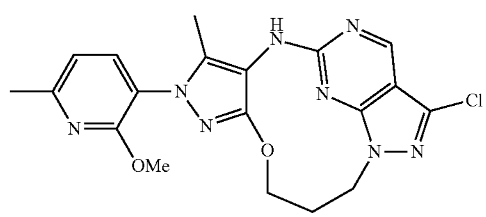 |
| 14 | 8-Chloro-2-(2-(1,1-difluoroethyl)pyridin-3-yl)-3-methyl-2,4,12,13-tetrahydro-11H-5,7-(azenometheno)dipyrazolo[3,4-b:5',1'-g][1]oxa[4,6,8]triazacycloundecine | 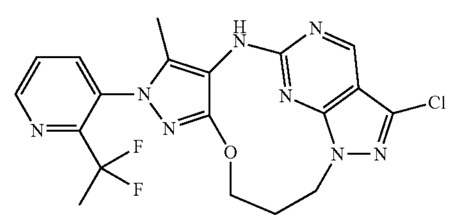 [SMILES: Cc1c2c(nn1-c1cccnc1C(C)(F)F)OCCCn1nc(Cl)c3cnc(nc31)N2] |
| 15 | 8-Chloro-2-(5-fluoro-2,6-dimethylpyridin-3-yl)-3-methyl-2,4,12,13-tetrahydro-11H-5,7-(azenometheno)dipyrazolo[3,4-b:5',1'-g][1]oxa[4,6,8]triazacycloundecine | 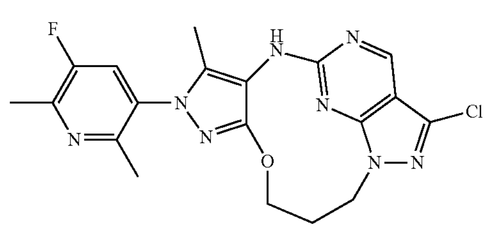 [SMILES: Cc1nc(C)c(-n2nc3c(c2C)Nc2ncc4c(Cl)nn(c4n2)CCCO3)cc1F] |

TABLE 1-continued

Compounds of the invention

| Compound number | Name | Structure |
|---|---|---|
| 16 | 8-Chloro-2-(2-cyclopropoxypyridin-3-yl)-3-methyl-2,4,12,13-tetrahydro-11H-5,7-(azenometheno)dipyrazolo[3,4-b:5',1'-g][1]oxa[4,6,8]triazacycloundecine | 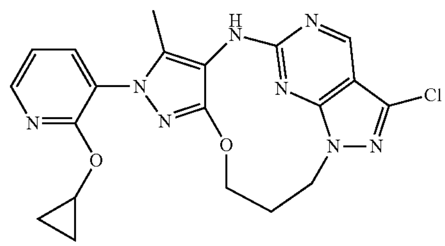 [SMILES: Cc1c2c(nn1-c1cccnc1OC1CC1)OCCCn1nc(Cl)c3cnc(nc31)N2] |
| 17 | 8-Chloro-3-methyl-2-(2-(trifluoromethyl)pyridin-3-yl)-2,4,12,13-tetrahydro-11H-5,7-(azenometheno)dipyrazolo[3,4-b:5',1'-g][1]oxa[4,6,8]triazacycloundecine | 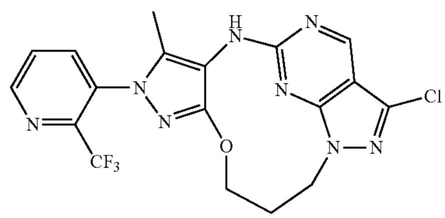 [SMILES: Cc1c2c(nn1-c1cccnc1C(F)(F)F)OCCCn1nc(Cl)c3cnc(nc31)N2] |
| 18 | 8-Chloro-2-(2-(fluoromethoxy)pyridin-3-yl)-3-methyl-2,4,12,13-tetrahydro-11H-5,7-(azenometheno)dipyrazolo [3,4-b:5',1'-g][1]oxa[4,6,8]triazacycloundecine | 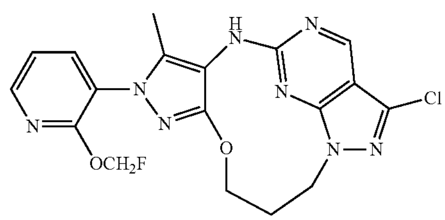 |
| 19 | 8-Chloro-2-(2-(difluoromethoxy)pyridin-3-yl)-3-methyl-2,4,12,13-tetrahydro-11H-5,7-(azenometheno)dipyrazolo[3,4-b:5',1'-g][1]oxa[4,6,8]triazacycloundecine | 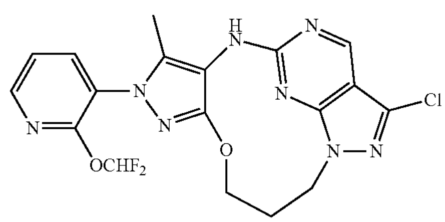 [SMILES: Cc1c2c(nn1-c1cccnc1OC(F)F)OCCCn1nc(Cl)c3cnc(nc31)N2] |
| 20 | 8-Chloro-3-methyl-2-(2-(trifluoromethoxy)pyridin-3-yl)-2,4,12,13-tetrahydro-11H-5,7-(azenometheno)dipyrazolo[3,4-b:5',1'-g][1]oxa[4,6,8]triazacycloundecine | 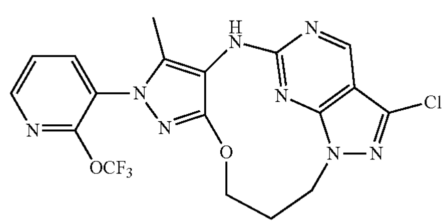 |
| 21 | 8-Chloro-2-(3-methoxypyridazin-4-yl)-3-methyl-2,4,12,13-tetrahydro-11H-5,7-(azenometheno)dipyrazolo[3,4-b:5',1'-g][1]oxa[4,6,8]triazacycloundecine | 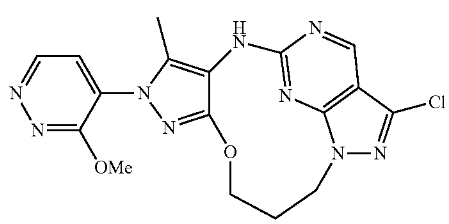 [SMILES: COc1nnccc1-n1nc2c(c1C)Nc1ncc3c(Cl)nn(c3n1)CCCO2] |

TABLE 1-continued

Compounds of the invention

| Compound number | Name | Structure |
|---|---|---|
| 22 | 8-Chloro-2-(4-methoxy-2-methylpyrimidin-5-yl)-3-methyl-2,4,12,13-tetrahydro-11H-5,7-(azenometheno)dipyrazolo[3,4-b:5',1'-g][1]oxa[4,6,8]triazacycloundecine | 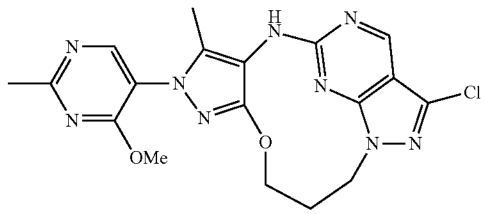 [SMILES: COc1nc(C)ncc1-n1nc2c(c1C)Nc1ncc3c(Cl)nn(c3n1)CCCO2] |
| 23 | 8-Chloro-2-(5-fluoro-2-(methoxy-d₃)pyridin-3-yl)-3-methyl-2,4,12,13-tetrahydro-11H-5,7-(azenometheno)dipyrazolo[3,4-b:5',1'-g][1]oxa[4,6,8]triazacycloundecine | 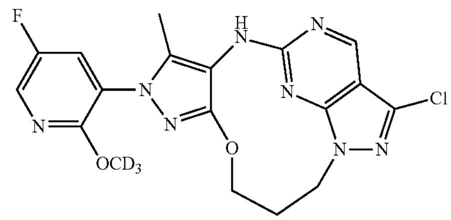 |
| 24 | 8-Chloro-2-(2-(methoxy-d₃)pyridin-3-yl)-3-methyl-2,4,12,13-tetrahydro-11H-5,7-(azenometheno)dipyrazolo[3,4-b:5',1'-g][1]oxa[4,6,8]triazacycloundecine | 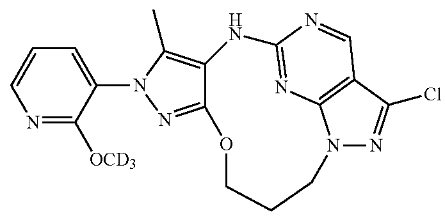 |
| 25 | 8-Chloro-2-(2,6-dimethylpyridin-3-yl)-3-(methyl-d₃)-2,4,12,13-tetrahydro-11H-5,7-(azenometheno)dipyrazolo[3,4-b:5',1'-g][1]oxa[4,6,8]triazacycloundecine | 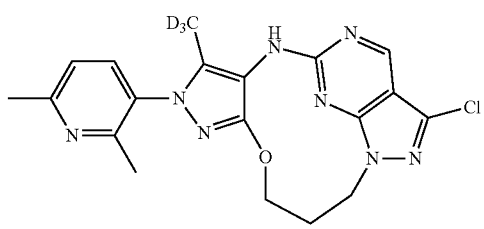 [SMILES: [2H]C([2H])([2H])c1c2c(nn1-c1ccc(C)nc1C)OCCCn1nc(Cl)c3cnc(nc31)N2] |
| 26 | 8-Chloro-3-(methyl-d₃)-2-(2-methylpyridin-3-yl)-2,4,12,13-tetrahydro-11H-5,7-(azenometheno)dipyrazolo[3,4-b:5',1'-g][1]oxa[4,6,8]triazacycloundecine | 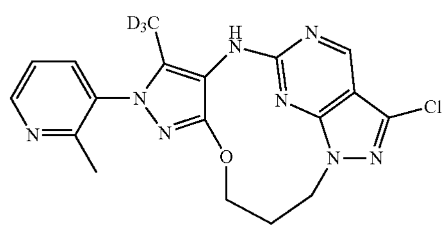 [SMILES: [2H]C([2H])([2H])c1c2c(nn1-c1cccnc1C)OCCCn1nc(Cl)c3cnc(nc31)N2] |
| 27 | 8-Chloro-2-(2,5-dimethylpyridin-3-yl)-3-(methyl-d₃)-2,4,12,13-tetrahydro-11H-5,7-(azenometheno)dipyrazolo[3,4-b:5',1'-g][1]oxa[4,6,8]triazacycloundecine | 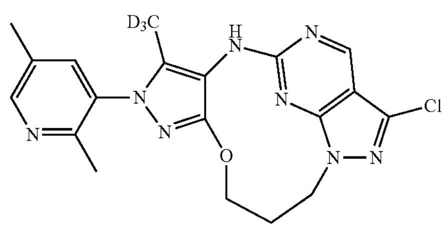 [SMILES: [2H]C([2H])([2H])c1c2c(nn1-c1cc(C)cnc1C)OCCCn1nc(Cl)c3cnc(nc31)N2] |

TABLE 1-continued

Compounds of the invention

| Compound number | Name | Structure |
|---|---|---|
| 28 | 8-Chloro-2-(2-methoxypyridin-3-yl)-3-(methyl-d₃)-2,4,12,13-tetrahydro-11H-5,7-(azenometheno)dipyrazolo[3,4-b:5',1'-g][1]oxa[4,6,8]triazacycloundecine | 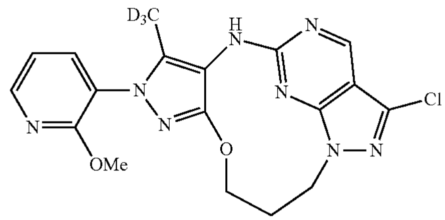 [SMILES: [2H]C([2H])([2H])c1c2c(nn1-c1cccnc1OC)OCCCn1nc(Cl)c3cnc(nc31)N2] |
| 29 | 8-Chloro-2-(5-fluoro-2-methoxypyridin-3-yl)-3-(methyl-d₃)-2,4,12,13-tetrahydro-11H-5,7-(azenometheno)dipyrazolo[3,4-b:5',1'-g][1]oxa[4,6,8]triazacycloundecine | 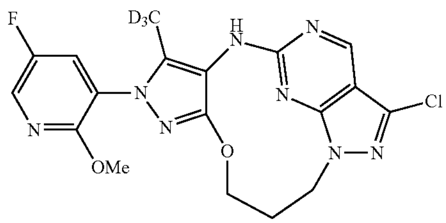 [SMILES: [2H]C([2H])([2H])c1c2c(nn1-c1cc(F)cnc1OC)OCCCn1nc(Cl)c3cnc(nc31)N2] |
| 30 | 8-Chloro-2-(5-fluoro-2-methylpyridin-3-yl)-3-(methyl-d₃)-2,4,12,13-tetrahydro-11H-5,7-(azenometheno)dipyrazolo[3,4-b:5',1'-g][1]oxa[4,6,8]triazacycloundecine | 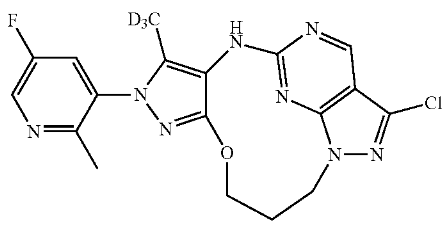 [SMILES: [2H]C([2H])([2H])c1c2c(nn1-c1cc(F)cnc1C)OCCCn1nc(Cl)c3cnc(nc31)N2] |

Definitions

In the present context, "alkyl" is intended to indicate a straight or branched saturated hydrocarbon. In particular, $C_1$-$C_3$-alkyl is intended to indicate such hydrocarbon having 1, 2 or 3 carbon atoms in the longest continuous carbon chain. Typical alkyl groups include, but are not limited to, methyl, ethyl, propyl, isopropyl, butyl, isobutyl, t-butyl and the like.

As used herein, the term "isotopically labelled $C_1$-$C_3$-alkyl" means that either one or more of the carbon or one or more of the hydrogen atom(s) in the alkyl group is replaced with a corresponding isotope such as $^{13}C$ and/or $^{14}C$ for carbon atom(s), or deuterium or tritium for hydrogen atom(s). In one embodiment at least one $^{13}C$ atom is replaced with a $^{14}C$ atom. In one embodiment at least one $^{12}C$ atom is replaced with a $^{14}C$ atom. In one embodiment at least one $^{12}C$ atom is replaced with a $^{13}C$ atom. In a further embodiment at least one hydrogen atom is replaced with deuterium. In an embodiment of the invention the hydrogen atoms are all replaced by deuterium. Representative examples of isotopically labelled alkyl include but are not limited to —CD₃, —CD₂CD₃. In a preferred embodiment, the isotopically labelled $C_1$-$C_3$-alkyl is —CD₃.

As used herein, the term "isotopically labelled O—$C_1$-$C_3$-alkyl" means that either one or more of the carbon or one or more of the hydrogen atom(s) in the alkyl group is replaced with a corresponding isotope such as $^{13}C$ and/or $^{14}C$ for carbon atom(s), or deuterium or tritium for hydrogen atom(s). In one embodiment at least one $^{13}C$ atom is replaced with a $^{14}C$ atom. In one embodiment at least one $^{12}C$ atom is replaced with a $^{14}C$ atom. In one embodiment at least one $^{12}C$ atom is replaced with a $^{13}C$ atom. In another embodiment at least one hydrogen atom is replaced with deuterium. In an embodiment of the invention the hydrogen atoms are all replaced by deuterium. Representative examples of isotopically labelled alkoxy include but are not limited to —O-CD₃, —O-CD₂CD₃. In a preferred embodiment, the isotopically labelled O—$C_1$-$C_3$-alkyl is —O-CD₃.

The term "alkoxy" as used herein refers to a group of formula —O-alkyl, wherein alkyl is defined as above. In particular, $C_1$-$C_3$-alkoxy is intended to indicate an alkoxy-group having 1, 2 or 3 hydrocarbon atoms in the longest continuous carbon chain. Examples of alkoxy groups include, but are not limited to, methoxy, ethoxy, propoxy, butoxy, isobutoxy, t-butoxy and the like.

The term "haloalkyl" or "haloalkoxy" is intended to refer to an alkyl or alkoxy group as defined hereinabove with 1, 2 or 3 hydrogens replaced by a halogen. Representative examples include but are not limited to CH₂F, CHF₂, CF₃, OCF₃, OCH₂F, and OCHF₂, Similarly, the term "fluoroalkyl" is intended to refer to an alkyl group as defined hereinabove, with 1, 2, or 3 hydrogens replaced by fluorine. Representative examples include but are not limited to CH₂F, CHF₂, and —CF₃.

In the present context, "halogen" is intended to indicate members of the 7$^{th}$ main group of the periodic table of the elements, such as bromine, fluorine, and chlorine.

The term "heteroatom" is intended to mean sulfur, oxygen, or nitrogen.

The term "cyano" as used herein, means at least one —CN group is appended to the parent molecular moiety.

The term "cyanoalkyl" as used herein is intended to indicate an alkyl group as defined herein, wherein at least one —CN group is appended to the parent molecular moiety.

The term "cyclic" as used herein refers to any cyclic structure, including heterocyclic, aromatic and heteroaromatic non-fused ring systems. The term "membered" is meant to denote the number of skeletal atoms that constitute the ring. Thus, for example, pyridyl, pyranyl, and pyrimidinyl are six-membered rings and pyrrolyl, and tetrahydrofuranyl are five-membered rings.

The term "cycloalkyl," as used herein, refers to a carbocyclic ring system containing three to ten carbon atoms, zero heteroatoms and zero double bonds. The cycloalkyl may be monocyclic or bicyclic, wherein the bicyclic ring is joined bridged, fused, or spirocyclic.

The terms "heterocycle", "heterocyclic" and "heterocyclyl" as used herein, alone or in combination, refers to saturated or unsaturated nonaromatic rings containing from 4 to 7 ring atoms where one or more of the ring atoms are heteroatoms. The heterocycle may be monocyclic or bicyclic, wherein the bicyclic ring is joined bridged, fused, or spirocyclic.

In the present context, the term "therapeutically effective amount" of a compound is intended to indicate an amount sufficient to alleviate or partially arrest the clinical manifesta-tions of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, e.g. by con-structing a matrix of values and testing different points in the matrix, which is all within the ordinary skills of a trained physician.

In the present context, the term "treatment" and "treating" means the management and care of a patient for the purpose of combating a disease. The term is intended to include the full spectrum of treatments for a given disease from which the patient is suffering, such as administration of the active compound to alleviate the symptoms or complications, to delay the progression of the disease, to alleviate or relief the symptoms and complications, and/or to cure or eliminate the disease. The patient to be treated is preferably a mammal, in particular a human being. In the present context, "disease" can be used synonymous with disorder, condition, malfunction, dysfunction, and the like.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

Embodiments of the Invention

In the following, embodiments of the invention are disclosed.

In a first aspect of the invention is provided a compound of formula IIa, or a pharmaceutically acceptable salt thereof, wherein:

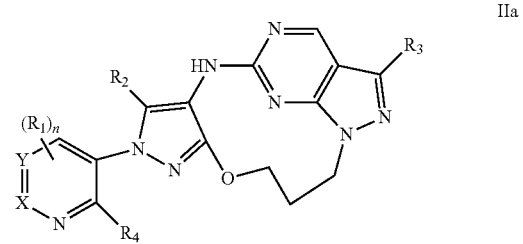

IIa

X is CH, $CR_1$ or N;

Y is CH, $CR_1$ or N;

$R_1$ is independently selected from the group consisting of a $C_1$-$C_3$ alkyl, a $C_1$-$C_3$ haloalkyl, and halogen;

$R_2$ is selected from a $C_1$-$C_3$ alkyl or an isotopically labelled $C_1$-$C_3$ alkyl;

$R_3$ is selected from the group consisting of a halogen, a cyano, and a $C_1$-$C_3$ haloalkyl;

$R_4$ is selected from the group consisting of a $C_1$-$C_3$ alkyl, an isotopically labelled $C_1$-$C_3$ alkyl, a $C_1$-$C_3$ haloalkyl, a O—$C_1$-$C_3$ alkyl, an isotopically labelled O—$C_1$-$C_3$ alkyl, a O—$C_1$-$C_3$ haloalkyl, and a O—$C_3$-$C_6$ cycloalkyl;

n is 0,1 or 2.

In an embodiment, the invention provides a compound of formula I, or a pharmaceutically acceptable salt thereof, wherein:

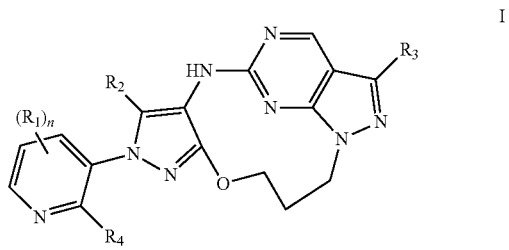

I $R_1$ is independently selected from the group consisting of a $C_1$-$C_3$ alkyl, a $C_1$-$C_3$ haloalkyl, and a halogen;

$R_2$ is selected from a $C_1$-$C_3$ alkyl or an isotopically labelled $C_1$-$C_3$ alkyl;

$R_3$ is selected from the group consisting of a halogen, a cyano, and a $C_1$-$C_3$ haloalkyl;

$R_4$ is selected from the group consisting of a $C_1$-$C_3$ alkyl, a O—$C_1$-$C_3$ haloalkyl, a O—$C_1$-$C_3$ alkyl, and a $C_1$-$C_3$ haloalkyl;

n is 0, 1 or 2.

In a further embodiment, is provided a compound of formula Ia, or a pharmaceutically acceptable salt thereof wherein:

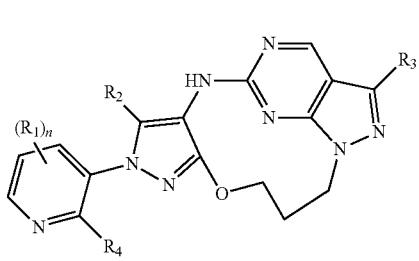

R₁ is selected from the group consisting of a $C_1$-$C_3$ alkyl, a $C_1$-$C_3$ haloalkyl, and a halogen;
R₂ is selected from a $C_1$-$C_3$ alkyl or an isotopically labelled $C_1$-$C_3$ alkyl;
R₃ is halogen;
R₄ is selected from the group consisting of a $C_1$-$C_3$ alkyl, a O—$C_1$-$C_3$ haloalkyl, a O—$C_1$-$C_3$ alkyl, and a $C_1$-$C_3$ haloalkyl;
n is 0 or 1.
In an embodiment X is CH or $CR_1$ and Y is CH or $CR_1$.
In an embodiment X is CH and Y is CH.
In an embodiment X is $CR_1$ and Y is $CR_1$.
In an embodiment X is CH and Y is $CR_1$.
In an embodiment X is $CR_1$ and Y is CH.
In an embodiment X is CH or $CR_1$ and Y is N.
In an embodiment X is N and Y is CH or $CR_1$.
In an embodiment X is N and Y is $CR_1$.
In an embodiment X is N and Y is CH.
In an embodiment X is CH and Y is N.
In an embodiment X is $CR_1$ and Y is N.
In an embodiment, R₁ is a $C_1$-$C_3$ alkyl.
In an embodiment, R₁ is —CH₃.
In an embodiment, R₁ is —CH₂CH₃.
In an embodiment, R₁ is a halogen.
In an embodiment, R₁ is fluoro.
In an embodiment, R₂ is selected from the group consisting of —CH₃, —CH₂CH₃, and —CD₃.
In an embodiment, R₂ is —CH₃.
In an embodiment, R₂ is —CH₂CH₃.
In an embodiment, R₂ is —CD₃.
In an embodiment, R₃ is a halogen.
In an embodiment, R₃ is chloro.
In an embodiment, R₄ is selected from the group consisting of —CH₃, —CH₂CH₃, —OCH₃, —OCH₂CH₃, —CHF₂, —CF₃, —O—$C_3$ cycloalkyl, O-cyclopropane, —OCH₂F, —OCHF₂, —OCF₃, and —OCD₃.
In an embodiment, R₄ is —CH₃.
In an embodiment, R₄ is —CH₂CH₃.
In an embodiment, R₄ is —OCH₃.
In an embodiment, R₄ is —OCH₂CH₃.
In an embodiment, R₄ is —CHF₂.
In an embodiment, R₄ is —CF₃.
In an embodiment, R₄ is —CF₂CH₃.
In an embodiment, R₄ is —O—$C_3$ cycloalkyl.
In an embodiment, R₄ is O-cyclopropane.
In an embodiment, R₄ is —OCH₂F.
In an embodiment, R₄ is —OCHF₂.
In an embodiment, R₄ is —OCF₃.
In an embodiment, R₄ is —OCD₃.
In an embodiment, n is 2.
In an embodiment, n is 1.
In an embodiment, n is 0.

In an embodiment, the compound of the invention is selected from the list consisting of:

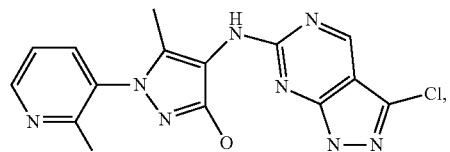

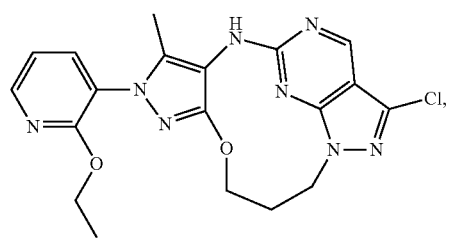

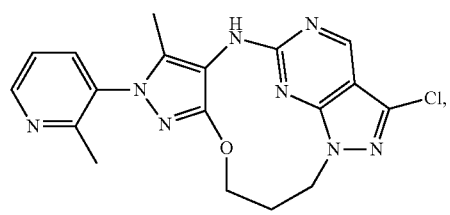

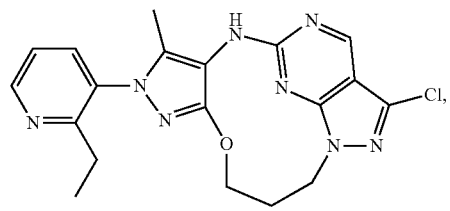

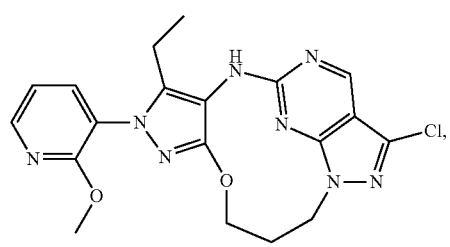

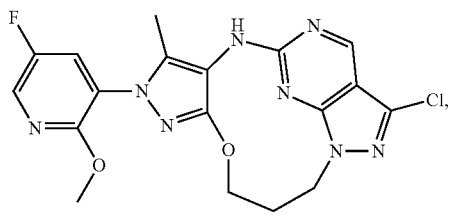

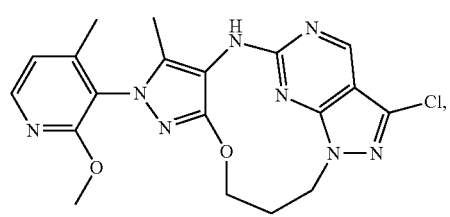

-continued
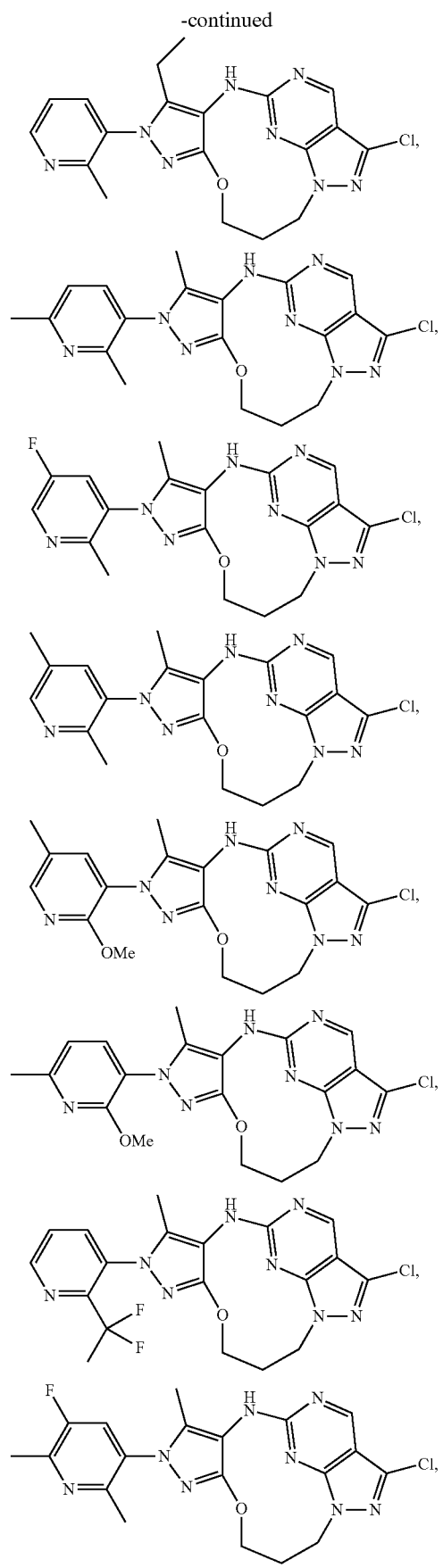
-continued
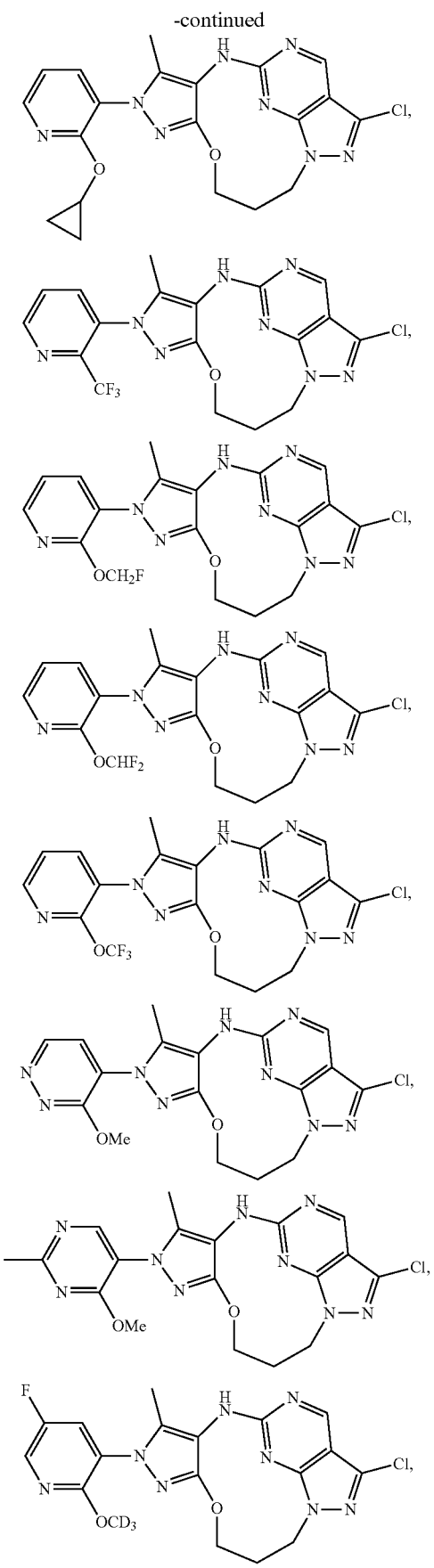

-continued

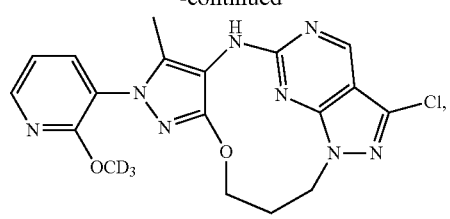

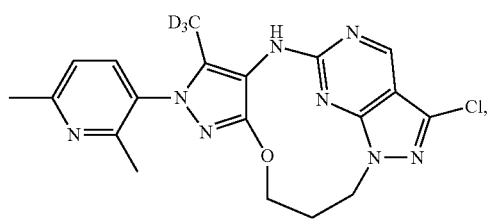

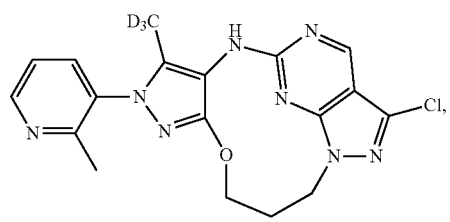

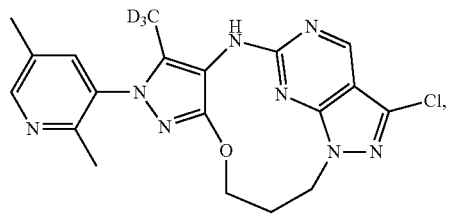

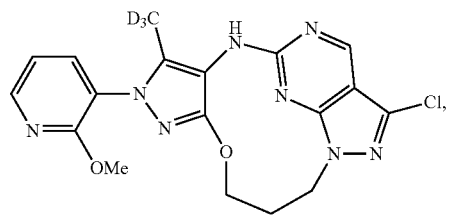

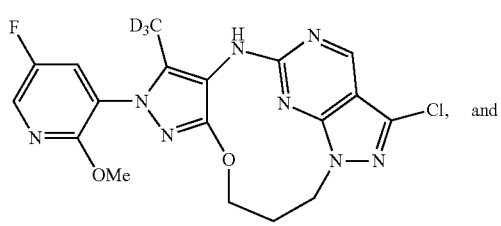, and

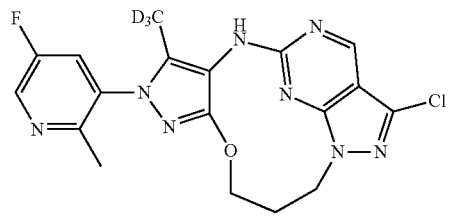

or a pharmaceutically acceptable salt thereof.

In an embodiment, the compound is

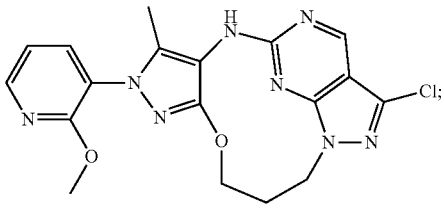

or a pharmaceutically acceptable salt thereof.
In an embodiment, the compound is

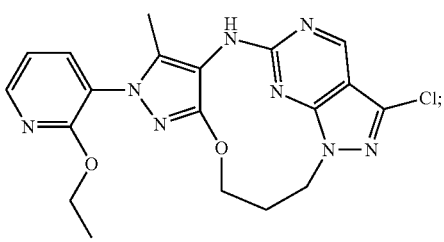 [SMILES: CCOc1ncccc1-n1nc2c(c1C)Nc1ncc3c(Cl)nn(c3n1)CCCO2]

or a pharmaceutically acceptable salt thereof.
In an embodiment, the compound is

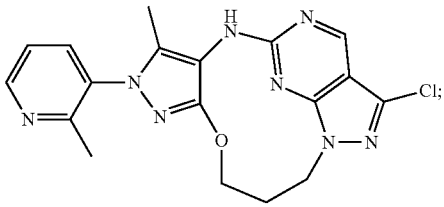 [SMILES: Cc1ncccc1-n1nc2c(c1C)Nc1ncc3c(Cl)nn(c3n1)CCCO2]

or a pharmaceutically acceptable salt thereof.
In an embodiment, the compound is

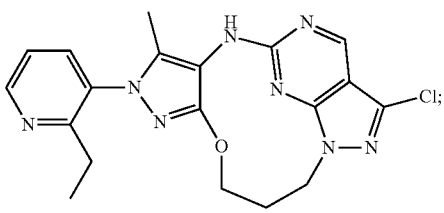

or a pharmaceutically acceptable salt thereof.
In an embodiment, the compound is

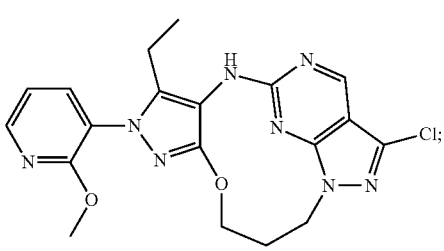 [SMILES: CCc1c2c(nn1-c1cccnc1OC)OCCCn1nc(Cl)c3cnc(nc31)N2]

or a pharmaceutically acceptable salt thereof.

In an embodiment, the compound is

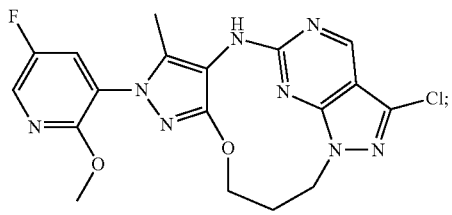 [SMILES: COc1ncc(F)cc1-n1nc2c(c1C)Nc1ncc3c(Cl)nn(c3n1)CCCO2]

or a pharmaceutically acceptable salt thereof.
In an embodiment, the compound is

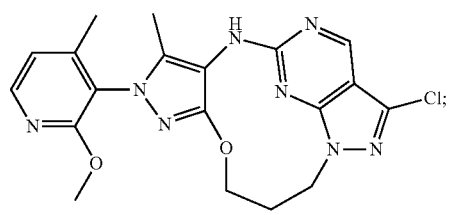

or a pharmaceutically acceptable salt thereof.
In an embodiment, the compound is

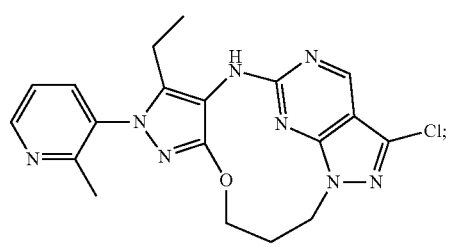 [SMILES: CCc1c2c(nn1-c1cccnc1C)OCCCn1nc(Cl)c3cnc(nc31)N2]

or a pharmaceutically acceptable salt thereof.
In an embodiment, the compound is

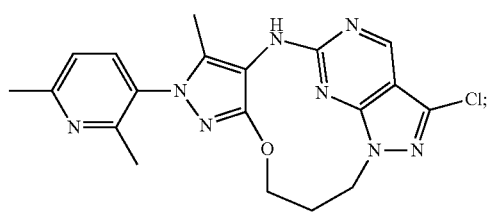 [SMILES: Cc1ccc(-n2nc3c(c2C)Nc2ncc4c(Cl)nn(c4n2)CCCO3)c(C)n1]

or a pharmaceutically acceptable salt thereof.
In an embodiment, the compound is

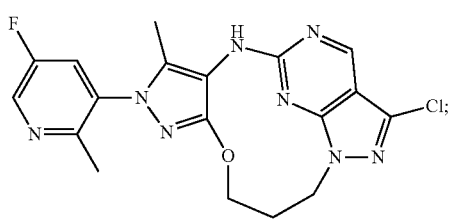 [SMILES: Cc1ncc(F)cc1-n1nc2c(c1C)Nc1ncc3c(Cl)nn(c3n1)CCCO2]

or a pharmaceutically acceptable salt thereof.

In an embodiment, the compound is

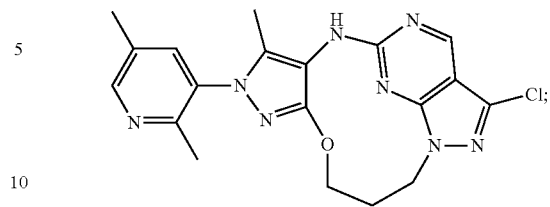

or a pharmaceutically acceptable salt thereof.
In an embodiment, the compound is

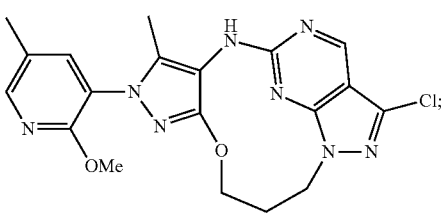 [SMILES: COc1ncc(C)cc1-n1nc2c(c1C)Nc1ncc3c(Cl)nn(c3n1)CCCO2]

or a pharmaceutically acceptable salt thereof.
In an embodiment, the compound is

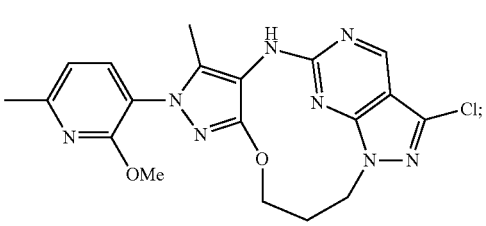 [SMILES: COc1nc(C)ccc1-n1nc2c(c1C)Nc1ncc3c(Cl)nn(c3n1)CCCO2]

or a pharmaceutically acceptable salt thereof.
In an embodiment, the compound is

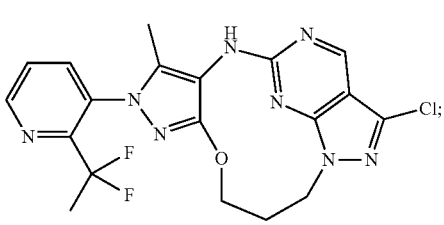 [SMILES: Cc1c2c(nn1-c1cccnc1C(C)(F)F)OCCCn1nc(Cl)c3cnc(nc31)N2]

or a pharmaceutically acceptable salt thereof.
In an embodiment, the compound is

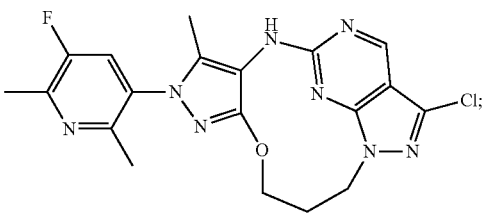 [SMILES: Cc1nc(C)c(-n2nc3c(c2C)Nc2ncc4c(Cl)nn(c4n2)CCCO3)cc1F]

or a pharmaceutically acceptable salt thereof.

In an embodiment, the compound is

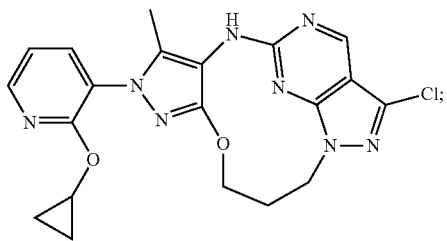 [SMILES: Cc1c2c(nn1-c1cccnc1OC1CC1)OCCCn1nc(Cl)c3cnc(nc31)N2]

or a pharmaceutically acceptable salt thereof.
In an embodiment, the compound is

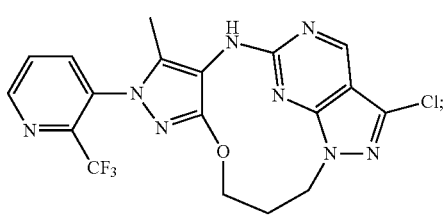

or a pharmaceutically acceptable salt thereof.
In an embodiment, the compound is

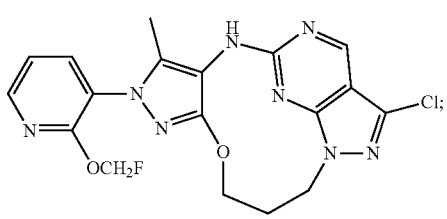

or a pharmaceutically acceptable salt thereof.
In an embodiment, the compound is

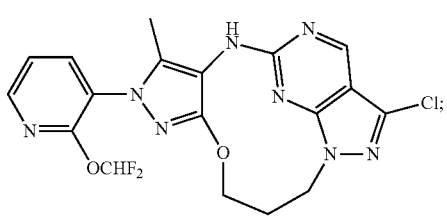 [SMILES: Cc1c2c(nn1-c1cccnc1OC(F)F)OCCCn1nc(Cl)c3cnc(nc31)N2]

or a pharmaceutically acceptable salt thereof.
In an embodiment, the compound is

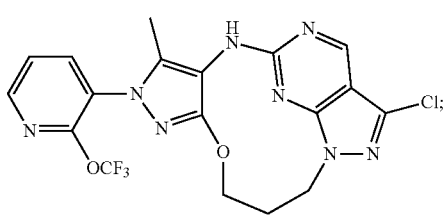 [SMILES: Cc1c2c(nn1-c1cccnc1OC(F)(F)F)OCCCn1nc(Cl)c3cnc(nc31)N2]

or a pharmaceutically acceptable salt thereof.

In an embodiment, the compound is

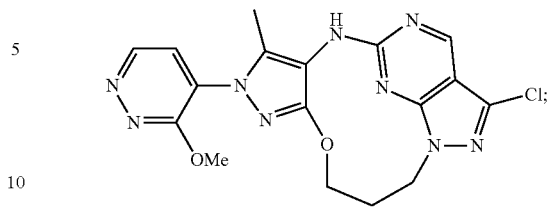

or a pharmaceutically acceptable salt thereof.
In an embodiment, the compound is

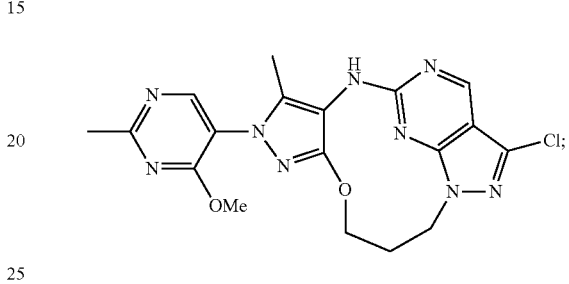

or a pharmaceutically acceptable salt thereof.
In an embodiment, the compound is

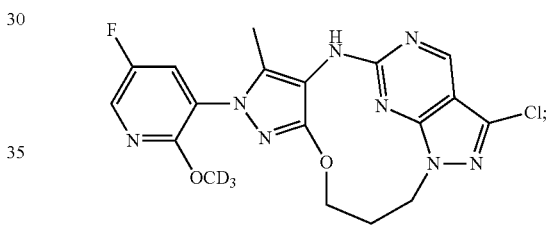

or a pharmaceutically acceptable salt thereof.
In an embodiment, the compound is

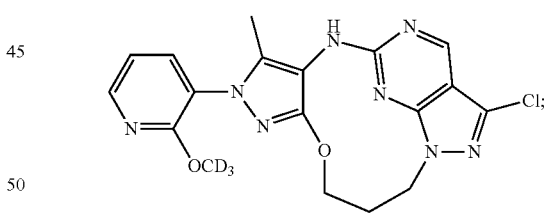

or a pharmaceutically acceptable salt thereof.
In an embodiment, the compound is

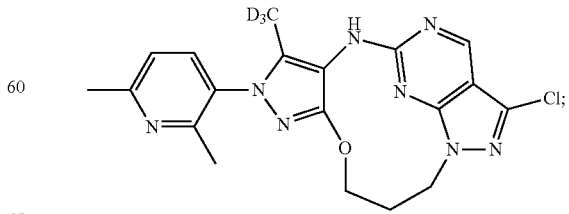

or a pharmaceutically acceptable salt thereof.

In an embodiment, the compound is

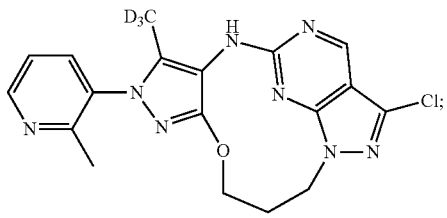 [SMILES: [2H]C([2H])([2H])c1c2c(nn1-c1cccnc1C)OCCCn1nc(Cl)c3cnc(nc31)N2]

or a pharmaceutically acceptable salt thereof.
In an embodiment, the compound is

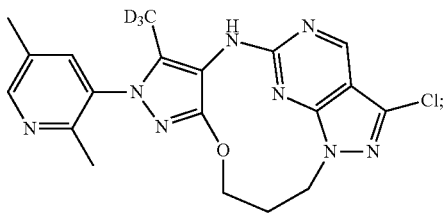 [SMILES: [2H]C([2H])([2H])c1c2c(nn1-c1cc(C)cnc1C)OCCCn1nc(Cl)c3cnc(nc31)N2]

or a pharmaceutically acceptable salt thereof.
In an embodiment, the compound is

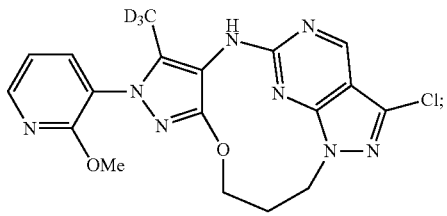 [SMILES: [2H]C([2H])([2H])c1c2c(nn1-c1cccnc1OC)OCCCn1nc(Cl)c3cnc(nc31)N2]

or a pharmaceutically acceptable salt thereof.
In an embodiment, the compound is

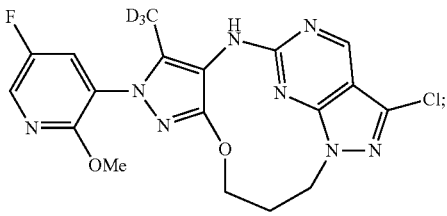 [SMILES: [2H]C([2H])([2H])c1c2c(nn1-c1cc(F)cnc1OC)OCCCn1nc(Cl)c3cnc(nc31)N2]

or a pharmaceutically acceptable salt thereof.
In an embodiment, the compound is

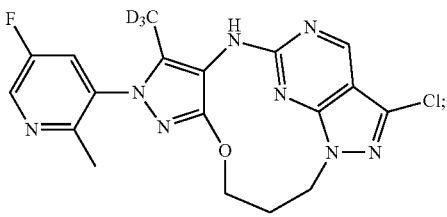 [SMILES: [2H]C([2H])([2H])c1c2c(nn1-c1cc(F)cnc1C)OCCCn1nc(Cl)c3cnc(nc31)N2]

or a pharmaceutically acceptable salt thereof.

In an embodiment the compound of the invention is selected from the list consisting of:

8-Chloro-2-(2-methoxypyridin-3-yl)-3-methyl-2,4,12,13-tetrahydro-11H-5,7-(azenome-theno)dipyrazolo[3,4-b:5',1'-g][1]oxa[4,6,8]triazacycloundecine;

8-Chloro-2-(2-ethoxypyridin-3-yl)-3-methyl-2,4,12,13-tetrahydro-11H-5,7-(azenome-theno)dipyrazolo[3,4-b:5',1'-g][1]oxa[4,6,8]triazacycloundecine;

8-Chloro-3-methyl-2-(2-methylpyridin-3-yl)-2,4,12,13-tetrahydro-11H-5,7-(azenome-theno)dipyrazolo[3,4-b:5',1'-g][1]oxa[4,6,8]triazacycloundecine;

8-Chloro-2-(2-ethylpyridin-3-yl)-3-methyl-2,4,12,13-tetrahydro-11H-5,7-(azenome-theno)dipyrazolo[3,4-b:5',1'-g][1]oxa[4,6,8]triazacycloundecine;

8-Chloro-3-ethyl-2-(2-methoxypyridin-3-yl)-2,4,12,13-tetrahydro-11H-5,7-(azenome-theno)dipyrazolo[3,4-b:5',1'-g][1]oxa[4,6,8]triazacycloundecine;

8-Chloro-2-(5-fluoro-2-methoxypyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(2-methoxy-4-methylpyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-3-ethyl-2-(2-methylpyridin-3-yl)-2,4,12,13-tetrahydro-11H-5,7-(azenome-theno)dipyrazolo[3,4-b:5',1'-g][1]oxa[4,6,8]triazacycloundecine;

8-Chloro-2-(2,6-dimethylpyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(5-fluoro-2-methylpyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(2,5-dimethylpyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(2-methoxy-5-methylpyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(2-methoxy-6-methylpyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(2-(1,1-difluoroethyl)pyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(5-fluoro-2,6-dimethylpyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(2-cyclopropoxypyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-3-methyl-2-(2-(trifluoromethyl)pyridin-3-yl)-2,4,12,13-tetrahydro-11H-5,7-(azenometheno)dipyrazolo[3,4-b:5',1'-g][1]oxa[4,6,8]triazacycloundecine;

8-Chloro-2-(2-(fluoromethoxy)pyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(2-(difluoromethoxy)pyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-3-methyl-2-(2-(trifluoromethoxy)pyridin-3-yl)-2,4,12,13-tetrahydro-11H-5,7-(azenometheno)dipyrazolo[3,4-b:5',1'-g][1]oxa[4,6,8]triazacycloundecine;

8-Chloro-2-(3-methoxypyridazin-4-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(4-methoxy-2-methylpyrimidin-5-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(5-fluoro-2-(methoxy-d$_3$)pyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(2-(methoxy-d$_3$)pyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(2,6-dimethylpyridin-3-yl)-3-(methyl-d$_3$)-2,4,12,13-tetrahydro-11H-5,7-(azenometheno)dipyrazolo[3,4-b:5',1'-g][1]oxa[4,6,8]triazacycloundecine;

8-Chloro-3-(methyl-d$_3$)-2-(2-methylpyridin-3-yl)-2,4,12,13-tetrahydro-11H-5,7-(azenometheno)dipyrazolo[3,4-b:5',1'-g][1]oxa[4,6,8]triazacycloundecine;

8-Chloro-2-(2,5-dimethylpyridin-3-yl)-3-(methyl-d$_3$)-2,4,12,13-tetrahydro-11H-5,7-(azenometheno)dipyrazolo[3,4-b:5',1'-g][1]oxa[4,6,8]triazacycloundecine;

8-Chloro-2-(2-methoxypyridin-3-yl)-3-(methyl-d$_3$)-2,4,12,13-tetrahydro-11H-5,7-(azenometheno)dipyrazolo[3,4-b:5',1'-g][1]oxa[4,6,8]triazacycloundecine;

8-Chloro-2-(5-fluoro-2-methoxypyridin-3-yl)-3-(methyl-d$_3$)-2,4,12,13-tetrahydro-11H-5,7-(azenometheno)dipyrazolo[3,4-b:5',1'-g][1]oxa[4,6,8]triazacycloundecine; and 8-Chloro-2-(5-fluoro-2-methylpyridin-3-yl)-3-(methyl-d$_3$)-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

In an embodiment the compound of the invention is 8-Chloro-2-(2-methoxypyridin-3-yl)-3-methyl-2,4,12,13-tetrahydro-11H-5,7-(azenome-theno)dipyrazolo[3,4-b:5',1'-g][1]oxa[4,6,8]triazacycloundecine; or a pharmaceutically acceptable salt thereof.

In an embodiment the compound of the invention is 8-Chloro-2-(2-ethoxypyridin-3-yl)-3-methyl-2,4,12,13-tetrahydro-11H-5,7-(azenome-theno)dipyrazolo[3,4-b:5',1'-g][1]oxa[4,6,8]triazacycloundecine; or a pharmaceutically acceptable salt thereof.

In an embodiment the compound of the invention is 8-Chloro-3-methyl-2-(2-methylpyridin-3-yl)-2,4,12,13-tetrahydro-11H-5,7-(azenome-theno)dipyrazolo[3,4-b:5',1'-g][1]oxa[4,6,8]triazacycloundecine; or a pharmaceutically acceptable salt thereof.

In an embodiment the compound of the invention is 8-Chloro-2-(2-ethylpyridin-3-yl)-3-methyl-2,4,12,13-tetrahydro-11H-5,7-(azenome-theno)dipyrazolo[3,4-b:5',1'-g][1]oxa[4,6,8]triazacycloundecine; or a pharmaceutically acceptable salt thereof.

In an embodiment the compound of the invention is 8-Chloro-3-ethyl-2-(2-methoxypyridin-3-yl)-2,4,12,13-tetrahydro-11H-5,7-(azenome-theno)dipyrazolo[3,4-b:5',1'-g][1]oxa[4,6,8]triazacycloundecine; or a pharmaceutically acceptable salt thereof.

In an embodiment the compound of the invention is 8-Chloro-2-(5-fluoro-2-methoxypyridin-3-yl)-3-methyl-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

In an embodiment the compound of the invention is 8-Chloro-2-(2-methoxy-4-methylpyridin-3-yl)-3-methyl-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

In an embodiment the compound of the invention is 8-Chloro-3-ethyl-2-(2-methylpyridin-3-yl)-2,4,12,13-tetrahydro-11H-5,7-(azenome-theno)dipyrazolo[3,4-b:5',1'-g][1]oxa[4,6,8]triazacycloundecine; or a pharmaceutically acceptable salt thereof.

In an embodiment the compound of the invention is 8-Chloro-2-(2,6-dimethylpyridin-3-yl)-3-methyl-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

In an embodiment the compound of the invention is 8-Chloro-2-(5-fluoro-2-methylpyridin-3-yl)-3-methyl-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

In an embodiment the compound of the invention is 8-Chloro-2-(2,5-dimethylpyridin-3-yl)-3-methyl-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

In an embodiment the compound of the invention is 8-Chloro-2-(2-methoxy-5-methylpyridin-3-yl)-3-methyl-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

In an embodiment the compound of the invention is 8-Chloro-2-(2-methoxy-6-methylpyridin-3-yl)-3-methyl-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

In an embodiment the compound of the invention is 8-Chloro-2-(2-(1,1-difluoroethyl)pyridin-3-yl)-3-methyl-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

In an embodiment the compound of the invention is 8-Chloro-2-(5-fluoro-2,6-dimethylpyridin-3-yl)-3-methyl-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

In an embodiment the compound of the invention is 8-Chloro-2-(2-cyclopropoxypyridin-3-yl)-3-methyl-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

In an embodiment the compound of the invention is 8-Chloro-3-methyl-2-(2-(trifluoromethyl)pyridin-3-yl)-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

In an embodiment the compound of the invention is 8-Chloro-2-(2-(fluoromethoxy)pyridin-3-yl)-3-methyl-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

In an embodiment the compound of the invention is 8-Chloro-2-(2-(difluoromethoxy)pyridin-3-yl)-3-methyl-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

In an embodiment the compound of the invention is 8-Chloro-3-methyl-2-(2-(trifluoromethoxy)pyridin-3-yl)-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

In an embodiment the compound of the invention is
8-Chloro-2-(3-methoxypyridazin-4-yl)-3-methyl-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

In an embodiment the compound of the invention is
8-Chloro-2-(4-methoxy-2-methylpyrimidin-5-yl)-3-methyl-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

In an embodiment the compound of the invention is
8-Chloro-2-(5-fluoro-2-(methoxy-$d_3$)pyridin-3-yl)-3-methyl-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

In an embodiment the compound of the invention is
8-Chloro-2-(2-(methoxy-$d_3$)pyridin-3-yl)-3-methyl-2,4,12,13-tetrahydro-11H-5,7-(azenome-theno)dipyrazolo[3,4-b:5',1'-g][1]oxa[4,6,8]triazacycloundecine; or a pharmaceutically acceptable salt thereof.

In an embodiment the compound of the invention is
8-Chloro-2-(2,6-dimethylpyridin-3-yl)-3-(methyl-$d_3$)-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

In an embodiment the compound of the invention is
8-Chloro-3-(methyl-$d_3$)-2-(2-methylpyridin-3-yl)-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

In an embodiment the compound of the invention is
8-Chloro-2-(2,5-dimethylpyridin-3-yl)-3-(methyl-$d_3$)-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

In an embodiment the compound of the invention is
8-Chloro-2-(2-methoxypyridin-3-yl)-3-(methyl-$d_3$)-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

In an embodiment the compound of the invention is
8-Chloro-2-(5-fluoro-2-methoxypyridin-3-yl)-3-(methyl-$d_3$)-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

In an embodiment the compound of the invention is
8-Chloro-2-(5-fluoro-2-methylpyridin-3-yl)-3-(methyl-$d_3$)-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

The compounds of the present invention may have one or more asymmetric centres and it is intended that any optical isomers (i.e. enantiomers or diastereomers) as separated, pure or partially purified optical isomers and any mixtures thereof including racemic mixtures, i.e. a mixture of stereoisomers, are included within the scope of the invention.

In this context is understood that when specifying the enantiomeric form, the compound is in enantiomeric excess, e.g. essentially in a pure form. Accordingly, one embodiment of the invention relates to a compound of the invention having an enantiomeric excess (ee) of at least 60%, at least 70%, at least 80%, at least 85%, at least 90%, at least 96%, preferably at least 98%.

Racemic forms can be resolved into the optical antipodes by known methods, for example by separation of diastereomeric salts thereof with an optically active acid and liberating the optically active amine compound by treatment with a base. Another method for resolving racemates into the optical antipodes is based upon chromatography on an optically active matrix. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials. Abso-lute stereochemistry may be determined by methods known to the skilled person, such as vi-brational circular dichroism (VCD) Spectroscopic analysis.

Furthermore, when a double bond or a fully or partially saturated ring system is present in the molecule geometric isomers may be formed. It is intended that any geometric isomers as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

In one embodiment of the invention a compound of formula I, formula IIa or formula Ia is isotopically labelled at the $R_2$ position. In a further embodiment of the invention, one or more of the hydrogen atoms of the compound of formula I, formula IIa or formula Ia are represented by deuterium. In a further embodiment of the invention, one or more of the hydrogen atoms at the $R_2$ position of the compound of formula I, formula IIa or formula Ia are represented by deuterium. In a further embodiment of the invention, all hydrogen atoms at the $R_2$ position of the compound of formula I, formula IIa or formula Ia are represented by deuterium. It is recognized that elements are present in natural isotopic abundances in most synthetic compounds and result in inherent incorporation of deuterium. However, the natural isotopic abundance of hydrogen isotopes such as deuterium is immaterial (about 0.015%) relative to the degree of stable isotopic substitution of compounds indicated herein. Thus, as used herein, designation of an atom as deuterium at a position indicates that the abundance of deuterium is significantly greater than the natural abundance of deuterium. Any atom not designated as a particular isotope is intended to represent any stable isotope of that atom, as will be apparent to the ordi-narily skilled artisan.

In one embodiment, designation of a position as "D" in a compound has a minimum deuterium incorporation of greater than about 60% at that position such as greater than about 70% at that position such as greater than about 80% at that position such as greater than about 85% at that position. In a further embodiment, designation of a position as "D" in a compound has a minimum deuterium incorporation of greater than about 90% at that position such as greater than about 95% at that position such as greater than about 97% at that position such as greater than about 99% at that position.

In a further aspect, the invention provides a pharmaceutical composition comprising a compound of formula I, formula IIa or formula Ia as disclosed herein or a pharmaceutically acceptable salt thereof and one or more pharmaceutically acceptable carriers.

In a further aspect, the invention provides compounds of formula I, formula IIa or formula Ia as disclosed herein or pharmaceutically acceptable salts thereof for use in therapy.

In a further aspect, the invention provides compounds of formula I, formula IIa or formula Ia as disclosed herein or pharmaceutically acceptable salts thereof for use in the treatment of a synucleinopathy.

In an embodiment, the invention provides compounds of formula I, formula IIa or formula Ia as disclosed herein or pharmaceutically acceptable salts thereof for use in the treatment of Lewy body dementia, multiple system atrophy, or Parkinson's disease.

In a further embodiment, the invention provides compounds of formula I, formula Ia or formula Ia as disclosed herein or pharmaceutically acceptable salts thereof for use in the treatment of Parkinson's disease.

In a further embodiment, the invention provides compounds of formula I, formula Ia or formula Ia as disclosed herein or pharmaceutically acceptable salts thereof for use in the treatment of a disease associated with LRRK2 such as Parkinson's disease.

In a further aspect, the invention provides use of compounds of formula I, formula Ia or formula Ia as disclosed herein or pharmaceutically acceptable salts thereof in the treatment of a synucleinopathy.

In an embodiment, the invention provides use of compounds of formula I, formula IIa or formula Ia as disclosed herein or pharmaceutically acceptable salts thereof in the treatment of Lewy body dementia, multiple system atrophy, or Parkinson's disease.

In a further embodiment, the invention provides use of compounds of formula I, formula IIa or formula Ia as disclosed herein or pharmaceutically acceptable salts thereof in the treatment of Parkinson's disease.

In a further embodiment, the invention provides use of compounds of formula I, formula IIa or formula Ia as disclosed herein or pharmaceutically acceptable salts thereof in the treatment of a disease associated with LRRK2 such as Parkinson's disease.

In a further aspect, the invention relates to the use of a compound of formula I, formula IIa or formula Ia as disclosed herein or a pharmaceutically acceptable salt thereof in the manufacture of a medicament for use in the treatment of a synucleinopathy.

In an embodiment, the invention relates to the use of a compound of formula I, formula IIa or formula Ia as disclosed herein or a pharmaceutically acceptable salt thereof in the manufacture of a medicament for use in the treatment of Lewy body dementia, multiple system atrophy, or Parkinson's disease.

In a further embodiment, the invention relates to the use of a compound of formula I, formula IIa or formula Ia as disclosed herein or a pharmaceutically acceptable salt thereof in the manufacture of a medicament for use in the treatment of Parkinson's disease.

In a further embodiment, the invention relates to the use of a compound of formula I, formula IIa or formula Ia as disclosed herein or a pharmaceutically acceptable salt thereof in the manufacture of a medicament for use in the treatment of a disease associated with LRRK2 such as Parkinson's disease.

In a further aspect, the invention relates to a method for the treatment of a disease associated with LRRK2 such as synucleinopathies, the method comprising the administration of a therapeutically effective amount of a compound of formula I, formula IIa or formula Ia as disclosed herein or a pharmaceutically acceptable salt thereof to a patient in need thereof.

In a further embodiment, the invention relates to a method for the treatment of a disease associated with LRRK2, wherein the disease is Lewy body dementia, multiple system atrophy, or Parkinson's disease; the method comprising the administration of a therapeutically effective amount of a compound of formula I, formula IIa or formula Ia as disclosed herein or a pharmaceutically acceptable salt thereof to a patient in need thereof.

In a further embodiment, the invention relates to a method for the treatment of Parkinson's disease, the method comprising the administration of a therapeutically effective amount of a compound of formula I, formula IIa or formula Ia as disclosed herein or a pharmaceutically acceptable salt thereof to a patient in need thereof.

In a further embodiment, the invention relates to a method for the treatment of a disease associated with LRRK2 such as Parkinson disease, the method comprising the administration of a therapeutically effective amount of a compound of formula I, formula IIa or formula Ia as disclosed herein or a pharmaceutically acceptable salt thereof to a patient in need thereof.

Pharmaceutically Acceptable Salts

The compounds of this invention are generally utilized as the free substance or as a pharmaceutically acceptable salt thereof. When a compound of formula I, formula IIa or formula Ia contains a free base, such salts may be prepared in a conventional manner by treating a solution or suspension of a free base of formula I, formula IIa or formula Ia with a molar equivalent of a pharmaceutically acceptable acid. Representative examples of suitable organic and inorganic acids are described below.

Pharmaceutically acceptable salts in the present context are intended to indicate non-toxic, i.e. physiologically acceptable salts. The term pharmaceutically acceptable salts includes salts formed with inorganic and/or organic acids such as hydrochloric acid, hydrobromic acid, phosphoric acid, nitrous acid, sulphuric acid, benzoic acid, citric acid, gluconic acid, lactic acid, maleic acid, succinic acid, tartaric acid, acetic acid, propionic acid, oxalic acid, maleic acid, fumaric acid, glutamic acid, pyroglutamic acid, salicylic acid and sulfonic acids, such as methanesul-fonic acid, ethanesulfonic acid, toluenesulfonic acid and benzene-sulfonic acid. Some of the acids listed above are di- or tri-acids, i.e. acids containing two or three acidic hydrogens, such as phosphoric acid, sulphuric acid, fumaric acid and maleic acid. Di- and tri-acids may form 1:1, 1:2 or 1:3 (tri-acids) salts, i.e. a salt formed between two or three molecules of the compound of the present invention and one molecule of the acid.

The term pharmaceutically acceptable salts include salts formed with inorganic and/or organic bases, such as alkali metal bases, such as sodium hydroxide, lithium hydroxide, potassium hydroxide, alkaline earth bases, such as calcium hydroxide and magnesium hydroxide, and organic bases, such as trimethylamine. Some of the bases listed above are di- or tri-bases, i.e. bases able to receive two or three acidic hydrogens, such as calcium hydroxide and magnesium hydroxide. Di- and tri-bases may form 1:1 or 1:2 salts, i.e. a salt formed between two molecules of the compound of the present invention and one molecule of the base.

Additional examples of useful acids and bases to form pharmaceutically acceptable salts can be found e.g. in Stahl and Wermuth (Eds.) "Handbook of Pharmaceutical salts. Properties, selection, and use", Wiley-VCH, 2008.

Pharmaceutical Composition

The above-mentioned compounds or pharmaceutically acceptable salts may be in a composition as the sole active pharmaceutical ingredient or in combination with other pharmaceutically active ingredients. Additionally, one or more pharmaceutically acceptable carriers or diluents may be in the composition.

The pharmaceutical compositions may be specifically formulated for administration by any suitable route such as the oral, rectal, nasal, pulmonary, topical (including buccal and sub-lingual), transdermal, intracisternal, intraperitoneal, vaginal, and parenteral (including subcutaneous, intramuscular, intrathecal, intravenous, and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragées, pills, lozenges, powders, and granules. Where appropriate, they can be prepared with coatings.

Liquid dosage forms for oral administration include solutions, emulsions, suspensions, syrups, and elixirs.

Pharmaceutical compositions for parenteral administration include sterile aqueous and nonaqueous injectable solutions, dispersions, suspensions, or emulsions as well as sterile powders to be reconstituted in sterile injectable solutions or dispersions prior to use.

Other suitable administration forms include suppositories, sprays, ointments, creams, gels, inhalants, dermal patches, implants, etc.

Conveniently, the compounds of the invention are administered in a unit dosage form containing said compounds in an amount of about 0.1 to 500 mg, such as 10 mg, 50 mg, 100 mg, 150 mg, 200 mg, or 250 mg of a compound of the present invention.

For parenteral administration, solutions of the compound of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous, and intraperitoneal administration. The sterile aqueous media employed are all readily available by standard techniques known to those skilled in the art.

Suitable pharmaceutical carriers include inert solid diluents or fillers, sterile aqueous solutions, and various organic solvents. Examples of solid carriers are lactose, terra alba, sucrose, cyclodextrin, talc, gelatine, agar, pectin, acacia, magnesium stearate, stearic acid, and lower alkyl ethers of cellulose. Examples of liquid carriers are syrup, peanut oil, olive oil, phosphor lipids, fatty acids, fatty acid amines, polyoxyethylene and water. The pharmaceutical compositions formed by combining the compound of the invention and the pharmaceutically acceptable carriers are then readily administered in a variety of dosage forms suitable for the disclosed routes of administration.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tablet, e.g. placed in a hard gelatine capsule in powder or pellet form or in the form of a troche or lozenge. The amount of solid carrier may vary but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants and/or diluents followed by compression of the mixture in a conventional tabletting machine. Examples of adjuvants or diluents comprise corn starch, potato starch, talcum, magnesium stearate, gelatine, lactose, gums, and the like. Any other adjuvants or additives usually used for such purposes such as colourings, flavourings, preservatives etc. may be used provided that they are compati-ble with the active ingredients.

Treating Diseases

As established above, LRRK2 inhibitors may be used in the treatment of Parkinson's disease and particular mention is made of Parkinson's disease associated with mutations in LRRK2, such as Gly2019Ser. Moreover, LRRK2 inhibitors are also expected to be useful in the treatment of other diseases which are associated with LRRK2. LRRK2 has been identified as a core compo-nent in Lewy body formation and is thus expected to be useful in the treatment of synucleinopathies such as Lewy body dementia [Neuropathol. Appl. Neurobiol., 34, 272-283, 2008]. Expression of LRRK2 mRNA is highly enriched in brain, lungs, kidney, spleen, and blood suggesting that functional impact of increased LRRK2 activity is likely to be most relevant in pathogenic and pathologic conditions associated with those regions. Support for that notion can be found in studies showing an increased risk of non-skin cancer in LRRK2 Gly2019Ser mutation carriers and especially for renal and lung cancer [Mov. Disorder, 25, 2536-2541, 2010]. Overexpression of LRRK2 by chromosomal amplification has also been identified in papillary renal and thyroid carcinomas. Also, genetic association of LRRK2 has been reported for diseases where aberrant responses of the immune system are involved. This is the case for inflammatory bowel diseases such as Crohn's disease and ulcerative colitis as well as for leprosy [*Nat. Genet.* 42, 1118-1125, 2010; *Inflamm. Bowel Dis.* 16, 557-558, 2010; N. Engl. J. Med. 361, 2609-2618, 2009; *Inflamm. Bowel Dis*].

Thus, in an embodiment is provided a compound, or pharmaceutically acceptable salts thereof, or a pharmaceutical composition according to the invention for use in the treatment of a disease in the central nervous system, such as a synucleinopthy selected from Lewy body dementia, multiple system atrophy, and Parkinson's disease.

In an embodiment, the disease in the central nervous system is Parkinson's disease.

In an embodiment, the Parkinson's disease is idiopathic Parkinson's disease, sporadic Parkinson's disease or Parkinson's disease in patients carrying a G2019S mutation in LRRK2.

In an embodiment, the Parkinson's disease is idiopathic Parkinson's disease, sporadic Parkinson's disease or Parkinson's disease in patients carrying one or more genetic mutations, which result in the expression of the G2019S variant of the LRRK2 protein.

In an embodiment, the Parkinson's disease is idiopathic Parkinson's disease, sporadic Parkinson's disease or Parkinson's disease in patients carrying one or more genetic mutations, which result in the expression of one or more of the G2019S, I2020T, G2385R, A419V, R1441G, R1441H, R1441C, R1628P and Y1699C variants of the LRRK2 protein.

In an embodiment, the Parkinson's disease is idiopathic Parkinson's disease, sporadic Parkinson's disease or Parkinson's disease in patients carrying one or more genetic mutations, which result in the expression of one or more of the M1646T, S1647T, Y2189C, N1437H, M1646T and N2081D variants of the LRRK2 protein.

In an embodiment, the Parkinson's disease is idiopathic Parkinson's disease, sporadic Parkinson's disease or Parkinson's disease in patients who do not carry one or more genetic mutations, which result in the expression of one or more of the N551K, R1398H and K1423K variants of the LRRK2 protein.

In an embodiment, the Parkinson's disease is idiopathic Parkinson's disease, sporadic Parkinson's disease or Parkinson's disease in patients carrying one or more LRRK2 genetic non-coding variants selected from rs76904798-T and Rs1491942-G.

In an embodiment, the Parkinson's disease is idiopathic Parkinson's disease.

In an embodiment, the Parkinson's disease is sporadic Parkinson's disease.

In an embodiment, the Parkinson's disease is in patients carrying a G2019S mutation in LRRK2.

In an embodiment, the Parkinson's disease is in patients carrying one or more genetic mutations, which result in the expression of the G2019S variant of the LRRK2 protein.

In an embodiment, the Parkinson's disease is in patients carrying one or more genetic mutations, which result in the expression of one or more of the G2019S, I2020T, G2385R, A419V, R1441G, R1441H, R1441C, R1628P and Y1699C variants of the LRRK2 protein.

In an embodiment, the Parkinson's disease is in patients carrying one or more genetic mutations, which result in the expression of one or more of the M1646T, S1647T, Y2189C, N1437H, M1646T and N2081D variants of the LRRK2 protein.

In an embodiment, the Parkinson's disease is in patients who does not carry one or more genetic mutations, which result in the expression of one or more of the N551K, R1398H and K1423K variants of the LRRK2 protein.

In an embodiment, the Parkinson's disease is in patients carrying one or more LRRK2 genetic non-coding variants selected from rs76904798-T and Rs1491942-G.

In an embodiment, the Parkinson's disease is in patients carrying one or more LRRK2 non-coding variants selected from rs76904798-T and Rs1491942-G.

In an embodiment, the Parkinson's disease is in patients carrying one or more mutated forms of LRRK2 selected from G2019S, I2020T, M1646T, G2385R, A419V, N551K, R1398H, K1423K, R1441G, R1441H, R1441C, R1628P, S1647T, Y1699C, and Y2189C.

In one embodiment, the compound of the present invention is administered in an amount from about 0.001 mg/kg body weight to about 100 mg/kg body weight per day. In particular, daily dosages may be in the range of 0.01 mg/kg body weight to about 50 mg/kg body weight per day. The exact dosages will depend upon the frequency and mode of administration, the sex, the age, the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 1-1000 mg/day of a compound, or pharmaceutically acceptable salt thereof of the present invention, such as 1-500 mg/day.

The compounds, or pharmaceutically acceptable salt thereof of the present invention may be administered alone as a pure compound or in a pharmaceutical composition comprising the compound or a pharmaceutical salt thereof and one or more pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, $22^{nd}$ Edition, Pharmaceutical Press, 2012. In the present context, "excipient", "carrier", "diluent", "adjuvant" and the like are used synonymously and are intended to mean the same.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

Monotherapy, and Adjunctive Treatment

The compounds of the invention may be administered as a monotherapy or as part of an adjunctive treatment regimen.

In an embodiment, the compounds of the invention may be administered as monotherapy in the treatment of a synucleinopathy, such as Lewy body dementia, multiple system atrophy or Parkinson's disease. Such monotherapy indicates that the compound of the invention is the only active ingredient administered to the patient to treat this specific disease, however such monotherapy does not exclude that the patient may be treated with other drugs to treat other conditions.

In a further embodiment, the compounds of the invention may be administered as part of an adjunctive treatment regimen targeting the synucleinopathy such as Lewy body dementia, multiple system atrophy or Parkinson's disease. Such adjunctive treatment indicates that the compound of the invention is administered adjunctive to an already existing treatment regimen targeting the synucleinopathy or the associated symptoms. Alternatively, the adjunctive treatment may also indicate that the compound of the invention is the first drug to be administered to treat the synucleinopathy and then subsequently another drug is added to the treatment regimen, which additional drug is also targeting the synucleinopathy or the associated symptoms.

In an embodiment, the compound of the invention is administered in combination with an additional compound for the combined treatment of a synucleinopathy such as Lewy body dementia, multiple system atrophy or Parkinson's disease.

In a specific embodiment, such additional compound may be selected from caspase inhibitors, calpain inhibitors, LRRK2 inhibitors, BACE1 inhibitors, antibodies against any form of Aβ peptides, inflammation inhibitors, LAG-3 antibodies, molecules inhibiting alphasynuclein aggregation, nicotine, caffeine, Monoamine oxidase B inhibitor, Levodopa/carbidopa, Dopamine agonists, COMT inhibitors, $A_2A$ antagonists, anti-alphasynuclein antibodies, Mitogen-activated protein kinase 14 inhibitors, USP30 inhibitors, Beta adrenoreceptor agonists, dopamine D1 PAMs, Toll-like receptor 2 antagonists, Carnitine palmitoyl transferase 1 inhibitors, Glutamate 5 receptor antagonists, Muscarinic M2 receptor antagonists, Muscarinic M3 receptor antagonists, Muscarinic M4 receptor antagonists, 5 Hydroxy tryptamine 1A receptor agonists, 5 Hydroxy tryptamine 4 receptor agonists, 5 Hydroxy tryptamine 3 receptor agonists, 5 Hydroxy tryptamine 2A receptor antagonists, Alpha 1a adrenoreceptor antagonists, Sigma 1 receptor agonists, Sigma 2 receptor antagonists, Dopamine D1 receptor agonists, Dopamine D2 receptor agonists, Dopamine D3 receptor agonists, Dopamine D5 receptor antagonists, dopamine reuptake inhibitors, DOPA decarboxylase inhibitors, Insulin-like growth factor 1 antagonists, Insulin-like growth factor 2 antagonists, Tyrosine kinase inhibitors, Ras inhibitors, Leucotriene D4 antagonists, Leucotriene receptor antagonists, PDE1 inhibitors, T-type calcium channel antagonists, Peroxiredoxin inhibitors, GLP-1R agonists, NMDA receptor blockers, Lipoxygenase inhibitors, and Peroxisome proliferator-activated receptor gamma agonists.

In a further embodiment the additional compound is selected from the list consisting of trihexyphenidyl, biperiden, metixene, procyclidine, profenamine, dexetimide, phenglutarimide, mazaticol, bornaprine, tropatepine, etanautine, orphenadrine, benzatropine, etybenzatropine, dopamine, levodopa, carbidopa, levodopa/carbidopa, melevodopa, etilevodopa, foslevodopa, amantadine, bromocriptine, pergolide, dihydroergocryptine mesylate, ropinirole, pramipexole, cabergoline, apomorphine, piribedil, rotigotine, selegiline, rasagiline, safinamide, tolcapone, entacapone, budipine, opicapone, istradefylline, pralnacasan, bapineuzemab, solanezumab, gantenerumab, crenezumab, aducanumab, glunozumab, prasinezumab, miglustat, eliglustat, ropinerole, neflamapimod, bosutinib, oxafuramine, nadolol, nilotinib, vodobatinib, clenbuterol, mevidalen, emeramide, tomaralimab, mitometin, dipraglurant, ezeprogind, blarcamesine, buntanetap, renzapride, tavapadon, pramiprexole, salbutamol, Infudopa, alirinetide, antraquinolol, a rasagiline prodrug, apomorphine, pramiprexole, radotinib, talineuren, montelukast, lenrispodun, pirepemat, suvecaltamide, sonlicromanol, L-Demethyl phencynonate hydrochloride, mesocarb, roluperidone, exenatide, befiradol, ketamine, pridopidine, utroloxestat, aplindore, finamine, phenlarmide, (R)-troloxamide quinone, cannibigerol, and kenterin.

Compounds Useful in Manufacturing of Compounds of the Invention

The compounds of the invention may be prepared by methods described in the experimental section, together with synthetic methods known in the art of organic chemistry, or modifications that are familiar to those of ordinary skill in the art.

In an aspect the invention provides compounds which are useful as intermediate compounds in a manufacturing process for compounds of the invention.

In an embodiment, such intermediate compounds are compounds of formula XVI, or a salt thereof, wherein:

XVI

X is CH, CR$_1$ or N;
Y is CH, CR$_1$ or N;
R$_1$ is independently selected from the group consisting of a C$_1$-C$_3$ alkyl, a C$_1$-C$_3$ haloalkyl, and halogen;
R$_2$ is selected from a C$_1$-C$_3$ alkyl or an isotopically labelled C$_1$-C$_3$ alkyl;
R$_3$ is selected from the group consisting of a halogen, a cyano, and a C$_1$-C$_3$ haloalkyl;
R$_4$ is selected from the group consisting of a C$_1$-C$_3$ alkyl, an isotopically labelled C$_1$-C$_3$ alkyl, a C$_1$-C$_3$ haloalkyl, a O—C$_1$-C$_3$ alkyl, an isotopically labelled O—C$_1$-C$_3$ alkyl, a O—C$_1$-C$_3$ haloalkyl, and a O—C$_3$-C$_6$ cycloalkyl;
n is 0, 1 or 2.

In another embodiment, such intermediate compounds are compounds of formula II, or a salt thereof, wherein:

II

R$_1$ is independently selected from the group consisting of a C$_1$-C$_3$ alkyl, a C$_1$-C$_3$ haloalkyl, and halogen;
R$_2$ is selected from a C$_1$-C$_3$ alkyl or an isotopically labelled C$_1$-C$_3$ alkyl;
R$_3$ is selected from the group consisting of a halogen, a cyano, and a C$_1$-C$_3$ haloalkyl;
R$_4$ is selected from the group consisting of a C$_1$-C$_3$ alkyl, an isotopically labelled C$_1$-C$_3$ alkyl, a C$_1$-C$_3$ haloalkyl, a O—C$_1$-C$_3$ alkyl, an isotopically labelled O—C$_1$-C$_3$ alkyl, a O—C$_1$-C$_3$ haloalkyl, and a O—C$_3$-C$_6$ cycloalkyl;
n is 0, 1 or 2.
In an embodiment X is CH or CR$_1$ and Y is CH or CR$_1$.
In an embodiment X is CH and Y is CH.
In an embodiment X is CR$_1$ and Y is CR$_1$.
In an embodiment X is CH and Y is CR$_1$.
In an embodiment X is CR$_1$ and Y is CH.
In an embodiment X is CH or CR$_1$ and Y is N.
In an embodiment X is N and Y is CH or CR$_1$.
In an embodiment X is N and Y is CR$_1$.
In an embodiment X is N and Y is CH.
In an embodiment X is CH and Y is N.
In an embodiment X is CR$_1$ and Y is N.
In an embodiment, R$_1$ is a C$_1$-C$_3$ alkyl.
In an embodiment, R$_1$ is —CH$_3$.
In an embodiment, R$_1$ is —CH$_2$CH$_3$.
In an embodiment, R$_1$ is a halogen.
In an embodiment, R$_1$ is fluoro.
In an embodiment, R$_2$ is selected from the group consisting of —CH$_3$, —CH$_2$CH$_3$, and —CD$_3$.
In an embodiment, R$_2$ is —CH$_3$.
In an embodiment, R$_2$ is —CH$_2$CH$_3$.
In an embodiment, R$_2$ is —CD$_3$.
In an embodiment, R$_3$ is a halogen.
In an embodiment, R$_3$ is chloro.
In an embodiment, R$_4$ is selected from the group consisting of —CH$_3$, —CH$_2$CH$_3$, —OCH$_3$, —OCH$_2$CH$_3$, —CHF$_2$, —CF$_3$, —O—C$_3$ cycloalkyl, O-cyclopropane, —OCH$_2$F, —OCHF$_2$, —OCF$_3$, and —OCD$_3$.

In an embodiment, R$_4$ is —CH$_3$.
In an embodiment, R$_4$ is —CH$_2$CH$_3$.
In an embodiment, R$_4$ is —OCH$_3$.
In an embodiment, R$_4$ is —OCH$_2$CH$_3$.
In an embodiment, R$_4$ is —CHF$_2$.
In an embodiment, R$_4$ is —CF$_3$.
In an embodiment, R$_4$ is —CF$_2$CH$_3$.
In an embodiment, R$_4$ is —O—C$_3$ cycloalkyl.
In an embodiment, R$_4$ is O-cyclopropane.
In an embodiment, R$_4$ is —OCH$_2$F.
In an embodiment, R$_4$ is —OCHF$_2$.
In an embodiment, R$_4$ is —OCF$_3$.
In an embodiment, R$_4$ is —OCD$_3$.
In an embodiment, n is 2.
In an embodiment, n is 1.
In an embodiment, n is 0.

In an embodiment, the invention provides a process for manufacturing a compound of the invention or a pharmaceutically acceptable salt thereof, which process comprises reducing an intermediate compound of type XVI with iron and ammonium chloride in a suitable solvent e.g. a mixture of ethanol and water.

In an embodiment, the invention provides a process for manufacturing a compound of the invention or a pharmaceutically acceptable salt thereof, which process comprises reducing an intermediate compound of type XVI with iron and ammonium chloride in a suitable solvent e.g. a mixture of ethanol and water followed by a cyclization step.

In an embodiment, the invention provides a process for manufacturing a compound of the invention or a pharmaceutically acceptable salt thereof, which process comprises reducing an intermediate of type II with iron and ammonium chloride in a suitable solvent e.g. a mixture of ethanol and water.

In an embodiment, the invention provides a process for manufacturing a compound of the invention or a pharmaceutically acceptable salt thereof, which process comprises reducing an intermediate of type II with iron and ammonium chloride in a suitable solvent e.g. a mixture of ethanol and water followed by a cyclization step.

Specific intermediate compounds of the invention are further exemplified in the experimental section.

SPECIFIC EMBODIMENTS OF THE INVENTION

In the following specific embodiments of the invention are disclosed.

The first embodiment is denoted E1, the second embodiment is denoted E2 and so forth.

E1. A compound of formula I, or a pharmaceutically acceptable salt thereof, wherein:

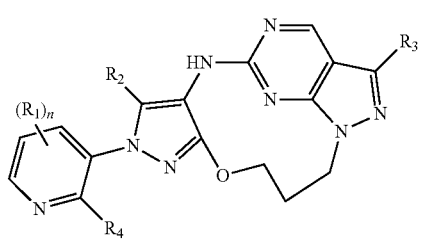

I

R$_1$ is independently selected from the group consisting of C$_1$-C$_3$ alkyl, a C$_1$-C$_3$ haloalkyl, and a halogen;
R$_2$ is selected from a C$_1$-C$_3$ alkyl or an isotopically labelled C$_1$-C$_3$ alkyl;
R$_3$ is selected from the group consisting of a halogen, a cyano, and a C$_1$-C$_3$ haloalkyl;
R$_4$ is selected from the group consisting of a C$_1$-C$_3$ alkyl, a O—C$_1$-C$_3$ haloalkyl, a O—C$_1$-C$_3$ alkyl, and a C$_1$-C$_3$ haloalkyl;
n is 0, 1 or 2.

E2. The compound of embodiment E1, or a pharmaceutically acceptable salt thereof, wherein the compound is a compound of formula Ia, wherein:

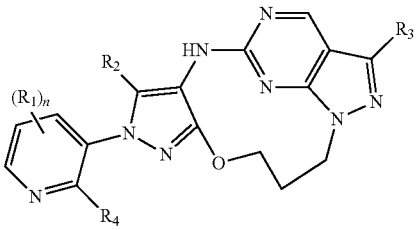

Ia

R$_1$ is selected from the group consisting of a C$_1$-C$_3$ alkyl, a C$_1$-C$_3$ haloalkyl, and a halogen;
R$_2$ is selected from a C$_1$-C$_3$ alkyl or an isotopically labelled C$_1$-C$_3$ alkyl;
R$_3$ is halogen;
R$_4$ is selected from the group consisting of a C$_1$-C$_3$ alkyl, a O—C$_1$-C$_3$ haloalkyl, a O—C$_1$-C$_3$ alkyl, and a C$_1$-C$_3$ haloalkyl;
n is 0 or 1.

E3. The compound according to any one of embodiments E1-E2, or a pharmaceutically acceptable salt thereof, wherein R$_1$ is a C$_1$-C$_3$ alkyl.

E4. The compound according to any one of embodiments E1-E3, or a pharmaceutically acceptable salt thereof, wherein R$_1$ is —CH$_3$.

E5. The compound according to any one of embodiments E1-E3, or a pharmaceutically acceptable salt thereof, wherein R$_1$ is —CH$_2$CH$_3$.

E6. The compound according to any one of embodiments E1-E3, or a pharmaceutically acceptable salt thereof, wherein R$_1$ is fluoro.

E7. The compound according to any one of embodiments E1-E6, or a pharmaceutically acceptable salt thereof, wherein R$_2$ is selected from the group consisting of —CH$_3$, —CH$_2$CH$_3$, and —CD$_3$.

E8. The compound according to any one of embodiments E1-E6, or a pharmaceutically acceptable salt thereof, wherein R$_2$ is —CH$_3$.

E9. The compound according to any one of embodiments E1-E6, or a pharmaceutically acceptable salt thereof, wherein R$_2$ is —CH$_2$CH$_3$.

E10. The compound according to any one of embodiments E1-E6, or a pharmaceutically acceptable salt thereof, wherein R$_2$ is —CD$_3$.

E11. The compound according to any one of embodiments E1-E10, or a pharmaceutically acceptable salt thereof, wherein R$_3$ is chloro.

E12. The compound according to any one of embodiments E1-E11, or a pharmaceutically acceptable salt thereof, wherein R$_4$ is selected from the group consisting of —CH$_3$, —CH$_2$CH$_3$, —OCH$_3$, and —OCH$_2$CH$_3$.

E13. The compound according to any one of embodiments E1-E11, or a pharmaceutically acceptable salt thereof, wherein $R_4$ is —CH$_3$.

E14. The compound according to any one of embodiments E1-E11, or a pharmaceutically acceptable salt thereof, wherein $R_4$ is —CH$_2$CH$_3$.

E15. The compound according to any one of embodiments E1-E11, or a pharmaceutically acceptable salt thereof, wherein $R_4$ is —OCH$_3$.

E16. The compound according to any one of embodiments E1-E11, or a pharmaceutically acceptable salt thereof, wherein $R_4$ is —OCH$_2$CH$_3$.

E17. The compound according to any one of embodiments E1-E11, or a pharmaceutically acceptable salt thereof, wherein n is 1.

E18. The compound according to any one of embodiments E1-E11, or a pharmaceutically acceptable salt thereof, wherein n is 0.

E19. The compound according to embodiment E1, wherein the compound is selected from the list consisting of:

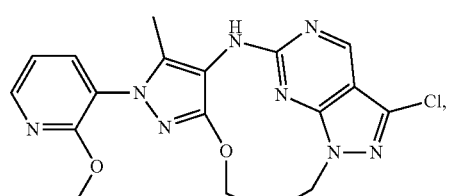

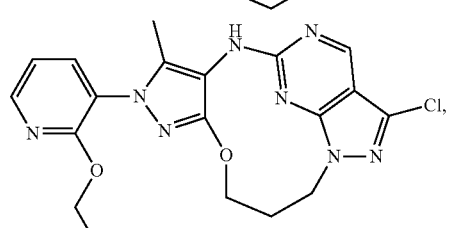

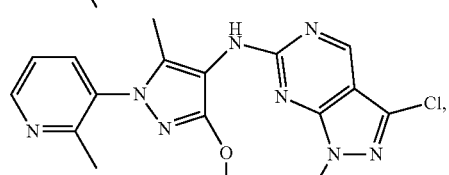

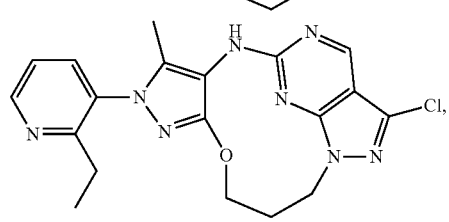

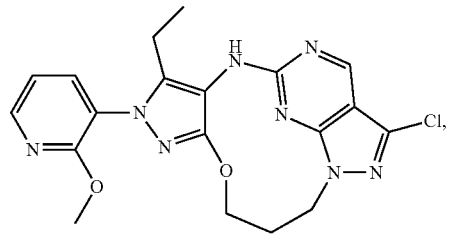

-continued

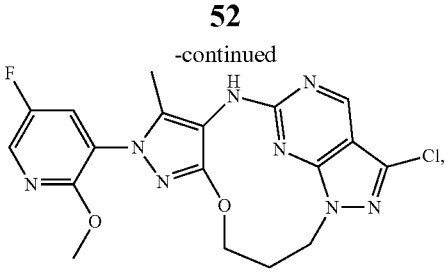

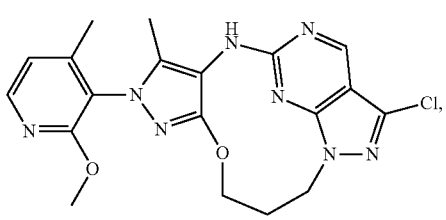

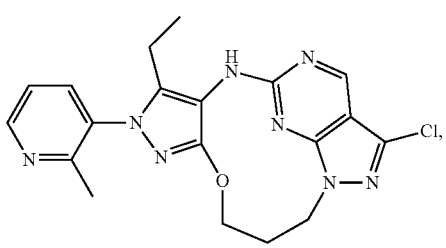

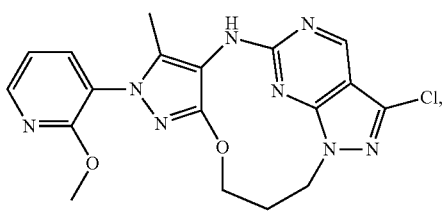 [SMILES: COc1ncccc1-n1nc2c(c1C)Nc1ncc3c(Cl)nn(c3n1)CCCO2]

or a pharmaceutically acceptable salt thereof.

E20. The compound according to embodiment E1, wherein the compound is or a pharmaceutically acceptable salt thereof.

E21. The compound according to embodiment E1, wherein the compound is

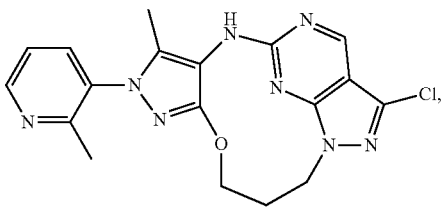 [SMILES: Cc1ncccc1-n1nc2c(c1C)Nc1ncc3c(Cl)nn(c3n1)CCCO2]

or a pharmaceutically acceptable salt thereof.

E22. The compound according to embodiment E1, wherein the compound is

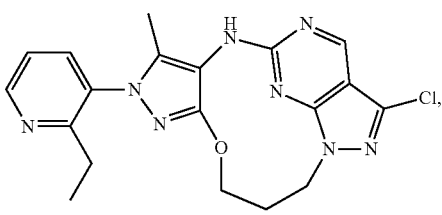 [SMILES: CCc1ncccc1-n1nc2c(c1C)Nc1ncc3c(Cl)nn(c3n1)CCCO2]

or a pharmaceutically acceptable salt thereof.

E23. The compound according to embodiment E1, wherein the compound is

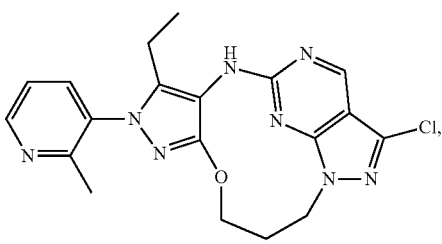 [SMILES: CCc1c2c(nn1-c1cccnc1C)OCCCn1nc(Cl)c3cnc(nc31)N2]

or a pharmaceutically acceptable salt thereof.

E24. A pharmaceutical composition comprising a compound or pharmaceutically acceptable salt thereof according to any one of the previous embodiments E1 to E23 and one or more pharmaceutically acceptable carriers or diluents.

E25. The compound according to any one of embodiments E1 to E23, or a pharmaceutically acceptable salt thereof for use in therapy.

E26. The compound according to any one of embodiments E1 to E23, or a pharmaceutically acceptable salt thereof, for use in the treatment of a disease or disorder in the central nervous system, such as a synucleinopathy selected from Lewy body dementia, multiple system atrophy, and Parkinson's disease.

E27. The compound according to embodiment E26, or a pharmaceutically acceptable salt thereof, wherein the Parkinson's disease is idiopathic Parkinson's disease, sporadic Parkinson's disease, Parkinson's disease in patients carrying a G2019S mutation in LRRK2, or Parkinson's disease in patients carrying one or more LRRK2 non-coding variants selected from rs76904798-T and Rs1491942-G.

E28. The compound according to embodiment E26, or a pharmaceutically acceptable salt thereof, wherein the Parkinson's disease is idiopathic Parkinson's disease, sporadic Parkinson's disease or Parkinson's disease in patients carrying one or more mutated forms of LRRK2 selected from G2019S, 12020T, M1646T, G2385R, A419V, N551K, R1398H, K1423K, R1441G, R1441H, R1441C, R1628P, S1647T, Y1699C, and Y2189C.

E29. The compound according to embodiment E26, or a pharmaceutically acceptable salt thereof, wherein the Parkinson's disease is idiopathic Parkinson's disease, sporadic Parkinson's disease or Parkinson's disease in patients carrying a G2019S mutation in LRRK2.

E30. The compound according to embodiment E26, or a pharmaceutically acceptable salt thereof, wherein the Parkinson's disease is idiopathic Parkinson's disease, sporadic Parkinson's disease or Parkinson's disease in patients carrying one or more LRRK2 non-coding variants selected from rs76904798-T and Rs1491942-G.

E31. The compound according to any one of embodiments E1 to E23, or a pharmaceutically acceptable salt thereof, for use in a method for the treatment of a disease or disorder characterized by increased LRRK2 kinase activity or by expression of one or more mutated forms of LRRK2 selected from G2019S, 12020T, M1646T, G2385R, A419V, N551K, R1398H, K1423K, R1441G, R1441H, R1441C, R1628P, S1647T, Y1699C, and Y2189C or a LRRK2 non-coding variant alone or in combination selected from rs76904798-T and Rs1491942-G.

E32. Use of a compound according to any one of embodiments E1 to E23, or a pharmaceutically acceptable salt thereof, in the manufacture of a medicament for the treatment of a disease or disorder in the central nervous system selected from Lewy body dementia, multiple system atrophy or Parkinson's disease.

E33. A method for the treatment of a disease or disorder in the central nervous system selected from Lewy body dementia, multiple system atrophy or Parkinson's disease comprising the administration of a therapeutically effective amount of a compound, or a pharmaceutically acceptable salt thereof, according to any one of embodiments E1 to E23 to a patient in need thereof.

E34. The compound, use or method according to any of the preceding embodiments, wherein the patient to be treated carries one or more genetic mutations, which result in the expression of the G2019S variant of the LRRK2 protein.

E35. The compound, use or method according to any of the preceding embodiments, wherein the patient to be treated carries one or more genetic mutations, which result in the expression of one or more of the G2019S, 12020T, G2385R, A419V, R1441G, R1441H, R1441C, R1628P and Y1699C variants of the LRRK2 protein.

E36. The compound, use or method according to any of the preceding embodiments, wherein the patient to be treated carries one or more genetic mutations, which result in the expression of one or more of the M1646T, S1647T, Y2189C, N1437H, M1646T and N2081D variants of the LRRK2 protein.

E37. The compound, use or method according to any of the preceding embodiments, wherein the patient to be treated does not carry one or more genetic mutations, which result in the expression of one or more of the N551K, R1398H and K1423K variants of the LRRK2 protein.

E38. The compound, use or method according to any of the preceding embodiments, wherein the patient to be treated carries one or more LRRK2 genetic non-coding variants selected from rs76904798-T and Rs1491942-G.

In the following further specific embodiments of the invention are disclosed.

The first further embodiment is denoted EE1, the second embodiment is denoted EE2 and so forth.

EE1. A compound of formula IIa, or a pharmaceutically acceptable salt thereof, wherein:

IIa

X is CH, $CR_1$ or N;

Y is CH, $CR_1$ or N;

$R_1$ is independently selected from the group consisting of a $C_1$-$C_3$ alkyl, a $C_1$-$C_3$ haloalkyl, and halogen;

$R_2$ is selected from a $C_1$-$C_3$ alkyl or an isotopically labelled $C_1$-$C_3$ alkyl;

$R_3$ is selected from the group consisting of a halogen, a cyano, and a $C_1$-$C_3$ haloalkyl;

$R_4$ is selected from the group consisting of a $C_1$-$C_3$ alkyl, an isotopically labelled $C_1$-$C_3$ alkyl, a $C_1$-$C_3$ haloalkyl, a O—$C_1$-$C_3$ alkyl, an isotopically labelled O—$C_1$-$C_3$ alkyl, a O—$C_1$-$C_3$ haloalkyl, and a O—$C_3$-$C_6$ cycloalkyl;

n is 0, 1 or 2.

EE2. A compound of formula I, or a pharmaceutically acceptable salt thereof, wherein:

I $R_1$ is independently selected from the group consisting of a $C_1$-$C_3$ alkyl, a $C_1$-$C_3$ haloalkyl, and a halogen;

$R_2$ is selected from a $C_1$-$C_3$ alkyl or an isotopically labelled $C_1$-$C_3$ alkyl;

$R_3$ is selected from the group consisting of a halogen, a cyano, and a $C_1$-$C_3$ haloalkyl;

$R_4$ is selected from the group consisting of a $C_1$-$C_3$ alkyl, a O—$C_1$-$C_3$ haloalkyl, a O—$C_1$-$C_3$ alkyl, and a $C_1$-$C_3$ haloalkyl;

n is 0, 1 or 2.

EE3. A compound of formula Ia, or a pharmaceutically acceptable salt thereof wherein:

Ia $R_1$ is selected from the group consisting of a $C_1$-$C_3$ alkyl, a $C_1$-$C_3$ haloalkyl, and a halogen;

$R_2$ is selected from a $C_1$-$C_3$ alkyl or an isotopically labelled $C_1$-$C_3$ alkyl;

$R_3$ is halogen;

$R_4$ is selected from the group consisting of a $C_1$-$C_3$ alkyl, a O—$C_1$-$C_3$ haloalkyl, a O—$C_1$-$C_3$ alkyl, and a $C_1$-$C_3$ haloalkyl;

n is 0 or 1.

EE4. The compound of embodiment EE1 or a pharmaceutically acceptable salt thereof, wherein X is CH or $CR_1$ and Y is CH or $CR_1$.

EE5. The compound of embodiment EE1 or a pharmaceutically acceptable salt thereof, wherein X is CH or $CR_1$ and Y is N.

EE6. The compound of embodiment EE1 or a pharmaceutically acceptable salt thereof, wherein X is N and Y is CH or $CR_1$.

EE7. The compound of any of embodiments EE1-EE6 or a pharmaceutically acceptable salt thereof, wherein $R_1$ is a $C_1$-$C_3$ alkyl.

EE8. The compound of any of embodiments EE1-EE7 or a pharmaceutically acceptable salt thereof, wherein $R_1$ is —$CH_3$.

EE9. The compound of any of embodiments EE1-EE7 or a pharmaceutically acceptable salt thereof, wherein $R_1$ is —$CH_2CH_3$.

EE10. The compound of any of embodiments EE1-EE6 or a pharmaceutically acceptable salt thereof, wherein $R_1$ is a halogen.

EE11. The compound of any of embodiments EE1-EE6 or a pharmaceutically acceptable salt thereof, wherein $R_1$ is fluoro.

EE12. The compound of any of embodiments EE1-EE11 or a pharmaceutically acceptable salt thereof, wherein $R_2$ is selected from the group consisting of —$CH_3$, —$CH_2CH_3$, and —$CD_3$.

EE13. The compound of any of embodiments EE1-EE12 or a pharmaceutically acceptable salt thereof, wherein $R_2$ is —$CH_3$.

EE14. The compound of any of embodiments EE1-EE12 or a pharmaceutically acceptable salt thereof, wherein $R_2$ is —$CH_2CH_3$.

EE15. The compound of any of embodiments EE1-EE12 or a pharmaceutically acceptable salt thereof, wherein $R_2$ is —$CD_3$.

EE16. The compound of any of embodiments EE1-EE15 or a pharmaceutically acceptable salt thereof, wherein $R_3$ is a halogen.

EE17. The compound of any of embodiments EE1-EE15 or a pharmaceutically acceptable salt thereof, wherein $R_3$ is chloro.

EE18. The compound of any of embodiments EE1-EE17 or a pharmaceutically acceptable salt thereof, wherein $R_4$ is selected from the group consisting of —$CH_3$, —$CH_2CH_3$, —OCH₃, —OCH₂CH₃, —CHF₂, —CF₃, —CF₂CH₃, —O—C₃ cycloalkyl, O-cyclopropane, —OCH₂F, —OCHF₂, —OCF₃, and —OCD₃.

EE19. The compound of any of embodiments EE1-EE18 or a pharmaceutically acceptable salt thereof, wherein R₄ is —CH₃.

EE20. The compound of any of embodiments EE1-EE18 or a pharmaceutically acceptable salt thereof, wherein R₄ is —CH₂CH₃.

EE21. The compound of any of embodiments EE1-EE18 or a pharmaceutically acceptable salt thereof, wherein R₄ is —OCH₃.

EE22. The compound of any of embodiments EE1-EE18 or a pharmaceutically acceptable salt thereof, wherein R₄ is —OCH₂CH₃.

EE23. The compound of any of embodiments EE1-EE18 or a pharmaceutically acceptable salt thereof, wherein R₄ is —CHF₂.

EE24. The compound of any of embodiments EE1-EE18 or a pharmaceutically acceptable salt thereof, wherein R₄ is —CF₃.

EE25. The compound of any of embodiments EE1-EE18 or a pharmaceutically acceptable salt thereof, wherein R₄ is —CF₂CH₃.

EE26. The compound of any of embodiments EE1-EE18 or a pharmaceutically acceptable salt thereof, wherein R₄ is —O—C₃ cycloalkyl.

EE27. The compound of any of embodiments EE1-EE18 or a pharmaceutically acceptable salt thereof, wherein R₄ is O-cyclopropane.

EE28. The compound of any of embodiments EE1-EE18 or a pharmaceutically acceptable salt thereof, wherein R₄ is —OCH₂F.

EE29. The compound of any of embodiments EE1-EE18 or a pharmaceutically acceptable salt thereof, wherein R₄ is —OCHF₂.

EE30. The compound of any of embodiments EE1-EE18 or a pharmaceutically acceptable salt thereof, wherein R₄ is —OCF₃.

EE31. The compound of any of embodiments EE1-EE18 or a pharmaceutically acceptable salt thereof, wherein R₄ is —OCD₃.

EE32. The compound of any of embodiments EE1-EE31 or a pharmaceutically acceptable salt thereof, wherein n is 2.

EE33. The compound of any of embodiments EE1-EE31 or a pharmaceutically acceptable salt thereof, wherein n is 1.

EE34. The compound of any of embodiments EE1-EE31 or a pharmaceutically acceptable salt thereof, wherein n is 0.

EE35. The compound of any of embodiments EE1-EE34 or a pharmaceutically acceptable salt thereof, wherein the compound is selected from the list consisting of:

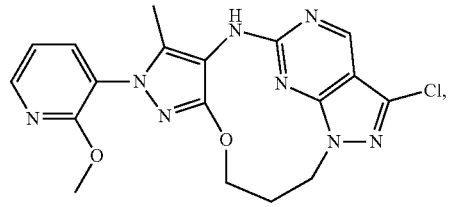 [SMILES: COc1ncccc1-n1nc2c(c1C)Nc1ncc3c(Cl)nn(c3n1)CCCO2]

-continued

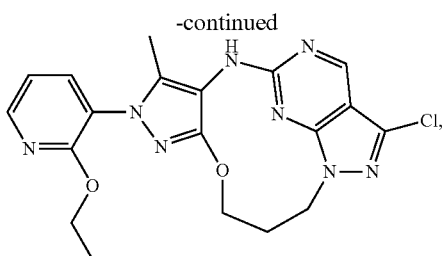

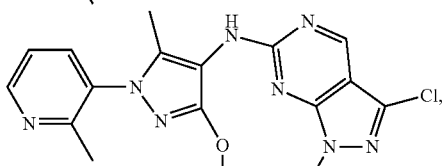

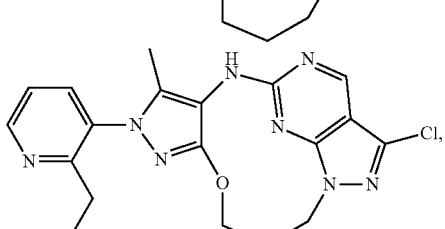

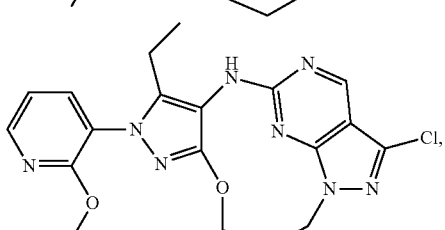

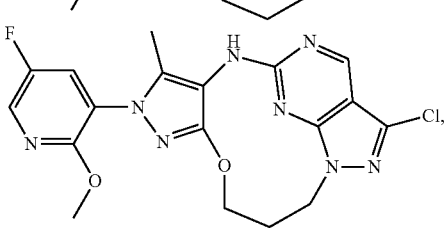

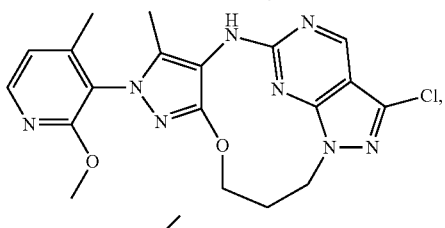

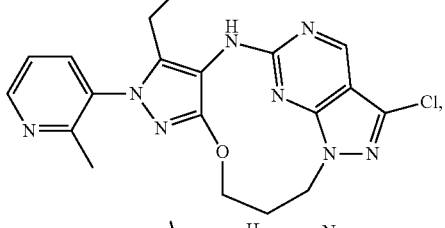

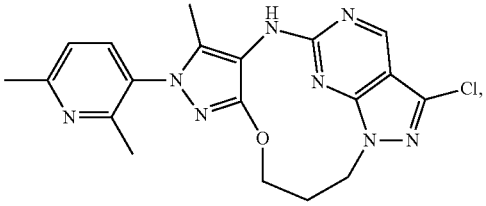

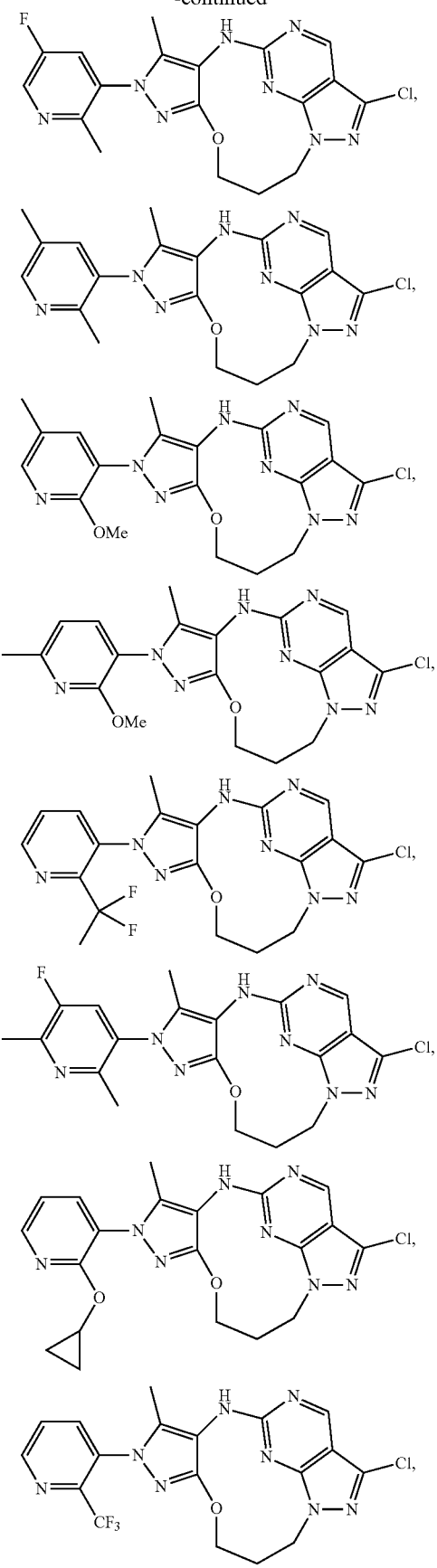
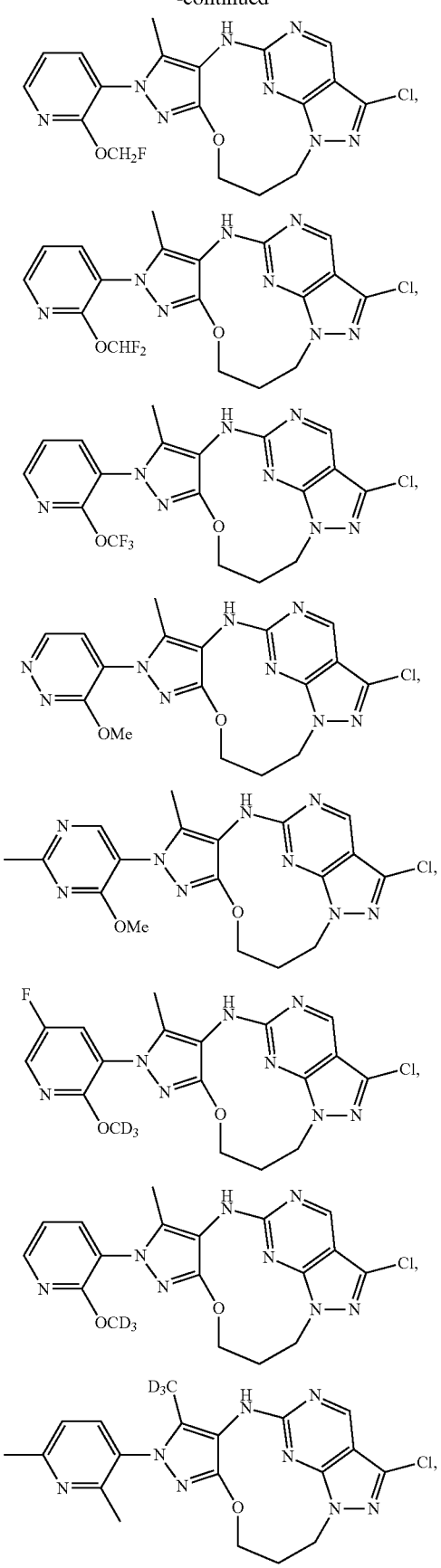

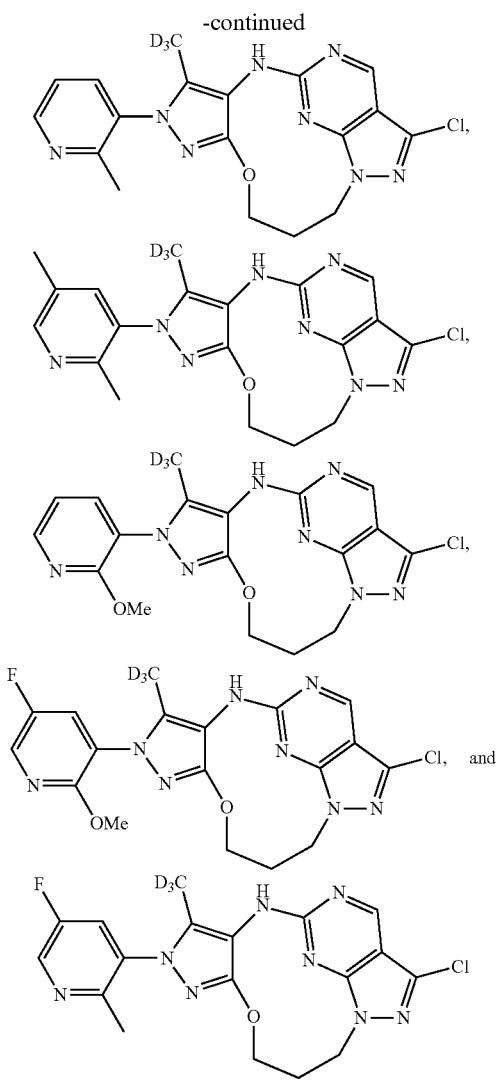

or a pharmaceutically acceptable salt thereof.

EE36. The compound of any of embodiments EE1-EE34 or a pharmaceutically salt thereof, wherein the compound is selected from the list consisting of:

8-Chloro-2-(2-methoxypyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(2-ethoxypyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-3-methyl-2-(2-methyl pyridin-3-yl)-2,4,12,13-tetrahydro-11H-5,7-(azenometheno)dipyrazolo[3,4-b:5',1'-g][1]oxa[4,6,8]triazacycloundecine;

8-Chloro-2-(2-ethylpyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-3-ethyl-2-(2-methoxypyridin-3-yl)-2,4,12,13-tetrahydro-11H-5,7-(azenometheno)dipyrazolo[3,4-b:5',1'-g][1]oxa[4,6,8]triazacycloundecine;

8-Chloro-2-(5-fluoro-2-methoxypyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(2-methoxy-4-methylpyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-3-ethyl-2-(2-methylpyridin-3-yl)-2,4,12,13-tetrahydro-11H-5,7-(azenometheno)dipyrazolo[3,4-b:5',1'-g][1]oxa[4,6,8]triazacycloundecine;

8-Chloro-2-(2,6-dimethylpyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(5-fluoro-2-methylpyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(2,5-dimethylpyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(2-methoxy-5-methylpyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(2-methoxy-6-methylpyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(2-(1,1-difluoroethyl)pyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(5-fluoro-2,6-dimethylpyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(2-cyclopropoxypyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-3-methyl-2-(2-(trifluoromethyl)pyridin-3-yl)-2,4,12,13-tetrahydro-11H-5,7-(azenometheno)dipyrazolo[3,4-b:5',1'-g][1]oxa[4,6,8]triazacycloundecine;

8-Chloro-2-(2-(fluoromethoxy)pyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(2-(difluoromethoxy)pyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-3-methyl-2-(2-(trifluoromethoxy)pyridin-3-yl)-2,4,12,13-tetrahydro-11H-5,7-(azenometheno)dipyrazolo[3,4-b:5',1'-g][1]oxa[4,6,8]triazacycloundecine;

8-Chloro-2-(3-methoxypyridazin-4-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(4-methoxy-2-methylpyrimidin-5-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(5-fluoro-2-(methoxy-$d_3$)pyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(2-(methoxy-$d_3$)pyridin-3-yl)-3-methyl-2,4,12,13-tetrahydro-11H-5,7-(azenometheno)dipyrazolo[3,4-b:5',1'-g][1]oxa[4,6,8]triazacycloundecine;

8-Chloro-2-(2,6-dimethylpyridin-3-yl)-3-(methyl-$d_3$)-2,4,12,13-tetrahydro-11H-5,7-(azenometheno)dipyrazolo[3,4-b:5',1'-g][1]oxa[4,6,8]triazacycloundecine;

8-Chloro-3-(methyl-$d_3$)-2-(2-methylpyridin-3-yl)-2,4,12,13-tetrahydro-11H-5,7-(azenometheno)dipyrazolo[3,4-b:5',1'-g][1]oxa[4,6,8]triazacycloundecine;

8-Chloro-2-(2,5-dimethylpyridin-3-yl)-3-(methyl-$d_3$)-2,4,12,13-tetrahydro-11H-5,7-(azenometheno)dipyrazolo[3,4-b:5',1'-g][1]oxa[4,6,8]triazacycloundecine;

8-Chloro-2-(2-methoxypyridin-3-yl)-3-(methyl-$d_3$)-2,4,12,13-tetrahydro-11H-5,7-(azenometheno)dipyrazolo[3,4-b:5',1'-g][1]oxa[4,6,8]triazacycloundecine;

8-Chloro-2-(5-fluoro-2-methoxypyridin-3-yl)-3-(methyl-$d_3$)-2,4,12,13-tetrahydro-11H-5,7-(azenometheno)dipyrazolo[3,4-b:5',1'-g][1]oxa[4,6,8]triazacycloundecine; and 8-Chloro-2-(5-fluoro-2-methylpyridin-3-yl)-3-(methyl-d₃)-2,4,12,13-tetrahydro-11H-5,7-(azenometheno)dipyrazolo[3,4-b:5',1'-g][1]oxa[4,6,8]triazacycloundecine; or a pharmaceutically acceptable salt thereof.

EE37. The compound of embodiments EE1-EE36 or a pharmaceutically acceptable salt thereof for use in therapy.

EE38. A pharmaceutical composition comprising a compound or pharmaceutically acceptable salt thereof of the previous embodiments EE1-EE36 and one or more pharmaceutically acceptable carriers or diluents.

EE39. The compound according to any one of embodiments EE1-EE36, or a pharmaceutically acceptable salt thereof, for use in the treatment of a disease or disorder in the central nervous system selected from Lewy body dementia, multiple system atrophy, and Parkinson's disease.

EE40. The compound according to embodiment EE39, or a pharmaceutically acceptable salt thereof, wherein the Parkinson's disease is idiopathic Parkinson's disease, sporadic Parkinson's disease, Parkinson's disease in patients carrying a G2019S mutation in LRRK2, or Parkinson's disease in patients carrying one or more LRRK2 non-coding variants selected from rs76904798-T and Rs1491942-G.

EE41. The compound according to embodiment EE39, or a pharmaceutically acceptable salt thereof, wherein the Parkinson's disease is idiopathic Parkinson's disease, sporadic Parkinson's disease or Parkinson's disease in patients carrying one or more mutated forms of LRRK2 selected from G2019S, 12020T, M1646T, G2385R, A419V, N551K, R1398H, K1423K, R1441G, R1441H, R1441C, R1628P, S1647T, Y1699C, and Y2189C.

EE42. The compound according to embodiment EE39, or a pharmaceutically acceptable salt thereof, wherein the Parkinson's disease is idiopathic Parkinson's disease, sporadic Parkinson's disease or Parkinson's disease in patients carrying a G2019S mutation in LRRK2.

EE43. The compound according to embodiment EE39, or a pharmaceutically acceptable salt thereof, wherein the Parkinson's disease is idiopathic Parkinson's disease, sporadic Parkinson's disease or Parkinson's disease in patients carrying one or more LRRK2 non-coding variants selected from rs76904798-T and Rs1491942-G.

EE44. The compound according to any one of embodiments EE1-EE36, or a pharmaceutically acceptable salt thereof, for use in a method for the treatment of a disease or disorder characterized by increased LRRK2 kinase activity or by expression of one or more mutated forms of LRRK2 selected from G2019S, 12020T, M1646T, G2385R, A419V, N551K, R1398H, K1423K, R1441G, R1441H, R1441C, R1628P, S1647T, Y1699C, and Y2189C or a LRRK2 non-coding variant alone or in combination selected from rs76904798-T and Rs1491942-G.

EE45. Use of a compound according to any one of embodiments EE1-EE36, or a pharmaceutically acceptable salt thereof, in the manufacture of a medicament for the treatment of a disease or disorder in the central nervous system selected from Lewy body dementia, multiple system atrophy or Parkinson's disease.

EE46. Use of a compound according to any one of embodiments EE1-EE36, or a pharmaceutically acceptable salt thereof, in the manufacture of a medicament for the treatment of Parkinson's disease.

EE47. A method for the treatment of a disease or disorder in the central nervous system selected from Lewy body dementia, multiple system atrophy or Parkinson's disease comprising the administration of a therapeutically effective amount of a compound, or a pharmaceutically acceptable salt thereof, according to any one of embodiments EE1-EE36 to a patient in need thereof.

EE47. The compound according to any one of embodiments EE1-EE36 or a pharmaceutically acceptable salt thereof, for use in the treatment of a disease or disorder characterized by increased LRRK2 kinase activity or by expression of one or more mutated forms of LRRK2 selected from G2019S, 12020T, M1646T, G2385R, A419V, N551K, R1398H, K1423K, R1441G, R1441H, R1441C, R1628P, S1647T, Y1699C, and Y2189C or a LRRK2 non-coding variant alone or in combination selected from rs76904798-T and Rs1491942-G.

In the following additional specific embodiments of the invention are disclosed.

The first additional embodiment is denoted I1, the second embodiment is denoted I2 and so forth.

I1. A compound of formula I, or a pharmaceutically acceptable salt thereof, wherein:

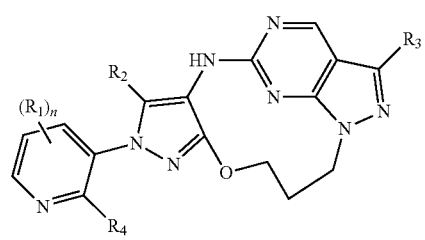

$R_1$ is independently selected from the group consisting of a $C_1$-$C_3$ alkyl, a $C_1$-$C_3$ haloalkyl, and a halogen;

$R_2$ is selected from a $C_1$-$C_3$ alkyl or an isotopically labelled $C_1$-$C_3$ alkyl;

$R_3$ is selected from the group consisting of a halogen, a cyano, and a $C_1$-$C_3$ haloalkyl;

$R_4$ is selected from the group consisting of a $C_1$-$C_3$ alkyl, a O—$C_1$-$C_3$ haloalkyl, a O—$C_1$-$C_3$ alkyl, and a $C_1$-$C_3$ haloalkyl;

n is 0, 1 or 2.

I2. The compound according to embodiment I1, or a pharmaceutically acceptable salt thereof, wherein the compound is a compound of formula Ia, wherein:

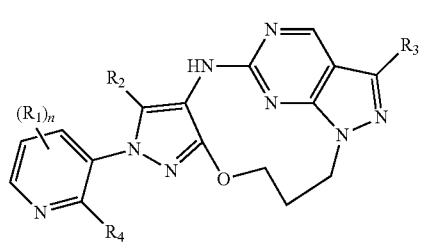

$R_1$ is selected from the group consisting of a $C_1$-$C_3$ alkyl, a $C_1$-$C_3$ haloalkyl, and a halogen;

$R_2$ is selected from a $C_1$-$C_3$ alkyl or an isotopically labelled $C_1$-$C_3$ alkyl;

$R_3$ is a halogen;

$R_4$ is selected from the group consisting of a $C_1$-$C_3$ alkyl, a O—$C_1$-$C_3$ haloalkyl, a O—$C_1$-$C_3$ alkyl, and a $C_1$-$C_3$ haloalkyl;

n is 0 or 1.

I3. The compound according to any one of embodiments I1-I2, or a pharmaceutically acceptable salt thereof, wherein $R_1$ is a $C_1$-$C_3$ alkyl.

I4. The compound according to any one of embodiments I1-I3, or a pharmaceutically acceptable salt thereof, wherein $R_1$ is —$CH_3$.

I5. The compound according to any one of embodiments I1-I4, or a pharmaceutically acceptable salt thereof, wherein $R_1$ is fluoro.

I6. The compound according to any one of embodiments I1-I5, or a pharmaceutically acceptable salt thereof, wherein $R_2$ is selected from the group consisting of —$CH_3$, —$CH_2CH_3$, and —$CD_3$.

I7. The compound according to any one of embodiments I1-I6, or a pharmaceutically acceptable salt thereof, wherein $R_3$ is chloro.

I8. The compound according to any one of embodiments I1-I7, or a pharmaceutically acceptable salt thereof, wherein $R_4$ is selected from the group consisting of —$CH_3$, —$CH_2CH_3$, —$OCH_3$, and —$OCH_2CH_3$.

I9. The compound according to any one of embodiments I1-I8, or a pharmaceutically acceptable salt thereof, wherein n is 1.

I10. The compound according to any one of embodiments I1-I7, or a pharmaceutically acceptable salt thereof, wherein n is 0.

I11. The compound according to embodiment I1, wherein the compound is selected from the list consisting of:

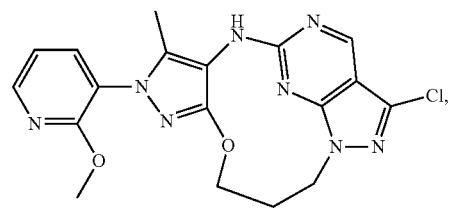

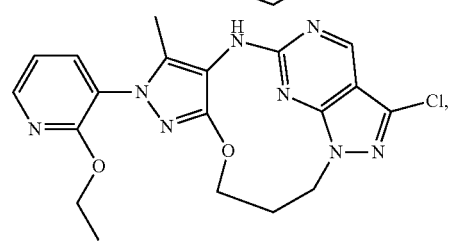

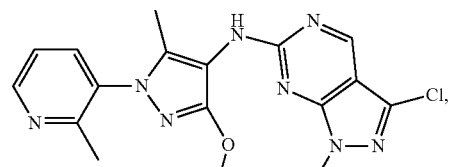

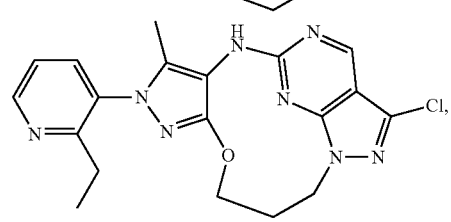

-continued

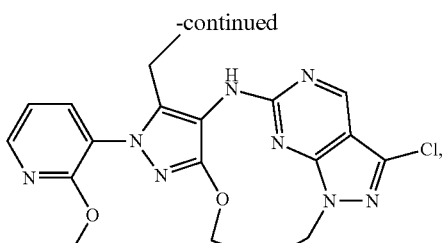

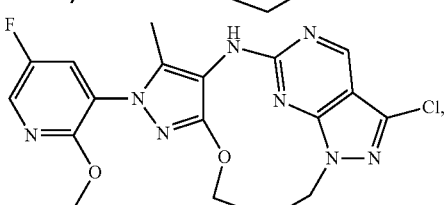

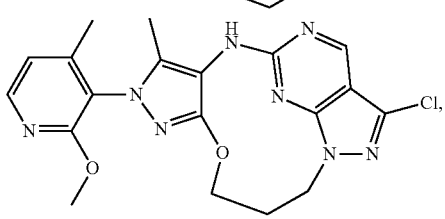

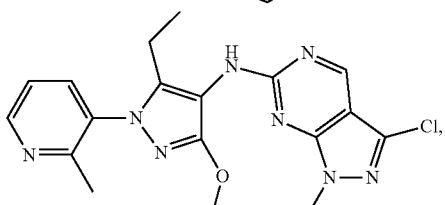

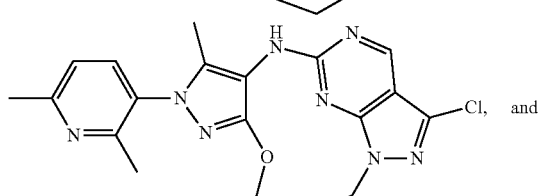

and

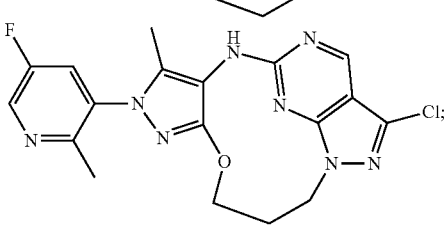

or a pharmaceutically acceptable salt thereof.

I12. A pharmaceutical composition comprising a compound according to any one of the previous embodiments I1 to I11 and one or more pharmaceutically acceptable carriers.

I13. A compound, or a pharmaceutically acceptable salt thereof according to any one of embodiments I1 to I11 for use in therapy.

I14. A compound according to any one of embodiments I1 to I11, or a pharmaceutically acceptable salt thereof, for use in the treatment of a disease in the central nervous system, such as synucleinopathy selected from Lewy body dementia, multiple system atrophy, or Parkinson's disease.

I15. The compound according to embodiments I14, or a pharmaceutically acceptable salt thereof, wherein the Parkinson's disease is idiopathic Parkinson's disease, sporadic Parkinson's disease or Parkinson's disease in patients carrying a G2019S mutation in LRRK2.

I16. A compound according to any one of embodiments I1 to I11, or a pharmaceutically acceptable salt thereof, for use in the treatment of a disease or disorder characterized by increased LRRK2 kinase activity or by expression of one or more mutated forms of LRRK2 selected from G2019S, I2020T, M1646T, G2385R, A419V, N551K, R1398H, K1423K, R1441G, R1441H, R1441C, R1628P, S1647T, Y1699C, and Y2189C or a LRRK2 non-coding variant alone or in combination selected from rs76904798-T and Rs1491942-G.

I17. Use of a compound according to any one of embodiments I1 to I11, or a pharmaceutically acceptable salt thereof, in the manufacture of a medicament for the treatment of a disease or disorder in the central nervous system, such as synucleinopathy selected from Lewy body dementia, multiple system atrophy, or Parkinson's disease.

I18. The use according to embodiment I17 wherein the Parkinson's disease is idiopathic Parkinson's disease, sporadic Parkinson's disease or Parkinson's disease in patients carrying a G2019S mutation in LRRK2, or Parkinson's disease in patients carrying one or more LRRK2 non-coding variants selected from rs76904798-T and Rs1491942-G.

I19. A method for the treatment of a disease or disorder in the central nervous system selected from Lewy body dementia, multiple system atrophy or Parkinson's disease comprising the administration of a therapeutically effective amount of the compound according to any one of embodiments I1 to I11, or a pharmaceutically acceptable salt thereof, to a patient in need thereof.

I20. The method according to embodiment I19 wherein the Parkinson's disease is idiopathic Parkinson's disease, sporadic Parkinson's disease, Parkinson's disease in patients carrying a G2019S mutation in LRRK2, or Parkinson's disease in patients carrying one or more LRRK2 non-coding variants alone selected from rs76904798-T and Rs1491942-G.

Experimental Section
Preparation of the Compounds of the Invention

The compounds of formula I, formula IIa or formula Ia may be prepared by methods described below, together with synthetic methods known in the art of organic chemistry, or modifications that are familiar to those of ordinary skill in the art. For example, the methods describe the use of selective protecting groups during the synthesis of the compounds of the invention. One skilled in the art would be able to select the appropriate protecting group for a particular reaction. Methods for protection and deprotection of such groups are well known in the art and may be found in Watts and Green et al., Protective Groups in Organic Synthesis, 2006, 4th Edition, Wiley Interscience, New York. The starting materials used herein are available commercially or may be prepared by routine methods known in the art, such as those method described in standard reference books such as "Compendium of Organic Synthetic Methods, Vol. I-XII" (published by Wiley Interscience). Preferred methods include, but are not limited to, those described below. The schemes are representative of methods useful in synthesizing the compounds of the present invention. They are not to constrain the scope of the invention in any way.

Scheme 1

Method 1

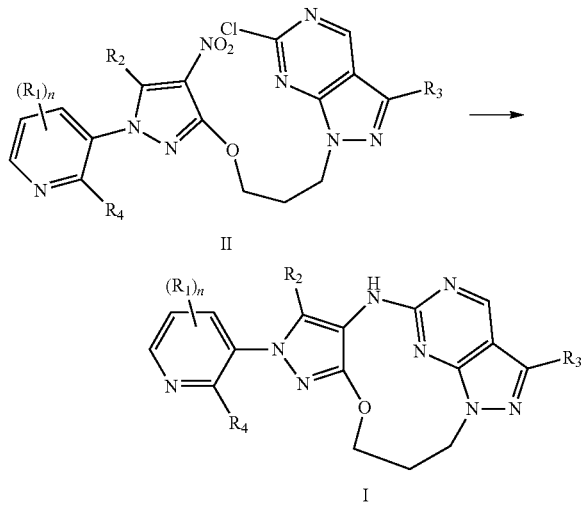

In brief, compounds of formula I can be prepared according to scheme 1. The compounds of formula I can for example be prepared through a one pot reduction-cyclization procedure by reducing an intermediate of type II with iron and ammonium chloride in a suitable solvent e.g. a mixture of ethanol and water followed by cyclization as described for Example 2.

Scheme 2

Method 2

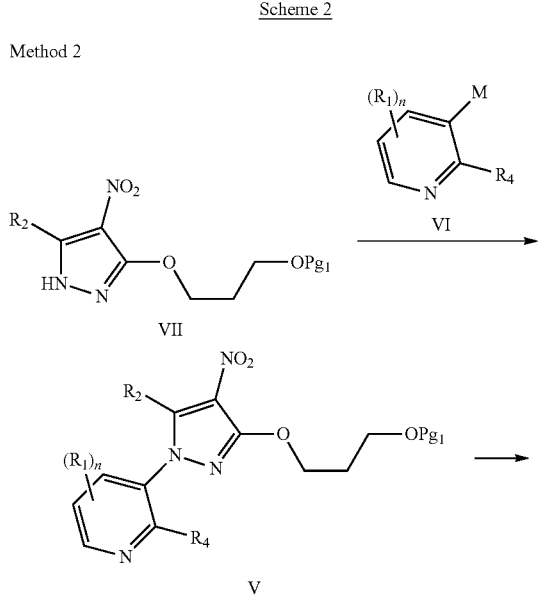

-continued

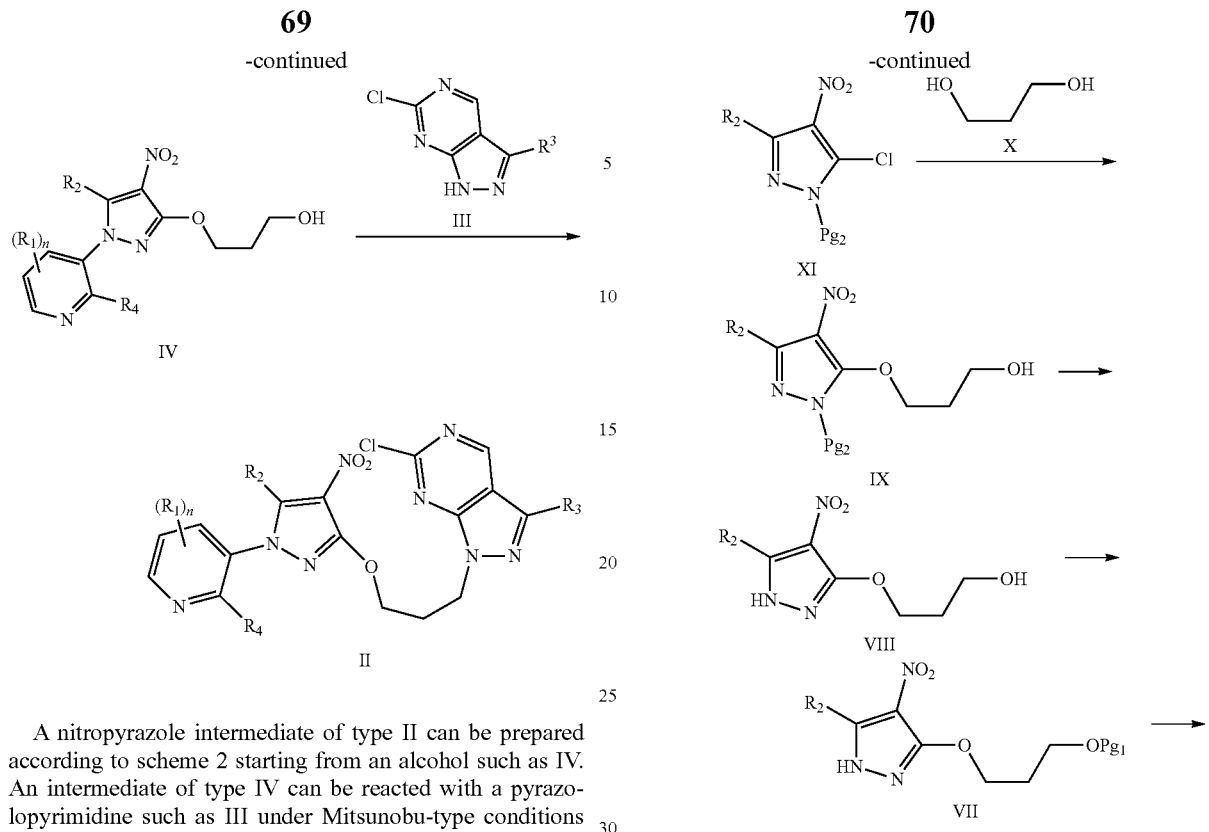

A nitropyrazole intermediate of type II can be prepared according to scheme 2 starting from an alcohol such as IV. An intermediate of type IV can be reacted with a pyrazolopyrimidine such as III under Mitsunobu-type conditions employing for example diisopropyl azodicarboxylate and triphenylphosphine in a solvent such as tetrahydrofuran to afford an intermediate of type II. Intermediates of type V (wherein $Pg_1$ is for example TBS) can be converted into an alchohol intermediate of type IV using for example a fluoride source such as tetrabutylammonium fluoride in an appropriate solvent for example tetrahydrofuran. A pyrazole intermediate of type V can be prepared through the coupling of an intermediate of type VII with a pyridine intermediate of type VI (wherein M is for example $B(OH)_2$. The coupling is exemplified by a Chan-Lam type coupling. The reaction can be performed by reacting an intermediate of type VII with a boronic acid intermediate VI in which M=$B(OH)_2$ in the presence of a copper salt such as copper(II) acetate, a base for example pyridine, a drying agent such as 4 Å molecular sieves under an oxygen atmosphere and a suitable solvent such as 1,2-dichloroethane.

The general synthetic sequence in scheme 2 is for example described in the synthesis of intermediate 3,6-dichloro-1-(3-((5-methyl-1-(2-methylpyridin-3-yl)-4-nitro-1H-pyrazol-3-yl)oxy)propyl)-1H-pyrazolo[3,4-d]pyrimidine.

Scheme 3

Method 3

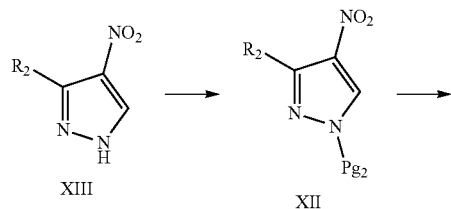

An intermediate of type VII (wherein $Pg_1$ is for example TBS) can be prepared according to scheme 3. Intermediates of type VII (wherein $Pg_1$ is for example TBS) can be prepared from an alcohol intermediate of type VIII using for example tert-butyldimethylsilyl chloride in the presence of a base such as imidazole and a catalyst such as 4-dimethylaminopyridine in an appropriate solvent such as dichloromethane. An alcohol intermediate such as VIII can be prepared from a nitropyazole such as IX (wherein $Pg_2$ is for example, 2-tetrahydropyranyl) by treatment with an acid such as aqueous hydrochloric acid in a suitable solvent for example methanol.

Alcohol intermediates of type IX can be prepared by reacting a chloro intermediate XI with propane-1,3-diol X in the presence of a base for example cesium fluoride in a solvent such as N,N-dimethylacetamide.

Chloro intermediates such as XI (wherein $Pg_2$ is for example, 2-tetrahydropyranyl) can be prepared from a nitropyrazole intermediate XII (wherein $Pg_2$ is for example, 2-tetrahydropyranyl) using a strong base for example lithium bis(trimethylsilyl)amide, and an electrophile for example hexachloroethane in a suitable solvent such as tetrahydrofuran.

A nitropyrazole intermediate of type XII (wherein $Pg_2$ is for example, 2-tetrahydropyranyl) can be prepared from a pyrazole such as XIII employing 3,4-dihydro-2H-pyran in the presence of an acid for example para-toluenesulfonic acid monohydrate in an appropriate solvent for example tetrahydrofuran.

The general synthetic sequence in scheme 3 is for example described in the synthesis of intermediate 5-(3-((tert-butyldimethylsilyl)oxy)propoxy)-3-methyl-4-nitro-1H-pyrazole.

Scheme 4

Method 4

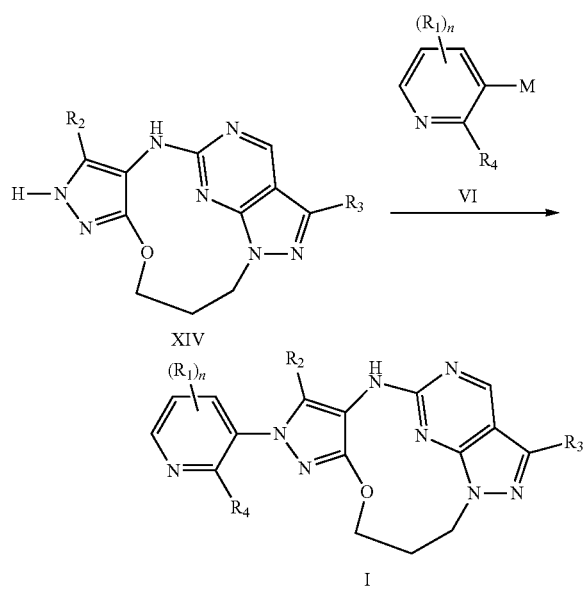

Alternatively, compounds of formula I can be prepared from a compound of formula XIV according to scheme 4. The compounds of formula I can be prepared by employing e.g. a copper-mediated coupling between an intermediate of type XIV and an intermediate of type VI (wherein M is for example B(OH)$_2$). The coupling is exemplified by but not limited to a Chan-Lam type coupling. The reaction can be performed by reacting an intermediate of type XIV with a boronic acid intermediate VI in which M=B(OH)$_2$ in the presence of a copper salt such as copper(II) acetate, a base for example pyridine, a drying agent such as 4 Å molecular sieves under an oxygen atmosphere and a suitable solvent such as 1,2-dichloroethane as described for Example 1.

Scheme 5

Method 5

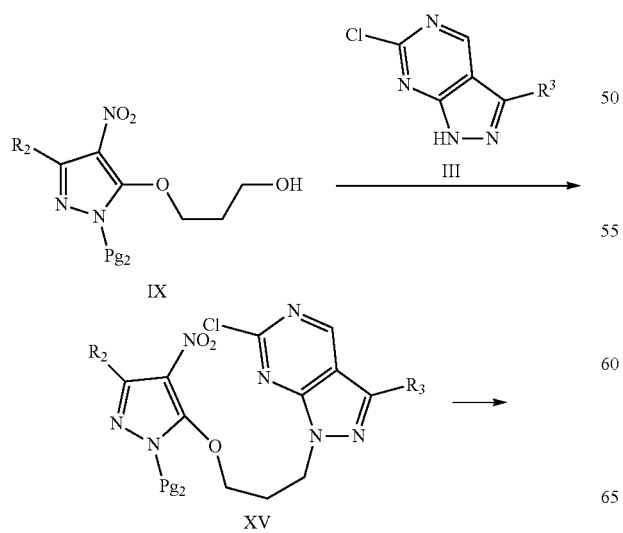

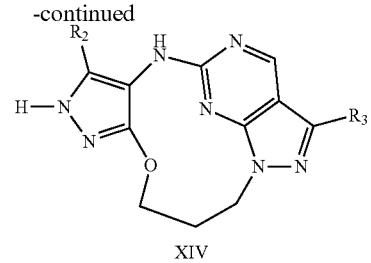

An intermediate such as XIV can be prepared according to scheme 5. The intermediates of type XIV can for example be prepared through a one pot procedure by reducing an intermediate of type XV (wherein Pg$_2$ is for example, 2-tetrahydropyranyl) with iron and ammonium chloride in a suitable solvent e.g. a mixture of ethanol and water.

Nitropyrazole intermediates like XV can be prepared by reaction a pyrazolopyrimidine like III with an alcohol such as IX (wherein Pg$_2$ is for example, 2-tetrahydropyranyl) employing Mitsunobu-like reaction conditions for example diisopropyl azodicarboxylate and triphenylphosphine in a solvent such as tetrahydrofuran.

The general synthetic sequence in scheme 5 is for example described in the synthesis of intermediate 8-chloro-3-methyl-2,4,12,13-tetrahydro-11H-5,7-(azenometheno)dipyrazolo[3,4-b:5',1'-g][1]oxa[4,6,8]triazacycloundecine.

Scheme 6

Method 6

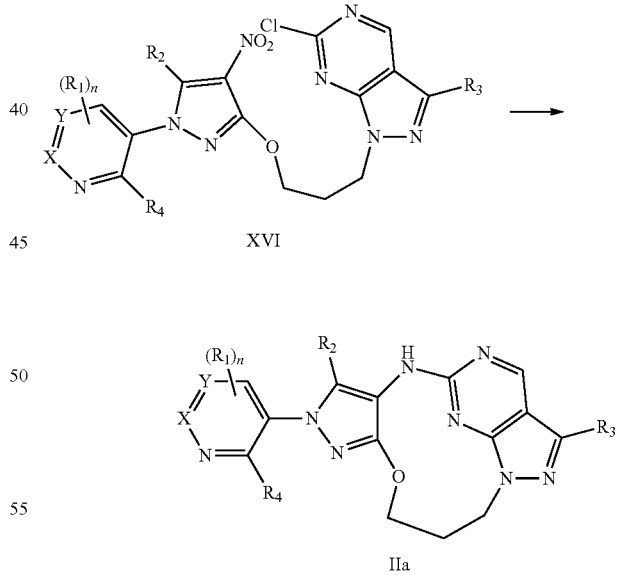

Compounds of formula IIa can be prepared according to scheme 6. The compounds of formula IIa can for example be prepared through a one pot reduction-cyclization procedure by reducing an intermediate of type XVI with iron and ammonium chloride in a suitable solvent e.g. a mixture of ethanol and water followed by cyclization as described for in Example 21.

Scheme 7

Method 7

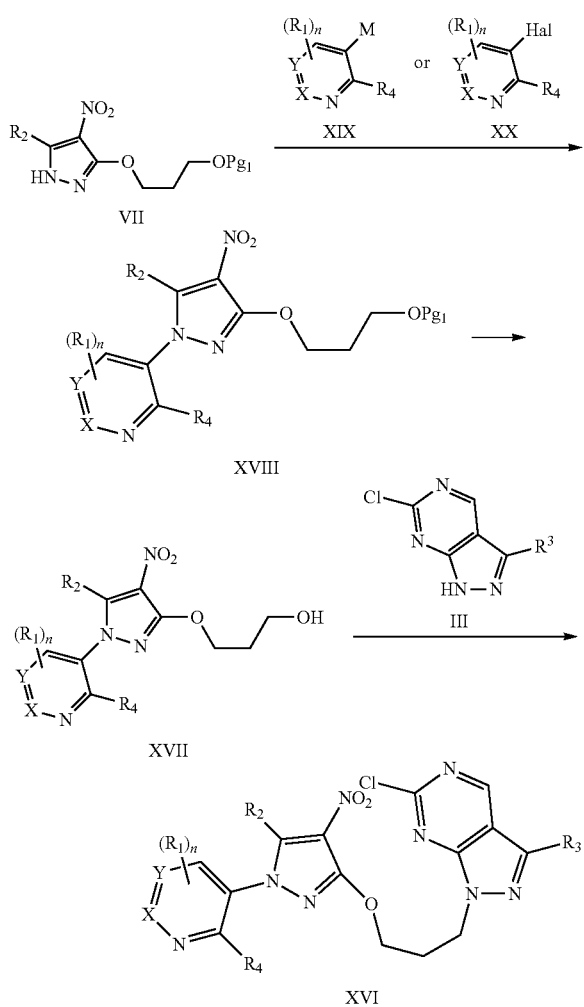

A nitropyrazole intermediate of type XVI can be prepared through a 3-step sequence according to scheme 7 starting from a nitropyrazole such as VII.

A pyrazole intermediate of type XVIII (wherein $Pg_1$ is for example TBS) can be prepared through the coupling of an intermediate of type VII (wherein $Pg_1$ is for example TBS) with an intermediate of type XIX (wherein M is for example $B(OH)_2$. The coupling is exemplified by a Chan-Lam type coupling. The reaction can be performed by reacting an intermediate of type VII (wherein $Pg_1$ is for example TBS) with a boronic acid intermediate XIX in which M=$B(OH)_2$ in the presence of a copper salt such as copper(II) triflate, a base for example N,N,N',N'-tetramethylethylenediamine under an oxygen atmosphere and a suitable solvent such as acetonitrile and dichloromethane. Alternatively, a pyrazole intermediate of type VII can be reacted with an intermediate of type XX (wherein Hal is e.g., Cl) to afford an intermediate such as XVIII in the presence of a base e.g., potassium carbonate and an appropriate solvent like acetonitrile.

Intermediates of type XVIII (wherein $Pg_1$ is for example TBS) can be converted into an alchohol intermediate of type XVII using for example a fluoride source such as tetrabutylammonium fluoride an appropriate solvent for example tetrahydrofuran.

An alcohol of intermediate such as XVII can be reacted with a pyrazolopyrimidine such as III under Mitsunobu-type conditions employing for example diisopropyl azodicarboxylate and triphenylphosphine in a solvent such as tetrahydrofuran to afford an intermediate of type XVI.

The general synthetic sequence in scheme 7 is for example described in the synthesis of the intermediates 3,6-dichloro-1-(3-((1-(3-methoxypyridazin-4-yl)-5-methyl-4-nitro-1H-pyrazol-3-yl)oxy)propyl)-1H-pyrazolo[3,4-d]pyrimidine and 3,6-dichloro-1-(3-((1-(4-methoxy-2-methylpyrimidin-5-yl)-5-methyl-4-nitro-1H-pyrazol-3-yl)oxy)propyl)-1H-pyrazolo[3,4-d]pyrimidine.

Scheme 8

Method 8

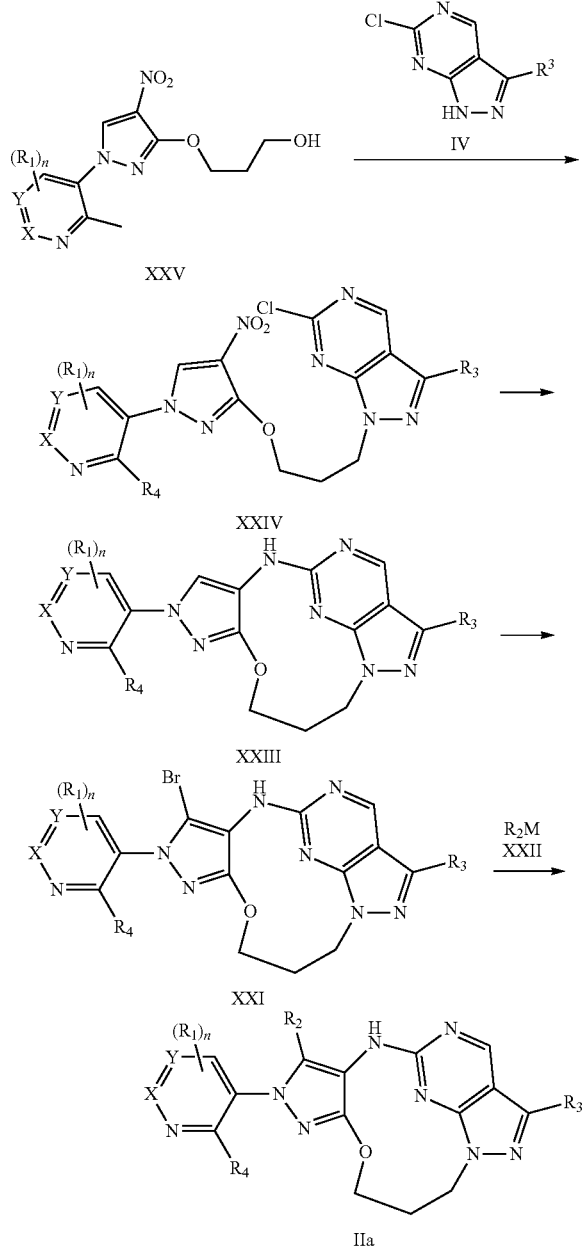

Alternatively, compounds of formula IIa can be prepared according to scheme 7 through a 4-step sequence starting from a nitropyrazole intermediate of type XXV.

Nitropyrazole intermediates such as XXIV can for example be synthesized through reaction of a pyrazolopyrimidine such as IV and an alcohol like XXV employing Mitsunobu-like reaction conditions. The Mitsunobu-like coupling can for example be conducted using e.g., triphenylphosphine and diisopropyl azodicarboxylate in a suitable solvent like tetrahydrofuran.

Intermediates of type XXIII can be synthesized from a nitropyrazole intermediate such as XXIV employing a one-pot reduction and cyclization procedure. The reduction and subsequent cyclization can be performed using for example iron in the presence of ammonium chloride in a suitable solvent such as a mixture of ethanol and water.

A bromo intermediate such as XXI can be prepared from a pyrazole like XXIII using a brominating agent for example 2,4,4,6-tetrabromocyclohexa-2,5-dien-1-one in a suitable solvent such as tetrahydrofuran.

A bromo intermediate of type XXI can be reacted with an organometallic species such as XXII (wherein M is for example Bpin, $B(OH)_2$, Sn(n-Bu)$_3$ or SnMe$_3$, Zn, ZnBr or ZnCl). The coupling is exemplified by but not limited to a Negishi-type cross-coupling. The reaction can be performed by reacting an intermediate of type XXI with an organozinc species such as $(CD_3)_2Zn$ in the presence of a catalyst like bis[tris(tert-butyl)phosphine]palladium, a base such as lithium bis(trimethylsilyl)amide in an appropriate solvent such as tetrahydrofuran to provide a compounds of formula IIa (wherein $R_2=CD_3$) as described for Example 25.

Scheme 9

Method 9

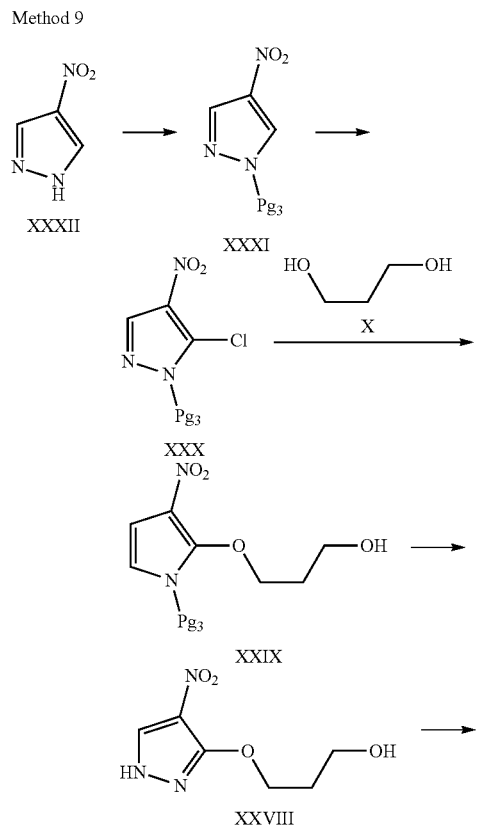

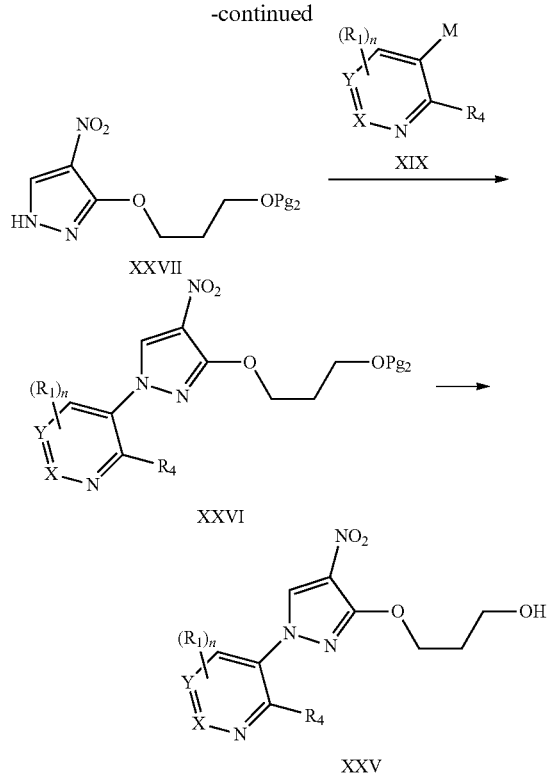

A method to prepare an intermediate of type XXV is depicted in scheme 9. A nitropyrazole intermediate of type XXXI (wherein Pg$_3$ is for example, 2-tetrahydropyranyl) can be prepared from a pyrazole of type XXXII using e.g., 3,4-dihydro-2H-pyran in the presence of an acid for example para-toluenesulfonic acid monohydrate in an appropriate solvent such as tetrahydrofuran.

Chloro intermediates such as XXX (wherein Pg$_3$ is for example, 2-tetrahydropyranyl) can be prepared from a nitropyrazole intermediate XXXI (wherein Pg$_3$ is for example, 2-tetrahydropyranyl) using a strong base for example lithium bis(trimethylsilyl)amide, and an electrophile for example hexachloroethane in a suitable solvent such as tetrahydrofuran.

Alcohol intermediates of type XXIX (wherein Pg$_3$ is for example, 2-tetrahydropyranyl) can be prepared by reacting a chloro intermediate XXX with a diol of type X in the presence of a base for example cesium fluoride in a solvent such as N,N-dimethylacetamide.

An intermediate of type XXIX (wherein Pg$_3$ is for example, 2-tetrahydropyranyl) can be converted into a pyrazole such as XXVIII by treatment with an acid such as aqueous hydrochloric acid in a suitable solvent for example methanol.

Intermediates of type XXVII (wherein Pg$_2$ is e.g., TBS) can be synthesized from an alcohol such as XXVIII using for example tert-butyldimethylsilyl chloride in the presence of a base such as imidazole and a catalyst such as 4-dimethylaminopyridine in an appropriate solvent such as dichloromethane.

Nitropyrazole intermediates of type XXVI (wherein Pg$_3$ is e.g., TBS) can synthesized from pyrazole intermediates such as XXVII and an intermediate of type XIX (wherein M is for example $B(OH)_2$). The coupling is exemplified by a Chan-Lam type coupling. The reaction can be performed by reacting an intermediate of type XXVII (wherein Pg$_2$ is for example TBS) with a boronic acid intermediate XIX in which M=B(OH)$_2$ in the presence of a copper salt such as copper(II) acetate, a base for example pyridine, and a drying agent such as 4 Å molecular sieves under an oxygen atmosphere in a suitable solvent such as 1,2-dichloroethane.

Finally, alcohol intermediates of type XXV can be prepared from a nitro pyrazole intermediate of type XXVI (wherein Pg$_2$ is e.g., TBS) using tetra-n-butyl ammonium fluoride in a suitable solvent such as tetrahydrofuran. The synthetic schemes 8 and 9 is for example detailed in the synthesis of 3-bromo-8-chloro-2-(2,6-dimethylpyridin-3-yl)-2,4,12,13-tetrahydro-11H-5,7-(azenometheno)dipyrazolo[3,4-b:5',1'-g][1]oxa[4,6,8]triazacycloundecine.

Abbreviations

Abbreviations used in the experimental may include, but are not limited to the following:
Boc: tert-butyloxycarbonyl; Bpin: pinacol boronate; BRIJ-35: polyoxyethylene (23) lauryl ether; C: Celsius; CPME: cyclopentyl methyl ether; c-Pr: cyclopropyl; DBAD: di-tert-butyl azodicarboxylate; DCM: dichloromethane; DIAD: diisopropyl azodicarboxylate; DIPEA: N,N-diisopropylethylamine; DMA: N,N-dimethylacetamide; DMF: N,N-dimethylformamide; DMSO: dimethylsulfoxide; DTBPF: 1,1-bis(di-tert-butylphosphino)ferrocene; DTT: dithiothreitol; EGTA: ethylene glycol-bis(β-aminoethyl ether)-N,N,N',N'-tetraacetic acid; Et: ethyl; EtOAc: ethyl acetate; g: gram; h: hour(s); HMDS: hexamethyldisilazane; L: liter; LDA: lithium diisopropylamide; M: molar; Me: methyl; mg: milligram; mL: milliliter; mmol: millimole; Ms: methanesulfonyl; n-Bu: n-butyl; NFSI: N-fluorobenzenesulfonimide; NMR: nuclear magnetic resonance; Ph: phenyl; Pin: pinacol; PG: protecting group; SFC: supercritical fluid chromatography; TBS: tert-butyl(dimethyl)silyl; TBAF. Tetra-n-butylammonium fluoride; TEA: triethylamine; THF: tetrahydrofuran; THP: tetrahydropyran; TMEDA: N,N,N',N'-tetramethylethylenediamine; TMS: trimethylsilyl; Tris: trisaminomethane; Ts: toluenesulfonyl.

Chemical Names

The chemical names for the Examples of the invention were generated using ChemDraw, version 20.0.0.41 by PerkinElmer Informatics, Inc.

Analytical Methods

LC-MS Methods

Method A: LC-MS were run on Agilent Prime-6125B UPLC-MS consisting of Agilent Prime including column manager, binary solvent manager, sample organizer, PDA detector (operating at 254 nm), ELS detector, and 6125B equipped with APPI-source operating in positive ion mode. LC-conditions: The column was Agilent Poroshell 120 EC-C18 1.9 µm; 3.0×30 mm operating at 50° C. with 1.5 mL/min of a binary gradient consisting of water+0.037% trifluoroacetic acid (A) and acetonitrile+0.018% trifluoroacetic acid(B). The retention times ($t_R$) are expressed in minutes based on UV-trace at 254 nm.
Gradient: 0.00 min 5% B
  1.20 min 80% B
  2.5 min 95% B
  2.51 min 5% B
  3.00 min 5% B
Total run time: 3.0 min Method B: LC-MS were run on Agilent LC1200-MS6150 UPLC-MS consisting of Agilent LC1200 including column manager, binary solvent manager, sample organizer, PDA detector (operating at 220&254 nm), ELS detector, and MS6150 equipped with APPI-source operating in positive ion mode. LC-conditions: The column was MERCK, RP-18 e 25×3.0 mm operating at 50° C. with 1.5 mL/min of a binary gradient consisting of water+0.037% trifluoroacetic acid (A) and acetonitrile+0.018% trifluoroacetic acid(B). The retention times ($t_R$) are expressed in minutes based on UV-trace at 220&254 nm.
Gradient: 0.00 min 5% B
  0.7 min 95% B
  1.1 min 95% B
  1.11 min 5% B
  1.5 min 5% B
Total run time: 1.5 min Method C: LC-MS were run on Agilent LC1200-MS6110 UPLC-MS consisting of Agilent LC1200 including column manager, binary solvent manager, sample organizer, PDA detector (operating at 220&254 nm), ELS detector, and MS6110 equipped with APPI-source operating in positive ion mode. LC-conditions: The column was Xbridge Shield, RP-18 e 50×2.1 mm operating at 30° C. with 1 mL/min of a binary gradient consisting of water(4 L)+NH$_3$—H$_2$O(0.8 mL) (A) and acetonitrile (B). The retention times ($t_R$) are expressed in minutes based on UV-trace at 220&254 nm.
Gradient: 0.00 min 10% B
  2 min 80% B
  2.48 min 80% B
  2.5 min 10% B
  3 min 10% B
Total run time: 3 min Method D:LC-MS were run on Waters Aquity UPLC-MS consisting of Waters Aquity including column manager, binary solvent manager, sample organizer, PDA detector (operating at 254 nm), ELS detector, and TQD-MS equipped with ESI-source operating in positive ion mode. LC-conditions: The column was Acquity UPLC BEH C18 1.7 µm; 2.1×50 mm operating at 60° C. with 1.2 ml/min of a binary gradient consisting of water+0.05% trifluoroacetic acid (A) and acetonitrile+5% water+0.03% trifluoroacetic acid. The retention times ($t_R$) are expressed in minutes based on UV-trace at 254 nm.
Gradient: 0.00 min 10% B
  1.00 min 100% B
  1.01 min 10% B
  1.15 min 10% B
Total run time: 1.15 min Method E:LC-MS were run on Waters Aquity UPLC-MS consisting of Waters Aquity including column manager, binary solvent manager, sample organizer, PDA detector (operating at 254 nm), ELS detector, and TQD-MS equipped with ESI-source operating in positive ion mode. LC-conditions: The column was Acquity UPLC HSS T3 1.8 µm; 2.1×50 mm operating at 60° C. with 1.2 ml/min of a binary gradient consisting of water+0.05% trifluoroacetic acid (A) and acetonitrile+5% water+0.035% trifluoroacetic acid. The retention times ($t_R$) are expressed in minutes based on UV-trace at 254 nm.
Gradient: 0.00 min 2% B
  1.00 min 100% B
  1.01 min 2% B
  1.15 min 2% B
Total run time: 1.15 min Method F: LC-MS were run on Agilent Prime-6125B UPLC-MS consisting of Agilent Prime including column manager, binary solvent manager, sample organizer, PDA detector (operating at 254 nm), ELS detector, and MS6125B equipped with APPI-source operating in positive ion mode. LC-conditions: The column was Agilent Poroshell 120 HPH-C18 1.9 µm 3.0×30 mm operating at 30° C. with 1.5 mL/min of a binary gradient consisting of water+0.05% NH$_3$—H$_2$O (A) and acetonitrile (B). The retention times (t$_R$) are expressed in minutes based on UV-trace at 254 nm.

Gradient: 0.00 min 5% B
1.2 min 80% B
2.5 min 95% B
2.51 min 5% B
3.0 min 5% B
Total run time: 3.0 min

NMR $^1$H NMR spectra were recorded at 600 MHz on a Bruker 600-Avance-III spectrometer, at 400 MHz on Bruker Avance AV-III-400 or Varian MR400 spectrometers. Chemical shift values are expressed in ppm-values relative to tetramethylsilane. The following abbreviations or their combinations are used for multiplicity of NMR signals: br=broad, d=doublet, m=multiplet, q=quartet, quint=quintet, s=singlet and t=triplet.

Preparation of Reagents

Reagent: Bis(methyl-d$_3$)zinc in THF-dibutyl ether-Toluene

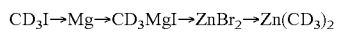

To a mixture of magnesium turnings (3.51 g, 145 mmol) and di-(n-butyl) ether (39.0 mL) was added DIBAL-H in toluene (1.00 mL, 1.00 molar, 1.00 mmol) at room temperature. The mixture was stirred for 15 min then iodomethane-d$_3$ (0.62 mL, 10 mmol) was added. The mixture was then heated to 40° C. and stirred for 15 minutes. Then additional iodomethane-d$_3$ (5.6 mL, 90 mmol) was added dropwise over a period of 30 minutes. The mixture was further stirred at 40° C. for 1.5 h. The mixture was cooled, and an aliquot was subjected to iodometric titration (I$_2$ in 2-MeTHF; slow addition of Grignard reagent) to determine the concentration=1.38 M.

To dried zinc(II) bromide (2.20 g, 9.77 mmol) under N$_2$ was added THF (4.40 mL). This was stirred for 10 min. Then di-(n-butyl) ether (4.40 mL) was slowly added to form a white suspension. Then CD$_3$MgI (1.38 M in n-Bu$_2$O) (14.2 mL, 1.38 M, 19.6 mmol) was added slowly over a period of 5 minutes at ~5° C. (ice-water cooling) to form a white suspension. The mixture was stirred for 30 minutes at room temperature. Then toluene (5.52 mL) was added, and the suspension was stirred for 15 min. The mixture was filtered under an inert atmosphere, and the filtrate was used in the subsequent reaction. Iodometric titration (I$_2$ in 2-MeTHF) to determine the concentration=0.71 M.

Reagent: (Methyl-d$_3$)boronic acid

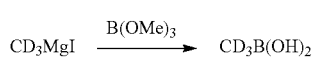

To a solution of trimethyl borate (3.68 g, 35.4 mmol) in THF (40 mL) was added iodo(trideuteriomethyl)magnesium (20 mL, 20 mmol, 1 M in diethyl ether) in a dropwise manner at −65° C. and the reaction was stirred at −65° C. for 2 hours. The reaction mixture was quenched with 1M aqueous HCl (10 mL) and the mixture was allowed to warm to 15° C. The mixture was diluted with brine (30 mL) and extracted with Et$_2$O (150 mL). The organic layer was washed with brine (30 mL×3), dried over Na$_2$SO$_4$, and concentrated under reduced pressure to afford (methyl-d$_3$) boronic acid (2.6 g, purity ~40 w % containing THF) of sufficient purity for the subsequent step.

Alternatively, (Methyl-d$_3$)boronic acid can be prepared in the following manner:

To a solution of trimethyl borate (6 g, 58 mmol) in THF (60 mL) was added (methyl-d$_3$)magnesium iodide (16.2 mL, 32 mmol, 2 M in n-Bu$_2$O) in a dropwise manner at −65° C. The mixture was stirred at −65° C. for 2 h. The mixture was quenched with 1M aqueous HCl (17 mL) and allowed to warm to 15° C. The mixture was diluted with brine (30 mL) and extracted with Et$_2$O (60 mL×7). The combined organic layers were washed with brine (30 mL×2) and dried over Na$_2$SO$_4$ and concentrated under reduced pressure to give (methyl-d$_3$)boronic acid (9.8 g, purity ~15 w % containing THF and n-Bu$_2$O).

Preparation of Intermediates

Intermediate: 3,6-Dichloro-1H-pyrazolo[3,4-d]pyrimidine

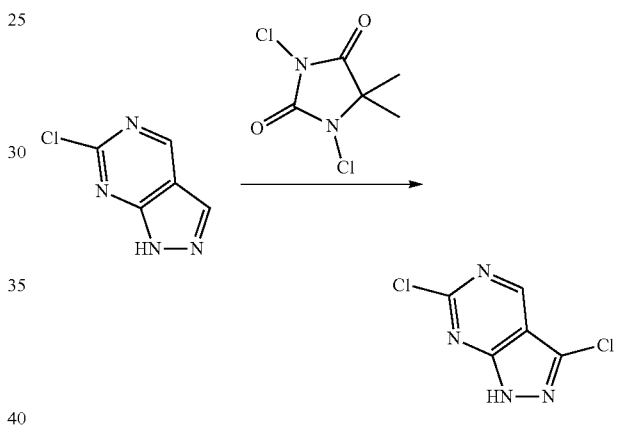

Three reactions were run in parallel: To a solution of 6-chloro-1H-pyrazolo[3,4-d]pyrimidine (8 g, 51.8 mmol) in MeCN (240 mL) was added 1,3-dichloro-5,5-dimethylimidazolidine-2,4-dione (7.14 g, 36.23 mmol). The mixture was stirred at 85° C. for 24 h. The reaction mixture was concentrated under reduced pressure. The residues from the three reactions were combined and purified by chromatography on silica gel (eluent: petroleum ether:EtOAc 100: 0→80:20) to afford 3,6-dichloro-1H-pyrazolo[3,4-d]pyrimidine (4.3 g) of sufficient purity for the subsequent step. $^1$H NMR (DMSO-d$_6$, 400 MHz) δ 14.55 (br s, 1H), 9.29 (s, 1H).

Intermediate: 5-(3-((tert-Butyldimethylsilyl)oxy) propoxy)-3-methyl-4-nitro-1H-pyrazole

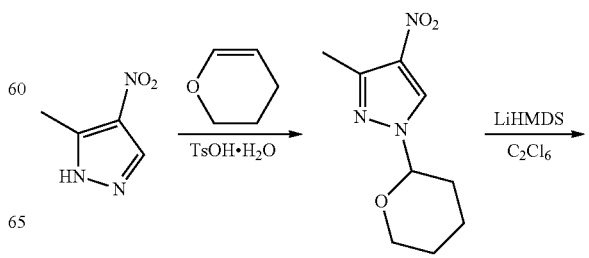

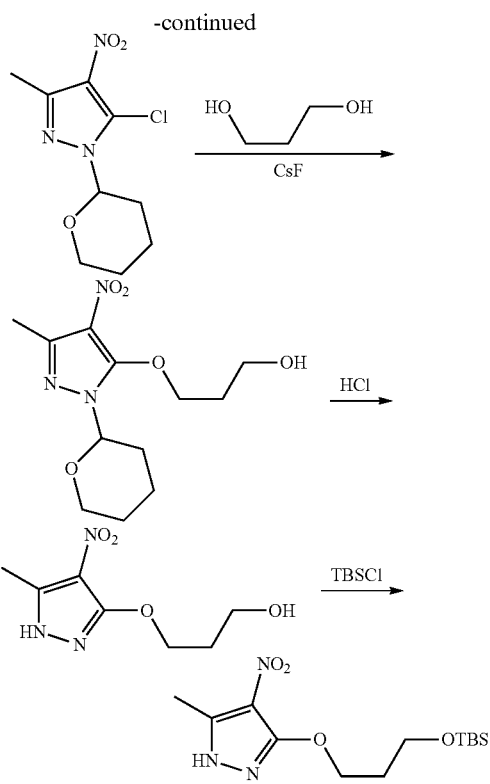

To a solution of 3-methyl-4-nitro-1H-pyrazole (12 g, 94.4 mmol) in THF (140 mL) was added TsOH·H₂O (898 mg, 4.7 mmol) and stirred at 20° C. for 30 minutes. 3,4-Dihydro-2H-pyran (10.2 g, 121 mmol) was added at 0° C. The mixture was stirred at 20° C. for 16 h. The mixture was concentrated under reduced pressure. The residue was purified by chromatography on silica gel (eluent: petroleum ether:EtOAc 100:0→80:20) to afford 3-methyl-4-nitro-1-(tetrahydro-2H-pyran-2-yl)-1H-pyrazole (12 g) of sufficient purity for the subsequent step.

To a solution of 3-methyl-4-nitro-1-(tetrahydro-2H-pyran-2-yl)-1H-pyrazole (12 g, 56.8 mmol) in THF (100 mL) was added LiHMDS (1 M in THF, 62.5 mL) at –65° C. and stirred at –65° C. for 30 minutes. Perchloroethane (14.80 g, 62.49 mmol) dissolved in THF (50 mL) was added and the mixture was stirred at –65° C. for 60 minutes and then allowed to warm to 20° C. for 10 minutes. The mixture was quenched with saturated aqueous NH₄Cl (200 mL) at 0° C. and then allowed to warm to 20° C. for 20 minutes and extracted with EtOAc (150 mL×3). The combined organic layers were washed with brine (80 mL) and concentrated under reduced pressure. The residue was purified by chromatography on silica gel (eluent: petroleum ether:EtOAc 100:0→90:10) to afford 5-chloro-3-methyl-4-nitro-1-(tetrahydro-2H-pyran-2-yl)-1H-pyrazole (7.9 g) of sufficient purity for the subsequent step.

To a solution of 5-chloro-3-methyl-4-nitro-1-(tetrahydro-2H-pyran-2-yl)-1H-pyrazole (19 g, 77.3 mmol) in DMA (150 mL) was added CsF (41.1 g, 271 mmol) and propane-1,3-diol (29.43 g, 386.7 mmol). The mixture was stirred at 50° C. for 16 h. The mixture was diluted with water (200 mL) and extracted with EtOAc (100 mL×3). The combined organic layers were washed with brine (100 mL×3). The organic layers were concentrated under reduced pressure. The residue was purified by chromatography on silica gel (eluent: petroleum ether:EtOAc 100:0→69:31) to afford 3-((3-methyl-4-nitro-1-(tetrahydro-2H-pyran-2-yl)-1H-pyrazol-5-yl)oxy)propan-1-ol (13.7 g) of sufficient purity for the subsequent step.

To a solution of 3-((3-methyl-4-nitro-1-(tetrahydro-2H-pyran-2-yl)-1H-pyrazol-5-yl)oxy)propan-1-ol (4 g, 14 mmol) in MeOH (20 mL) was added HCl (12 M, 14.0 mL). The mixture was stirred at 20° C. for 16 h and then heated to 60° C. for 2 h. The mixture was concentrated and pH adjusted to 10 with 4M aqueous NaOH. The resulting mixture were concentrated under reduced pressure. The residue was purified by chromatography on silica gel (eluent: petroleum ether:EtOAc 100:0→20:80) to afford 3-((3-methyl-4-nitro-1H-pyrazol-5-yl)oxy)propan-1-ol (2.7 g) of sufficient purity for the subsequent step. ¹H NMR (DMSO-d₆, 400 MHz) δ 12.94 (br s, 1H), 4.55 (t, J=4.8 Hz, 1H), 4.28 (t, J=6.4 Hz, 2H), 3.60-3.49 (m, 2H), 2.47 (s, 3H), 1.92-1.82 (m, 2H).

To a solution of 3-((3-methyl-4-nitro-1H-pyrazol-5-yl)oxy)propan-1-ol (2.7 g, 13 mmol) in DCM (30 mL) was added imidazole (1.46 g, 21.5 mmol), TBSCI (4.05 g, 26.8 mmol), and DMAP (820 mg, 6.71 mmol). The mixture was stirred at 20° C. for 16 h. The mixture was concentrated under reduced pressure. The residue was purified by chromatography on silica gel (eluent: petroleum ether:EtOAc 100:0→79:21) to afford 5-(3-((tert-butyldimethylsilyl)oxy)propoxy)-3-methyl-4-nitro-1H-pyrazole (3.7 g) of sufficient purity for the subsequent step. ¹H NMR (CD₃OD, 400 MHz) δ 4.40 (t, J=6.4 Hz, 2H), 3.84 (t, J=6.0 Hz, 2H), 2.61 (s, 3H), 2.03 (t, J=6.0 Hz, 2H), 0.89 (s, 9H), 0.05 (s, 6H).

Intermediate: 5-(3-((tert-Butyldimethylsilyl)oxy)propoxy)-3-ethyl-4-nitro-1H-pyrazole

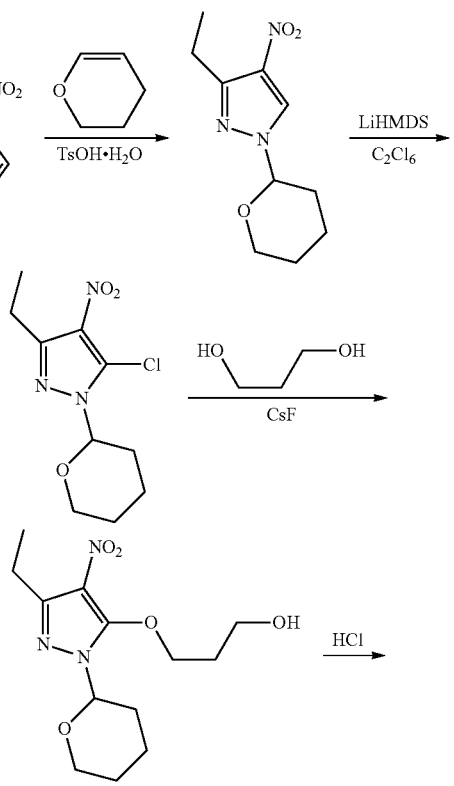

-continued

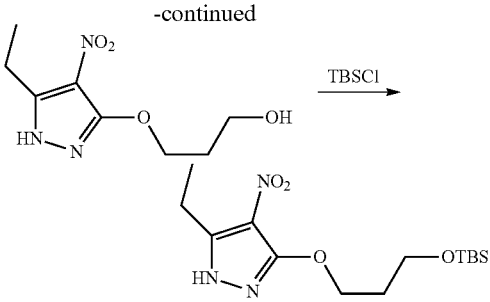

To a solution of 3-ethyl-4-nitro-1H-pyrazole (12.5 g, 88.6 mmol) in THF (150 mL) was added TsOH·H₂O (843 mg, 4.43 mmol). The mixture was stirred at 25° C. for 15 minutes. 3,4-Dihydro-2H-pyran (9.54 g, 113 mmol) was added while stirring at 0° C. The mixture was stirred at 25° C. for 16 h. The mixture was concentrated under reduced pressure. The residue was purified by chromatography on silica gel (eluent: petroleum ether:EtOAc 100:0→90:10) to afford 3-ethyl-4-nitro-1-tetrahydropyran-2-yl-pyrazole (19 g) of sufficient purity for the subsequent step. $^1$H NMR (CDCl₃, 400M Hz) 68.33 (s, 1H), 5.34-5.30 (m, 1H), 4.13-4.06 (m, 1H), 3.76-3.66 (m, 1H), 2.98 (q, J=7.6 Hz, 2H), 2.19-2.09 (m, 1H), 2.02-1.96 (m, 1H), 1.77-1.63 (m, 4H), 1.28 (t, J=7.6 Hz, 3H).

To a solution of 3-ethyl-4-nitro-1-tetrahydropyran-2-yl-pyrazole (19 g, 84 mmol) in THF (80 mL) was added LiHMDS (1 M in THF, 92.8 mL) at −65° C. and the reaction was stirred at −65° C. for 30 minutes. 1,1,1,2,2,2-hexachloroethane (22 g, 93 mmol) dissolved in THF (60 mL) was added and the mixture was stirred at −65° C. for 2 h and then allowed to warm to 20° C. for 10 minutes. The mixture was quenched with saturated aqueous NH₄Cl solution (200 mL) at 0° C. and then allowed to warm to 20° C. for 20 min and extracted with EtOAc (200 mL×3). The combined organic layers were washed with brine (80 mL×3) and concentrated under reduced pressure. The residue was purified by chromatography on silica gel (eluent: petroleum ether:EtOAc 100:0→95:5) to afford 5-chloro-3-ethyl-4-nitro-1-tetrahydropyran-2-yl-pyrazole (17 g) of sufficient purity for the subsequent step. $^1$H NMR (CDCl₃, 400 MHz) δ 5.52 (dd, J=2.8, 10.0 Hz, 1H), 4.13-4.03 (m, 1H), 3.76-3.64 (m, 1H), 2.98(q, J=7.2 Hz, 2H), 2.51-2.36 (m, 1H), 2.22-2.10 (m, 1H), 1.95-1.85 (m, 1H), 1.81-1.60 (m, 3H), 1.29 (t, J=7.2 Hz, 3H).

To a solution of 5-chloro-3-ethyl-4-nitro-1-(tetrahydro-2H-pyran-2-yl)-1H-pyrazole (12 g, 46.2 mmol) and propane-1,3-diol (17.6 g, 231 mmol) in DMA (150 mL) was added CsF (21.1 g, 139 mmol). The mixture was stirred at 50° C. for 16 h. The mixture was diluted with water (200 mL) and extracted with EtOAc (150 mL×4). The combined organic layers were washed with brine (100 mL×4) and then concentrated under reduced pressure. The residue was purified by chromatography on silica gel (eluent: petroleum ether:EtOAc 100:0→60:40) to afford 3-((3-ethyl-4-nitro-1-(tetrahydro-2H-pyran-2-yl)-1H-pyrazol-5-yl)oxy)propan-1-ol (14 g) of sufficient purity for the subsequent step.

To a solution of 3-((3-ethyl-4-nitro-1-(tetrahydro-2H-pyran-2-yl)-1H-pyrazol-5-yl)oxy)propan-1-ol (14 g, 47 mmol) in MeOH (140 mL) was added concentrated aqueous HCl (24 mL). The mixture was stirred at 60° C. for 3 h. To the mixture was added NaOH and pH adjusted to 8 while stirring at 0° C. The mixture was concentrated under reduced pressure. The residue was purified by chromatography on silica gel (eluent: petroleum ether:EtOAc 100:0→10:90) to afford 3-((3-ethyl-4-nitro-1H-pyrazol-5-yl)oxy)propan-1-ol (8.5 g) of sufficient purity for the subsequent step. $^1$H NMR (DMSO-d₆, 400 MHz) δ 12.95 (br s, 1H), 4.54 (br, 1H), 4.29 (t, J=6.8 Hz, 2H), 3.54 (t, J=6.0 Hz, 2H), 2.89 (q, J=7.6 Hz, 2H), 1.92-1.83 (m, 2H), 1.20 (t, J=7.6 Hz, 3H).

To a solution of 3-((3-ethyl-4-nitro-1H-pyrazol-5-yl)oxy) propan-1-ol (8.5 g, 40 mmol) in DCM (70 mL) was added DMAP (1.45 g, 11.9 mmol), imidazole (4.30 g, 63.2 mmol), and TBSCl (11.9 g, 80.0 mmol). The mixture was stirred at 25° C. for 16 h. The mixture was concentrated under reduced pressure. The residue was purified by chromatography on silica gel (eluent: petroleum ether:EtOAc 100:0→70:30) to afford 5-(3-((tert-butyldimethylsilyl)oxy)propoxy)-3-ethyl-4-nitro-1H-pyrazole (8.5 g) of sufficient purity for the subsequent step. $^1$H NMR (CDCl₃, 400 MHz) δ 4.40 (t, J=6.4 Hz, 2H), 3.83 (t, J=6.0 Hz, 2H), 3.04 (q, J=7.6 Hz, 2H), 2.09-1.99 (m, 2H), 1.33 (t, J=7.6 Hz, 3H), 0.88 (s, 9H), 0.05 (s, 6H).

Intermediate: 8-Chloro-3-methyl-2,4,12,13-tetrahydro-11H-5,7-(azenometheno)dipyrazolo[3,4-b:5', 1'-g][1]oxa[4,6,8]triazacycloundecine

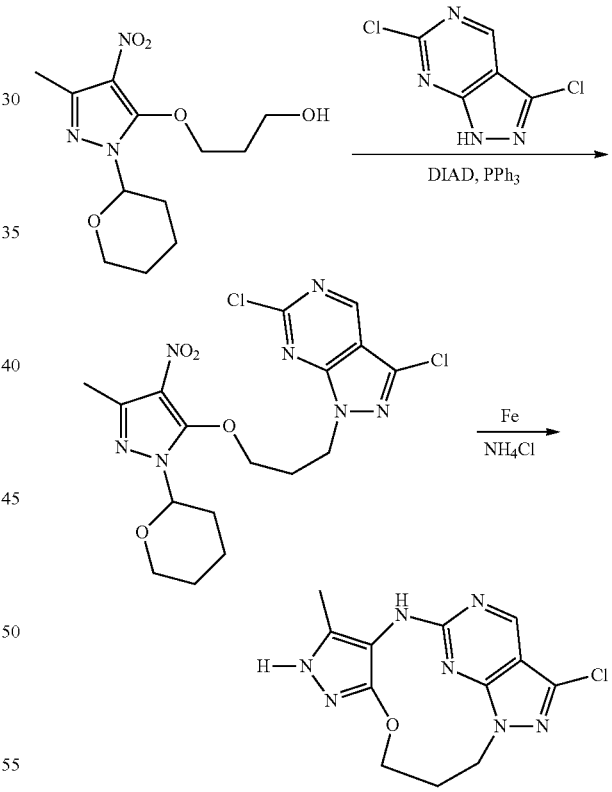

A mixture of 3-((3-methyl-4-nitro-1-(tetrahydro-2H-pyran-2-yl)-1H-pyrazol-5-yl)oxy)propan-1-ol (2.00 g, 7.01 mmol), 3,6-dichloro-1H-pyrazolo[3,4-d]pyrimidine (1.32 g, 7.01 mmol), PPh₃ (2.76 g, 10.5 mmol), and DIAD (2.13 g, 10.5 mmol) in THF (20 mL) was stirred at 15° C. for 16 h. The mixture was concentrated under reduced pressure. The residue was purified by chromatography on silica gel (eluent: petroleum ether:EtOAc 100:0→70:30). The crude product was dissolved in a mixture of EtOAc 40 mL and petroleum ether 20 mL at 50° C. for 20 minutes. The mixture was allowed to cool to 20° C., filtered, and the filter cake was dried to afford 3,6-dichloro-1-(3-((3-methyl-4-nitro-1-(tetrahydro-2H-pyran-2-yl)-1H-pyrazol-5-yl)oxy)propyl)-1H-pyrazolo[3,4-d]pyrimidine (2.3 g) of sufficient purity for the subsequent step. $^1$H NMR (CDCl$_3$, 400M Hz) δ 9.01 (s, 1H), 5.43 (dd, J=2.8, 10.4 Hz, 1H), 4.70 (t, J=6.8 Hz, 2H), 4.59-4.46 (m, 1H), 4.44-4.34 (m, 1H), 4.08-4.00 (m, 1H), 3.74-3.60 (m, 1H), 2.57-2.47 (m, 5H), 2.43-2.31 (m, 1H), 2.17-2.06 (m, 1H), 1.93-1.79 (m, 1H), 1.78-1.67 (m, 2H), 1.27 (d, J=6.4 Hz, 1H).

To a solution of 3,6-dichloro-1-(3-((3-methyl-4-nitro-1-(tetrahydro-2H-pyran-2-yl)-1H-pyrazol-5-yl)oxy)propyl)-1H-pyrazolo[3,4-d]pyrimidine (2.3 g, 5.0 mmol) in EtOH (300 mL) was added Fe (1.41 g, 25.2 mmol) and then a solution of NH$_4$Cl (1.35 g, 25.2 mmol) in H$_2$O (20 mL). The mixture was stirred at 80° C. for 32 h. The mixture was concentrated under reduced pressure. The residue was purified by chromatography on silica gel (eluent: petroleum ether:EtOAc:DCM:MeOH 100:0:0:0→0:100:0:0→0:0:100:0→0:0:90:10) to afford 8-chloro-3-methyl-2,4,12,13-tetrahydro-11H-5,7-(azenometheno)dipyrazolo[3,4-b:5',1'-g][1]oxa[4,6,8]-triazacycloundecine (500 mg) of sufficient purity for the subsequent step. $^1$H NMR (DMSO-d, 400 MHz) δ 11.68 (br s, 1H), 9.33 (s, 1H), 8.77 (s, 1H), 4.44-4.24 (m, 4H), 2.18 (s, 3H), 1.82-1.72 (m, 2H). LC-MS (method A) (m/z)=306.1 (MH)$^+$ t$_R$=1.19 minutes.

Intermediate: 3,6-Dichloro-1-(3-((1-(2-ethoxypyridin-3-yl)-5-methyl-4-nitro-1H-pyrazol-3-yl)oxy)propyl)-1H-pyrazolo[3,4-d]pyrimidine

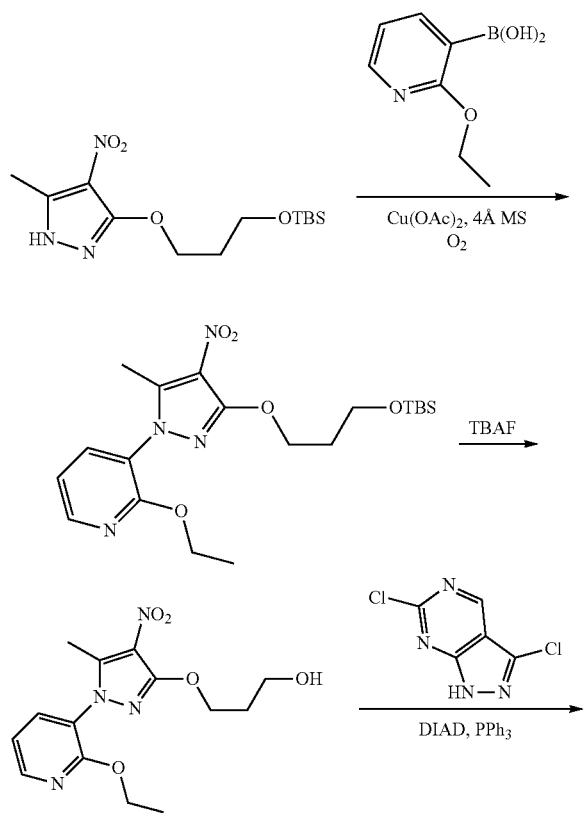

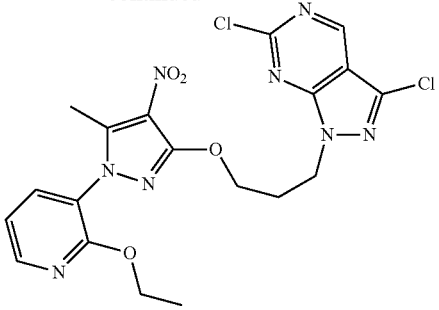

To a solution of 5-(3-((tert-butyldimethylsilyl)oxy)propoxy)-3-methyl-4-nitro-1H-pyrazole (600 mg, 1.90 mmol) and (2-ethoxy-3-pyridyl)boronic acid (635 mg, 3.80 mmol) in DCE (20 mL) was added Cu(OAc)$_2$ (518 mg, 2.85 mmol), pyridine (602 mg, 7.61 mmol) and 4 Å MS (600 mg). The mixture was stirred under an O$_2$-atmosphere at 50° C. for 16 h. Additional (2-ethoxy-3-pyridyl)boronic acid (300 mg, 1.78 mmol) was added. The reaction mixture was stirred for another 16 h. The reaction mixture was filtered. The filtrate was concentrated under reduced pressure. The residue was purified by chromatography on silica gel (eluent: petroleum ether:EtOAc 100:0→80:20) to afford 3-(3-(3-((tert-butyldimethylsilyl)oxy)propoxy)-5-methyl-4-nitro-1H-pyrazol-1-yl)-2-ethoxypyridine (742 mg) of sufficient purity for the subsequent step. 1H NMR (CDCl$_3$, 400 MHz) δ 8.30 (dd, J=2.0, 4.8 Hz, 1H), 7.70 (dd, J=2.0, 8.0 Hz, 1H), 7.06 (dd, J=4.8, 7.6 Hz, 1H), 4.53-4.39 (m, 4H), 3.85 (t, J=6.0 Hz, 2H), 2.48 (s, 3H), 2.14-2.00 (m, 2H), 1.36 (t, J=7.2 Hz, 3H), 0.92 (s, 9H), 0.06 (s, 6H).

To a solution of 3-(3-(3-((tert-butyldimethylsilyl)oxy)propoxy)-5-methyl-4-nitro-1H-pyrazol-1-yl)-2-ethoxypyridine (735 mg, 1.68 mmol) in THF (10 mL) was added TBAF (1 M in THF, 2.5 mL). The mixture was stirred at 20° C. for 1 h. The reaction mixture was concentrated under reduced pressure. The residue was purified by chromatography on silica gel (eluent: petroleum ether:EtOAc 100:0→30:70) to afford 3-((1-(2-ethoxypyridin-3-yl)-5-methyl-4-nitro-1H-pyrazol-3-yl)oxy)propan-1-ol (474 mg) of sufficient purity for the subsequent step. $^1$H NMR (CDCl$_3$, 400M Hz) δ 8.30 (dd, J=2.0, 4.8 Hz, 1H), 7.68 (dd, J=2.0, 7.6 Hz, 1H), 7.06 (dd, J=4.8, 7.6 Hz, 1H), 4.53 (t, J=6.0 Hz, 2H), 4.46 (q, J=6.8 Hz, 2H), 3.86 (t, J=5.6 Hz, 2H), 2.47 (s, 3H), 2.14-2.06 (m, 2H), 1.36 (t, J=6.8 Hz, 3H).

To a solution of 3-((1-(2-ethoxypyridin-3-yl)-5-methyl-4-nitro-1H-pyrazol-3-yl)oxy)propan-1-ol (250 mg, 0.78 mmol) and 3,6-dichloro-1H-pyrazolo[3,4-d]pyrimidine (147 mg, 0.776 mmol) in THF (15 mL) was added PPh$_3$ (610 mg, 2.33 mmol) followed by DIAD (471 mg, 2.33 mmol) at 5° C. The resulting mixture was stirred at 20° C. for 16 h. The reaction mixture was filtered, and the filtrate was concentrated under reduced pressure. The residue was purified by chromatography on silica gel (eluent: petroleum ether:EtOAc 100:0→55:45) to afford 3,6-dichloro-1-(3-((1-(2-ethoxypyridin-3-yl)-5-methyl-4-nitro-1H-pyrazol-3-yl)oxy)propyl)-1H-pyrazolo[3,4-d]pyrimidine (163 mg) of sufficient purity for the subsequent step. $^1$H NMR (CDCl$_3$, 400 MHz) δ 8.97 (s, 1H), 8.30 (dd, J=2.0, 4.8 Hz, 1H), 7.67 (dd, J=2.0, 7.6 Hz, 1H), 7.14-6.96 (m, 1H), 4.69 (t, J=6.4 Hz, 2H), 4.52-4.42 (m, 2H), 4.38 (t, J=5.6 Hz, 2H), 2.55-2.49 (m, 2H), 2.47 (s, 3H), 1.36 (t, J=7.2 Hz, 3H).

Intermediate: 3,6-Dichloro-1-(3-((5-methyl-1-(2-methylpyridin-3-yl)-4-nitro-1H-pyrazol-3-yl)oxy)propyl)-1H-pyrazolo[3,4-d]pyrimidine

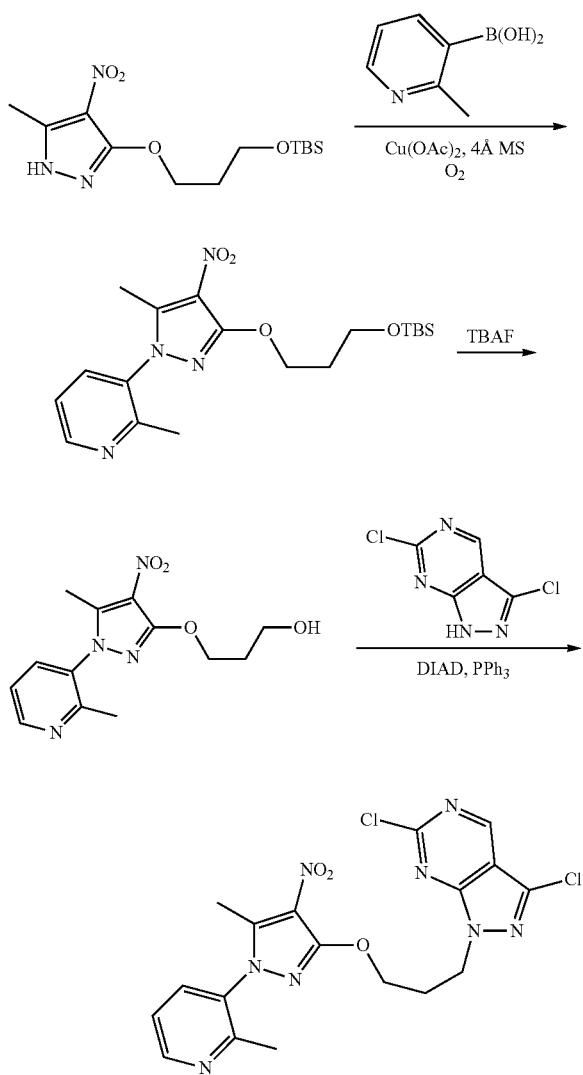

To a solution of 5-(3-((tert-butyldimethylsilyl)oxy)propoxy)-3-methyl-4-nitro-1H-pyrazole (400 mg, 1.27 mmol) and (2-methyl-3-pyridyl)boronic acid (521 mg, 3.80 mmol) in DCE (20 mL) was added Cu(OAc)$_2$ (345 mg, 1.90 mmol), pyridine (401 mg, 5.07 mmol) and 4 Å MS (400 mg). The mixture was stirred under an O$_2$-atmosphere at 50° C. for 16 h. Additional (2-methyl-3-pyridyl) boronic acid (260 mg, 1.88 mmol) was added. The reaction mixture was stirred for another 16 h. The reaction mixture was filtered, and the filtrate was concentrated under reduced pressure. The residue was purified by chromatography on silica gel (eluent: petroleum ether:EtOAc 100:0→55:45) to afford 3-(3-(3-((tert-butyldimethylsilyl)oxy)propoxy)-5-methyl-4-nitro-1H-pyrazol-1-yl)-2-methylpyridine (430 mg) of sufficient purity for the subsequent step. 1H NMR (CDCl$_3$, 400 MHz) δ 8.70 (dd, J=1.2, 4.8 Hz, 1H), 7.60 (dd, J=1.2, 8.0 Hz, 1H), 7.36 (dd, J=4.8, 8.0 Hz, 1H), 4.44 (t, J=6.0 Hz, 2H), 3.85 (t, J=6.0 Hz, 2H), 2.46 (s, 3H), 2.39 (s, 3H), 2.01-2.12 (m, 2H), 0.89 (s, 9H), 0.08 (s, 6H).

To a solution of 3-(3-(3-((tert-butyldimethylsilyl)oxy)propoxy)-5-methyl-4-nitro-1H-pyrazol-1-yl)-2-methylpyridine (425 mg, 1.05 mmol) in THF (10 mL) was added TBAF (1 M in THF, 1.57 mL). The resulting mixture was stirred at 20° C. for 1 h. The mixture was concentrated under reduced pressure. The residue was purified by chromatography on silica gel (eluent: petroleum ether:EtOAc (10 v % MeOH) 50:50→0:100) to afford 3-((5-methyl-1-(2-methylpyridin-3-yl)-4-nitro-1H-pyrazol-3-yl)oxy)propan-1-ol (279 mg) of sufficient purity for the subsequent step. 1H NMR (CDCl$_3$, 400 MHz) δ 8.71 (d, J=4.0 Hz, 1H), 7.60 (d, J=6.8 Hz, 1H), 7.36 (dd, J=4.8, 7.6 Hz, 1H), 4.53 (t, J=5.6 Hz, 2H), 3.89 (t, J=5.6 Hz, 2H), 2.46 (s, 3H), 2.39 (s, 3H), 2.15-2.07 (m, 2H).

To a solution of 3-((5-methyl-1-(2-methylpyridin-3-yl)-4-nitro-1H-pyrazol-3-yl)oxy)propan-1-ol (274 mg, 0.937 mmol) and 3,6-dichloro-1H-pyrazolo[3,4-d]pyrimidine (177 mg, 0.937 mmol) in THF (20 mL) was added PPh$_3$ (738 mg, 2.81 mmol) followed by DIAD (569 mg, 2.81 mmol) at 5° C. The resulting mixture was stirred at 20° C. for 16 h. The reaction mixture was filtered, and the filtrate was concentrated under reduced presure. The residue was purified by chromatography on silica gel (eluent: petroleum ether:EtOAc (10 v % MeOH) 100:0→35:65) to afford a residue that was washed with MeOH (5 mL) and filtered. The filter cake was isolated to afford 3,6-dichloro-1-(3-((5-methyl-1-(2-methylpyridin-3-yl)-4-nitro-1H-pyrazol-3-yl)oxy)propyl)-1H-pyrazolo[3,4-d]pyrimidine (188 mg) of sufficient purity for the subsequent step. $^1$H NMR (CDCl$_3$, 400 MHz) δ 8.97 (s, 1H), 8.69 (dd, J=1.2, 4.8 Hz, 1H), 7.57 (d, J=8.0 Hz, 1H), 7.35 (dd, J=4.8, 8.0 Hz, 1H), 4.70 (t, J=6.0 Hz, 2H), 4.36 (t, J=6.0 Hz, 2H), 2.51-2.46 (m, 2H), 2.45 (s, 3H), 2.35 (s, 3H).

Intermediate: 3,6-Dichloro-1-(3-((1-(2-ethylpyridin-3-yl)-5-methyl-4-nitro-1H-pyrazol-3-yl)oxy)propyl)-1H-pyrazolo[3,4-d]pyrimidine

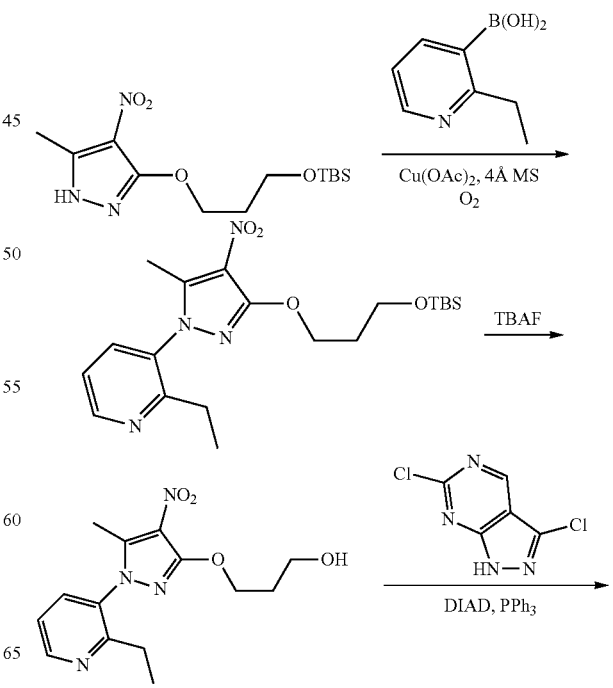

-continued

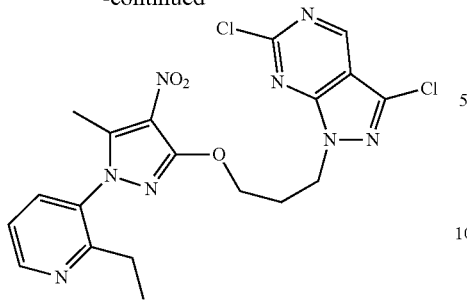

To a solution of 5-(3-((tert-butyldimethylsilyl)oxy) propoxy)-3-methyl-4-nitro-1H-pyrazole (400 mg, 1.27 mmol) and (2-ethyl-3-pyridyl)boronic acid (383 mg, 2.54 mmol) in DCE (16 mL) was added Cu(OAc)$_2$ (345 mg, 1.90 mmol), pyridine (401 mg, 5.07 mmol) and 4 Å MS (400 mg). The mixture was stirred under an O$_2$-atmosphere at 50° C. for 16 h. Additional (2-ethyl-3-pyridyl) boronic acid (190 mg, 1.23 mmol) was added. The reaction mixture was stirred for another 16 h at 50° C. The mixture was filtered, and the filtrate was concentrated under reduced pressure. The residue was purified by chromatography on silica gel (eluent: petroleum ether:EtOAc 100:0→35:65) to afford 3-(3-(3-((tert-butyldimethylsilyl)oxy)propoxy)-5-methyl-4-nitro-1H-pyrazol-1-yl)-2-ethylpyridine (300 mg) of sufficient purity for the subsequent step.

To a solution of 3-(3-(3-((tert-butyldimethylsilyl)oxy) propoxy)-5-methyl-4-nitro-1H-pyrazol-1-yl)-2-ethylpyridine (295 mg, 0.70 mmol) in THF (8 mL) was added TBAF (1 M in THF, 1.05 mL). The mixture was stirred at 20° C. for 1 h. The mixture was concentrated under reduced pressure. The residue was purified by chromatography on silica gel (eluent: petroleum ether:EtOAc (10 v % MeOH) 80:20→30:70) to afford 3-((1-(2-ethylpyridin-3-yl)-5-methyl-4-nitro-1H-pyrazol-3-yl)oxy)propan-1-ol (136 mg) of sufficient purity for the subsequent step. 1H NMR (CDCl$_3$ 400 MHz) δ 8.76 (dd, J=1.2, 4.8 Hz, 1H), 7.57 (dd, J=1.6, 8.0 Hz, 1H), 7.35 (dd, J=4.8, 7.6 Hz, 1H), 4.52 (t, J=5.6 Hz, 2H), 3.89 (t, J=5.6 Hz, 2H), 2.62 (q, J=7.2 Hz, 2H), 2.17-2.07 (m, 2H), 1.26 (t, J=7.2 Hz, 3H).

To a solution of 3-((1-(2-ethylpyridin-3-yl)-5-methyl-4-nitro-1H-pyrazol-3-yl)oxy)propan-1-ol (136 mg, 0.44 mmol) and 3,6-dichloro-1H-pyrazolo[3,4-d]pyrimidine (84 mg, 0.44 mmol) in THF (10 mL) was added PPh$_3$ (349 mg, 1.33 mmol) followed by DIAD (269 mg, 1.33 mmol) at 5° C. The resulting mixture was stirred at 20° C. for 16 h. The reaction mixture was concentrated under reduced pressure. The residue was purified by chromatography on silica gel (eluent: petroleum ether:EtOAc (10 v % MeOH) 100:0→30:70) and the residue was further purified by preparative HPLC (Instrument: Gilson GX-215 Liquid Handler, SHIMADZU LC-20AP, SHIMADZU SPD-20A, column: Welch Xtimate C18 150×30 mm×5 μm, mobile phase A: water (NH$_3$H$_2$O+NH$_4$HCO$_3$), mobile phase B: MeCN, gradient: B from 47% to 77% in 8 min then hold at 100% for 2 min, flow rate (mL/min): 30, column temperature: 30° C., wavelength: 220 nm 254 nm) give afford 3,6-dichloro-1-(3-((1-(2-ethylpyridin-3-yl)-5-methyl-4-nitro-1H-pyrazol-3-yl)oxy)propyl)-1H-pyrazolo[3,4-d]pyrimidine (40 mg) of sufficient purity for the subsequent step. $^1$H NMR (CDCl$_3$, 400 MHz) δ 8.97 (s, 1H), 8.74 (dd, J=1.6, 4.8 Hz, 1H), 7.55 (dd, J=1.6, 7.6 Hz, 1H), 7.34 (dd, J=4.8, 7.6 Hz, 1H), 4.70 (t, J=6.4 Hz, 2H), 4.36 (t, J=5.6 Hz, 2H), 2.61-2.47 (m, 4H), 2.44 (s, 3H), 1.23 (t, J=6.8 Hz, 3H).

Intermediate: 3,6-Dichloro-1-(3-((5-ethyl-1-(2-methoxypyridin-3-yl)-4-nitro-1H-pyrazol-3-yl)oxy) propyl)-1H-pyrazolo[3,4-d]pyrimidine

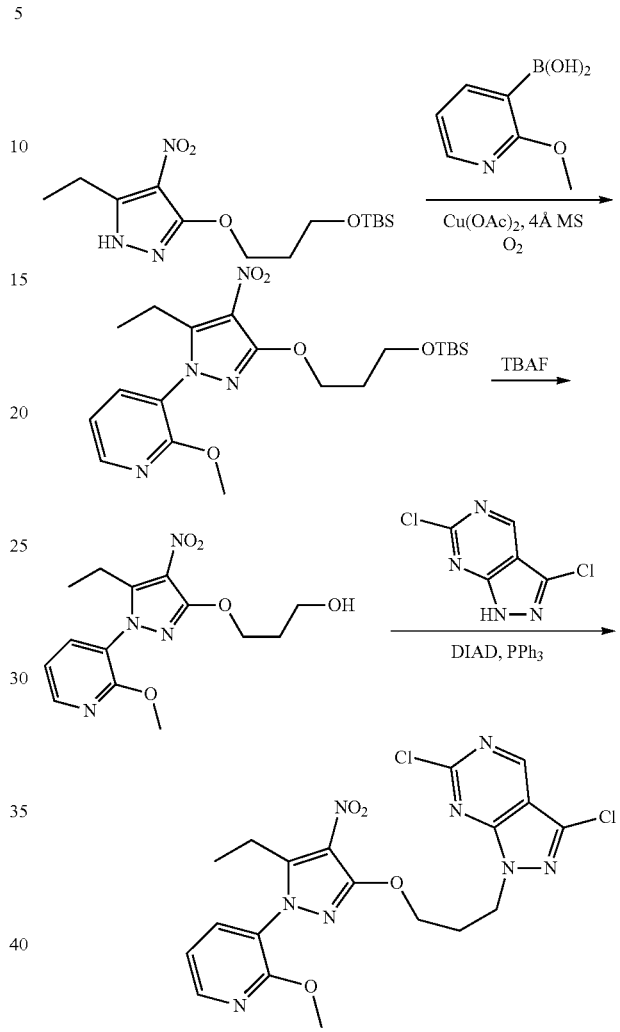

A mixture of 5-(3-((tert-butyldimethylsilyl)oxy) propoxy)-3-ethyl-4-nitro-1H-pyrazole (600 mg, 1.82 mmol), (2-methoxy-3-pyridyl)boronic acid (557 mg, 3.64 mmol), Cu(OAc)$_2$ (496 mg, 2.73 mmol), pyidine (576 mg, 7.28 mmol), and 4 Å MS (600 mg) in DCE (20 mL) was heated for 16 h at 50° C. under an O$_2$-atmosphere (15 psi). The mixture was concentrated under reduced pressure. The residue was purified by chromatography on silica gel (eluent: petroleum ether:EtOAc 100:0→50:50) to afford 3-(3-(3-((tert-butyldimethylsilyl)oxy)propoxy)-5-ethyl-4-nitro-1H-pyrazol-1-yl)-2-methoxypyridine (430 mg) of sufficient purity for the subsequent step. LC-MS (Method B) (m/z)= 437.2 (MH)$^+$ t$_R$=1.12 minutes.

To a solution of 3-(3-(3-((tert-butyldimethylsilyl)oxy) propoxy)-5-ethyl-4-nitro-1H-pyrazol-1-yl)-2-methoxypyridine (400 mg, 0.92 mmol) in THF (2 mL) was added TBAF (1 M in THF, 1.37 mL). The mixture was stirred at 25° C. for 1 h. The mixture was concentrated under reduced pressure. The residue was purified by chromatography on silica gel (eluent: petroleum ether:EtOAc 100:0→50:50) to afford 3-((5-ethyl-1-(2-methoxypyridin-3-yl)-4-nitro-1H-pyrazol-3-yl)oxy)propan-1-ol (220 mg) of sufficient purity for the subsequent step. $^1$H NMR (CDCl$_3$, 400 MHz) δ 8.34 (dd, J=1.6, 4.8 Hz, 1H), 7.65 (dd, J=1.6, 7.6 Hz, 1H), 7.08 (dd, J=4.8, 7.5 Hz, 1H), 4.52 (t, J=6.0 Hz, 2H), 3.98 (s, 3H), 3.86 (t, J=5.6 Hz, 2H), 2.91-2.61 (m, 2H), 2.14-2.07 (m, 2H), 1.15 (t, J=7.6 Hz, 3H).

To a solution of 3-((5-ethyl-1-(2-methoxypyridin-3-yl)-4-nitro-1H-pyrazol-3-yl)oxy)propan-1-ol (200 mg, 0.62 mmol) and 3,6-dichloro-1H-pyrazolo[3,4-d]pyrimidine (120 mg, 0.64 mmol) in THF (10 mL) was added PPh$_3$ (500 mg, 1.91 mmol) and DIAD (400 mg, 1.98 mmol). The mixture was stirred at 25° C. for 16 h. The mixture was concentrated under reduced pressure. The residue was purified by chromatography on silica gel (eluent: petroleum ether:EtOAc 100:0→30:70) to afford 3,6-dichloro-1-(3-((5-ethyl-1-(2-methoxypyridin-3-yl)-4-nitro-1H-pyrazol-3-yl)oxy)propyl)-1H-pyrazolo[3,4-d]pyrimidine (250 mg) of sufficient purity for the subsequent step.

Intermediate: 3,6-Dichloro-1-(3-((1-(5-fluoro-2-methoxypyridin-3-yl)-5-methyl-4-nitro-1H-pyrazol-3-yl)oxy)propyl)-1H-pyrazolo[3,4-d]pyrimidine

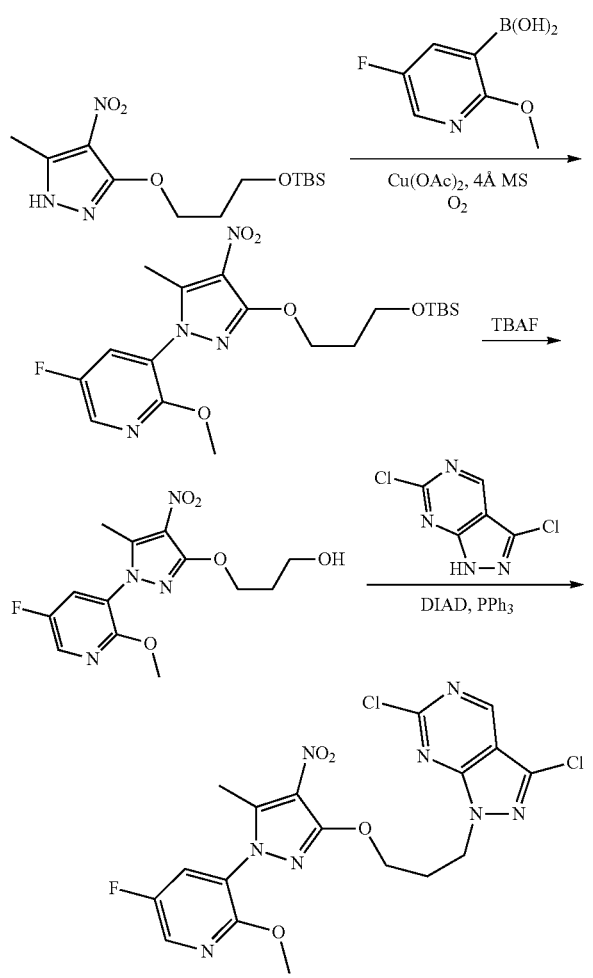

A mixture of 5-(3-((tert-butyldimethylsilyl)oxy)propoxy)-3-methyl-4-nitro-1H-pyrazole (800 mg, 2.54 mmol), (5-fluoro-2-methoxypyridin-3-yl)boronic acid (520 mg, 3.04 mmol), pyridine (802 mg, 10.1 mmol), Cu(OAc)$_2$ (691 mg, 3.80 mmol), and 4 Å MS (800 mg) in DCE (30 mL) was degassed and purged with O$_2$×3 and then the mixture was stirred at 50° C. for 15 h under an O$_2$-atmosphere. Additional (5-fluoro-2-methoxypyridin-3-yl)boronic acid (450 mg, 2.63 mmol) was added to the mixture and the reaction was stirred at 50° C. for another 15 h under an O$_2$-atmosphere. The reaction mixture was concentrated under reduced pressure. The residue was purified by chromatography on silica gel (eluent: petroleum ether:EtOAc 100:0→90:10) to afford 3-(3-(3-((tert-butyldimethylsilyl)oxy)propoxy)-5-methyl-4-nitro-1H-pyrazol-1-yl)-5-fluoro-2-methoxypyridine (420 mg) of sufficient purity for the subsequent step. $^1$H NMR (CDCl$_3$, 400 MHz) δ8.20 (d, J=2.8 Hz, 1H), 7.54 (dd, J=2.8, 7.2 Hz, 1H), 4.42 (t, J=6.4 Hz, 2H), 3.98 (s, 3H), 3.83 (t, J=6.0 Hz, 2H), 2.48 (s, 3H), 2.08-2.03 (m, 2H), 0.88 (s, 9H), 0.05 (s, 6H).

To a solution of 3-(3-(3-((tert-butyldimethylsilyl)oxy)propoxy)-5-methyl-4-nitro-1H-pyrazol-1-yl)-5-fluoro-2-methoxypyridine (410 mg, 0.93 mmol) in THF (10 mL) was added TBAF (1 M in THF, 1.40 mL). The mixture was stirred at 20° C. for 1 h. The reaction mixture was concentrated under reduced pressure. The residue was purified by chromatography on silica gel (eluent: petroleum ether:EtOAc 100:0→50:50) to afford 3-((1-(5-fluoro-2-methoxypyridin-3-yl)-5-methyl-4-nitro-1H-pyrazol-3-yl)oxy)propan-1-ol(270 mg). LC-MS (Method B) (m/z)=327.1 (MH)$^+$ t$_R$=0.78 minutes.

DIAD (483 mg, 2.39 mmol) was added to a solution of 3-((1-(5-fluoro-2-methoxypyridin-3-yl)-5-methyl-4-nitro-1H-pyrazol-3-yl)oxy)propan-1-ol (260 mg, 0.80 mmol), 3,6-dichloro-1H-pyrazolo[3,4-d]pyrimidine (151 mg, 0.80 mmol), and PPh$_3$ (627 mg, 2.39 mmol) in THF (20 mL) at 0° C. The mixture was stirred at 20° C. for 15 h. The reaction mixture was concentrated under reduced pressure. The residue was purified by chromatography on silica gel (eluent: petroleum ether:EtOAc 100:0→80:20) to afford 3,6-dichloro-1-(3-((1-(5-fluoro-2-methoxypyridin-3-yl)-5-methyl-4-nitro-1H-pyrazol-3-yl)oxy)propyl)-1H-pyrazolo[3,4-d]pyrimidine (600 mg) of sufficient purity for the subsequent step. LC-MS (Method B) (m/z)=497.0 (MH)$^+$ t$_R$=0.96 minutes.

Intermediate: 3,6-Dichloro-1-(3-((1-(2-methoxy-4-methylpyridin-3-yl)-5-methyl-4-nitro-1H-pyrazol-3-yl)oxy)propyl)-1H-pyrazolo[3,4-d]pyrimidine

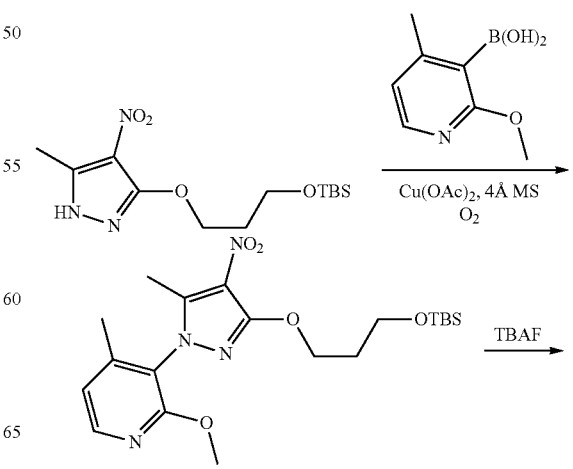

93

-continued

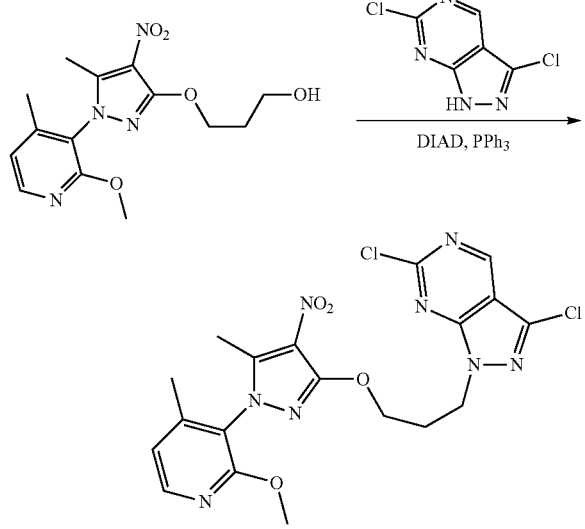

A mixture of 5-(3-((tert-butyldimethylsilyl)oxy) propoxy)-3-methyl-4-nitro-1H-pyrazole (800 mg, 2.54 mmol), (2-methoxy-4-methylpyridin-3-yl)boronic acid (508 mg, 3.04 mmol), Cu(OAc)$_2$ (691 mg, 3.80 mmol), pyridine (802 mg, 10.1 mmol), and 4 Å MS (800 mg) in DCE (40 mL) was degassed and purged with O$_2$×3, and then the mixture was stirred at 50° C. for 32 h under an O$_2$-atmosphere. The mixture was concentrated under reduced pressure. The residue was purified by chromatography on silica gel (eluent: petroleum ether:EtOAc 95:5→70:30) to afford 3-(3-(3-((tert-butyldimethylsilyl)oxy)propoxy)-5-methyl-4-nitro-1H-pyrazol-1-yl)-2-methoxy-4-methylpyridine (340 mg) of sufficient purity for the subsequent step. LC-MS (Method B) (m/z)=437.2 (MH)$^+$ $t_R$=1.11 minutes.

To a solution of 3-(3-(3-((tert-butyldimethylsilyl)oxy) propoxy)-5-methyl-4-nitro-1H-pyrazol-1-yl)-2-methoxy-4-methylpyridine (340 mg, 0.78 mmol) in THF (6 mL) was added TBAF (1.17 mL, 1M in THF) at 0° C. and the reaction was stirred at 30° C. for 2 h. The mixture was concentrated under reduced presure. The residue was purified by chromatography on silica gel (eluent: petroleum ether:EtOAc 95:5→50:50) to afford 3-((1-(2-methoxy-4-methylpyridin-3-yl)-5-methyl-4-nitro-1H-pyrazol-3-yl)oxy)propan-1-ol (200 mg) of sufficient purity for the subsequent step. $^1$H NMR (CDCl$_3$, 400 MHz) δ 8.17 (d, J=5.2 Hz, 1H), 6.92 (d, J=5.2 Hz, 1H), 4.51 (t, J=5.6 Hz, 2H), 3.95 (s, 3H), 3.86 (t, J=5.6 Hz, 2H), 2.39 (s, 3H), 2.14 (s, 3H), 2.13-2.06 (m, 2H).

To a solution of 3-((1-(2-methoxy-4-methylpyridin-3-yl)-5-methyl-4-nitro-1H-pyrazol-3-yl)oxy)propan-1-ol (200 mg, 0.62 mmol), 3,6-dichloro-1H-pyrazolo[3,4-d]pyrimidine (117 mg, 0.62 mmol), and PPh$_3$ (326 mg, 1.24 mmol) in THF (20 mL) was added dropwise DIAD (251 mg, 1.24 mmol) at 0° C. The mixture was stirred at 30° C. for 16 h. The mixture was concentrated under reduced pressure. The residue was purified by chromatography on silica gel (eluent: petroleum ether:EtOAc 20:80→50:50) to afford 3,6-dichloro-1-(3-((1-(2-methoxy-4-methylpyridin-3-yl)-5-methyl-4-nitro-1H-pyrazol-3-yl)oxy)propyl)-1H-pyrazolo [3,4-d]pyrimidine (240 mg) of sufficient purity for the subsequent step. LC-MS (Method B) (m/z)=493.0 (MH)$^+$ $t_R$=0.94 minutes.

94

Intermediate: 3,6-Dichloro-1-(3-((5-ethyl-1-(2-methylpyridin-3-yl)-4-nitro-1H-pyrazol-3-yl)oxy)propyl)-1H-pyrazolo[3,4-d]pyrimidine

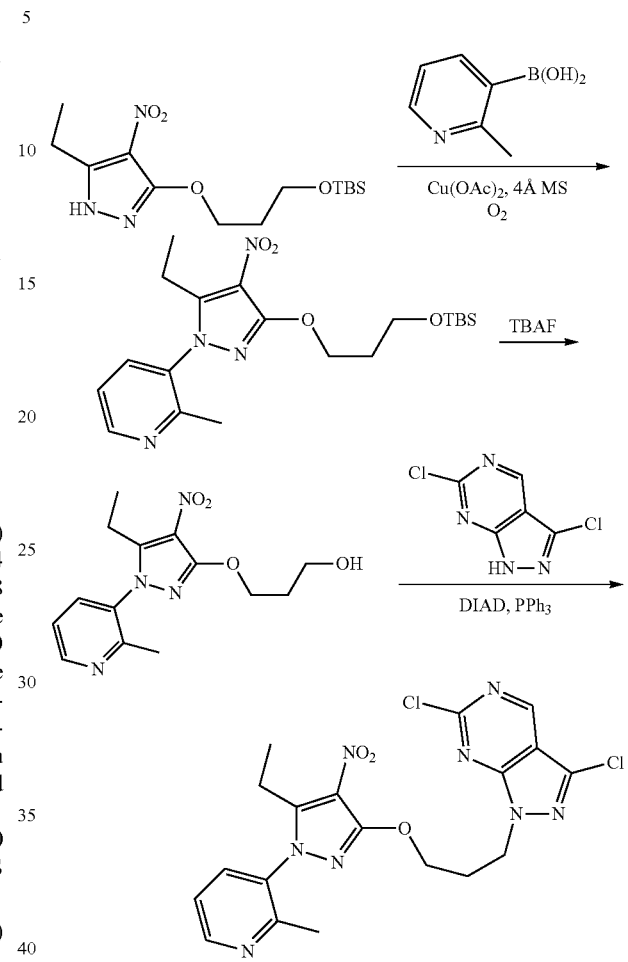

A mixture of 5-(3-((tert-butyldimethylsilyl)oxy) propoxy)-3-ethyl-4-nitro-1H-pyrazole (750 mg, 2.28 mmol), (2-methylpyridin-3-yl)boronic acid (468 mg, 3.41 mmol), Cu(OAc)$_2$ (620 mg, 3.41 mmol), pyridine (720 mg, 9.11 mmol), and 4 Å MS (750 mg) in DCE (20 mL) was degassed and purged with O$_2$×3 and then the mixture was stirred at 50° C. for 15 h under an O$_2$-atmospher. Additional (2-methylpyridin-3-yl)boronic acid (470 mg, 3.41 mmol) was added to the mixture and the reaction was stirred at 50° C. for another 15 h. The mixture was concentrated under reduced pressure. The residue was purified by chromatography on silica gel (eluent: petroleum ether:EtOAc 100: 0→70:30) to afford 3-(3-(3-((tert-butyldimethylsilyl)oxy) propoxy)-5-ethyl-4-nitro-1H-pyrazol-1-yl)-2-methylpyridine (1 g) of sufficient purity for the subsequent step.

To a solution of 3-(3-(3-((tert-butyldimethylsilyl)oxy) propoxy)-5-ethyl-4-nitro-1H-pyrazol-1-yl)-2-methylpyridine (1 g, 2.38 mmol) in THF (10 mL) was added TBAF (1 M in THF, 3.6 mL). The mixture was stirred at 20° C. for 1 h. The reaction mixture was concentrated under reduced pressure. The residue was purified by chromatography on silica gel (eluent: petroleum ether:EtOAc 100:0→70:30) to afford 3-((5-ethyl-1-(2-methylpyridin-3-yl)-4-nitro-1H-pyrazol-3-yl)oxy)propan-1-ol (330 mg) of sufficient purity for the subsequent step.

A solution of DIAD (634 mg, 3.13 mmol) was added to a solution of 3-((5-ethyl-1-(2-methylpyridin-3-yl)-4-nitro-1H-pyrazol-3-yl)oxy)propan-1-ol (320 mg, 1.04 mmol), 3,6-dichloro-1H-pyrazolo[3,4-d]pyrimidine (197 mg, 1.04 mmol), and PPh₃ (822 mg, 3.13 mmol) in THF (15 mL) at 0° C. The mixture was stirred at 20° C. for 15 h. The reaction mixture was concentrated under reduced pressure. The residue was purified by chromatography on silica gel (eluent: petroleum ether:EtOAc 100:0→60:40) to afford 3,6-dichloro-1-(3-((5-ethyl-1-(2-methylpyridin-3-yl)-4-nitro-1H-pyrazol-3-yl)oxy)propyl)-1H-pyrazolo[3,4-d]pyrimidine (700 mg) of sufficient purity for the subsequent step.

Intermediate: 3,6-Dichloro-1-(3-((1-(2,6-dimethylpyridin-3-yl)-5-methyl-4-nitro-1H-pyrazol-3-yl)oxy)propyl)-1H-pyrazolo[3,4-d]pyrimidine

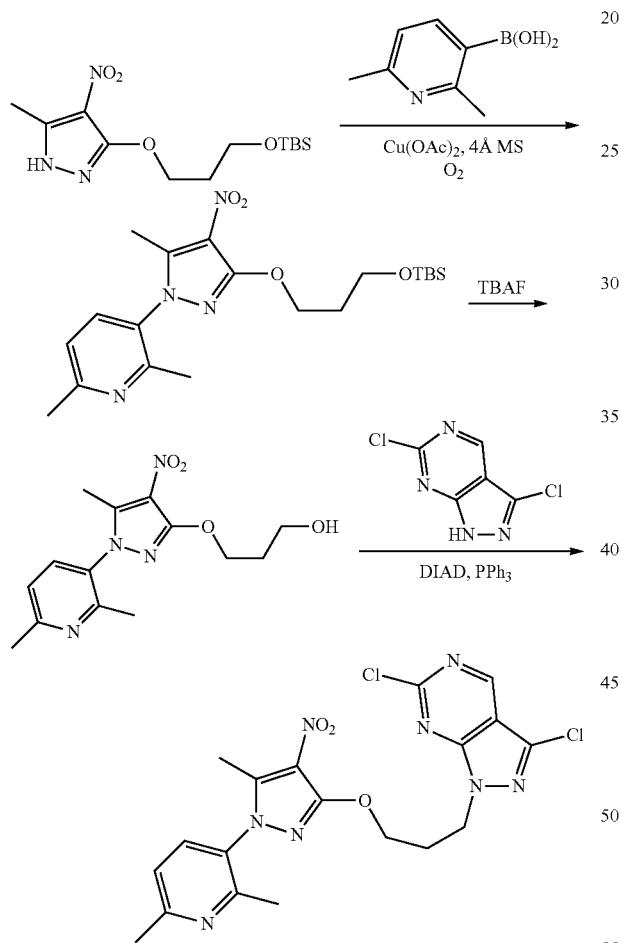

A mixture of 5-(3-((tert-butyldimethylsilyl)oxy)propoxy)-3-methyl-4-nitro-1H-pyrazole (800 mg, 2.54 mmol), (2,6-dimethylpyridin-3-yl)boronic acid (459 mg, 3.04 mmol), Cu(OAc)₂ (691 mg, 3.80 mmol), pyridine (802 mg, 10.14 mmol), and 4 Å MS (800 mg) in DCE (40 mL) was degassed and purged with O₂×3, and then the mixture was stirred at 50° C. for 32 h under an O₂-atmosphere. The mixture was concentrated under reduced pressure. The residue was purified by chromatography on silica gel (eluent: petroleum ether:EtOAc 95:5→20:80) followed by preparative HPLC ((Instrument: Gilson GX-281 Liquid Handler, Gilson 322 Pump, Gilson 156 UV Detector column: Xtimate C18 150×40 mm×10 μm, mobile mhase A: water (NH₃H₂O+ NH₄HCO₃), mobile phase B: MeCN, gradient: B from 60% to 90% in 8 minutes then hold at 100% for 3 minutes, flow rate (mL/min): 55, column temperature: 30° C., wavelength: 220 nm & 254 nm) to afford 3-(3-(3-((tert-butyldimethylsilyl)oxy)propoxy)-5-methyl-4-nitro-1H-pyrazol-1-yl)-2,6-dimethylpyridine (180 mg) of sufficient purity for the subsequent step. LC-MS (Method C) (m/z)=421.2 (MH)⁺ $t_R$=2.41 minutes.

To a solution of 3-(3-(3-((tert-butyldimethylsilyl)oxy)propoxy)-5-methyl-4-nitro-1H-pyrazol-1-yl)-2,6-dimethylpyridine (170 mg, 0.40 mmol) in THF (6 mL) was added TBAF (606 μL, 1M in THF) at 0° C. and the reaction was stirred at 30° C. for 2 h. The mixture was concentrated under reduced pressure. The residue was purified by chromatography on silica gel (eluent: petroleum ether:EtOAc 95:5→30:70) to afford 3-((1-(2,6-dimethylpyridin-3-yl)-5-methyl-4-nitro-1H-pyrazol-3-yl)oxy)propan-1-ol (120 mg) of sufficient purity for the subsequent step.

To a solution of 3-((1-(2,6-dimethylpyridin-3-yl)-5-methyl-4-nitro-1H-pyrazol-3-yl)oxy)propan-1-ol (120 mg, 0.39 mmol), 3,6-dichloro-1H-pyrazolo[3,4-d]pyrimidine (74 mg, 0.39 mmol), and PPh₃ (206 mg, 0.78 mmol) in THF (8 mL) was added dropwise DIAD (158 mg, 0.78 mmol) at 0° C. The mixture was stirred at 30° C. for 16 h. The mixture was concentrated under reduced pressure. The residue was purified by chromatography on silica gel (eluent: petroleum ether:EtOAc 80:20→30:70) to afford 3,6-dichloro-1-(3-((1-(2,6-dimethylpyridin-3-yl)-5-methyl-4-nitro-1H-pyrazol-3-yl)oxy)propyl)-1H-pyrazolo[3,4-d]pyrimidine (220 mg) of sufficient purity for the subsequent step. LC-MS (Method C) (m/z)=477.1 (MH)⁺ $t_R$=1.91 minutes.

Intermediate: 3,6-Dichloro-1-(3-((1-(5-fluoro-2-methylpyridin-3-yl)-5-methyl-4-nitro-1H-pyrazol-3-yl)oxy)propyl)-1H-pyrazolo[3,4-d]pyrimidine

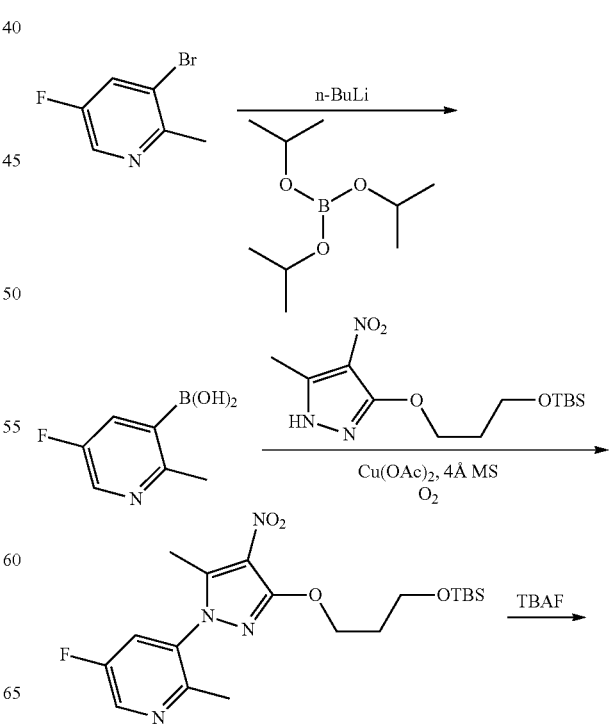

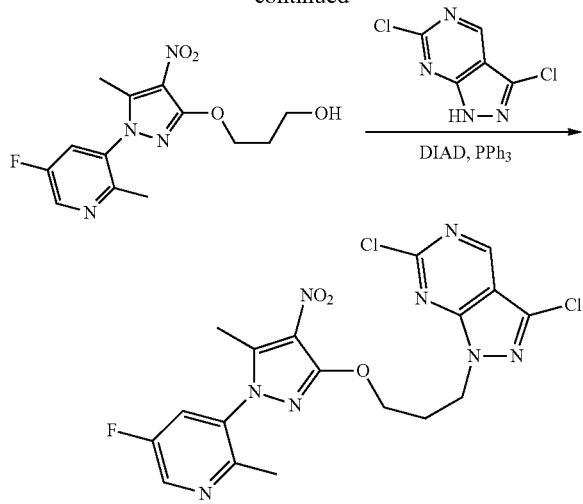

To a solution of 3-bromo-5-fluoro-2-methylpyridine (1.5 g, 7.9 mmol) and triisopropyl borate (2.38 g, 12.6 mmol) in THF (23 mL) was added n-BuLi (4.7 mL, 12 mmol, 2.5 M in hexane) at −65° C. After stirring at −65° C. for 1 h, the mixture was stirred at 0° C. for an additional 1 h. H$_2$O (30 mL) and EtOAc (30 mL) were added to the reaction and the mixture was stirred at 25° C. for 30 minutes. The mixture was neutralized with 1.0 M aqueous HCl and extracted with EtOAc (4×30 mL). The organic layer was dried over Na$_2$SO$_4$, filtered, and concentrated under reduced pressure to afford (5-fluoro-2-methylpyridin-3-yl)boronic acid (1.14 g) of sufficient purity for the subsequent step.

A mixture of 5-(3-((tert-butyldimethylsilyl)oxy) propoxy)-3-methyl-4-nitro-1H-pyrazole (900 mg, 2.40 mmol), (5-fluoro-2-methylpyridin-3-yl)boronic acid (1.11 g, 7.19 mmol), pyridine (758 mg, 9.59 mmol), Cu(OAc)$_2$ (653 mg, 3.59 mmol) and 4 Å MS (900 mg) in DCE (30 mL) was degassed and purged with N$_2$×3, and then the mixture was stirred at 50° C. for 36 h under an O$_2$-atmosphere. The reaction mixture was concentrated under reduced pressure. The residue was purified by chromatography on silica gel (eluent: petroleum ether:EtOAc 100:0→85:15) to afford 3-(3-(3-((tert-butyldimethylsilyl)oxy)propoxy)-5-methyl-4-nitro-1H-pyrazol-1-yl)-5-fluoro-2-methylpyridine (225 mg) of sufficient purity for the subsequent step. $^1$H NMR (CDCl$_3$, 400 MHz) δ 8.59 (d, J=2.8 Hz, 1H), 7.38 (dd, J=2.4, 7.2 Hz, 1H), 4.42 (t, J=6.4 Hz, 2H), 3.83 (t, J=6.0 Hz, 2H), 2.47 (s, 3H), 2.35 (s, 3H), 2.15-2.03 (m, 2H), 0.88 (s, 9H), 0.05 (s, 6H).

To a solution of 3-(3-(3-((tert-butyldimethylsilyl)oxy) propoxy)-5-methyl-4-nitro-1H-pyrazol-1-yl)-5-fluoro-2-methylpyridine (290 mg, 0.68 mmol) in THF (6 mL) was added TBAF (1 M in THF, 1.02 mL) at 0° C. and the reaction mixture was stirred at 25° C. for 1 h. The reaction mixture was concentrated under reduced pressure. The residue was purified by chromatography on silica gel (eluent: petroleum ether:EtOAc 100:0→40:60) to afford 3-((1-(5-fluoro-2-methylpyridin-3-yl)-5-methyl-4-nitro-1H-pyrazol-3-yl)oxy) propan-1-ol (187 mg) of sufficient purity for the subsequent step. LC-MS (Method B) (m/z)=311.1 (MH)$^+$t$_R$=0.72 minutes.

To a solution of 3-((1-(5-fluoro-2-methylpyridin-3-yl)-5-methyl-4-nitro-1H-pyrazol-3-yl)oxy)propan-1-ol (160 mg, 0.51 mmol) in THF (16 mL) was added 3,6-dichloro-1H-pyrazolo[3,4-d]pyrimidine (117 mg, 0.619 mmol), PPh$_3$ (406 mg, 1.55 mmol), and DIAD (313 mg, 1.55 mmol) at 0° C. The mixture was stirred at 25° C. for 12 h. The reaction mixture was concentrated under reduced pressure. The residue was purified by chromatography on silica gel (eluent: petroleum ether:EtOAc 100:0→45:55) to afford 3,6-dichloro-1-(3-((1-(5-fluoro-2-methylpyridin-3-yl)-5-methyl-4-nitro-1H-pyrazol-3-yl)oxy)propyl)-1H-pyrazolo[3,4-d] pyrimidine (200 mg) of sufficient purity for the subsequent step. LC-MS (Method B) (m/z)=481.0 (MH)$^+$t$_R$=0.92 minutes.

Intermediate: 3,6-Dichloro-1-(3-((1-(2,5-dimethylpyridin-3-yl)-5-methyl-4-nitro-1H-pyrazol-3-yl) oxy)propyl)-1H-pyrazolo[3,4-d]pyrimidine

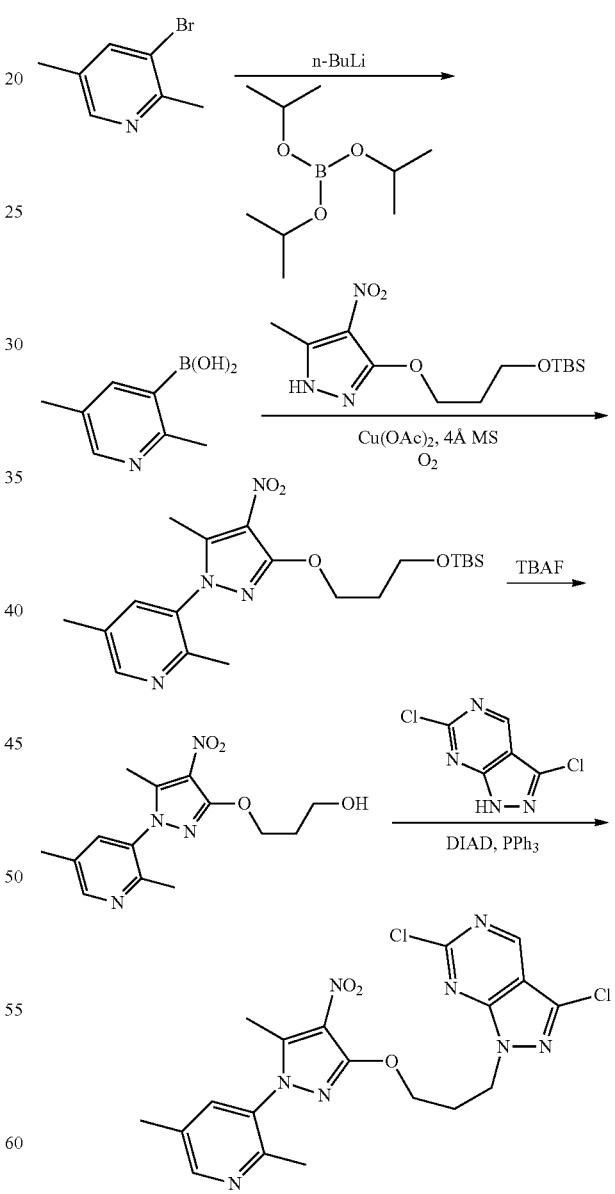

n-BuLi (13 mL, 33 mmol, 2.5 M in hexane) was added in a dropwise manner to 3-bromo-2,5-dimethyl-pyridine (3 g, 16 mmol) and triisopropyl borate (6.07 g, 32.3 mmol) in THF (50 mL) at −78° C. The mixture was stirred at −78° C. for 3 h. The mixture was quenched with aqueous NH₄Cl (20 mL) and then extracted with EtOAc (20 mL×4). The combined organic layers were concentrated under reduced pressure to afford (2,5-dimethyl-3-pyridyl)boronic acid (2 g) of sufficient purity for the subsequent step.

A mixture of 5-(3-((tert-butyldimethylsilyl)oxy)propoxy)-3-methyl-4-nitro-1H-pyrazole (800 mg, 2.54 mmol), (2,5-dimethyl-3-pyridyl)boronic acid (500 mg, 3.31 mmol), Cu(OAc)₂ (691 mg, 3.80 mmol), pyridine (803 mg, 10.1 mmol) and 4 Å MS (800 mg) in DCE (20 mL) was degassed and purged with O₂×3, and then stirred at 50° C. for 16 h under an O₂-atmosphere. Additional (2,5-dimethyl-3-pyridyl)boronic acid (300 mg, 1.99 mmol) was added and the reaction was stirred at 50° C. for another 6 h. The mixture was concentrated under reduced pressure. The residue was purified by chromatography on silica gel (eluent: petroleum ether:EtOAc 100:0→75:25) to afford 3-(3-(3-((tert-butyldimethylsilyl)oxy)propoxy)-5-methyl-4-nitro-1H-pyrazol-1-yl)-2,5-dimethylpyridine (900 mg) of sufficient purity for the subsequent step.

To a solution of 3-(3-(3-((tert-butyldimethylsilyl)oxy)propoxy)-5-methyl-4-nitro-1H-pyrazol-1-yl)-2,5-dimethylpyridine (900 mg, 2.14 mmol) in THF (20 mL) was added TBAF (3.2 mL, 3.2 mmol, 1 M in THF). The mixture was stirred at 25° C. for 2 h. The mixture was concentrated under reduced pressure. The residue was purified by chromatography on silica gel (eluent: petroleum ether:EtOAc 100:0→10:90) to afford 3-((1-(2,5-dimethylpyridin-3-yl)-5-methyl-4-nitro-1H-pyrazol-3-yl)oxy)propan-1-ol (550 mg) of sufficient purity for the subsequent step.

A mixture of 3-((1-(2,5-dimethylpyridin-3-yl)-5-methyl-4-nitro-1H-pyrazol-3-yl)oxy)propan-1-ol (300 mg, 0.98 mmol), 3,6-dichloro-1H-pyrazolo[3,4-d]pyrimidine (185 mg, 0.98 mmol), PPh₃ (780 mg, 2.97 mmol), and DIAD (600 mg, 2.97 mmol) in THF (25 mL) was stirred at 25° C. for 16 h. The mixture was concentrated under reduced pressure. The residue was purified by chromatography on silica gel (eluent: petroleum ether:EtOAc 100:0→30:70) to afford 3,6-dichloro-1-(3-((1-(2,5-dimethylpyridin-3-yl)-5-methyl-4-nitro-1H-pyrazol-3-yl)oxy)propyl)-1H-pyrazolo[3,4-d]pyrimidine (570 mg) of sufficient purity for the subsequent step.

Intermediate: 3,6-Dichloro-1-(3-((1-(2-methoxy-5-methylpyridin-3-yl)-5-methyl-4-nitro-1H-pyrazol-3-yl)oxy)propyl)-1H-pyrazolo[3,4-d]pyrimidine

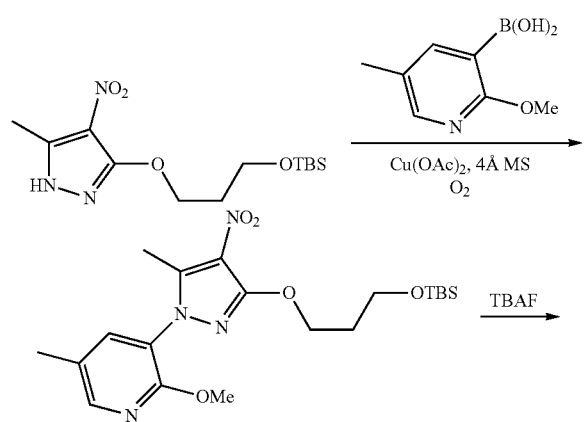

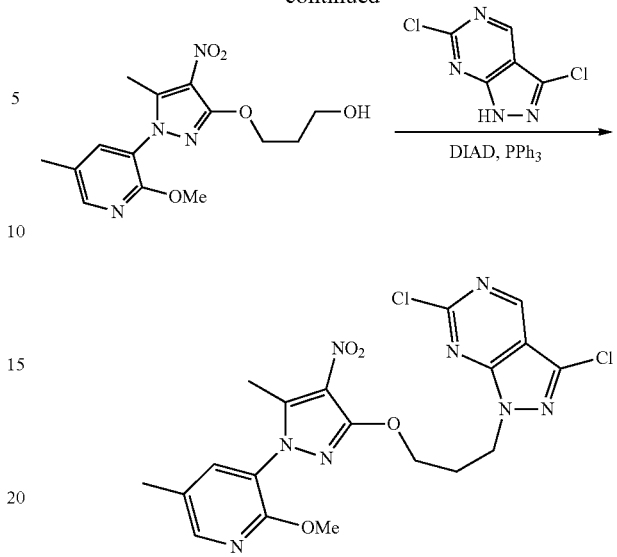

A mixture of 3-(3-((tert-butyldimethylsilyl)oxy)propoxy)-5-methyl-4-nitro-1H-pyrazole (500 mg, 1.59 mmol), (2-methoxy-5-methylpyridin-3-yl)boronic acid (318 mg, 1.90 mmol), pyridine (502 mg, 6.35 mmol), 4 Å MS (500 mg), and Cu(OAc)₂ (432 mg, 2.38 mmol) in DCE (20 mL) was degassed and purged with O₂×3 and then stirred at 50° C. for 15 h under an O₂-atmosphere. Additional (2-methoxy-5-methylpyridin-3-yl)boronic acid (318 mg, 1.90 mmol) was added to the mixture and reaction was stirred at 50° C. for another 15 h. The reaction mixture was concentrated under reduced pressure. The residue was purified by chromatography on silica gel (eluent: petroleum ether:EtOAc 100:0→10:90) to afford 3-(3-(3-((tert-butyldimethylsilyl)oxy)propoxy)-5-methyl-4-nitro-1H-pyrazol-1-yl)-2-methoxy-5-methylpyridine (410 mg) of sufficient purity for the subsequent step.

To a solution of 3-(3-(3-((tert-butyldimethylsilyl)oxy)propoxy)-5-methyl-4-nitro-1H-pyrazol-1-yl)-2-methoxy-5-methylpyridine (410 mg, 0.939 mmol) in THF (10 mL) was added TBAF (1.41 mL, 1.41 mmol, 1 M in THF). The mixture was stirred at 20° C. for 1 h. The reaction mixture was concentrated under reduced pressure. The residue was purified by chromatography on silica gel (eluent: petroleum ether:EtOAc 100:0→50:50) to afford 3-((1-(2-methoxy-5-methylpyridin-3-yl)-5-methyl-4-nitro-1H-pyrazol-3-yl)oxy)propan-1-ol (220 mg) of sufficient purity for the subsequent step.

A solution of DIAD (396 mg, 1.96 mmol) was added to a solution of 3-((1-(2-methoxy-5-methylpyridin-3-yl)-5-methyl-4-nitro-1H-pyrazol-3-yl)oxy)propan-1-ol (210 mg, 0.612 mmol), 3,6-dichloro-1H-pyrazolo[3,4-d]pyrimidine (124 mg, 0.656 mmol), and PPh₃ (513 mg, 1.96 mmol) in THF (10 mL) at 0° C. The mixture was stirred at 20° C. for 15 h. The reaction mixture was concentrated under reduced pressure. The residue was purified by chromatography on silica gel (eluent: petroleum ether:EtOAc 100:0→80:20) to afford 3,6-dichloro-1-(3-((1-(2-methoxy-5-methylpyridin-3-yl)-5-methyl-4-nitro-1H-pyrazol-3-yl)oxy)propyl)-1H-pyrazolo[3,4-d]pyrimidine (500 mg) of sufficient purity for the subsequent step.

Intermediate: 3,6-Dichloro-1-(3-((1-(2-methoxy-6-methylpyridin-3-yl)-5-methyl-4-nitro-1H-pyrazol-3-yl)oxy)propyl)-1H-pyrazolo[3,4-d]pyrimidine

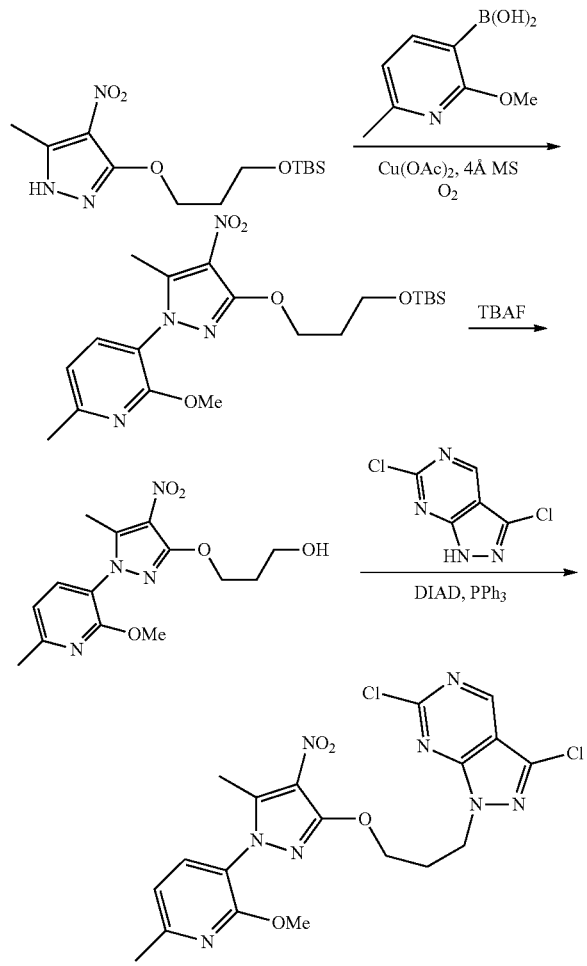

A mixture of 5-(3-((tert-butyldimethylsilyl)oxy)propoxy)-3-methyl-4-nitro-1H-pyrazole (800 mg, 2.54 mmol), (2-methoxy-6-methylpyridin-3-yl)boronic acid (847 mg, 5.07 mmol), 4 Å MS (800 mg), pyridine (802 mg, 10.1 mmol), and Cu(OAc)$_2$ (691 mg, 3.80 mmol) in DCE (25 mL) was heated for 16 h at 50° C. under an O$_2$-atmosphere. The reaction mixture was concentrated under reduced pressure. The residue was purified by chromatography on silica gel (eluent: petroleum ether:EtOAc 100:0→85:15) to afford 3-(3-(3-((tert-butyldimethylsilyl)oxy)propoxy)-5-methyl-4-nitro-1H-pyrazol-1-yl)-2-methoxy-6-methylpyridine (860 mg) of sufficient purity for the subsequent step.

To a solution of 3-(3-(3-((tert-butyldimethylsilyl)oxy)propoxy)-5-methyl-4-nitro-1H-pyrazol-1-yl)-2-methoxy-6-methylpyridine (850 mg, 1.95 mmol) in THF (9 mL) was added TBAF (2.92 mL, 2.92 mmol, 1 M in THF) and stirred at 25° C. for 1.5 h. The reaction mixture was concentrated under reduced pressure. The residue was purified by chromatography on silica gel (eluent: petroleum ether:EtOAc 100:0→40:60) to afford 3-((1-(2-methoxy-6-methylpyridin-3-yl)-5-methyl-4-nitro-1H-pyrazol-3-yl)oxy)propan-1-ol (620 mg) of sufficient purity for the subsequent step.

To a solution of 3-((1-(2-methoxy-6-methylpyridin-3-yl)-5-methyl-4-nitro-1H-pyrazol-3-yl)oxy)propan-1-ol (600 mg, 1.86 mmol) in THF (50 mL) was added 3,6-dichloro-1H-pyrazolo[3,4-d]pyrimidine (422 mg, 2.23 mmol), PPh$_3$ (1.46 g, 5.58 mmol), and DIAD (1.13 g, 5.58 mmol) at 0° C. The mixture was stirred at 25° C. for 16 h. The reaction mixture was concentrated under reduced pressure. The residue was purified by chromatography on silica gel (eluent: petroleum ether:EtOAc 100:0→85:15) to afford 3,6-dichloro-1-(3-((1-(2-methoxy-6-methylpyridin-3-yl)-5-methyl-4-nitro-1H-pyrazol-3-yl)oxy)propyl)-1H-pyrazolo[3,4-d]pyrimidine (1.3 g) of sufficient purity for the subsequent step.

Intermediate: 3,6-Dichloro-1-(3-((1-(2-(1,1-difluoroethyl)pyridin-3-yl)-5-methyl-4-nitro-1H-pyrazol-3-yl)oxy)propyl)-1H-pyrazolo[3,4-d]pyrimidine

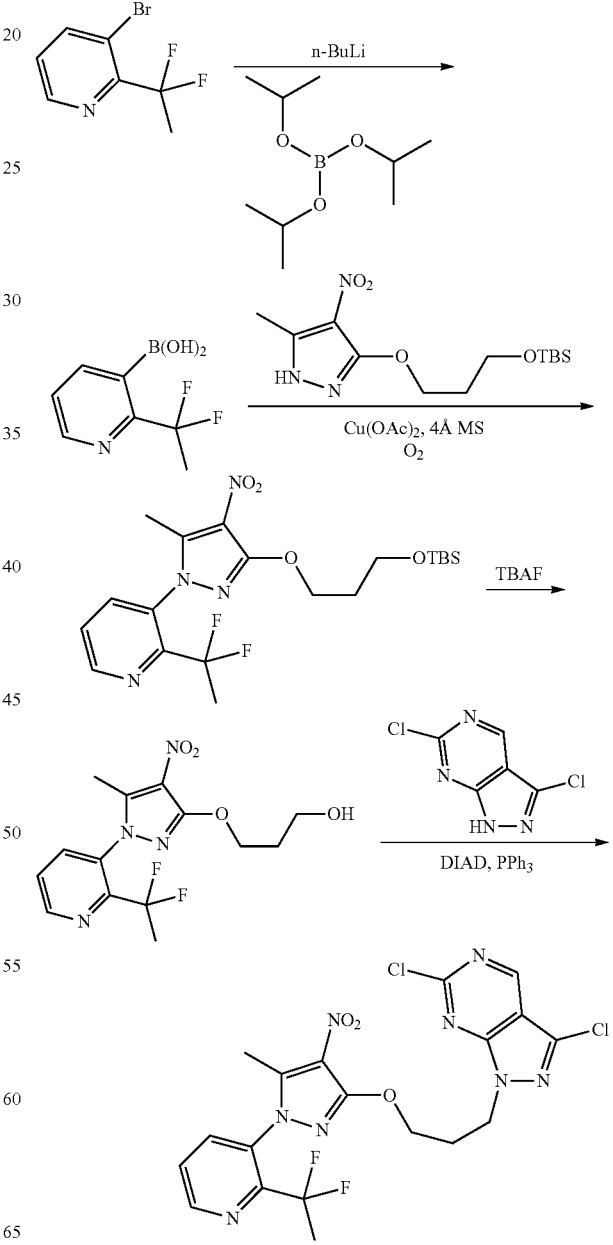

To a solution of 3-bromo-2-(1,1-difluoroethyl)pyridine (3.3 g, 15 mmol) and triisopropyl borate (8.39 g, 44.6 mmol) in THF (50 mL) was added dropwise n-BuLi (8.3 mL, 21 mmol, 2.5 M in hexane) at −78° C. The reaction mixture was stirred at −78° C. for 2 h. The reaction mixture was quenched with saturated aqueous NH$_4$Cl (50 mL) and extracted with EtOAc (100 mL×3). The combined organic layers were dried over Na$_2$SO$_4$ and concentrated under reduced pressure to afford (2-(1,1-difluoroethyl)pyridin-3-yl)boronic acid (2.5 g) of sufficient purity for the subsequent step.

A mixture of 5-(3-((tert-butyldimethylsilyl)oxy) propoxy)-3-methyl-4-nitro-1H-pyrazole (1.0 g, 3.2 mmol), (2-(1,1-difluoroethyl)pyridin-3-yl)boronic acid (900 mg, 4.81 mmol), Cu(OAc)$_2$ (864 mg, 4.76 mmol), pyridine (1.00 g, 12.7 mmol) and 4 Å MS (1 g) in DCE (20 mL) was degassed and purged with O$_2$×3 and then stirred at 60° C. for 15 h under an O$_2$-atmosphere. Additional [2-(1,1-difluoroethyl)-3-pyridyl]boronic acid (900 mg, 4.81 mmol) was added to the mixture and the reaction was stirred at 60° C. for another 15 h. The reaction mixture was concentrated under reduced pressure. The residue was purified by chromatography on silica gel (eluent: petroleum ether:EtOAc 100:0→60:40) to afford 3-(3-(3-((tert-butyldimethylsilyl)oxy)propoxy)-5-methyl-4-nitro-1H-pyrazol-1-yl)-2-(1,1-difluoroethyl)pyridine (1.2 g) of sufficient purity for the subsequent step.

To a solution of 3-(3-(3-((tert-butyldimethylsilyl)oxy) propoxy)-5-methyl-4-nitro-1H-pyrazol-1-yl)-2-(1,1-difluoroethyl)pyridine (1.2 g, 2.63 mmol) in THF (20 mL) was added TBAF (1 M in THF, 3.9 mL). The mixture was stirred at 20° C. for 17 hours. The reaction mixture was concentrated. The residue was purified by chromatography on silica gel (eluent: petroleum ether:EtOAc 100:0→0:100) to afford 3-((1-(2-(1,1-difluoroethyl)pyridin-3-yl)-5-methyl-4-nitro-1H-pyrazol-3-yl)oxy)propan-1-ol (260 mg) of sufficient purity for the subsequent step.

DIAD (443 mg, 2.19 mmol) was added to a solution of 3-((1-(2-(1,1-difluoroethyl)pyridin-3-yl)-5-methyl-4-nitro-1H-pyrazol-3-yl)oxy)propan-1-ol (250 mg, 0.730 mmol), 3,6-dichloro-1H-pyrazolo[3,4-d]pyrimidine (139 mg, 0.735 mmol), and PPh$_3$ (575 mg, 2.19 mmol) in THF (10 mL) at 0° C. The mixture was stirred at 20° C. for 1 h and concentrated under reduced pressure. The residue was purified by chromatography on silica gel (eluent: petroleum ether:EtOAc 100:0→50:50) to afford 3,6-dichloro-1-(3-((1-(2-(1,1-difluoroethyl)pyridin-3-yl)-5-methyl-4-nitro-1H-pyrazol-3-yl)oxy)propyl)-1H-pyrazolo[3,4-d]pyrimidine (370 mg) of sufficient purity for the subsequent step.

Intermediate: 3,6-Dichloro-1-(3-((1-(5-fluoro-2,6-dimethylpyridin-3-yl)-5-methyl-4-nitro-1H-pyrazol-3-yl)oxy)propyl)-1H-pyrazolo[3,4-d]pyrimidine

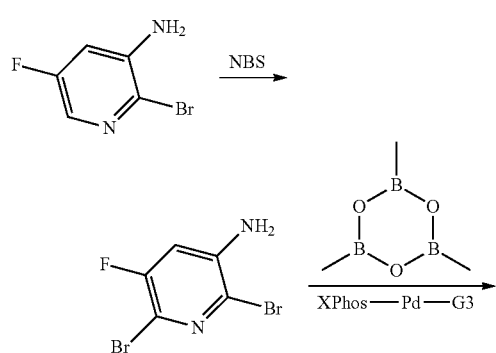

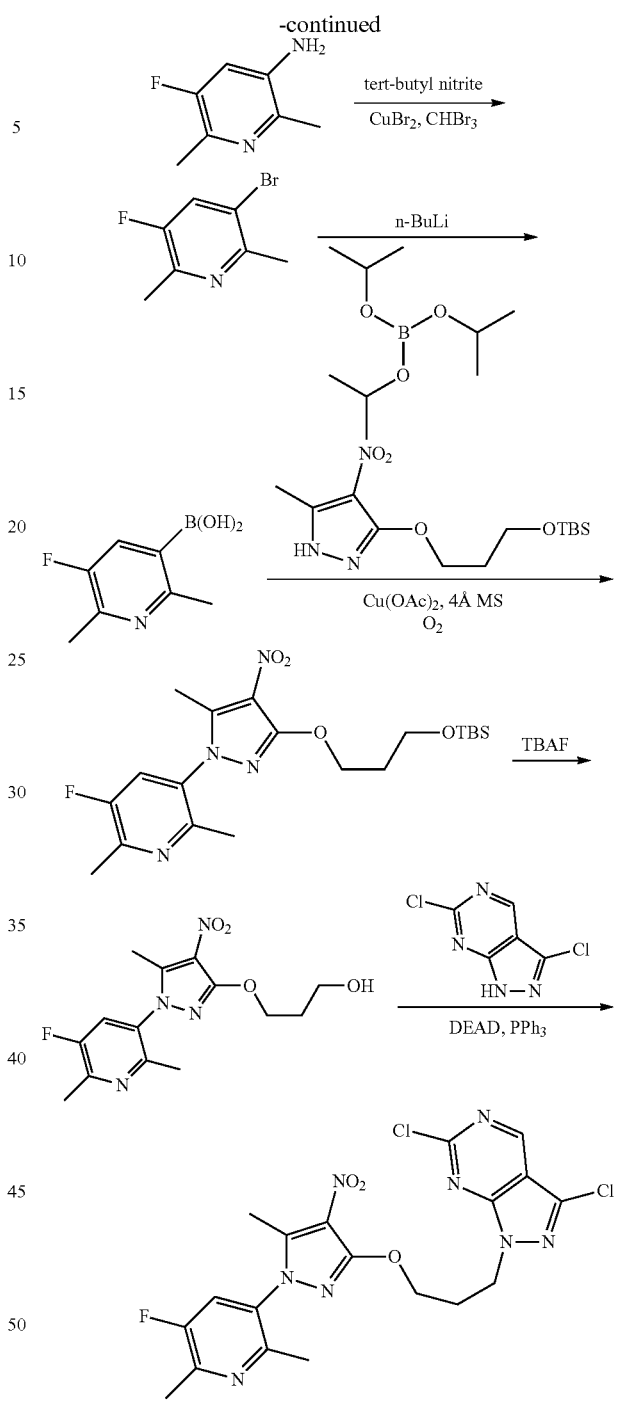

To 2-bromo-5-fluoropyridin-3-amine (5 g, 26 mmol) in MeCN (200 ml) was added NBS (4.66 g, 26.2 mmol) in a portionwise manner at 0° C. The mixture was stirred at 0° C. for 3 h. The mixture was concentrated under reduced pressure, diluted with water (50 mL), and extracted with ethyl acetate (50 mL×3). The combined organic layers were dried over anhydrous Na$_2$SO$_4$ and filtered. The filtrate was concentrated under reduced pressure. The residue was purified by chromatography on silica gel (eluent: petroleum ether: EtOAc 100:0→90:10) to afford 2,6-dibromo-5-fluoropyridin-3-amine (7.71 g) of sufficient purity for the subsequent step.

2,4,6-trimethyl-1,3,5,2,4,6-trioxatriborinane (16.3 g, 129 mmol) was added to a stirred suspension of 2,6-dibromo-5-fluoropyridin-3-amine (13.0 g, 51.8 mmol), K₃PO₄ (22.0 g, 104 mmol), and XPhos Pd G₃ (4.38 g, 5.18 mmol) in 1,4-dioxane (450 mL). The mixture was stirred at 95° C. for 12 h. The reaction mixture was concentrated under reduced pressure. The residue was purified by chromatography on silica gel (eluent: petroleum ether:EtOAc 100:0→30:70) to afford 5-fluoro-2,6-dimethylpyridin-3-amine (5.26 g) of sufficient purity for the subsequent step.

To a solution of 5-fluoro-2,6-dimethylpyridin-3-amine (5.26 g, 37.5 mmol) and CuBr₂ (10.1 g, 45.0 mmol) in CHBr₃ (100 mL) was added tert-butyl nitrite (4.64 g, 45.0 mmol) in a dropwise manner at 20° C. The solution was stirred at 20° C. for 12 h. The reaction mixture was concentrated under reduced pressure. The residue was purified by chromatography on silica gel (eluent: petroleum ether:EtOAc 100:0→90:10) to afford 3-bromo-5-fluoro-2,6-dimethylpyridine (3.8 g) of sufficient purity for the subsequent step.

To a mixture of 3-bromo-5-fluoro-2,6-dimethylpyridine (4.57 g, 22.4 mmol), triisopropyl borate (5.05 g, 26.9 mmol) in THF (115 mL) was added n-BuLi (10.8 mL, 27 mmol, 2.5 M in hexane) in a dropwise manner at −65° C. Upon complete addition the mixture was stirred at −65° C. for another 2 h. The reaction mixture was quenched with saturated aqueous NH₄Cl (20 mL) and water (20 mL) and extracted with EtOAc (5×30 mL). The combined organic layers were dried over Na₂SO₄ and concentrated under reduced pressure to afford (5-fluoro-2,6-dimethylpyridin-3-yl)boronic acid (2.44 g) of sufficient purity for the subsequent step.

A mixture of 5-(3-((tert-butyldimethylsilyl)oxy)propoxy)-3-methyl-4-nitro-1H-pyrazole (1.1 g, 3.5 mmol), (5-fluoro-2,6-dimethylpyridin-3-yl)boronic acid (2.36 g, 14.0 mmol), Cu(OAc)₂ (950 mg, 5.23 mmol), pyridine (1.10 g, 14.0 mmol) and 4 Å MS (1.1 g) in DCE (25 mL) was heated for 16 h at 50° C. under an O₂-atmosphere. The reaction mixture was concentrated under reduced pressure. The residue was purified by chromatography on silica gel (eluent: petroleum ether:EtOAc 100:0→85:15) to afford 3-(3-(3-((tert-butyldimethylsilyl)oxy)propoxy)-5-methyl-4-nitro-1H-pyrazol-1-yl)-5-fluoro-2,6-dimethylpyridine (1.15 g) of sufficient purity for the subsequent step.

To a solution of 3-(3-(3-((tert-butyldimethylsilyl)oxy)propoxy)-5-methyl-4-nitro-1H-pyrazol-1-yl)-5-fluoro-2,6-dimethylpyridine (1.15 g, 2.62 mmol) in THF (10 mL) was added TBAF (3.9 mL, 3.9 mmol, 1 M in THF) and stirred at 20° C. for 2 h. The reaction mixture was concentrated under reduced pressure. The residue was purified by chromatography on silica gel (eluent: petroleum ether:EtOAc 100:0→40:60) to afford 3-((1-(5-fluoro-2,6-dimethylpyridin-3-yl)-5-methyl-4-nitro-1H-pyrazol-3-yl)oxy)propan-1-ol (700 mg) of sufficient purity for the subsequent step.

To a solution 3-((1-(5-fluoro-2,6-dimethylpyridin-3-yl)-5-methyl-4-nitro-1H-pyrazol-3-yl)oxy)propan-1-ol (350 mg, 1.08 mmol) in THF (35 mL) was added 3,6-dichloro-1H-pyrazolo[3,4-d]pyrimidine (224 mg, 1.19 mmol), PPh₃ (849 mg, 3.24 mmol), and DEAD (564 mg, 3.24 mmol) at 0° C. The mixture was stirred at 20° C. for 1 h. The reaction mixture was concentrated under reduced pressure. The residue was purified by chromatography on silica gel (eluent: petroleum ether:EtOAc 100:0→70:30) to afford 3,6-dichloro-1-(3-((1-(5-fluoro-2,6-dimethylpyridin-3-yl)-5-methyl-4-nitro-1H-pyrazol-3-yl)oxy)propyl)-1H-pyrazolo[3,4-d]pyrimidine (710 mg) of sufficient purity for the subsequent step.

Intermediate: 3,6-Dichloro-1-(3-((1-(2-cyclopropoxypyridin-3-yl)-5-methyl-4-nitro-1H-pyrazol-3-yl)oxy)propyl)-1H-pyrazolo[3,4-d]pyrimidine

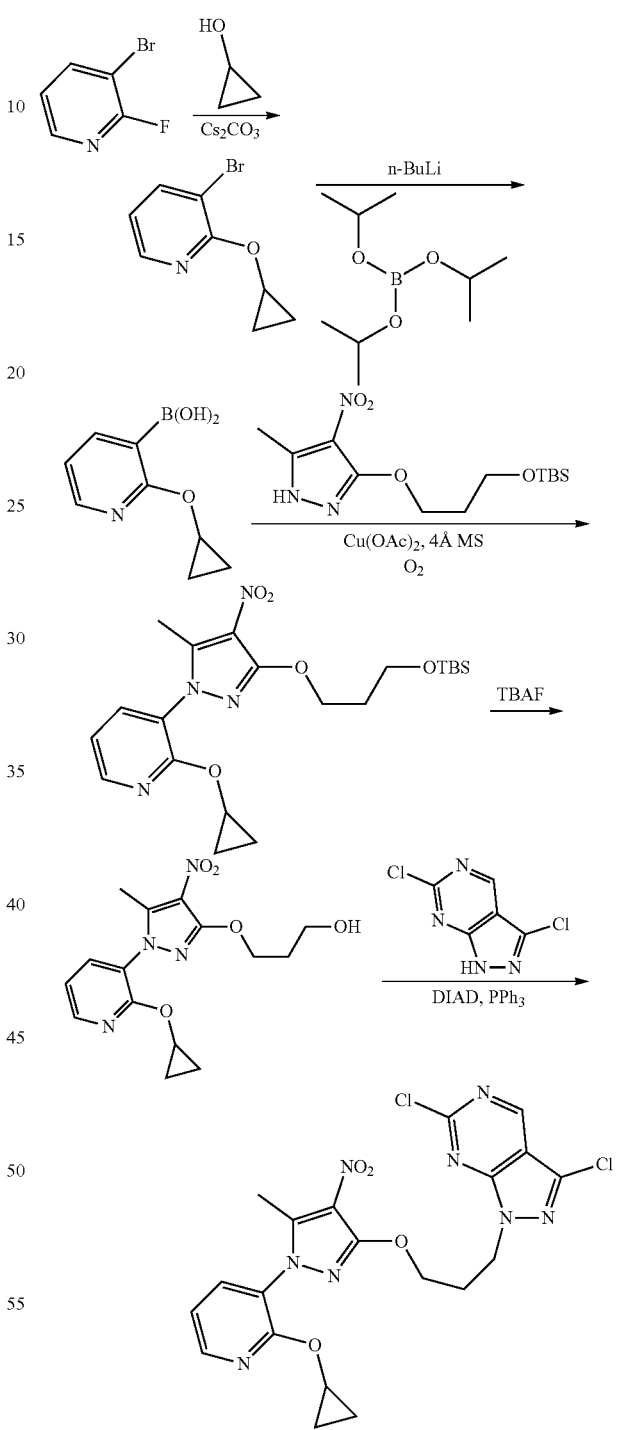

To a solution of 3-bromo-2-fluoropyridine (5.0 g, 28 mmol) in DMF (60 mL) was added Cs₂CO₃ (13.89 g, 42.62 mmol) and cyclopropanol (4.95 g, 85.23 mmol). The mixture was stirred at 20° C. for 15 h. The reaction mixture was diluted with water (50 mL) and extracted with EtOAc (100 mL×3). The combined organic layers were washed with brine (100 mL×3), dried over Na$_2$SO$_4$, and concentrated under reduced pressure. The residue was purified by chromatography on silica gel (eluent: petroleum ether:EtOAc 100:0→98:2) to afford 3-bromo-2-cyclopropoxypyridine (3.2 g) of sufficient purity for the subsequent step.

To a solution of 3-bromo-2-cyclopropoxypyridine (3 g, 14 mmol) and triisopropyl borate (7.91 g, 42.0 mmol) in THF (50 mL) was added n-BuLi (8.41 mL, 21 mmol, 2.5 M in hexane) in a dropwise manner at −78° C. The reaction mixture was stirred at −78° C. for 1.5 h. The reaction mixture was quenched with saturated aqueous NH$_4$Cl (20 mL) and extracted with EtOAc (50 mL×3). The combined organic layers were dried over Na$_2$SO$_4$ and concentrated under reduced pressure to afford (2-cyclopropoxypyridin-3-yl)boronic acid (2.2 g) of sufficient purity for the subsequent step.

A mixture of 5-(3-((tert-butyldimethylsilyl)oxy) propoxy)-3-methyl-4-nitro-1H-pyrazole (1.0 g, 3.2 mmol), (2-cyclopropoxypyridin-3-yl)boronic acid (1.13 g, 6.31 mmol), Cu(OAc)$_2$ (864 mg, 4.76 mmol), pyridine (1.00 g, 12.7 mmol), and 4 Å MS (1 g) in DCE (20 mL) was degassed and purged with O$_2$×3 and then stirred at 60° C. for 15 h under an O$_2$-atmosphere. The reaction mixture was concentrated under reduced pressure. The residue was purified by chromatography on silica gel (eluent: petroleum ether:EtOAc 100:0→80:20) to afford 3-(3-(3-((tert-butyldimethylsilyl)oxy)propoxy)-5-methyl-4-nitro-1H-pyrazol-1-yl)-2-cyclopropoxypyridine (600 mg) of sufficient purity for the subsequent step.

To a solution of 3-(3-(3-((tert-butyldimethylsilyl)oxy) propoxy)-5-methyl-4-nitro-1H-pyrazol-1-yl)-2-cyclopropoxypyridine (600 mg, 1.34 mmol) in THF (20 mL) was added TBAF (2 mL, 2 mmol, 1 M in THF). The mixture was stirred at 20° C. for 15 h. The reaction mixture was concentrated under reduced pressure. The residue was purified by chromatography on silica gel (eluent: petroleum ether: EtOAc 100:0→0:100) to afford 3-((1-(2-cyclopropoxypyridin-3-yl)-5-methyl-4-nitro-1H-pyrazol-3-yl)oxy)propan-1-ol (410 mg) of sufficient purity for the subsequent step.

DIAD (726 mg, 3.59 mmol) was added to a solution of 3-((1-(2-cyclopropoxypyridin-3-yl)-5-methyl-4-nitro-1H-pyrazol-3-yl)oxy)propan-1-ol (400 mg, 1.20 mmol), 3,6-dichloro-1H-pyrazolo[3,4-d]pyrimidine (228 mg, 1.21 mmol), and PPh$_3$ (942 mg, 3.59 mmol) in THF (10 mL) at 0° C. The mixture was stirred at 20° C. for 1 h. The reaction mixture was concentrated under reduced pressure. The residue was purified by chromatography on silica gel (eluent: petroleum ether:EtOAc 100:0→70:30) to afford 3,6-dichloro-1-(3-((1-(2-cyclopropoxypyridin-3-yl)-5-methyl-4-nitro-1H-pyrazol-3-yl)oxy)propyl)-1H-pyrazolo[3,4-d]pyrimidine (420 mg) of sufficient purity for the subsequent step.

Intermediate: 3,6-Dichloro-1-(3-((5-methyl-4-nitro-1-(2-(trifluoromethyl)pyridin-3-yl)-1H-pyrazol-3-yl) oxy)propyl)-1H-pyrazolo[3,4-d]pyrimidine

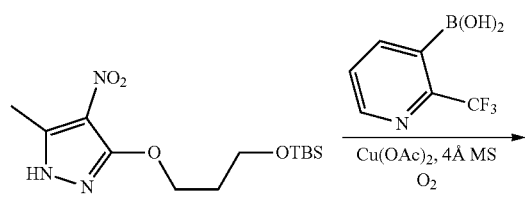

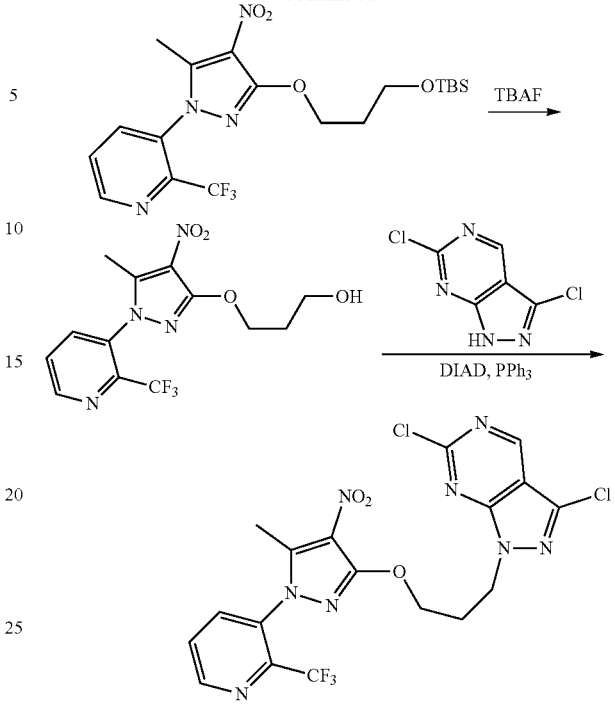

A mixture of 5-(3-((tert-butyldimethylsilyl)oxy)propoxy)-3-methyl-4-nitro-1H-pyrazole (1.00 g, 3.17 mmol), (2-(trifluoromethyl)pyridin-3-yl)boronic acid (726 mg, 3.80 mmol), Cu(OAc)$_2$ (864 mg, 4.76 mmol), pyridine (1.00 g, 12.7 mmol) and 4 Å MS (1 g) in DCE (40 mL) was degassed and purged with O$_2$×3 and stirred at 80° C. for 16 h under an O$_2$-atmosphere. The residue was purified by chromatography on silica gel (eluent: petroleum ether:EtOAc 83:17→67:33) followed by preparative HPLC (Instrument: Gilson GX-281 Liquid Handler, Gilson 322 Pump, Gilson 156 UV Detector, Column: Xtimate C18 150×40 mm×10 μm, Mobile Phase A: water (NH$_3$H$_2$O+NH$_4$HCO$_3$), Mobile phase B: MeCN, Gradient: B from 60% to 90% in 8 min then hold at 100% for 3 min, Flow Rate (mL/min): 55, Column temperature: 30° C., Wavelength: 220 nm, 254 nm) to afford 3-(3-(3-((tert-butyldimethylsilyl)oxy)propoxy)-5-methyl-4-nitro-1H-pyrazol-1-yl)-2-(trifluoromethyl)pyridine (50 mg) of sufficient purity for the subsequent step.

To a solution of 3-(3-(3-((tert-butyldimethylsilyl)oxy) propoxy)-5-methyl-4-nitro-1H-pyrazol-1-yl)-2-(trifluoromethyl)pyridine (100 mg, 0.22 mmol) in THF (8 mL) was added TBAF (0.326 mL, 0.22 mmol, 1M in THF) at 0° C. and the reaction was stirred at 30° C. for 2 h. The mixture was concentrated under reduced pressure. The residue was purified by chromatography on silica gel (eluent: petroleum ether:EtOAc 95:5→30:70) to afford 3-((5-methyl-4-nitro-1-(2-(trifluoromethyl)pyridin-3-yl)-1H-pyrazol-3-yl)oxy)propan-1-ol (70 mg) of sufficient purity for the subsequent step.

To a solution of 3-((5-methyl-4-nitro-1-(2-(trifluoromethyl)pyridin-3-yl)-1H-pyrazol-3-yl)oxy)propan-1-ol (65 mg, 0.19 mmol), 3,6-dichloro-1H-pyrazolo[3,4-d]pyrimidine (43 mg, 0.23 mmol), and PPh$_3$ (246 mg, 0.94 mmol) in THF (5 mL) was added DIAD (190 mg, 0.94 mmol) in a dropwise manner at 0° C. The mixture was stirred at 25° C. for 16 h. The mixture was concentrated under reduced pressure. The residue was purified by chromatography on silica gel (eluent: petroleum ether:EtOAc 100:0→70:30) to afford 3,6-dichloro-1-(3-((5-methyl-4-nitro-1-(2-(trifluoromethyl)pyridin-3-yl)-1H-pyrazol-3-yl)oxy)propyl)-1H-pyrazolo[3,4-d]pyrimidine (250 mg) of sufficient purity for the subsequent step.

Intermediate: 3,6-Dichloro-1-(3-((1-(2-(fluoromethoxy)pyridin-3-yl)-5-methyl-4-nitro-1H-pyrazol-3-yl)oxy)propyl)-1H-pyrazolo[3,4-d]pyrimidine

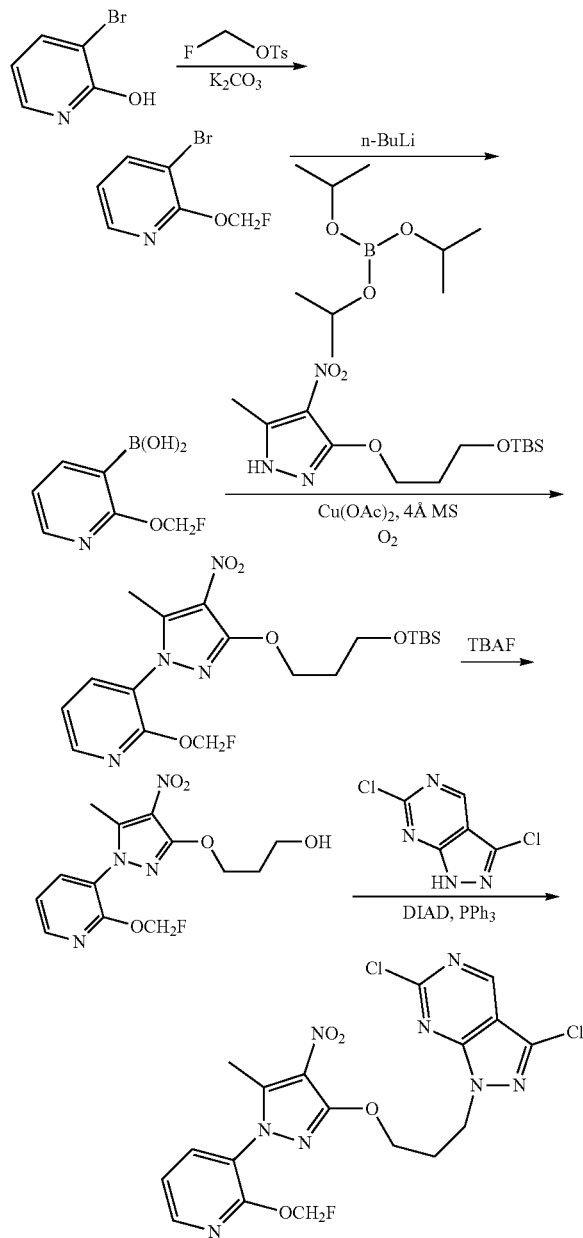

A mixture of 3-bromopyridin-2-ol (13 g, 751 mmol), fluoromethyl 4-methylbenzenesulfonate (30.52 g, 149.4 mmol), and K₂CO₃ (20.65 g, 149.4 mmol) in DMF (170 mL) was degassed and purged with N₂×3 and then stirred at 50° C. for 12 h. The reaction mixture was diluted with water (120 mL) and extracted with EtOAc (3×100 mL). The combined organic layers were washed with brine (3×100 mL), dried over Na₂SO₄, and concentrated under reduced pressure. The residue was purified by chromatography on silica gel (eluent: petroleum ether:EtOAc 100:0→95:5) to afford 3-bromo-2-(fluoromethoxy)pyridine (7 g) of sufficient purity for the subsequent step.

To a solution of 3-bromo-2-(fluoromethoxy)pyridine (7.0 g, 34 mmol) and triisopropyl borate (12.78 g, 67.96 mmol) in THF (100 mL) was added n-BuLi (20.4 mL, 51 mmol, 2.5 M in hexane) at −65° C. The mixture was stirred at −65° C. for 1.5 h followed by 1.5 h stirring at 0° C. The reaction mixture was quenched with saturated aqueous NH₄Cl (100 mL) and extracted with EtOAc (6×100 mL). The combined organic layers were dried over Na₂SO₄ and concentrated under reduced pressure to afford (2-(fluoromethoxy)pyridin-3-yl)boronic acid (5.4 g) of sufficient purity for the subsequent step.

A mixture of 5-(3-((tert-butyldimethylsilyl)oxy)propoxy)-3-methyl-4-nitro-1H-pyrazole (1.0 g, 3.2 mmol), (2-(fluoromethoxy)pyridin-3-yl)boronic acid (1.19 g, 6.97 mmol), pyridine (1.00 g, 12.7 mmol), Cu(OAc)₂ (864 mg, 4.76 mmol), and 4 Å MS (1 g) in DCE (15 mL) was heated for 16 h at 50° C. under an O₂-atmosphere. The reaction mixture was concentrated under reduced pressure. The residue was purified by chromatography on silica gel (eluent: petroleum ether:EtOAc 100:0→80:20) to afford 3-(3-(3-((tert-butyldimethylsilyl)oxy)propoxy)-5-methyl-4-nitro-1H-pyrazol-1-yl)-2-(fluoromethoxy)pyridine (120 mg) of sufficient purity for the subsequent step.

To a solution of 3-(3-(3-((tert-butyldimethylsilyl)oxy)propoxy)-5-methyl-4-nitro-1H-pyrazol-1-yl)-2-(fluoromethoxy)pyridine (500 mg, 1.13 mmol) in THF (5 mL) was added TBAF (1.7 mL, 1.7 mmol 1 M in THF) and stirred at 20° C. for 2 h. The reaction mixture was concentrated under reduced pressure. The residue was purified by chromatography on silica gel (eluent: petroleum ether:EtOAc 100:0→40:60) to afford 3-((1-(2-(fluoromethoxy)pyridin-3-yl)-5-methyl-4-nitro-1H-pyrazol-3-yl)oxy)propan-1-ol (250 mg) of sufficient purity for the subsequent step.

To a solution of 3-((1-(2-(fluoromethoxy)pyridin-3-yl)-5-methyl-4-nitro-1H-pyrazol-3-yl)oxy)propan-1-ol (340 mg, 1.04 mmol) in THF (25 mL) was added 3,6-dichloro-1H-pyrazolo[3,4-d]pyrimidine (197 mg, 1.04 mmol), PPh₃ (820 mg, 3.13 mmol), and DIAD (632 mg, 3.13 mmol) at 0° C. The mixture was stirred at 20° C. for 0.5 h. The reaction mixture was concentrated under reduced pressure. The residue was purified by chromatography on silica gel (eluent: petroleum ether:EtOAc 100:0→60:40) to afford 3,6-dichloro-1-(3-((1-(2-(fluoromethoxy)pyridin-3-yl)-5-methyl-4-nitro-1H-pyrazol-3-yl)oxy)propyl)-1H-pyrazolo[3,4-d]pyrimidine (385 mg) of sufficient purity for the subsequent step.

Intermediate: 3,6-Dichloro-1-(3-((1-(2-(difluoromethoxy)pyridin-3-yl)-5-methyl-4-nitro-1H-pyrazol-3-yl)oxy)propyl)-1H-pyrazolo[3,4-d]pyrimidine

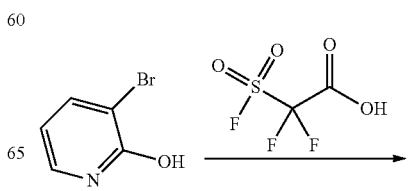

111

-continued

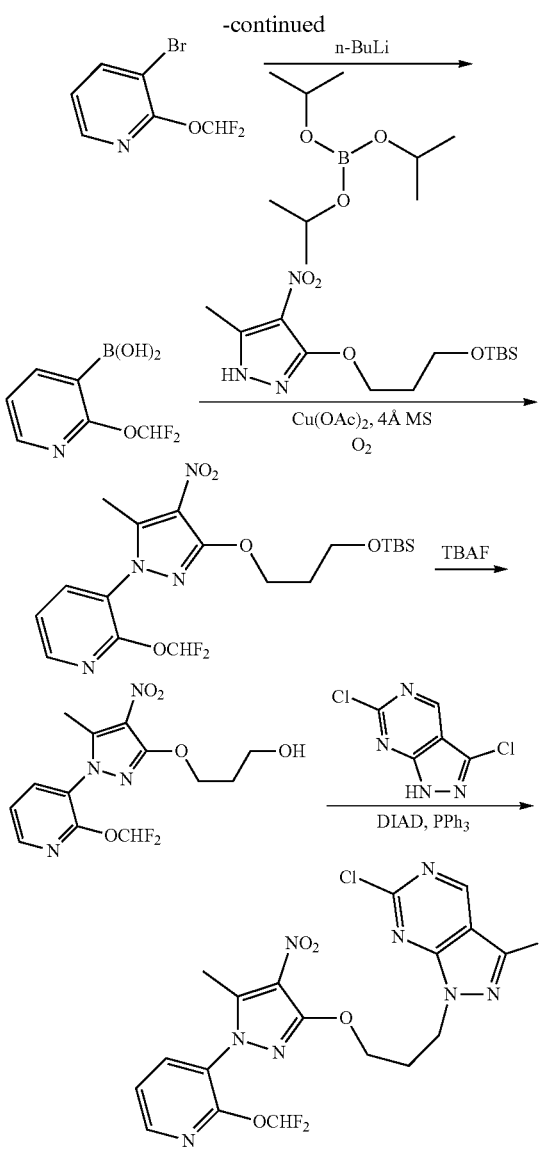

To a solution of 3-bromopyridin-2-ol (5.0 g, 29 mmol) in MeCN (140 mL) was added 2,2-difluoro-2-(fluorosulfonyl) acetic acid (6.14 g, 34.5 mmol) and Na$_2$SO$_4$ (4.49 g, 31.6 mmol). The mixture was stirred at 15° C. for 16 h. The reaction mixture was diluted with water (100 mL) and extracted with EtOAc (3×100 mL). The combined organic layers were dried over Na$_2$SO$_4$ and concentrated under reduced pressure. The residue was purified by chromatography on silica gel (eluent: petroleum ether:EtOAc 100: 0→95:5) to afford 3-bromo-2-(difluoromethoxy)pyridine (5.7 g) of sufficient purity for the subsequent step.

To a solution of 3-bromo-2-(difluoromethoxy)pyridine (6.6 g, 29 mmol) and triisopropyl borate (11.08 g, 58.93 mmol) in THF (100 mL) was added n-BuLi (17.7 mL, 44 mmol, 2.5 M in hexane) at −65° C. and stirred at −65° C. for 4.5 h. The reaction mixture was quenched with saturated aqueous NH$_4$Cl (40 mL) and extracted with EtOAc (3×100 mL). The combined organic layers were dried over Na$_2$SO$_4$ and concentrated under reduced pressure. The residue was purified by chromatography on silica gel (eluent: petroleum ether:EtOAc 100:0→80:20) to afford (2-(difluoromethoxy) pyridin-3-yl)boronic acid (4 g) of sufficient purity for the subsequent step.

112

A mixture of 5-(3-((tert-butyldimethylsilyl)oxy) propoxy)-3-methyl-4-nitro-1H-pyrazole (1.0 g, 3.2 mmol), (2-(difluoromethoxy)pyridin-3-yl)boronic acid (1.20 g, 6.34 mmol), pyridine (1.00 g, 12.7 mmol), Cu(OAc)$_2$ (864 mg, 4.76 mmol) and 4 Å MS (1 g) in DCE (15 mL) was heated for 16 h at 60° C. under an O$_2$-atmosphere. The reaction mixture was concentrated under reduced pressure. The residue was purified by chromatography on silica gel (eluent: petroleum ether:EtOAc 100:0→75:25) to afford 3-(3-(3-((tert-butyldimethylsilyl)oxy)propoxy)-5-methyl-4-nitro-1H-pyrazol-1-yl)-2-(difluoromethoxy)pyridine (160 mg) of sufficient purity for the subsequent step.

To a solution of 3-(3-(3-((tert-butyldimethylsilyl)oxy) propoxy)-5-methyl-4-nitro-1H-pyrazol-1-yl)-2-(difluoromethoxy)pyridine (320 mg, 0.698 mmol) in THF (8 mL) was added TBAF (1.1 mL, 1.1 mmol, 1 M in THF) and stirred at 20° C. for 2 h. The reaction mixture was concentrated under reduced pressure. The residue was purified by chromatography on silica gel (eluent: petroleum ether:EtOAc 100:0→0:100) to afford 3-((1-(2-(difluoromethoxy) pyridin-3-yl)-5-methyl-4-nitro-1H-pyrazol-3-yl)oxy)propan-1-ol (170 mg) of sufficient purity for the subsequent step.

To a solution of 3-((1-(2-(difluoromethoxy)pyridin-3-yl)- 5-methyl-4-nitro-1H-pyrazol-3-yl)oxy)propan-1-ol (160 mg, 0.465 mmol) in THF (16 mL) was added 3,6-dichloro-1H-pyrazolo[3,4-d]pyrimidine (88 mg, 0.47 mmol), PPh$_3$ (366 mg, 1.40 mmol), and DIAD (282 mg, 1.39 mmol) at 0° C. The mixture was stirred at 20° C. for 0.5 h. The reaction mixture was concentrated under reduced pressure. The residue was purified by chromatography on silica gel (eluent: petroleum ether:EtOAc 100:0→60:40) to afford 3,6-dichloro-1-(3-((1-(2-(difluoromethoxy)pyridin-3-yl)-5-methyl-4-nitro-1H-pyrazol-3-yl)oxy)propyl)-1H-pyrazolo [3,4-d]pyrimidine (200 mg) of sufficient purity for the subsequent step.

Intermediate: 3,6-Dichloro-1-(3-((5-methyl-4-nitro-1-(2-(trifluoromethoxy)pyridin-3-yl)-1H-pyrazol-3-yl)oxy)propyl)-1H-pyrazolo[3,4-d]pyrimidine

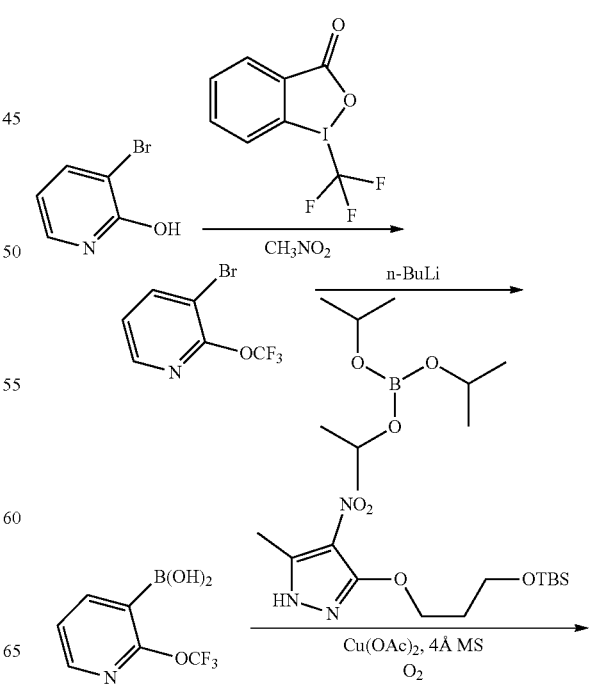

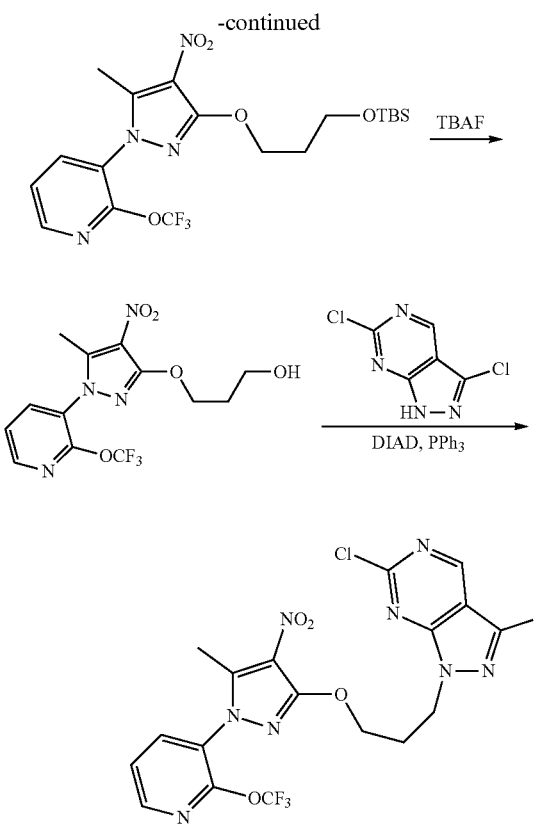

A mixture of 3-bromopyridin-2-ol (24.78 g, 142.40 mmol), 1-(trifluoromethyl)-1λ³-benzo[d][1,2]iodaoxol-3 (1H)-one (15 g, 47 mmol) in CH₃NO₂(342 g, 5.61 mol) was degassed and purged with N₂×3, and then stirred at 100° C. for 16 h. The mixture was diluted with water (300 mL) and extracted with DCM (2×300 mL). The organic layers were dried over Na₂SO₄, filtered, and concentrated under reduced pressure. The residue was purified by chromatography on silica gel (eluent: petroleum ether:EtOAc 100:0) to afford 3-bromo-2-(trifluoromethoxy)pyridine (5.6 g) of sufficient purity for the subsequent step.

To a solution of 3-bromo-2-(trifluoromethoxy)pyridine (6.0 g, 25 mmol) and triisopropyl borate (7.46 g, 39.7 mmol) in THF (100 mL) was added n-BuLi (14.9 mL, 37 mmol, 2.5 M in hexane) at −65° C. and stirred at −65° C. for 3 h. The reaction mixture was quenched with saturated aqueous NH₄Cl (100 mL) and extracted with EtOAc (6×60 mL). The combined organic layers were dried over Na₂SO₄ and concentrated under reduced pressure. The residue was purified by chromatography on silica gel (eluent: petroleum ether:EtOAc 100:0→75:25) to afford (2-(trifluoromethoxy)pyridin-3-yl)boronic acid (2.5 g) of sufficient purity for the subsequent step.

A mixture of 5-(3-((tert-butyldimethylsilyl)oxy)propoxy)-3-methyl-4-nitro-1H-pyrazole (1.0 g, 3.2 mmol), (2-(trifluoromethoxy)pyridin-3-yl)boronic acid (655 mg, 3.17 mmol), Cu(OAc)₂ (864 mg, 4.76 mmol), pyridine (1.00 g, 12.7 mmol) and 4 Å MS (1 g) in DCE (100 mL) was heated for 16 h at 60° C. under an O₂-atmosphere. The reaction mixture was concentrated under reduced pressure. The residue was purified by chromatography on silica gel (eluent: petroleum ether:EtOAc 100:0→80:20) to afford 3-(3-(3-((tert-butyldimethylsilyl)oxy)propoxy)-5-methyl-4-nitro-1H-pyrazol-1-yl)-2-(trifluoromethoxy)pyridine (55 mg) of sufficient purity for the subsequent step.

To a solution of 3-(3-(3-((tert-butyldimethylsilyl)oxy)propoxy)-5-methyl-4-nitro-1H-pyrazol-1-yl)-2-(trifluoromethoxy)pyridine (220 mg, 0.462 mmol) in THF (5 mL) was added TBAF (0.692 mL, 0.69 mmol, 1 M in THF) and stirred at 20° C. for 3 h. The reaction mixture was concentrated under reduced pressure The residue was purified by chromatography on silica gel (eluent: petroleum ether:EtOAc 100:0→30:70) to afford 3-((5-methyl-4-nitro-1-(2-(trifluoromethoxy)pyridin-3-yl)-1H-pyrazol-3-yl)oxy)propan-1-ol (130 mg) of sufficient purity for the subsequent step.

To a solution of 3-((5-methyl-4-nitro-1-(2-(trifluoromethoxy)pyridin-3-yl)-1H-pyrazol-3-yl)oxy)propan-1-ol (110 mg, 0.304 mmol) in toluene (11 mL) was added 3,6-dichloro-1H-pyrazolo[3,4-d]pyrimidine (57 mg, 0.30 mmol), PPh₃ (239 mg, 0.911 mmol), and DIAD (184 mg, 0.911 mmol) at 0° C. The mixture was stirred at 60° C. for 0.4 h. The reaction mixture was concentrated under reduced pressure. The residue was purified by chromatography on silica gel (eluent: petroleum ether:EtOAc 100:0→60:40) to afford 3,6-dichloro-1-(3-((5-methyl-4-nitro-1-(2-(trifluoromethoxy)pyridin-3-yl)-1H-pyrazol-3-yl)oxy)propyl)-1H-pyrazolo[3,4-d]pyrimidine (90 mg) of sufficient purity for the subsequent step.

Intermediate: 3,6-Dichloro-1-(3-((1-(3-methoxypyridazin-4-yl)-5-methyl-4-nitro-1H-pyrazol-3-yl)oxy)propyl)-1H-pyrazolo[3,4-d]pyrimidine

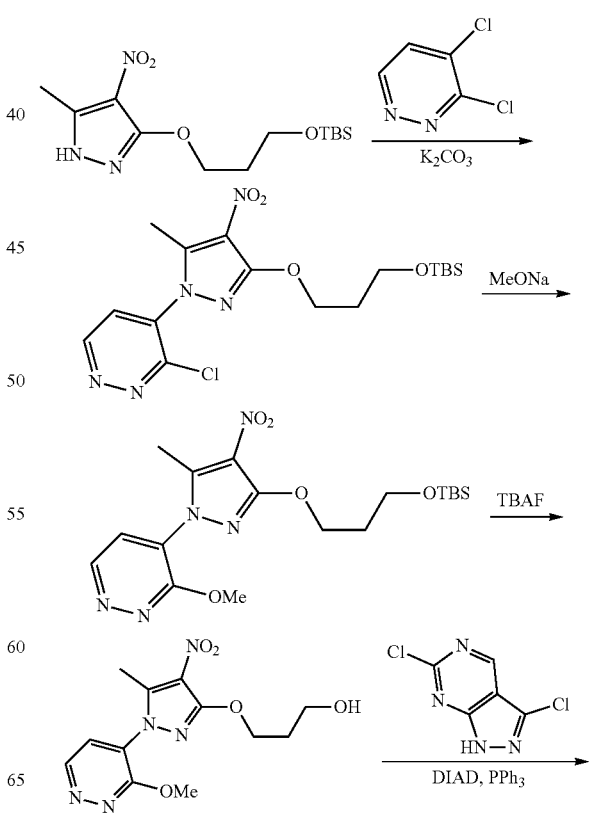

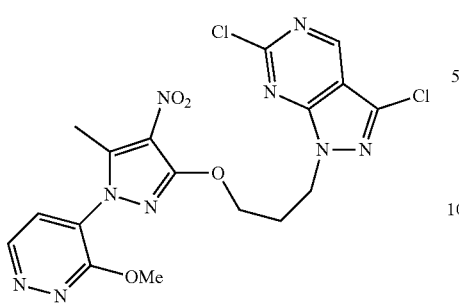

A mixture of 5-(3-((tert-butyldimethylsilyl)oxy)propoxy)-3-methyl-4-nitro-1H-pyrazole (1.0 g, 3.2 mmol), 3,4-dichloropyridazine (472 mg, 3.17 mmol), K₂CO₃ (789 mg, 5.71 mmol) in MeCN (50 mL) was degassed and purged with N₂×3 and then stirred at 60° C. for 48 h. The reaction mixture diluted with water (20 mL) and extracted with EtOAc (3×40 mL). The combined organic layers were dried over Na₂SO₄ and concentrated under reduced pressure. The residue was purified by chromatography on silica gel (eluent: petroleum ether:EtOAc 100:0→70:30) to afford 4-(3-(3-((tert-butyldimethylsilyl)oxy)propoxy)-5-methyl-4-nitro-1H-pyrazol-1-yl)-3-chloropyridazine (400 mg) of sufficient purity for the subsequent step.

To a solution of 4-(3-(3-((tert-butyldimethylsilyl)oxy)propoxy)-5-methyl-4-nitro-1H-pyrazol-1-yl)-3-chloropyridazine (140 mg, 0.327 mmol) in MeOH (5 mL) was added NaOMe (118 mg, 0.654 mmol, 30 w % in MeOH) at 0° C. The mixture was stirred at 25° C. for 1 h. The reaction mixture was diluted with water (10 mL) and extracted with EtOAc (3×10 mL). The combined organic layers were dried over Na₂SO₄ and concentrated under reduced pressure to afford 4-(3-(3-((tert-butyldimethylsilyl)oxy)propoxy)-5-methyl-4-nitro-1H-pyrazol-1-yl)-3-methoxypyridazine (120 mg) of sufficient purity for the subsequent step.

To a solution of 4-(3-(3-((tert-butyldimethylsilyl)oxy)propoxy)-5-methyl-4-nitro-1H-pyrazol-1-yl)-3-methoxypyridazine (100 mg, 0.236 mmol) in THF (5 mL) was added TBAF (0.354 mL, 0.35 mmol, 1 M in THF) and stirred at 25° C. for 1 h. The reaction mixture was concentrated under reduced pressure. The residue was purified by chromatography on silica gel (eluent: petroleum ether:EtOAc 100:0→0:100) to afford 3-((1-(3-methoxypyridazin-4-yl)-5-methyl-4-nitro-1H-pyrazol-3-yl)oxy)propan-1-ol (45 mg) of sufficient purity for the subsequent step.

To a solution of 3-((1-(3-methoxypyridazin-4-yl)-5-methyl-4-nitro-1H-pyrazol-3-yl)oxy)propan-1-ol (110 mg, 0.356 mmol) in THF (10 mL) was added 3,6-dichloro-1H-pyrazolo[3,4-d]pyrimidine (81 mg, 0.43 mmol), PPh₃ (280 mg, 1.07 mmol), and DIAD (216 mg, 1.07 mmol) at 0° C. The mixture was stirred at 25° C. for 16 h. The reaction mixture was concentrated under reduced pressure. The residue was purified by chromatography on silica gel (eluent: petroleum ether:EtOAc 100:0→10:90) to afford 3,6-dichloro-1-(3-((1-(3-methoxypyridazin-4-yl)-5-methyl-4-nitro-1H-pyrazol-3-yl)oxy)propyl)-1H-pyrazolo[3,4-d]pyrimidine (165 mg) of sufficient purity for the subsequent step.

Intermediate: 3,6-Dichloro-1-(3-((1-(4-methoxy-2-methylpyrimidin-5-yl)-5-methyl-4-nitro-1H-pyrazol-3-yl)oxy)propyl)-1H-pyrazolo[3,4-d]pyrimidine

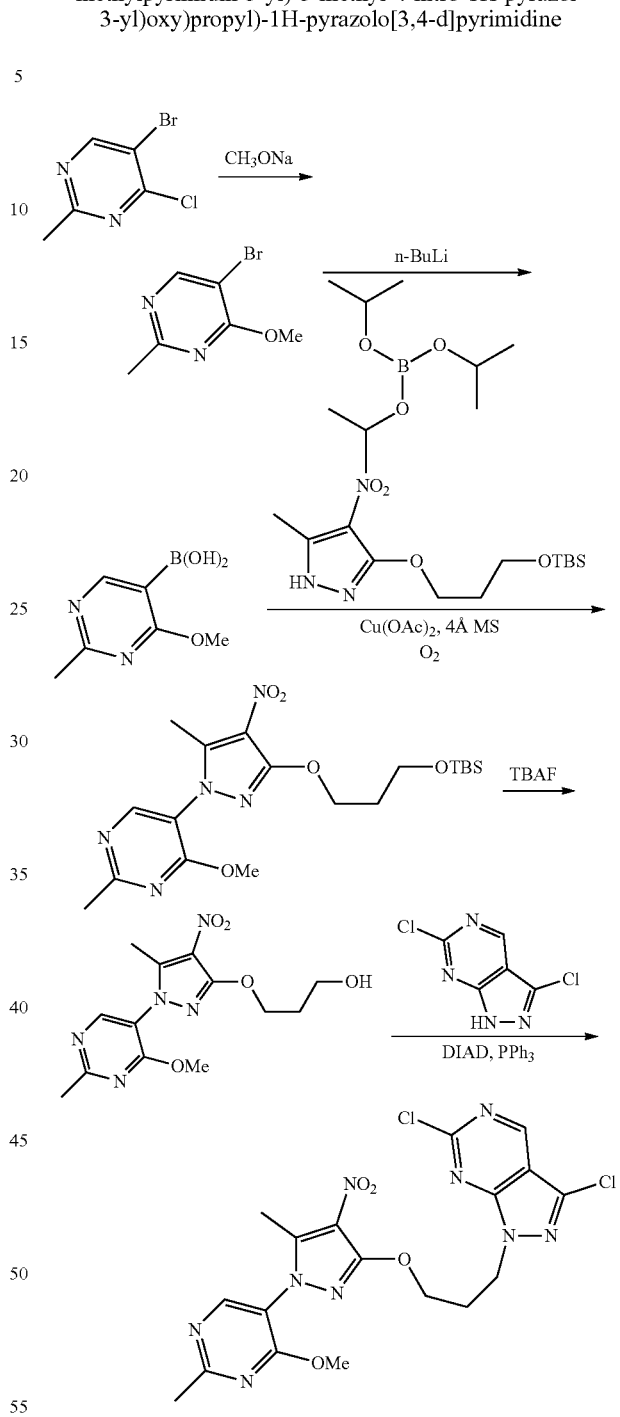

To a solution of 5-bromo-4-chloro-2-methyl-pyrimidine (3.0 g, 14 mmol) in MeOH (50 mL) was added NaOMe (43.5 mL, 44 mmol, 1 M in MeOH) at 0° C. The mixture was stirred at 0° C. for 1 h. The mixture was diluted with water (30 mL) and extracted with EtOAc (50 mL×3). The combined organic layers were dried over Na₂SO₄, filtered, and concentrated under reduced pressure to afford 5-bromo-4-methoxy-2-methyl-pyrimidine (2.9 g) of sufficient purity for the subsequent step.

To a solution of 5-bromo-4-methoxy-2-methyl-pyrimidine (3.4 g, 17 mmol) and triisopropyl borate (6.30 g, 33.5 mmol) in THF (40 mL) was added n-BuLi (8.0 mL, 20 mmol, 2.5 M in hexane) at −65° C. The mixture was stirred at −65° C. for 2 h and allowed to warm to 20° C. and stirred at 20° C. for 16 h. The reaction was quenched by addition of aqueous HCl (10 mL, 1 M) and pH adjusted to 6 using 1M aqueous HCl. The mixture was extracted with EtOAc (50 mL×8) and the combined organic layers were dried over Na$_2$SO$_4$, filtered, and concentrated under reduced pressure to afford (4-methoxy-2-methyl-pyrimidin-5-yl)boronic acid (2.03 g) of sufficient purity for the subsequent step.

A mixture of (4-methoxy-2-methyl-pyrimidin-5-yl)boronic acid (906 mg, 5.39 mmol), 5-(3-((tert-butyldimethylsilyl)oxy)propoxy)-3-methyl-4-nitro-1H-pyrazole (1.0 g, 3.2 mmol), TMEDA (1.11 g, 9.51 mmol), and Cu(OTf)$_2$ (3.44 g, 9.51 mmol) in MeCN (9 mL) and DCM (6 mL) was degassed and purged with O$_2$×3 and then stirred at 20° C. for 16 h under an O$_2$-atmosphere. The mixture was concentrated under reduced pressure. The residue was purified by chromatography on silica gel (eluent: petroleum ether:EtOAc 100:0→80:20) followed by preparative HPLC (Instrument: Gilson GX-281 Liquid Handler, Gilson 322 Pump, Gilson 156 UV Detector; Column: Xtimate C18 150×40 mm×10 μm; Mobile Phase A: water (0.05% NH$_3$H$_2$O+10 mM NH$_4$HCO$_3$); Mobile phase B: MeCN; Gradient: B from 70% to 100% in 8 min then hold at 100% for 3 min; Flow Rate (mL/min): 55; Column temperature: ° C.; Wavelength: 220 nm 254 nmbasic condition) to afford 5-(3-(3-((tert-butyldimethylsilyl)oxy)propoxy)-5-methyl-4-nitro-1H-pyrazol-1-yl)-4-methoxy-2-methylpyrimidine (460 mg) of sufficient purity for the subsequent step.

To a solution of 5-(3-(3-((tert-butyldimethylsilyl)oxy)propoxy)-5-methyl-4-nitro-1H-pyrazol-1-yl)-4-methoxy-2-methylpyrimidine (460 mg, 1.05 mmol) in THF (10 mL) was added TBAF (1.6 mL, 1.6 mmol, 1 M in THF). The mixture was stirred at 20° C. for 2 h. The mixture was concentrated under reduced pressure. The residue was purified by chromatography on silica gel (eluent: petroleum ether:EtOAc 100:0→0:100) to afford 3-((1-(4-methoxy-2-methylpyrimidin-5-yl)-5-methyl-4-nitro-1H-pyrazol-3-yl)oxy)propan-1-ol (330 mg) of sufficient purity for the subsequent step.

A mixture of 3-((1-(4-methoxy-2-methylpyrimidin-5-yl)-5-methyl-4-nitro-1H-pyrazol-3-yl)oxy)propan-1-ol (330 mg, 1.02 mmol), 3,6-dichloro-1H-pyrazolo[3,4-d]pyrimidine (193 mg, 1.02 mmol), PPh$_3$ (900 mg, 3.43 mmol), and DIAD (730 mg, 3.61 mmol) in THF (10 mL) was stirred at 15° C. for 2 h. The mixture was concentrated unduced pressure. The residue was purified by chromatography on silica gel (eluent: petroleum ether:EtOAc 100:0→60:40) to afford 3,6-dichloro-1-(3-((1-(4-methoxy-2-methylpyrimidin-5-yl)-5-methyl-4-nitro-1H-pyrazol-3-yl)oxy)propyl)-1H-pyrazolo[3,4-d]pyrimidine (900 mg) of sufficient purity for the subsequent step.

Intermediate: 3,6-Dichloro-1-(3-((1-(5-fluoro-2-(methoxy-d$_3$)pyridin-3-yl)-5-methyl-4-nitro-1H-pyrazol-3-yl)oxy)propyl)-1H-pyrazolo[3,4-d]pyrimidine

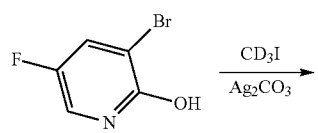

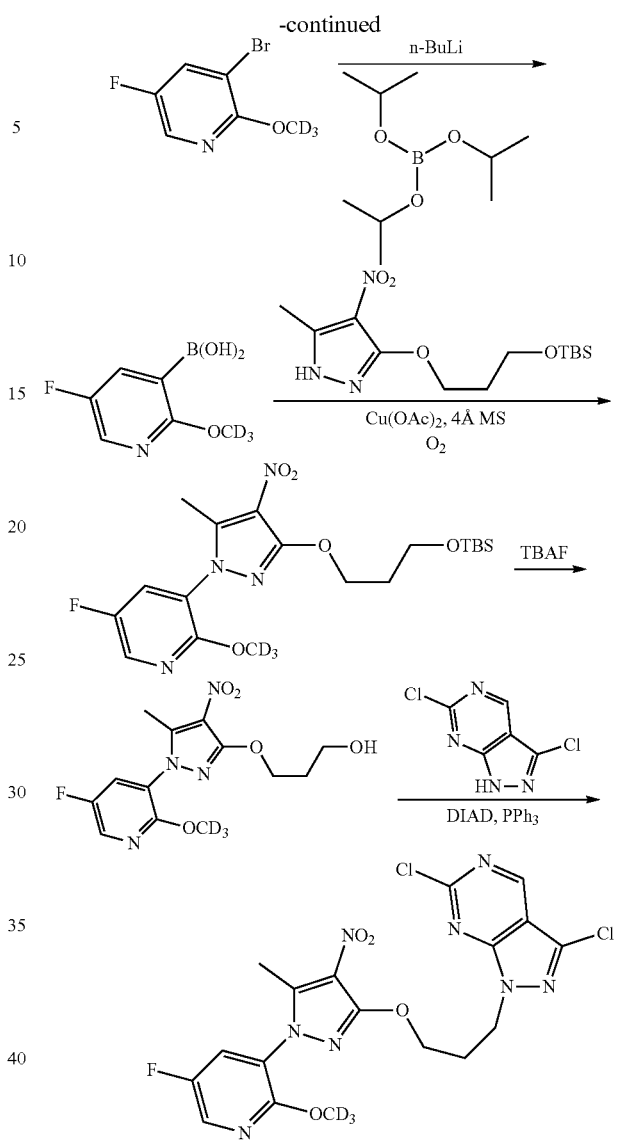

To a solution of 3-bromo-5-fluoro-pyridin-2-ol (10 g, 52 mmol) in toluene (150 mL) was added Ag$_2$CO$_3$ (10.05 g, 36.46 mmol) and trideuterio(iodo)methane (9.0 g, 62 mmol) at 5° C. The mixture was stirred at 25° C. for 16 h. The mixture was concentrated under reduced pressure. The residue was purified by chromatography on silica gel (eluent: petroleum ether:EtOAc 100:0→95:5) to afford 3-bromo-5-fluoro-2-(trideuteriomethoxy)pyridine (7.6 g) of sufficient purity for the subsequent step.

n-BuLi (8.61 mL, 22 mmol, 2.5 M in hexane) was slowly added to a solution of 3-bromo-5-fluoro-2-(trideuteriomethoxy)pyridine (3.0 g, 14 mmol) and triisopropyl borate (6.82 g, 36.3 mmol) in THF (30 mL) at −65° C. The mixture was stirred at −65° C. for 2 h and then allowed to warm to 25° C. and stirred for 14 h. The mixture was adjusted to pH 6 with aqueous HCl (1 M) and concentrated under reduced pressure. The residue was purified by chromatography on silica gel (eluent: petroleum ether:EtOAc 100:0→70:30) to afford (5-fluoro-2-(methoxy-d$_3$)pyridin-3-yl)boronic acid (2 g) of sufficient purity for the subsequent step.

A mixture of 5-(3-((tert-butyldimethylsilyl)oxy)propoxy)-3-methyl-4-nitro-1H-pyrazole (2.0 g, 6.3 mmol), (5-fluoro-2-(methoxy-d₃)pyridin-3-yl)boronic acid (1.32 g, 7.61 mmol), Cu(OAc)₂, (1.73 g, 9.51 mmol), pyridine (2.01 g, 25.4 mmol), and 4 Å MS (2 g) in DCE (40 mL) was degassed and purged with O₂×3. The mixture was stirred at 50° C. for 16 h under an O₂-atmosphere. Additional (5-fluoro-2-(methoxy-d₃)pyridin-3-yl)boronic acid (600 mg, 3.45 mmol) was added and the mixture was stirred at 50° C. for 16 h. The mixture was concentrated under reduced pressure. The residue was purified by chromatography on silica gel (eluent: petroleum ether:EtOAc 100:0→80:20) to afford 3-(3-(3-((tert-butyldimethylsilyl)oxy)propoxy)-5-methyl-4-nitro-1H-pyrazol-1-yl)-5-fluoro-2-(methoxy-d₃)pyridine (900 mg) of sufficient purity for the subsequent step.

To a solution of 3-(3-(3-((tert-butyldimethylsilyl)oxy)propoxy)-5-methyl-4-nitro-1H-pyrazol-1-yl)-5-fluoro-2-(methoxy-d₃)pyridine (800 mg, 1.80 mmol) in THF (10 mL) was added TBAF (2.7 mL, 2.7 mmol, 1 M in THF). The mixture was stirred at 25° C. for 1 h. The mixture was concentrated under reduced pressure. The residue was purified by chromatography on silica gel (eluent: petroleum ether:EtOAc 100:0→30:70) to afford 3-((1-(5-fluoro-2-(methoxy-d₃)pyridin-3-yl)-5-methyl-4-nitro-1H-pyrazol-3-yl)oxy)propan-1-ol (500 mg) of sufficient purity for the subsequent step.

To a mixture of 3-((1-(5-fluoro-2-(methoxy-d₃)pyridin-3-yl)-5-methyl-4-nitro-1H-pyrazol-3-yl)oxy)propan-1-ol (300 mg, 0.900 mmol), 3,6-dichloro-1H-pyrazolo[3,4-d]pyrimidine (172 mg, 0.910 mmol), PPh₃ (717 mg, 2.73 mmol) in THF (20 mL) was added DIAD (553 mg, 2.73 mmol) at 0° C. The mixture was stirred at 25° C. for 16 h. The mixture was concentrated under reduced pressure. The residue was purified by chromatography on silica gel (eluent: petroleum ether:EtOAc 100:0→80:20) to afford 3,6-dichloro-1-(3-((1-(5-fluoro-2-(methoxy-d₃)pyridin-3-yl)-5-methyl-4-nitro-1H-pyrazol-3-yl)oxy)propyl)-1H-pyrazolo[3,4-d]pyrimidine (380 mg) of sufficient purity for the subsequent step.

Intermediate: 3,6-Dichloro-1-(3-((1-(2-(methoxy-d₃)pyridin-3-yl)-5-methyl-4-nitro-1H-pyrazol-3-yl)oxy)propyl)-1H-pyrazolo[3,4-d]pyrimidine

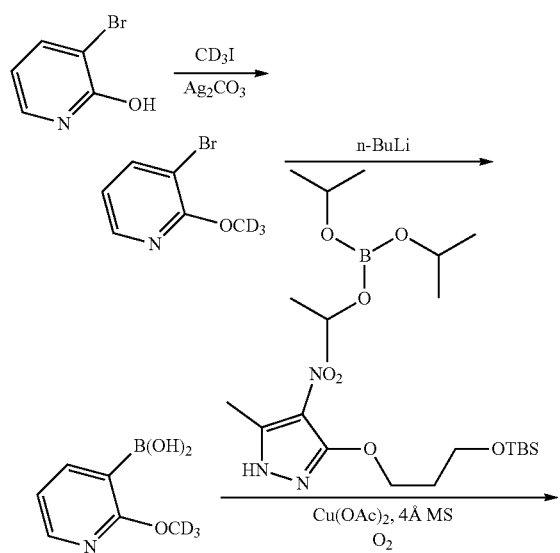

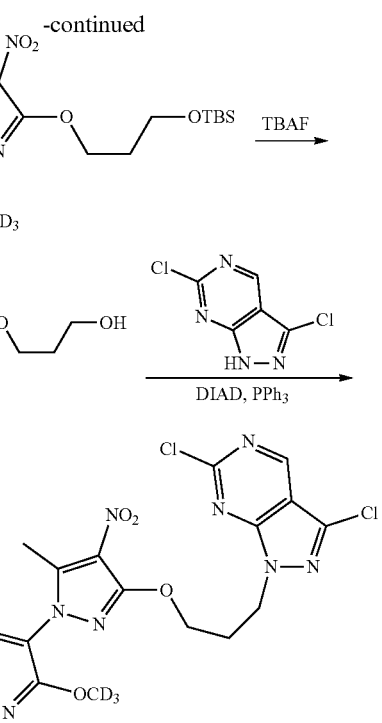

To a solution of 3-bromopyridin-2-ol (5.0 g, 29 mmol) in CHCl₃ (50 mL) was added Ag₂CO₃ (15.85 g, 57.47 mmol) and trideuterio(iodo)methane (8.33 g, 57.5 mmol). The mixture was stirred at 20° C. for 15 h. The mixture was concentrated under reduced pressure. The residue was purified by chromatography on silica gel (eluent: petroleum ether:EtOAc 100:0→95:5) to afford 3-bromo-2-(methoxy-d₃)pyridine (3.85 g) of sufficient purity for the subsequent step.

To a solution of 3-bromo-2-(methoxy-d₃)pyridine (4.2 g, 22 mmol) in THF (40 mL) was added n-BuLi (9.67 mL, 24 mmol, 2.5 M, in hexane) in a dropwise manner at −78° C. The reaction mixture was stirred at −78° C. for 30 minutes, then triisopropyl borate (8.27 g, 44.0 mmol) was added and the mixture was stirred 20° C. for 14.5 h. The reaction mixture was quenched with saturated aqueous NH₄Cl (20 mL) and extracted with EtOAc (50 mL×3). The combined organic layers were dried over Na₂SO₄ and concentrated under reduced pressure to afford (2-(methoxy-d₃)pyridin-3-yl)boronic acid (2 g) of sufficient purity for the subsequent step.

A mixture of 5-(3-((tert-butyldimethylsilyl)oxy)propoxy)-3-methyl-4-nitro-1H-pyrazole (600 mg, 1.90 mmol), (2-(methoxy-d₃)pyridin-3-yl)boronic acid (890 mg, 5.71 mmol), Cu(OAc)₂ (518 mg, 2.85 mmol), pyridine (602 mg, 7.61 mmol) and 4 Å MS (600 mg) in DCE (20 mL) was degassed and purged with O₂×3. The mixture was stirred at 50° C. for 15 h under an O₂-atmosphere, Additional (2-(methoxy-d₃)pyridin-3-yl)boronic acid (890 mg, 5.71 mmol) was added to the mixture and the reaction was stirred at 50° C. for another 15 h. The reaction mixture was concentrated under reduced pressure. The residue was purified by chromatography on silica gel (eluent: petroleum ether:EtOAc 100:0→70:30) to afford 3-(3-(3-((tert-butyldimethylsilyl)oxy)propoxy)-5-methyl-4-nitro-1H-pyrazol-1-yl)-2-(methoxy-d₃)pyridine (700 mg) of sufficient purity for the subsequent step.

To a solution of 3-(3-(3-((tert-butyldimethylsilyl)oxy)propoxy)-5-methyl-4-nitro-1H-pyrazol-1-yl)-2-(methoxy-d₃)pyridine (690 mg, 1.62 mmol) in THF (10 mL) was added TBAF (2.4 mL, 2.4 mmol, 1 M in THF). The mixture was stirred at 20° C. for 1 h. The reaction mixture was concentrated under reduced pressure. The residue was purified by chromatography on silica gel (eluent: petroleum ether:EtOAc 100:0→40:60) to afford 3-((1-(2-(methoxy-d₃)pyridin-3-yl)-5-methyl-4-nitro-1H-pyrazol-3-yl)oxy)propan-1-ol (380 mg) of sufficient purity for the subsequent step.

A solution of DIAD (721 mg, 3.57 mmol) was added to a solution of 3-((1-(2-(methoxy-d₃)pyridin-3-yl)-5-methyl-4-nitro-1H-pyrazol-3-yl)oxy)propan-1-ol (370 mg, 1.19 mmol), 3,6-dichloro-1H-pyrazolo[3,4-d]pyrimidine (225 mg, 1.19 mmol), and PPh₃ (935 mg, 3.57 mmol) in THF (20 mL) at 0° C. The mixture was stirred at 20° C. for 13 h. The reaction mixture was concentrated under reduced pressure. The residue was purified by chromatography on silica gel (eluent: petroleum ether:EtOAc 100:0→70:30) to afford 3,6-dichloro-1-(3-((1-(2-(methoxy-d₃)pyridin-3-yl)-5-methyl-4-nitro-1H-pyrazol-3-yl)oxy)propyl)-1H-pyrazolo[3,4-d]pyrimidine (310 mg) of sufficient purity for the subsequent step.

Intermediate: 3-Bromo-8-chloro-2-(2,6-dimethylpyridin-3-yl)-2,4,12,13-tetrahydro-11H-5,7-(azenometheno)dipyrazolo[3,4-b:5',1'-g][1]oxa[4,6,8]triazacycloundecine

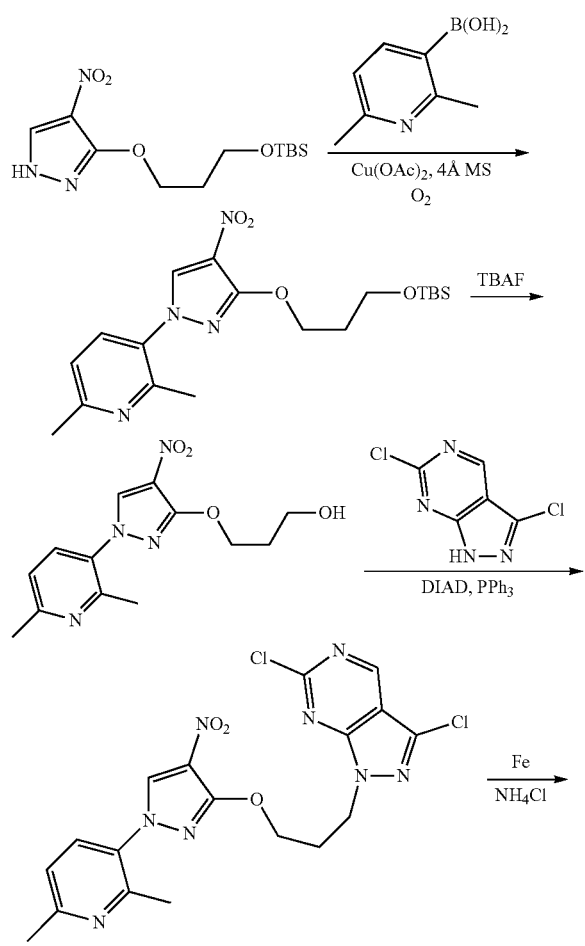

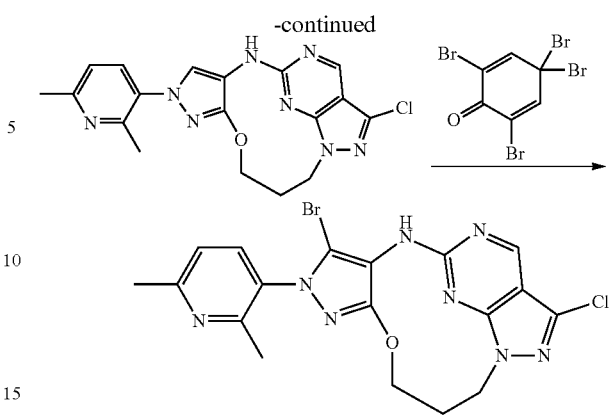

A mixture of 5-(3-((tert-butyldimethylsilyl)oxy)propoxy)-4-nitro-1H-pyrazole (1.0 g, 3.2 mmol), (2,6-dimethyl-3-pyridyl)boronic acid (1.0 g, 6.6 mmol), Cu(OAc)₂ (904 mg, 4.98 mmol), pyridine (1.05 g, 13.27 mmol), and 4 Å MS (1 g) in DCE (60 mL) was degassed and purged with oxygen× 3. The mixture was stirred at 60° C. for 16 h under an O₂-atmosphere. The mixture was concentrated under reduced pressure. The residue was purified by chromatography on silica gel (eluent: petroleum ether:EtOAc 100:0→40:60) to afford 3-(3-(3-((tert-butyldimethylsilyl)oxy)propoxy)-4-nitro-1H-pyrazol-1-yl)-2,6-dimethylpyridine (1.3 g) of sufficient purity for the subsequent step.

To a solution of 3-(3-(3-((tert-butyldimethylsilyl)oxy)propoxy)-4-nitro-1H-pyrazol-1-yl)-2,6-dimethylpyridine (1.5 g, 3.7 mmol) in THF (20 mL) was added TBAF (5.5 mL, 5.5 mmol, 1 M in THF) and the mixture was stirred at 25° C. for 1 h. The reaction mixture was concentrated under reduced pressure. The residue was purified by chromatography on silica gel (eluent: petroleum ether:EtOAc (10 v % MeOH) 100:0→50:50) to afford 3-((1-(2,6-dimethylpyridin-3-yl)-4-nitro-1H-pyrazol-3-yl)oxy)propan-1-ol (0.71 g) of sufficient purity for the subsequent step.

To a mixture of 3-((1-(2,6-dimethylpyridin-3-yl)-4-nitro-1H-pyrazol-3-yl)oxy)propan-1-ol (0.64 g, 2.19 mmol), 3,6-dichloro-1H-pyrazolo[3,4-d]pyrimidine (414 mg, 2.19 mmol), and PPh₃ (1.72 g, 6.57 mmol) in THF (40 mL) was added DIAD (1.33 g, 6.57 mmol) at 0° C. The mixture was stirred at 25° C. for 5 h. The mixture was concentrated under reduced pressure. The residue was purified by chromatography on silica gel (eluent: petroleum ether:EtOAc (10 v % MeOH and 10 v % DCM) 100:0→70:30) to afford 3,6-dichloro-1-(3-((1-(2,6-dimethylpyridin-3-yl)-4-nitro-1H-pyrazol-3-yl)oxy)propyl)-1H-pyrazolo[3,4-d]pyrimidine (0.8 g) of sufficient purity for the subsequent step.

To a mixture of 3,6-dichloro-1-(3-((1-(2,6-dimethylpyridin-3-yl)-4-nitro-1H-pyrazol-3-yl)oxy)propyl)-1H-pyrazolo[3,4-d]pyrimidine (0.70 g, 1.5 mmol) and NH₄Cl (404 mg, 7.55 mmol) in a mixture of EtOH (70 mL) and H₂O (7 mL) was added Fe (422 mg, 7.55 mmol) at 20° C. The mixture was stirred at 80° C. for 16 h. Additional NH₄Cl (400 mg) was added and the mixture was stirred at 80° C. for another 7 h. The mixture was filtered and concentrated under reduced pressure. The residue was purified by chromatography on silica gel (eluent: petroleum ether:EtOAc (10 v % DCM) 100:0→50:50) to afford 8-chloro-2-(2,6-dimethylpyridin-3-yl)-2,4,12,13-tetrahydro-11H-5,7-(azenometheno)dipyrazolo[3,4-b:5',1'-g][1]oxa[4,6,8]triazacycloundecine (0.55 g) of sufficient purity for the subsequent step.

A solution of 2,4,4,6-tetrabromocyclohexa-2,5-dien-1-one (0.38 g, 0.94 mmol) in THF (2 mL) was added dropwise to a solution of 8-chloro-2-(2,6-dimethylpyridin-3-yl)-2,4,12,13-tetrahydro-11H-5,7-(azenometheno)dipyrazolo[3,4-b:5',1'-g][1]oxa[4,6,8]triazacycloundecine (0.31 g, 0.78 mmol) in THF (60 mL) at 20° C. The mixture was stirred for 2 h at 20° C. Additional 2,4,4,6-tetrabromocyclohexa-2,5-dien-1-one (0.38 g, 0.84 mmol) in THF (2 mL) was added to the mixture and stirred for 15 h at 20° C. The mixture was concentrated under reduced pressure. The residue was purified by chromatography on silica gel (eluent: petroleum ether:EtOAc (10 v % MeOH) 100:0→50:50) followed by preparative SFC (Instrument: Berger, MULTIGRAM-II, Column: DAICEL CHIRALPAK AD 250×30 mm I.D. 10 μm, Mobile phase: supercritical $CO_2$/EtOH (0.1% $NH_3 \cdot H_2O$, v %)=40/60, Flow Rate: 80 mL/min, Column Temperature: 38° C., Nozzle Pressure: 100 bar (10 MPa), Nozzle Temperature: 60° C., Evaporator Temperature: 20° C., Trimmer Temperature: 25° C., Wavelength: 220 nm) to afford 3-bromo-8-chloro-2-(2,6-dimethylpyridin-3-yl)-2,4,12,13-tetrahydro-11H-5,7-(azenometheno)dipyrazolo[3,4-b:5',1'-g][1]oxa[4,6,8]triazacycloundecine (0.17 g) of sufficient purity for the subsequent step.

Intermediate: 3-Bromo-8-chloro-2-(2-methylpyridin-3-yl)-2,4,12,13-tetrahydro-11H-5,7-(azenometheno)dipyrazolo[3,4-b:5',1'-g][1]oxa[4,6,8]triazacycloundecine

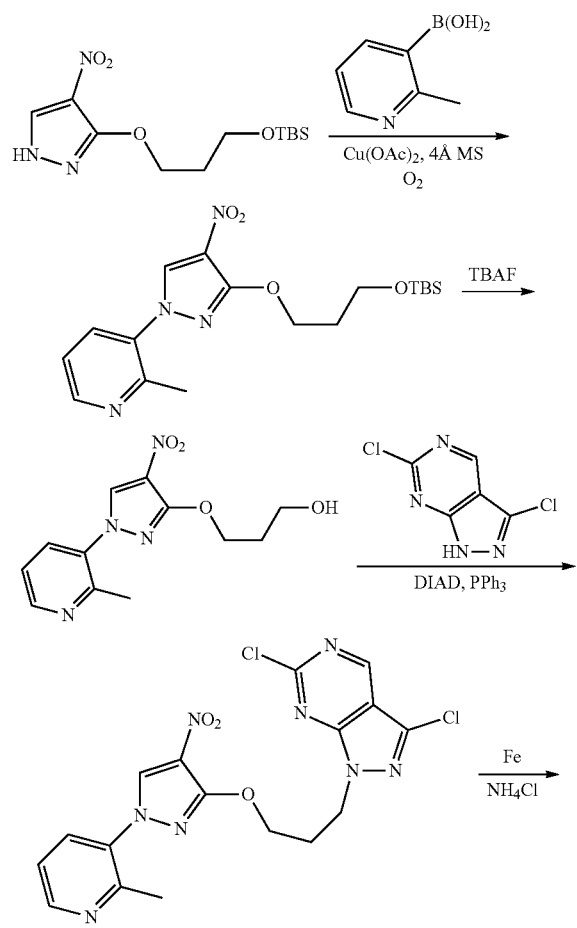

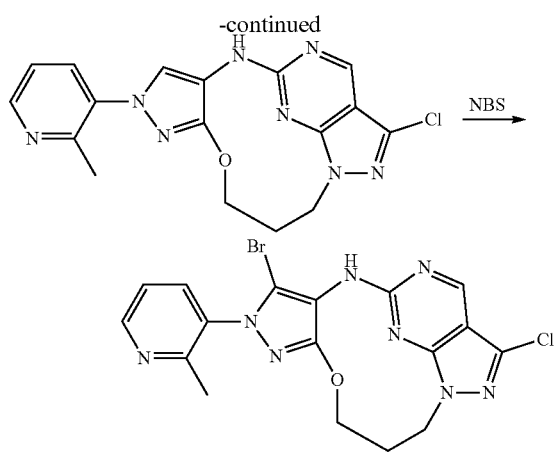

A mixture of 3-(3-((tert-butyldimethylsilyl)oxy)propoxy)-4-nitro-1H-pyrazole (8.0 g, 27 mmol), (2-methyl-3-pyridyl)boronic acid (4.36 g, 31.9 mmol), pyridine (8.40 g, 106 mmol), Cu(OAc)$_2$ (7.23 g, 39.9 mmol), and 4 Å MS (8 g) in DCE (200 mL) was degassed and purged with $O_2$×3, and then stirred at 50° C. for 15 h under an $O_2$-atmosphere. Additional (2-methyl-3-pyridyl)boronic acid (4.36 g, 3.19 mmol) was added to the mixture and the mixture was stirred at 50° C. for 15 h. The reaction mixture was concentrated under reduced pressure. The residue was purified by chromatography on silica gel (eluent: petroleum ether:EtOAc 100:0→90:10) to afford 3-(3-(3-((tert-butyldimethylsilyl)oxy)propoxy)-4-nitro-1H-pyrazol-1-yl)-2-methylpyridine (8.6 g) of sufficient purity for the subsequent step.

To a solution of 3-(3-(3-((tert-butyldimethylsilyl)oxy)propoxy)-4-nitro-1H-pyrazol-1-yl)-2-methylpyridine (8.6 g, 22 mmol) in THF (100 mL) was added TBAF (32.9 mL, 33 mmol, 1 M in THF). The mixture was stirred at 20° C. for 15 h. The reaction mixture was concentrated under reduced pressure. The residue was purified by chromatography on silica gel (eluent: petroleum ether:EtOAc 100:0→0:100) to afford 3-((1-(2-methylpyridin-3-yl)-4-nitro-1H-pyrazol-3-yl)oxy)propan-1-ol (5.3 g) of sufficient purity for the subsequent step.

A solution of DIAD (6.54 g, 32.3 mmol) was added to a solution of 3-((1-(2-methylpyridin-3-yl)-4-nitro-1H-pyrazol-3-yl)oxy)propan-1-ol (3.0 g, 11 mmol), 3,6-dichloro-1H-pyrazolo[3,4-d]pyrimidine (2.04 g, 10.8 mmol), and PPh$_3$ (8.48 g, 32.3 mmol) in THF (200 mL) at 0° C. The mixture was stirred at 20° C. for 1 h. The reaction mixture was concentrated under reduced pressure. The residue was purified by chromatography on silica gel (eluent: petroleum ether:EtOAc 100:0→20:80) to afford 3,6-dichloro-1-(3-((1-(2-methylpyridin-3-yl)-4-nitro-1H-pyrazol-3-yl)oxy)propyl)-1H-pyrazolo[3,4-d]pyrimidine (12 g) of sufficient purity for the subsequent step. All the above material was dissolved in EtOH (300 mL) and H$_2$O (30 mL). Fe (7.46 g, 134 mmol) and NH$_4$Cl (7.20 g, 134 mmol) were added. The mixture was stirred at 80° C. for 15 h. The reaction mixture was concentrated under reduced pressure. The residue was purified by chromatography on silica gel (eluent: petroleum ether:EtOAc 100:0→0:100) and triturated with MeOH (20 mL) to afford 8-chloro-2-(2-methylpyridin-3-yl)-2,4,12,13-tetrahydro-11H-5,7-(azenometheno)dipyrazolo[3,4-b:5',1'-g][1]oxa[4,6,8]triazacycloundecine (1.5 g) of sufficient purity for the subsequent step.

A solution of NBS (391 mg, 2.19 mmol) in THF (10 mL) was added dropwise to a solution of 8-chloro-2-(2-methylpyridin-3-yl)-2,4,12,13-tetrahydro-11H-5,7-(azenometheno)dipyrazolo[3,4-b:5',1'-g][1]oxa[4,6,8]triazacycloundecine (700 mg, 1.83 mmol) in THF (100 mL) at 20° C. The mixture was stirred at 20° C. for 15 h. Additional NBS (160 mg, 0.899 mmol) was added to the mixture and the mixture was stirred at 20° C. for 3 h. The reaction mixture was concentrated under reduced pressure. The residue was purified by chromatography on silica gel (eluent: petroleum ether:EtOAc 100:0→0:100) to afford 3-bromo-8-chloro-2-(2-methylpyridin-3-yl)-2,4,12,13-tetrahydro-11H-5,7-(azenometheno)dipyrazolo[3,4-b:5',1'-g][1]oxa[4,6,8]triazacycloundecine (320 mg) of sufficient purity for the subsequent step.

Intermediate: 3-Bromo-8-chloro-2-(2,5-dimethylpyridin-3-yl)-2,4,12,13-tetrahydro-11H-5,7-(azenometheno)dipyrazolo[3,4-b:5',1'-g][1]oxa[4,6,8]triazacycloundecine

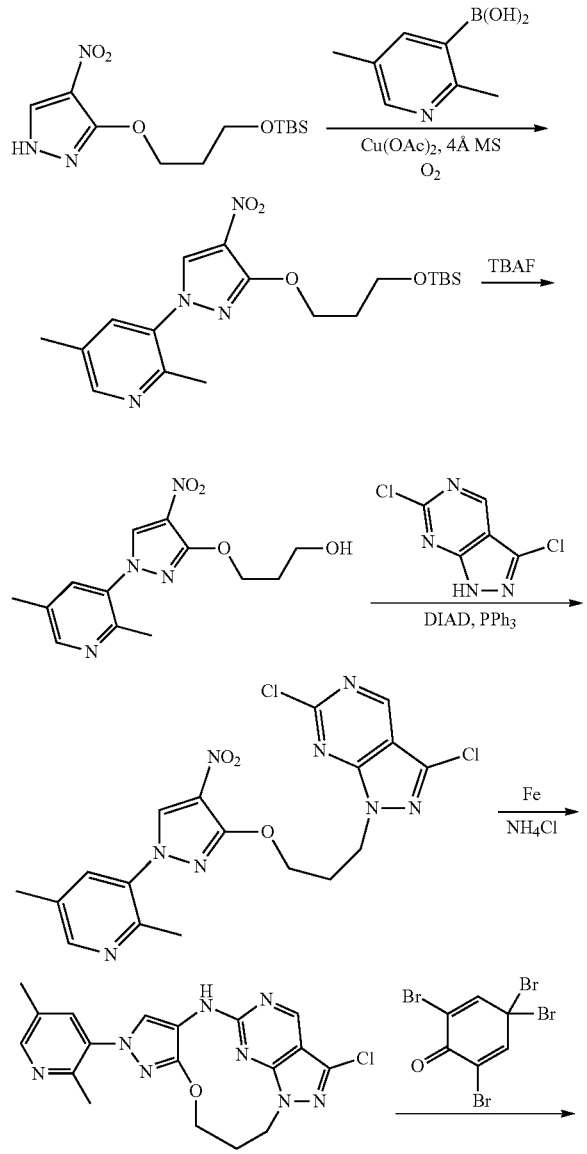

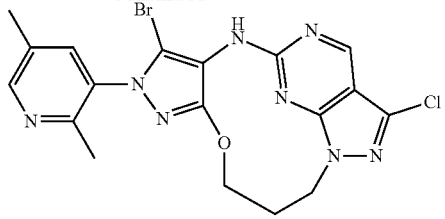

A mixture of 3-(3-(((tert-butyldimethylsilyl)oxy)propoxy)-4-nitro-1H-pyrazole (2.0 g, 6.6 mmol), (2,5-dimethylpyridin-3-yl)boronic acid (1.20 g, 7.96 mmol), Cu(OAc)$_2$ (1.81 g, 9.95 mmol), pyridine (2.10 g, 26.5 mmol), and 4 Å MS (2 g) in DCE (100 mL) was degassed and purged with O$_2$×3 and stirred at 50° C. for 16 h under an O$_2$-atmosphere. To the mixture was added (2,5-dimethylpyridin-3-yl)boronic acid (1 g) and stirred at 50° C. for another 16 h. The mixture was concentrated under reduced pressure. The residue was purified by chromatography on silica gel (eluent: petroleum ether:EtOAc 100:0→85:15) to afford 3-(3-(3-((tert-butyldimethylsilyl)oxy)propoxy)-4-nitro-1H-pyrazol-1-yl)-2,5-dimethylpyridine (2.5 g) of sufficient purity for the subsequent step.

To a solution of 3-(3-(3-((tert-butyldimethylsilyl)oxy)propoxy)-4-nitro-1H-pyrazol-1-yl)-2,5-dimethylpyridine (2.5 g, 6.2 mmol) in THF (30 mL) was added TBAF (9.2 mL, 9.2 mmol, 1 M in THF). The mixture was stirred at 20° C. for 2 h. The mixture was concentrated under reduced pressure. The residue was purified by chromatography on silica gel (eluent: petroleum ether:EtOAc 100:0→0:100) to afford 3-((1-(2,5-dimethylpyridin-3-yl)-4-nitro-1H-pyrazol-3-yl)oxy)propan-1-ol (1.6 g) of sufficient purity for the subsequent step.

A mixture of 3-((1-(2,5-dimethylpyridin-3-yl)-4-nitro-1H-pyrazol-3-yl)oxy)propan-1-ol (1.6 g, 5.5 mmol), 3,6-dichloro-1H-pyrazolo[3,4-d]pyrimidine (1.03 g, 5.47 mmol), PPh$_3$ (2.87 g, 10.95 mmol), and DIAD (2.21 g, 10.95 mmol) in THF (50 mL) was degassed and purged with N$_2$×3 and stirred at 20° C. for 1 h. The mixture was concentrated under reduced pressure. The residue was purified by chromatography on silica gel (eluent: petroleum ether:EtOAc 100:0→50:50) to afford 3,6-dichloro-1-(3-((1-(2,5-dimethylpyridin-3-yl)-4-nitro-1H-pyrazol-3-yl)oxy)propyl)-1H-pyrazolo[3,4-d]pyrimidine (4.5 g) of sufficient purity for the subsequent step.

To a solution of 3,6-dichloro-1-(3-((1-(2,5-dimethylpyridin-3-yl)-4-nitro-1H-pyrazol-3-yl)oxy)propyl)-1H-pyrazolo[3,4-d]pyrimidine (4 g, 8.6 mmol) in EtOH (300 mL) was added Fe (2.41 g, 43.2 mmol) and a solution of NH$_4$Cl (2.31 g, 43.2 mmol) in H$_2$O (10 mL). The mixture was stirred at 80° C. for 16 h. The mixture was concentrated under reduced pressure. The residue was purified by chromatography on silica gel (eluent: petroleum ether:EtOAc 100:0→0:100) to afford 8-chloro-2-(2,5-dimethylpyridin-3-yl)-2,4,12,13-tetrahydro-11H-5,7-(azenometheno)dipyrazolo[3,4-b:5',1'-g][1]oxa[4,6,8]triazacycloundecine (850 mg) of sufficient purity for the subsequent step.

To a solution of 8-chloro-2-(2,5-dimethylpyridin-3-yl)-2,4,12,13-tetrahydro-11H-5,7-(azenometheno)dipyrazolo[3,4-b:5',1'-g][1]oxa[4,6,8]triazacycloundecine (450 mg, 1.13 mmol) in THF (15 mL) was added a solution of 2,4,4,6-tetrabromocyclohexa-2,5-dien-1-one (563 mg, 1.37 mmol) in THF (5 mL). The mixture was stirred at 20° C. for 16 hours. Additional 2,4,4,6-tetrabromocyclohexa-2,5-dien-1-one (270 mg, 0.659 mmol) in THF (1 mL) was added and the reaction was stirred at 20° C. for 16 h. The mixture was concentrated under reduced pressure. The residue was purified by chromatography on silica gel (eluent: petroleum ether:EtOAc 100:0→0:100) to afford 3-bromo-8-chloro-2-(2,5-dimethylpyridin-3-yl)-2,4,12,13-tetrahydro-11H-5,7-(azenometheno)dipyrazolo[3,4-b:5',1'-g][1]oxa[4,6,8]triazacycloundecine (220 mg) of sufficient purity for the subsequent step.

Intermediate: 3-Bromo-8-chloro-2-(2-methoxypyridin-3-yl)-2,4,12,13-tetrahydro-11H-5,7-(azenometheno)dipyrazolo[3,4-b:5',1'-g][1]oxa[4,6,8]triazacycloundecine

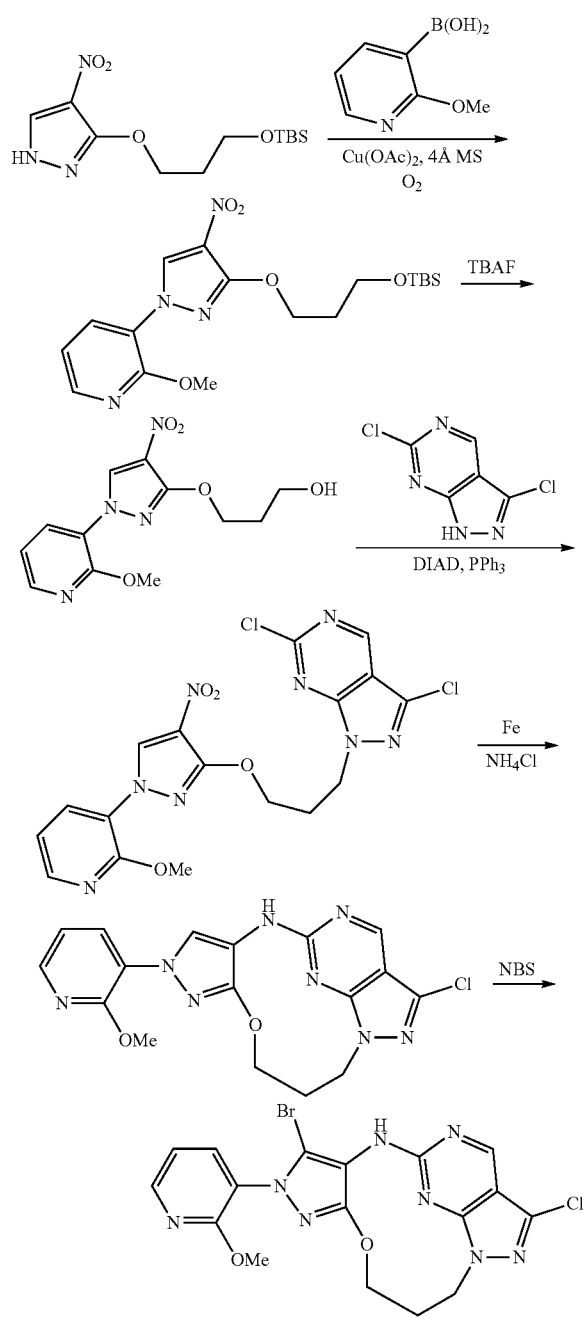

A mixture of 5-(3-((tert-butyldimethylsilyl)oxy)propoxy)-4-nitro-1H-pyrazole (5.0 g, 17 mmol), (2-methoxy-3-pyridyl)boronic acid (3.04 g, 19.9 mmol), Cu(OAc)₂ (4.52 g, 24.9 mmol), pyridine (5.25 g, 66.4 mmol) and 4 Å MS (5 g) in DCE (100 mL) was degassed and purged with O₂×3 and stirred at 50° C. for 16 h under an O₂-atmosphere. To the mixture was added (2-methoxy-3-pyridyl)boronic acid(2 g) and stirred at 50° C. for 16 h. The mixture was concentrated under reduced pressure. The residue was purified by chromatography on silica gel (eluent: petroleum ether:EtOAc 100:0→85:15) to afford 3-(3-(3-((tert-butyldimethylsilyl)oxy)propoxy)-4-nitro-1H-pyrazol-1-yl)-2-methoxypyridine (5.4 g) of sufficient purity for the subsequent step.

To a solution of 3-(3-(3-((tert-butyldimethylsilyl)oxy)propoxy)-4-nitro-1H-pyrazol-1-yl)-2-methoxypyridine (5.4 g, 13 mmol) in THF (40 mL) was added TBAF (19.8 mL, 20 mmol, 1 M in THF). The mixture was stirred at 25° C. for 2 h. The mixture was concentrated under reduced pressure. The residue was purified by chromatography on silica gel (eluent: petroleum ether:EtOAc 100:0→50:50) to afford 3-((1-(2-methoxypyridin-3-yl)-4-nitro-1H-pyrazol-3-yl)oxy)propan-1-ol (3.6 g) of sufficient purity for the subsequent step.

A mixture of 3-[1-(2-methoxy-3-pyridyl)-4-nitro-pyrazol-3-yl]oxypropan-1-ol (3.6 g, 12 mmol), 3,6-dichloro-1H-pyrazolo[3,4-d]pyrimidine (2.31 g, 12.2 mmol), PPh₃ (9.63 g, 36.7 mmol), and DIAD(7.42 g, 36.7 mmol) in THF (100 mL) was stirred at 25° C. for 3 h. The mixture was concentrated under reduced pressure. The residue was purified by chromatography on silica gel (eluent: petroleum ether:EtOAc 100:0→70:30) to afford 3,6-dichloro-1-(3-((1-(2-methoxypyridin-3-yl)-4-nitro-1H-pyrazol-3-yl)oxy)propyl)-1H-pyrazolo[3,4-d]pyrimidine of sufficient purity for the subsequent step.

To a solution of 3,6-dichloro-1-(3-((1-(2-methoxypyridin-3-yl)-4-nitro-1H-pyrazol-3-yl)oxy)propyl)-1H-pyrazolo[3,4-d]pyrimidine (2.4 g, 5.2 mmol) and Fe (1.44 g, 25.8 mmol) in EtOH (400 mL) was added a solution of NH₄Cl (1.38 g, 25.8 mmol) in H₂O (100 mL). The mixture was stirred at 80° C. for 16 h. Additional NH₄Cl (1.4 g, 26 mmol) was added and the mixture was stirred at 80° C. for another 16 h. A final portion of NH₄Cl (0.3 g, 6 mmol) was added and the mixture was stirred at 80° C. for 16 h. The mixture was concentrated under reduced pressure. The residue was purified by chromatography on silica gel (eluent: petroleum ether:EtOAc 100:0→0:100) to afford 8-chloro-2-(2-methoxypyridin-3-yl)-2,4,12,13-tetrahydro-11H-5,7-(azenometheno)dipyrazolo[3,4-b:5',1'-g][1]oxa[4,6,8]triazacycloundecine (240 mg) of sufficient purity for the subsequent step.

To a solution of 8-chloro-2-(2-methoxypyridin-3-yl)-2,4,12,13-tetrahydro-11H-5,7-(azenometheno)dipyrazolo[3,4-b:5',1'-g][1]oxa[4,6,8]triazacycloundecine (330 mg, 0.83 mmol) in THF (34 mL) was added NBS (177 mg, 0.99 mmol). The mixture was stirred at 20° C. for 16 h. A solution of NBS (90 mg, 0.51 mmol) in THF (1 mL) was added, the mixture was stirred at 20° C. for another 16 h. Finally, a solution of NBS (60 mg, 0.33 mmol) in THF (0.5 mL) was added and the mixture was stirred at 20° C. for 16 h. The mixture was concentrated under reduced pressure. The residue was purified by chromatography on silica gel (eluent: petroleum ether:EtOAc 100:0→40:60) to afford 3-bromo-8-chloro-2-(2-methoxypyridin-3-yl)-2,4,12,13-tetrahydro-11H-5,7-(azenometheno)dipyrazolo[3,4-b:5',1'-g][1]oxa[4,6,8]triazacycloundecine (150 mg) of sufficient purity for the subsequent step.

Intermediate: 3-Bromo-8-chloro-2-(5-fluoro-2-methoxypyridin-3-yl)-2,4,12,13-tetrahydro-11H-5,7-(azenometheno)dipyrazolo[3,4-b:5',1'-g][1]oxa[4,6,8]triazacycloundecine

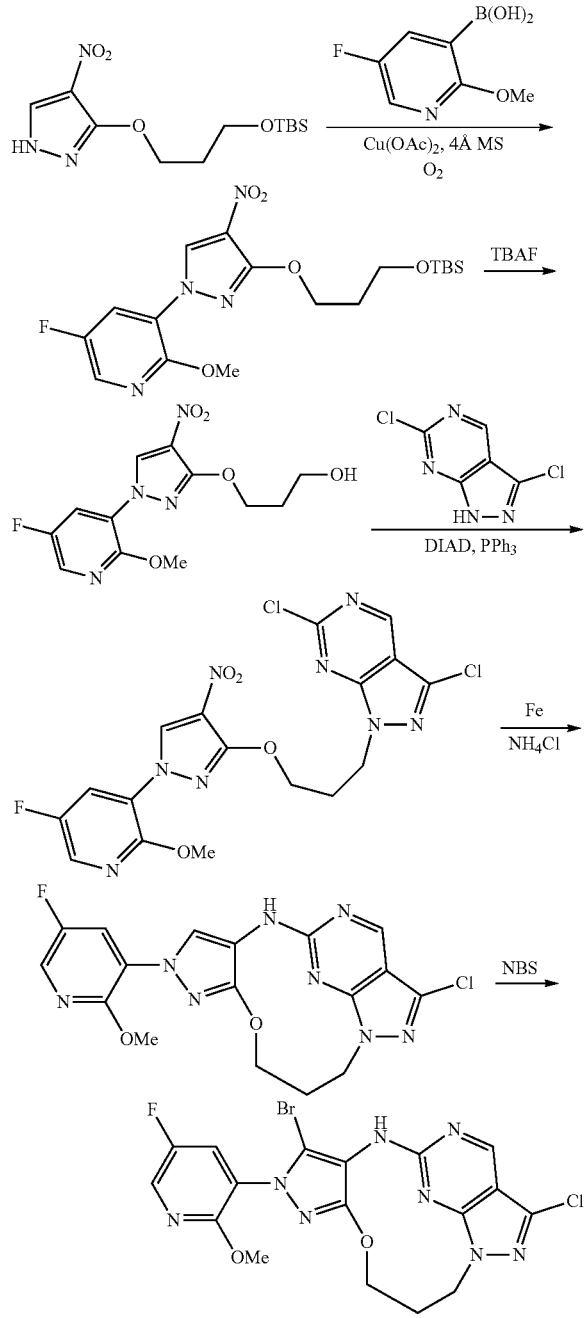

A mixture of 3-(3-((tert-butyldimethylsilyl)oxy)propoxy)-4-nitro-1H-pyrazole (3.0 g, 10 mmol), (5-fluoro-2-methoxy-3-pyridyl)boronic acid (1.7 g, 10 mmol), Cu(OAc)$_2$ (2.71 g, 14.9 mmol), pyridine (3.15 g, 39.8 mmol), and 4 Å MS (3 g) in DCE (60 mL) was degassed and purged with oxygen×3 and stirred at 50° C. for 16 h under an O$_2$-atmosphere. Additional (5-fluoro-2-methoxy-3-pyridyl)boronic acid (1.7 g) was added to the mixture and the reaction was stirred at 50° C. for 16 h. The mixture was concentrated under reduced pressure. The residue was purified by chromatography on silica gel (eluent: petroleum ether:EtOAc 100:0→70:30) to afford 3-(3-(3-((tert-butyldimethylsilyl)oxy)propoxy)-4-nitro-1H-pyrazol-1-yl)-5-fluoro-2-methoxypyridine (2.8 g) of sufficient purity for the subsequent step.

To a solution of 3-(3-(3-((tert-butyldimethylsilyl)oxy)propoxy)-4-nitro-1H-pyrazol-1-yl)-5-fluoro-2-methoxypyridine (4.7 g, 11 mmol) in THF (50 mL) was added TBAF (16.5 mL, 17 mmol, 1 M in THF) and stirred at 25° C. for 1 h. The reaction mixture was concentrated under reduced pressure. The residue was purified by chromatography on silica gel (eluent: petroleum ether:EtOAc (10 v % MeOH) 100:0→50:50) to afford 3-((1-(5-fluoro-2-methoxypyridin-3-yl)-4-nitro-1H-pyrazol-3-yl)oxy)propan-1-ol (3.3 g) of sufficient purity for the subsequent step.

To a mixture of 3-((1-(5-fluoro-2-methoxypyridin-3-yl)-4-nitro-1H-pyrazol-3-yl)oxy)propan-1-ol (1.65 g, 5.28 mmol), 3,6-dichloro-1H-pyrazolo[3,4-d]pyrimidine (1 g, 5.28 mmol), and PPh$_3$ (4.16 g, 15.9 mmol) in THF (200 mL) was added DIAD (3.21 g, 15.9 mmol) at 0° C. The mixture was stirred at 25° C. for 15 h. The mixture was concentrated under reduced pressure. The residue was purified by chromatography on silica gel (eluent: petroleum ether:EtOAc (10 v % MeOH, 10 v % DCM) 100:0→70:30) to afford 3,6-dichloro-1-(3-((1-(5-fluoro-2-methoxypyridin-3-yl)-4-nitro-1H-pyrazol-3-yl)oxy)propyl)-1H-pyrazolo[3,4-d]pyrimidine (3 g) of sufficient purity for the subsequent step.

To a mixture of 3,6-dichloro-1-(3-((1-(5-fluoro-2-methoxypyridin-3-yl)-4-nitro-1H-pyrazol-3-yl)oxy)propyl)-1H-pyrazolo[3,4-d]pyrimidine (1.2 g, 2.5 mmol) and NH$_4$Cl (598 mg, 11.2 mmol) in a mixture of EtOH (120 mL) and H$_2$O (12 mL) was added Fe (624 mg, 11.2 mmol) at 20° C. The mixture was stirred at 80° C. for 16 h. Additional NH$_4$Cl (600 mg, 11.2 mmol) was added to the mixture and the reaction was stirred at 80° C. for another 16 h. The mixture was filtered and concentrated under reduced pressure. The residue was purified by chromatography on silica gel (eluent: petroleum ether:EtOAc (10 v % DCM) 100:0→50:50) to afford 8-chloro-2-(5-fluoro-2-methoxypyridin-3-yl)-2,4,12,13-tetrahydro-11H-5,7-(azenometheno)dipyrazolo[3,4-b:5',1'-g][1]oxa[4,6,8]triazacycloundecine (0.7 g) of sufficient purity for the subsequent step.

A solution of NBS (164 mg, 0.92 mmol) in CHCl$_3$ (5 mL) was added dropwise to a solution of 8-chloro-2-(5-fluoro-2-methoxypyridin-3-yl)-2,4,12,13-tetrahydro-11H-5,7-(azenometheno)dipyrazolo[3,4-b:5',1'-g][1]oxa[4,6,8]triazacycloundecine (0.32 g, 0.77 mmol) in CHCl$_3$ (35 mL) at 25° C. The mixture was stirred for 16 h at 25° C. Additional NBS (100 mg, 0.562 mmol) in CHCl$_3$ (2 mL) was added in a dropwise manner and the mixture was stirred at 25° C. for 16 h. The mixture was concentrated under reduced pressure. The residue was purified by chromatography on silica gel (eluent: petroleum ether:EtOAc (10 v % MeOH, 10 v % DCM) 100:0→80:20) followed by SFC (Instrument: Thar SFC Prep 80, Column: DAICEL CHIRALCEL OD-H 250× 30 mm I.D. 5 μm, Mobile phase: supercritical CO$_2$/EtOH (0.1% NH$_3$·H$_2$O, v %)=70/30, Flow Rate: 80 mL/min, Column Temperature: 38° C., Nozzle Pressure: 100 bar (10 MPa), Nozzle Temperature: 60° C., Evaporator Temperature: 20° C., Trimmer Temperature: 25° C., Wavelength: 220 nm) to afford 3-bromo-8-chloro-2-(5-fluoro-2-methoxypyridin-3-yl)-2,4,12,13-tetrahydro-11H-5,7-(azenometheno)dipyrazolo[3,4-b:5',1'-g][1]oxa[4,6,8]triazacycloundecine (0.3 g) of sufficient purity for the subsequent step.

131

Intermediate: 3-Bromo-8-chloro-2-(5-fluoro-2-methylpyridin-3-yl)-2,4,12,13-tetrahydro-11H-5,7-(azenometheno)dipyrazolo[3,4-b:5',1'-g][1]oxa[4,6,8]triazacycloundecine

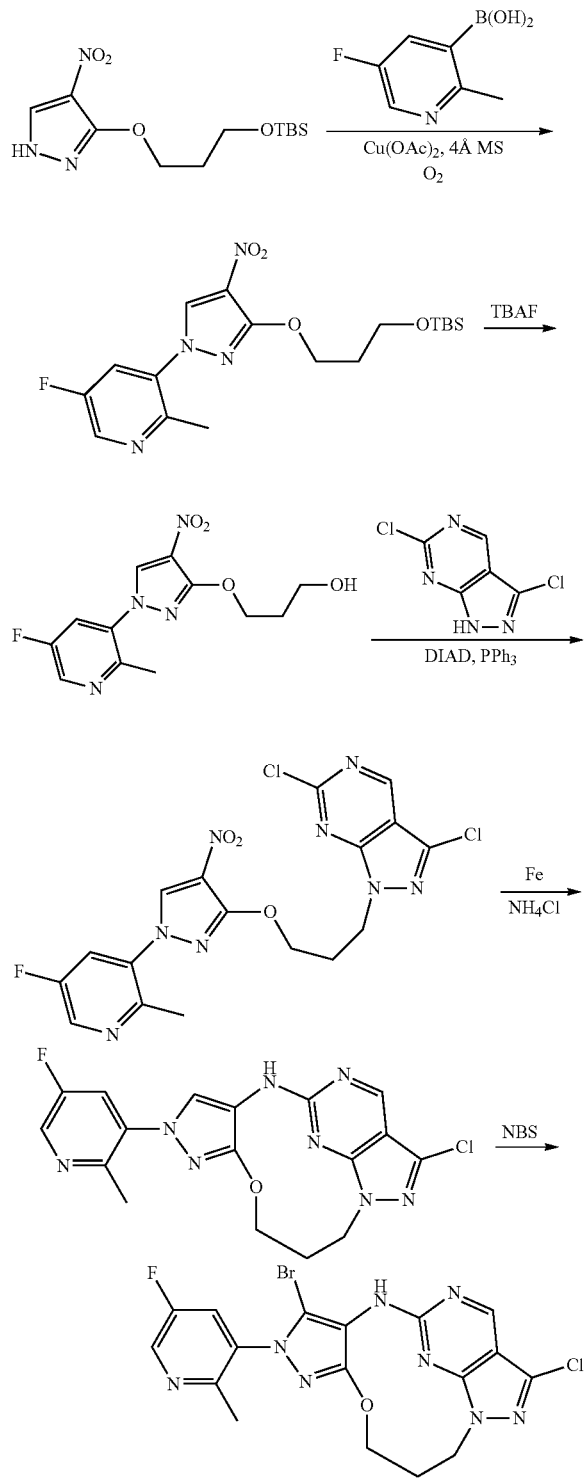

A mixture of 3-(3-((tert-butyldimethylsilyl)oxy)propoxy)-4-nitro-1H-pyrazole (6.0 g, 20 mmol), (5-fluoro-2-methylpyridin-3-yl)boronic acid (3.39 g, 21.9 mmol), Cu(OAc)₂ (5.42 g, 29.9 mmol), pyridine (6.30 g, 79.6 mmol) and 4 Å MS (6 g) in DCE (60 mL) was degassed and purged with O₂×3 and the mixture was stirred at 50° C. for 16 h under an O₂-atmosphere. Additional (5-fluoro-2-methylpyridin-3-yl)boronic acid (1.0 g, 6.5 mmol) was added and the mixture was stirred at 50° C. for another 16 h. The mixture was concentrated under reduced pressure. The residue was purified by chromatography on silica gel (eluent: petroleum ether:EtOAc 100:0→80:20) to afford 3-(3-(3-((tert-butyldimethylsilyl)oxy)propoxy)-4-nitro-1H-pyrazol-1-yl)-2-methoxypyridine (5.8 g) of sufficient purity for the subsequent step.

To a solution of 3-(3-(3-((tert-butyldimethylsilyl)oxy)propoxy)-4-nitro-1H-pyrazol-1-yl)-2-methoxypyridine (5.8 g, 14 mmol) in THF (60 mL) was added TBAF (21.2 mL, 21 mmol, 1 M in THF). The mixture was stirred at 20° C. for 1 h. The mixture was concentrated under reduced pressure. The residue was purified by chromatography on silica gel (eluent: petroleum ether:EtOAc 100:0→70:30) to afford 3-[1-(5-fluoro-2-methyl-3-pyridyl)-4-nitro-pyrazol-3-yl]oxypropan-1-ol (3.05 g) of sufficient purity for the subsequent step.

To a mixture of 3-[1-(5-fluoro-2-methyl-3-pyridyl)-4-nitro-pyrazol-3-yl]oxypropan-1-ol (2.9 g, 10 mmol), 3,6-dichloro-1H-pyrazolo[3,4-d]pyrimidine (1.85 g, 9.79 mmol), and PPh₃ (7.70 g, 29.4 mmol) in THF (160 mL) was added DIAD (5.94 g, 29.4 mmol). The mixture was stirred at 20° C. for 0.5 h. The mixture was concentrated under reduced pressure. The residue was purified by chromatography on silica gel (eluent: petroleum ether:EtOAc 100:0→70:30) to afford 3,6-dichloro-1-(3-((1-(5-fluoro-2-methylpyridin-3-yl)-4-nitro-1H-pyrazol-3-yl)oxy)propyl)-1H-pyrazolo[3,4-d]pyrimidine (3.7 g) of sufficient purity for the subsequent step.

To a solution of 3,6-dichloro-1-(3-((1-(5-fluoro-2-methylpyridin-3-yl)-4-nitro-1H-pyrazol-3-yl)oxy)propyl)-1H-pyrazolo[3,4-d]pyrimidine (2.7 g, 5.8 mmol) in EtOH (300 mL) and H₂O (30 mL) was added Fe (1.61 g, 28.9 mmol) and NH₄Cl (1.85 g, 34.7 mmol). The mixture was stirred at 80° C. for 16 h. The mixture was concentrated under reduced pressure. The residue was purified by chromatography on silica gel (eluent: petroleum ether:EtOAc 100:0→30:70) and triturated with EtOAc to afford 8-chloro-2-(5-fluoro-2-methylpyridin-3-yl)-2,4,12,13-tetrahydro-11H-5,7-(azenometheno)dipyrazolo[3,4-b:5',1'-g][1]oxa[4,6,8]triazacycloundecine (750 mg) of sufficient purity for the subsequent step.

To a solution of 8-chloro-2-(5-fluoro-2-methylpyridin-3-yl)-2,4,12,13-tetrahydro-11H-5,7-(azenometheno)dipyrazolo[3,4-b:5',1'-g][1]oxa[4,6,8]triazacycloundecine (670 mg, 1.67 mmol) in CHCl₃ (100 mL) was added a solution of NBS (328 mg, 1.84 mmol) in CHCl₃ (50 mL) dropwise at 20° C. over 20 minutes. The mixture was stirred at 20° C. for 16 hours. Additional NBS (150 mg, 0.843 mmol) in CHCl₃ (20 mL) was added and the mixture was stirred at 20° C. for 2 h. A final solution of NBS (50 mg, 0.28 mmol) in CHCl₃ (5 mL) was added and the reaction was stirred at 20° C. for 1 hour. The mixture was washed with water (30 mL×2) and concentrated under reduced pressure. The residue was purified by chromatography on silica gel (eluent: petroleum ether:EtOAc 100:0→70:30) and triturated with EtOAc to afford 3-bromo-8-chloro-2-(5-fluoro-2-methylpyridin-3-yl)-2,4,12,13-tetrahydro-11H-5,7-(azenometheno)dipyrazolo[3,4-b:5',1'-g][1]oxa[4,6,8]triazacycloundecine (420 mg) of sufficient purity for the subsequent step.

Compounds of the Invention

Example 1: 8-Chloro-2-(2-methoxypyridin-3-yl)-3-methyl-2,4,12,13-tetrahydro-11H-5,7-(azenometheno)dipyrazolo[3,4-b:5',1'-g][1]oxa[4,6,8]triazacycloundecine

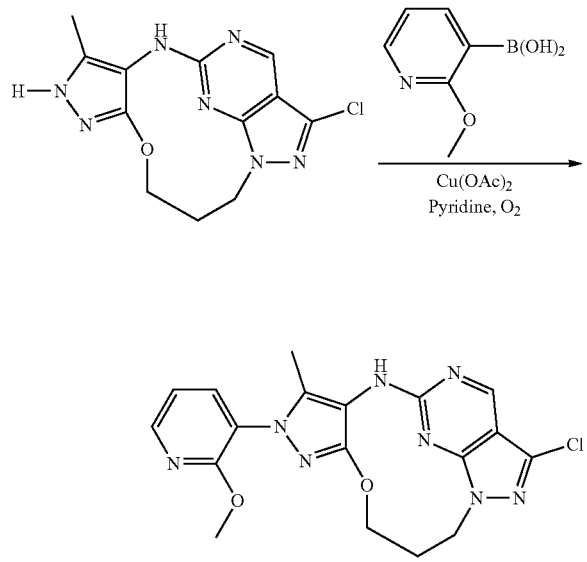

Two reactions were run in parallel at the same scale and under similar conditions: A mixture of 8-chloro-3-methyl-2,4,12,13-tetrahydro-11H-5,7-(azenometheno)dipyrazolo[3,4-b:5',1'-g][1]oxa[4,6,8]triazacycloundecine (250 mg, 0.82 mmol), (2-methoxy-3-pyridyl)boronic acid (188 mg, 1.23 mmol), Cu(OAc)$_2$ (225 mg, 1.24 mmol), pyridine (259 mg, 3.27 mmol) and 4 Å MS (250 mg) in DCE (6 mL) was degassed and purged with O$_2$ three times, and then the mixture was stirred at 65° C. for 16 h under an O$_2$-atmosphere (15 Psi). The mixture was concentrated under reduced pressure. The residue was purified by chromatography on silica gel (eluent: petroleum ether:EtOAc 100:0→0:100). The residue from the two reactions were combined and further purified by preparative SFC purification (instrument: Thar SFC Prep 80, column: DAICEL CHIRALCEL OJ (250×30 mm), particle size 10 µm, mobile phase: CO$_2$/EtOH (0.1% NH$_3$—H$_2$O, v %)=65/35, flow rate 70 mL/min, column temperature: 38° C., nozzle pressure: 100 bar (10 MPa), nozzle Temperature: 60° C., evaporator temperature: 20° C., trimmer temperature: 25° C.) to afford the title compound (70 mg). $^1$H NMR (CDCl$_3$, 400 MHz) δ 8.70 (s, 1H), 8.24 (dd, J=1.6, 5.6 Hz, 1H), 7.71 (dd, J=2.0, 7.6 Hz, 1H), 7.04 (dd, J=4.8, 7.2 Hz, 1H), 6.69 (br s, 1H), 4.58-4.52 (m, 2H), 4.51-4.47 (m, 2H), 4.00 (s, 3H), 2.18 (s, 3H), 2.08-1.79 (m, 2H). LC-MS (Method A) (m/z)=413.1 (MH)$^+$t$_R$=1.49 minutes.

Example 2: 8-Chloro-2-(2-ethoxypyridin-3-yl)-3-methyl-2,4,12,13-tetrahydro-11H-5,7-(azenometheno)dipyrazolo[3,4-b:5',1'-g][1]oxa[4,6,8]triazacycloundecine

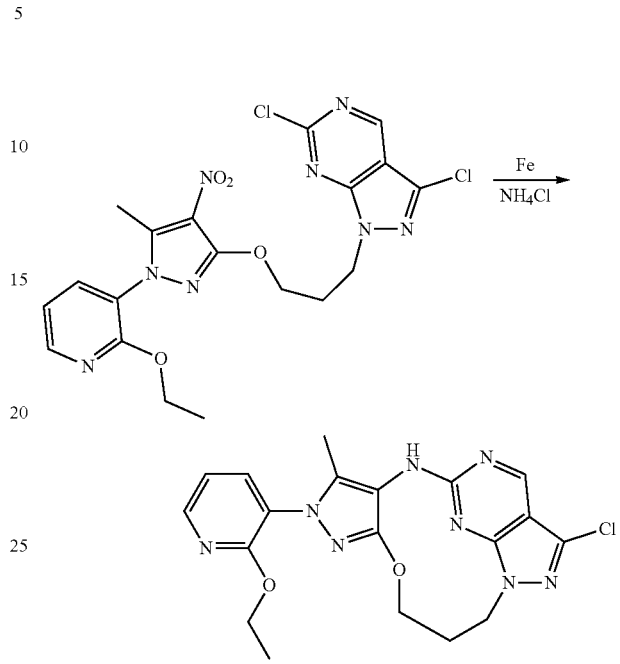

To a solution of 3,6-dichloro-1-(3-((1-(2-ethoxypyridin-3-yl)-5-methyl-4-nitro-1H-pyrazol-3-yl)oxy)propyl)-1H-pyrazolo[3,4-d]pyrimidine (160 mg, 0.32 mmol) in EtOH (16 mL) and H$_2$O (4 mL) was added Fe (91 mg, 1.62 mmol) and NH$_4$Cl (87 mg, 1.62 mmol). The resulting mixture was stirred at 80° C. for 16 h. The mixture was filtered and concentrated. The residue was purified by chromatography on silica gel (eluent: petroleum ether:EtOAc 100:0→40:60) to afford the title compound (58 mg). $^1$H NMR (DMSO-d$_6$, 400 MHz) δ 9.55 (s, 1H), 8.83 (s, 1H), 8.26 (d, J=3.6 Hz, 1H), 7.79 (d, J=7.2 Hz, 1H), 7.29-7.06 (m, 1H), 4.50-4.24 (m, 6H), 2.12 (s, 3H), 1.97-1.64 (m, 2H), 1.31 (t, J=6.8 Hz, 3H). LC-MS (Method A) (m/z)=427.2 (MH)$^+$t$_R$=1.55 minutes.

Example 3: 8-Chloro-3-methyl-2-(2-methylpyridin-3-yl)-2,4,12,13-tetrahydro-11H-5,7-(azenometheno)dipyrazolo[3,4-b:5',1'-g][1]oxa[4,6,8]triazacycloundecine

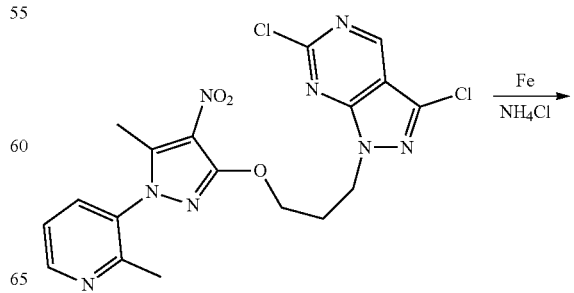

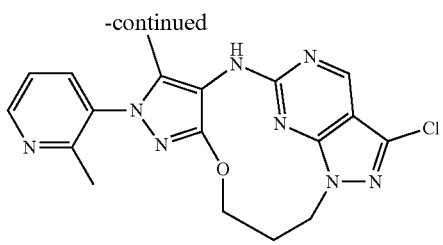

The compound was prepared in a manner similar to Example 2 using 3,6-dichloro-1-(3-((5-methyl-1-(2-methylpyridin-3-yl)-4-nitro-1H-pyrazol-3-yl)oxy)propyl)-1H-pyrazolo[3,4-d]pyrimidine (188 mg, 0.41 mmol), Fe (113 mg, 2.03 mmol), and NH$_4$Cl (109 mg, 2.03 mmol) in EtOH (20 mL) and H$_2$O (5 mL) at 80° C. for 16 h followed by work-up, purification by chromatography on silica gel (eluent: petroleum ether:EtOAc (10 v % MeOH) 100:0→15:85), and preparative SFC (Instrument: PREPSFC150Mgm, Column: DAICEL CHIRALPAK AD 250×30 mm, particle size 10 μm, mobile phase: supercritical CO$_2$/EtOH (0.1% NH$_3$·H$_2$O, v %)=40/60, flow rate: 120 mL/min, column temperature: 38° C., nozzle pressure: 100 bar (10 MPa), nozzle temperature: 60° C., evaporator temperature: 20° C., trimmer temperature: 25° C., Wavelength: 220 nm) to afford the title compound (90 mg). $^1$H NMR (CDCl$_3$, 400 MHz) δ 9.61 (s, 1H), 8.84 (s, 1H), 8.57 (dd, J=1.2, 4.8 Hz, 1H), 7.80 (dd, J=1.6, 8.0 Hz, 1H), 7.41 (dd, J=4.8, 8.0 Hz, 1H), 4.39-4.34 (m, 4H), 2.28 (s, 3H), 2.10 (s, 3H), 2.00-1.63 (m, 2H). LC-MS (Method A) (m/z)=397.1 (MH)$^+$t$_R$ 1.21 minutes.

Example 4: 8-Chloro-2-(2-ethylpyridin-3-yl)-3-methyl-2,4,12,13-tetrahydro-11H-5,7-(azenometheno)dipyrazolo[3,4-b:5',1'-g][1]oxa[4,6,8]triazacycloundecine

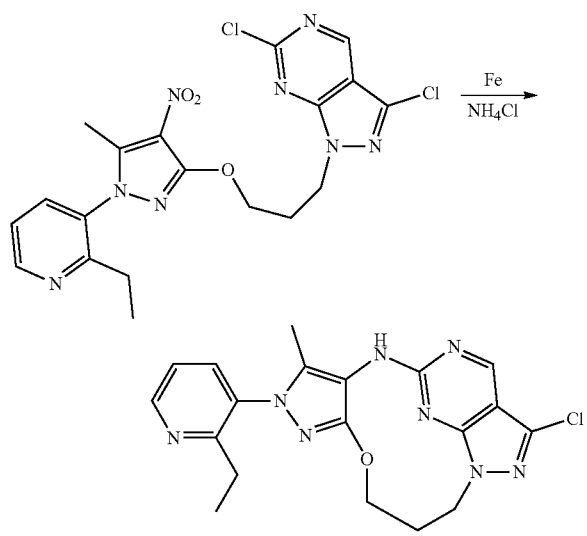

The compound was prepared in a manner similar to Example 2 using of 3,6-dichloro-1-(3-((1-(2-ethylpyridin-3-yl)-5-methyl-4-nitro-1H-pyrazol-3-yl)oxy)propyl)-1H-pyrazolo[3,4-d]pyrimidine (40 mg, 0.84 mmol), Fe (23 mg, 0.42 mmol), and NH$_4$Cl (22 mg, 0.41 mmol) in EtOH (8 mL) and H$_2$O (2 mL) at 80° C. for 16 h followed by work-up, purification by chromatography on silica gel (eluent: petroleum ether:EtOAc (10 v % MeOH) 90:10→35:65), and preparative SFC (Instrument: Thar SFC Prep 80, column: DAICEL CHIRALPAK AD 250×30 mm, particle size 10 μm, mobile phase: supercritical CO$_2$/IPA (0.1% NH$_3$·H$_2$O, v %)=60/40, flow rate: 80 mL/min, column temperature: 38° C., nozzle pressure: 100 bar (10 MPa), nozzle temperature: 60° C., evaporator temperature: 20° C., trimmer temperature: 25° C., wavelength: 220 nm) to afford the title compound (15 mg). $^1$H NMR (CDCl$_3$, 400 MHz,) δ 8.71 (s, 1H), 8.67 (dd, J=1.2, 4.8 Hz, 1H), 7.60 (dd, J=1.2, 8.0 Hz, 1H), 7.31-7.28 (m, 1H), 6.73 (br s, 1H), 4.55-4.46 (m, 4H), 2.68 (q, J=7.6 Hz, 2H), 2.14 (s, 3H), 2.04-1.92 (m, 2H), 1.26 (t, J=7.6 Hz, 3H). LC-MS (Method A) (m/z)= 411.1 (MH)$^+$t$_R$=1.32 minutes.

Example 5: 8-Chloro-3-ethyl-2-(2-methoxypyridin-3-yl)-2,4,12,13-tetrahydro-11H-5,7-(azenometheno)dipyrazolo[3,4-b:5',1'-g][1]oxa[4,6,8]triazacycloundecine

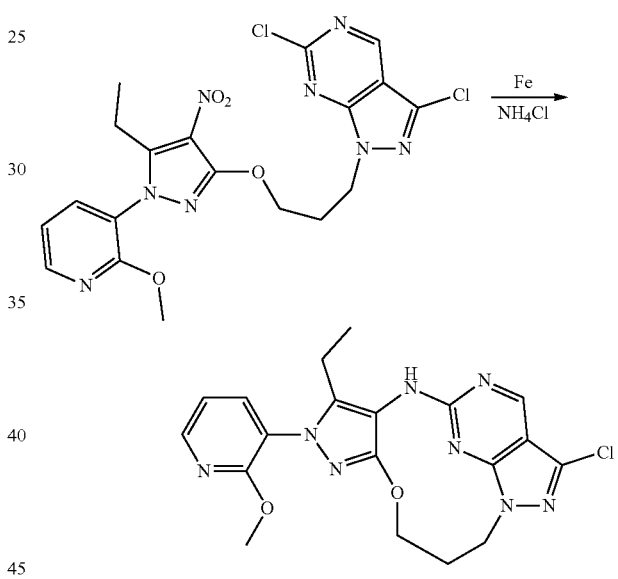

The compound was prepared in a manner similar to Example 2 using 3,6-dichloro-1-(3-((5-ethyl-1-(2-methoxypyridin-3-yl)-4-nitro-1H-pyrazol-3-yl)oxy)propyl)-1H-pyrazolo[3,4-d]pyrimidine (240 mg, 0.48 mmol), Fe (144 mg, 2.58 mmol), and NH$_4$Cl (144 mg, 2.69 mmol) in EtOH (20 mL) and H$_2$O (5 mL) at 80° C. for 16 h followed by work-up, purification by chromatography on silica gel (eluent: petroleum ether:EtOAc 100:0→0:100), and preparative SFC (instrument: Thar SFC Prep 80, column: DAICEL CHIRALCEL OD-H 250×30 mm, particle size 5 μm, mobile phase: CO$_2$/EtOH (0.1% NH$_3$—H$_2$O, v %)=70/30, flow rate 80 mL/min, column temperature: 38° C., nozzle pressure: 100 bar (10 MPa), nozzle Temperature: 60° C., evaporator temperature: 20° C., trimmer temperature: 25° C., wavelength: 220 nm) to afford the title compound (42 mg). $^1$H NMR (CDCl$_3$, 400 MHz) δ 8.70 (s, 1H), 8.25 (dd, J=1.6, 4.8 Hz, 1H), 7.69 (dd, J=1.6, 7.6 Hz, 1H), 7.03 (dd, J=4.2, 7.6 Hz, 1H), 6.82 (br s, 1H), 4.57-4.41 (m, 4H), 3.98 (s, 3H), 2.57 (q, J=7.6 Hz, 2H), 2.07-1.86 (m, 2H), 1.12 (t, J=7.6 Hz, 3H). LC-MS (Method A)) (m/z)=427.2 (MH)$^+$t$_R$=1.53 minutes.

Example 6: 8-Chloro-2-(5-fluoro-2-methoxypyridin-3-yl)-3-methyl-2,4,12,13-tetrahydro-11H-5,7-(azenometheno)dipyrazolo[3,4-b:5',1'-g][1]oxa[4,6,8]triazacycloundecine

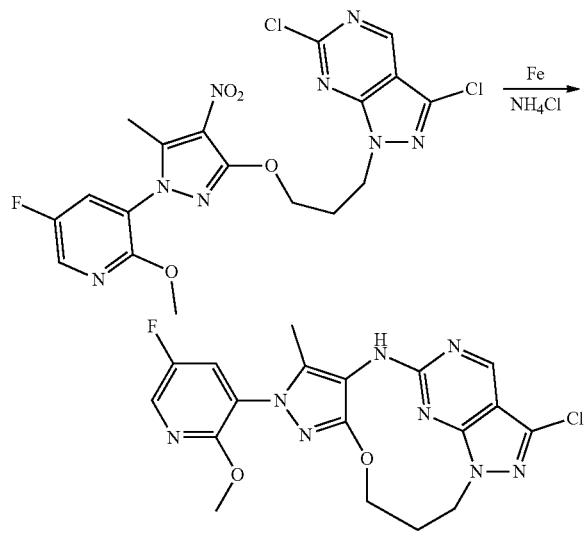

The compound was prepared in a manner similar to Example 2 using 3,6-dichloro-1-(3-((1-(5-fluoro-2-methoxypyridin-3-yl)-5-methyl-4-nitro-1H-pyrazol-3-yl)oxy)propyl)-1H-pyrazolo[3,4-d]pyrimidine (580 mg, 1.17 mmol), Fe (348 mg, 6.23 mmol), and NH$_4$Cl (348 mg, 6.51 mmol) in EtOH (30 mL) and H$_2$O (3 mL) at 80° C. for 13 h followed by work-up, purification by chromatography on silica gel (eluent: petroleum ether:EtOAc 100:0→60:40), and preparative SFC (Instrument: Thar SFC Prep 80, column: DAICEL CHIRALPAK AD 250×30 mm, particle size 10 μm, mobile phase: supercritical CO$_2$/IPA (0.1% NH$_3$·H$_2$O, v %)=75/25, flow rate: 100 mL/min, column temperature: 38° C., nozzle pressure: 100 bar (10 MPa), nozzle temperature: 60° C., evaporator temperature: 20° C., trimmer temperature: 25° C.; wavelength: 220 nm) to afford the title compound (120 mg). $^1$H NMR (CDCl$_3$, 400 MHz) δ8.70 (s, 1H), 8.10 (d, J=2.8 Hz, 1H), 7.55 (dd, J=2.8, 7.6 Hz, 1H), 6.88 (br s, 1H), 4.57-4.45 (m, 4H), 3.98 (s, 3H), 2.21 (s, 3H), 2.04-1.87 (m, 2H). LC-MS (Method A) (m/z)= 431.1 (MH)$^+$ t$_R$=1.59 minutes.

Example 7: 8-Chloro-2-(2-methoxy-4-methylpyridin-3-yl)-3-methyl-2,4,12,13-tetrahydro-11H-5,7-(azenometheno)dipyrazolo[3,4-b:5',1'-g][1]oxa[4,6,8]triazacycloundecine

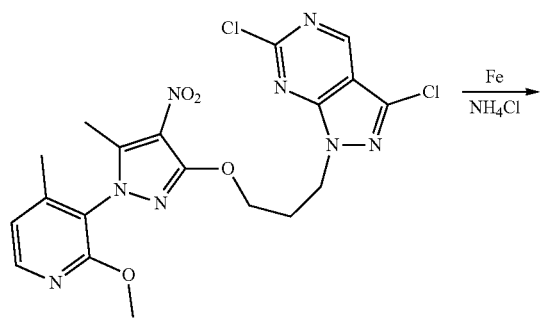

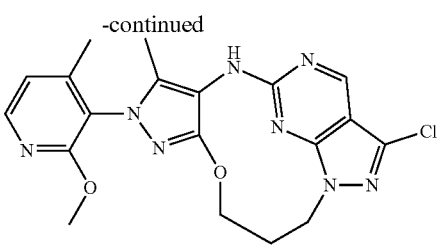

The compound was prepared in a manner similar to Example 2 using 3,6-dichloro-1-(3-((1-(2-methoxy-4-methylpyridin-3-yl)-5-methyl-4-nitro-1H-pyrazol-3-yl)oxy)propyl)-1H-pyrazolo[3,4-d]pyrimidine (240 mg, 0.49 mmol), Fe (136 mg, 2.43 mmol), and NH$_4$Cl (130 mg, 2.43 mmol) in EtOH (10 mL) and H$_2$O (1.5 mL) at 80° C. for 16 h followed by work-up, purification by chromatography on silica gel (eluent: petroleum ether:EtOAc 80:20→50:50), and preparative SFC ((Instrument: SFC-80Q, column: DAICEL CHIRALCEL OD-H (250 mm×30 mm), particle size, 5 μm, mobile phase: supercritical CO$_2$/EtOH (0.1% NH$_3$·H$_2$O, v %)=75/25, rate: 80 mL/min, column temperature: 38° C., nozzle pressure: 100 bar (10 MPa), nozzle temperature: 60° C., evaporator temperature: 20° C., trimmer temperature: 25° C., wavelength: 220 nm) to afford the title compound (50 mg). $^1$H NMR (CDCl$_3$, 400 MHz,) δ 8.70 (s, 1H), 8.10 (d, J=5.2 Hz, 1H), 6.88 (d, J=5.2 Hz, 1H), 6.75 (br s, 1H), 4.63-4.39 (m, 4H), 3.94 (s, 3H), 2.16 (s, 3H), 2.08 (s, 3H), 2.06-1.86 (m, 2H). LC-MS (Method A) (m/z)= 427.2 (MH)$^+$ t$_R$=1.51 minutes.

Example 8: 8-Chloro-3-ethyl-2-(2-methylpyridin-3-yl)-2,4,12,13-tetrahydro-11H-5,7-(azenometheno)dipyrazolo[3,4-b:5',1'-g][1]oxa[4,6,8]triazacycloundecine

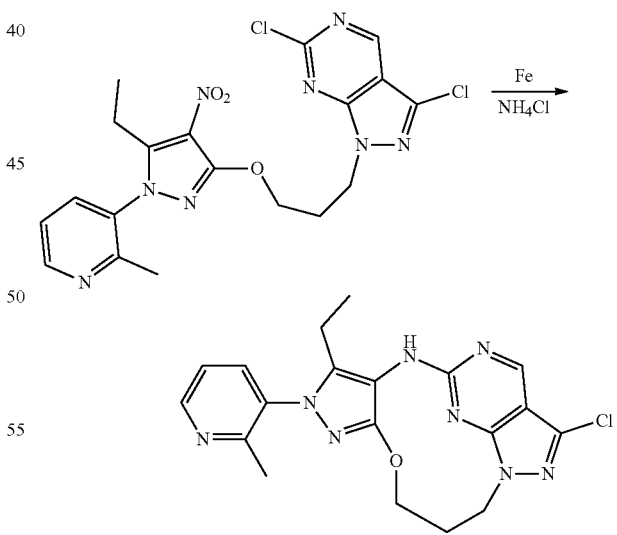

The compound was prepared in a manner similar to Example 2 using 3,6-dichloro-1-(3-((5-ethyl-1-(2-methylpyridin-3-yl)-4-nitro-1H-pyrazol-3-yl)oxy)propyl)-1H-pyrazolo[3,4-d]pyrimidine (680 mg, 1.42 mmol), Fe (408 mg, 7.31 mmol), and NH$_4$Cl (408 mg, 7.63 mmol) in EtOH (40 mL) and H$_2$O (4 mL) at 80° C. for 15 h. After stirring for 15 h, additional Fe (408 mg, 7.31 mmol) and NH$_4$Cl (408 mg, 7.63 mmol) were added and the reaction was stirred at 80° C. for 20 h, followed by work-up, purification by chromatography on silica gel (eluent: petroleum ether:EtOAc 100:0→0:100), and preparative SFC (instrument: Thar SFC Prep 80, column: DAICEL CHIRALCEL OD-H 250× 30 mm, particle size 5 μm, mobile phase: $CO_2$/EtOH (0.1% $NH_3$—$H_2O$, v %)=75/25, flow rate 70 mL/min, column temperature: 38° C., nozzle pressure: 100 bar (10 MPa), nozzle Temperature: 60° C., evaporator temperature: 20° C., trimmer temperature: 25° C., wavelength: 220 nm) to afford the title compound (100 mg). $^1$H NMR (400 MHz, $CDCl_3$) δ 8.71 (s, 1H), 8.62 (dd, J=1.6, 4.8 Hz, 1H), 7.63 (dd, J=1.6, 8.0 Hz, 1H), 7.30 (dd, J=4.8, 8.0 Hz, 1H), 6.71 (br s, 1H), 4.56-4.45 (m, 4H), 2.55 (q, J=7.6 Hz, 2H), 2.41 (s, 3H), 2.05-1.90 (m, 2H), 1.09 (t, J=7.6 Hz, 3H). LC-MS (Method A) (m/z)=411.1 $(MH)^+ t_R$=1.33 minutes.

Example 9: 8-Chloro-2-(2,6-dimethylpyridin-3-yl)-3-methyl-2,4,12,13-tetrahydro-11H-5,7-(azenometheno)dipyrazolo[3,4-b:5',1'-g][1]oxa[4,6,8]triazacycloundecine

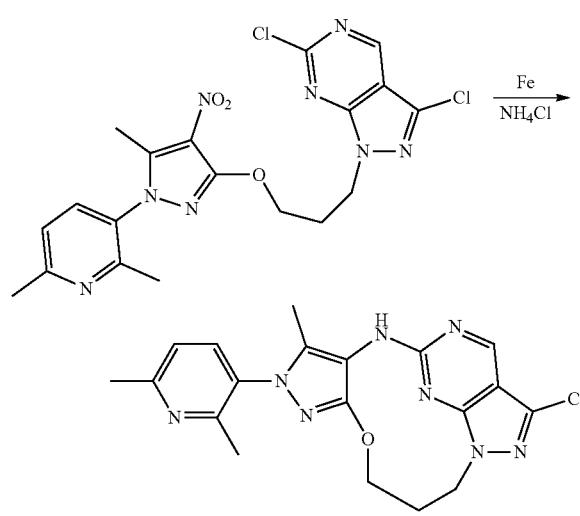

The compound was prepared in a manner similar to Example 2 using 3,6-dichloro-1-(3-((1-(2,6-dimethylpyridin-3-yl)-5-methyl-4-nitro-1H-pyrazol-3-yl)oxy)propyl)-1H-pyrazolo[3,4-d]pyrimidine (220 mg, 0.46 mmol), Fe (129 mg, 2.30 mmol), and $NH_4Cl$ (123 mg, 2.30 mmol) in EtOH (10 mL) and $H_2O$ (1.5 mL) at 80° C. for 16 h followed by work-up, purification by chromatography on silica gel (eluent: petroleum ether:EtOAc 83:17→0:100), and preparative SFC (Instrument: Thar SFC Prep 80, column: DAICEL CHIRALCEL OJ (250 mm×30 mm), particle size 10 μm, mobile phase: supercritical $CO_2$/EtOH (0.1% $NH_3 \cdot H_2O$, v %)=75/25, rate: 70 mL/min, column temperature: 38° C., nozzle pressure: 100 bar (10 MPa), nozzle temperature: 60° C., evaporator temperature: 20° C., trimmer temperature: 25° C., wavelength: 220 nm) to afford the title compound (45 mg). $^1$H NMR ($CDCl_3$, 400 MHz) δ 8.70 (s, 1H), 7.50 (d, J=8.0 Hz, 1H), 7.14 (d, J=8.0 Hz, 1H), 6.70 (br s, 1H), 4.55-4.45 (m, 4H), 2.63 (s, 3H), 2.38 (s, 3H), 2.13 (s, 3H), 2.02-1.93 (m, 2H). LC-MS (Method A) (m/z)=411.2 $(MH)^+ t_R$=1.20 minutes.

Example 10: 8-Chloro-2-(5-fluoro-2-methylpyridin-3-yl)-3-methyl-2,4,12,13-tetrahydro-11H-5,7-(azenometheno)dipyrazolo[3,4-b:5',1'-g][1]oxa[4,6,8]triazacycloundecine

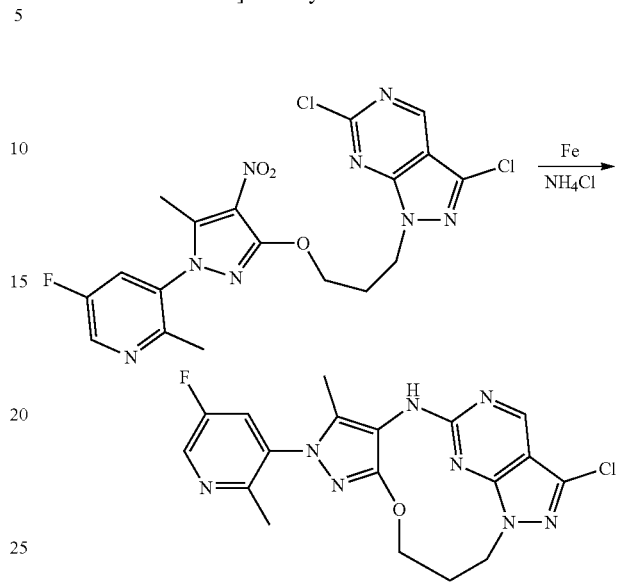

The compound was prepared in a manner similar to Example 2 using 3,6-dichloro-1-(3-((1-(5-fluoro-2-methyl pyridin-3-yl)-5-methyl-4-nitro-1H-pyrazol-3-yl)oxy)propyl)-1H-pyrazolo[[3,4-d]pyrimidine (180 mg, 0.37 mmol), Fe (104 mg, 1.87 mmol), and $NH_4Cl$ (100 mg, 1.87 mmol) in EtOH (18 mL) and $H_2O$ (1.8 mL) at 80° C. for 16 h followed by work-up, purification by chromatography on silica gel (eluent: petroleum ether:EtOAc 0:100→45:55), and preparative SFC ((Instrument: SFC-80Q, column: DAICEL CHIRALPAK AD (250 mm×30 mm), particle size 10 μm, mobile phase: supercritical $CO_2$/EtOH (0.1% $NH_3 \cdot H_2O$, v %)=50/50, flow rate: 80 mL/min, column temperature: 38° C., nozzle pressure: 100 bar (10 MPa), nozzle temperature: 60° C., evaporator temperature: 20° C., trimmer temperature: 25° C., wavelength: 220 nm) to afford the title compound (60 mg). $^1$H NMR (DSMO-$d_6$, 400 MHz) δ 9.63 (s, 1H), 8.83 (s, 1H), 8.62 (d,J=2.4 Hz, 1H), 7.95 (dd, J=2.8, 8.8 Hz, 1H), 4.45-4.35 (m, 4H) 2.27 (s, 3H), 2.13 (s, 3H), 1.87 (m, 2H). LC-MS (Method A)(m/z)=415.1$(MH)^+ t_R$=1.47 minutes.

Example 11: 8-Chloro-2-(2,5-dimethylpyridin-3-yl)-3-methyl-2,4,12,13-tetrahydro-11H-5,7-(azenometheno)dipyrazolo[3,4-b:5',1'-g][1]oxa[4,6,8]triazacycloundecine

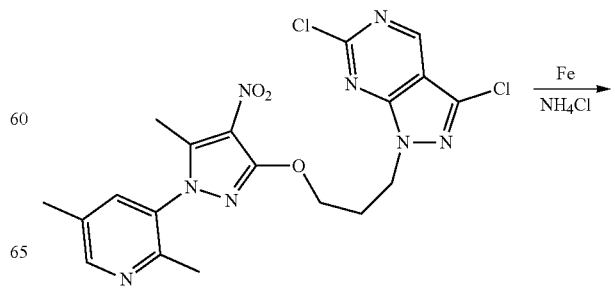

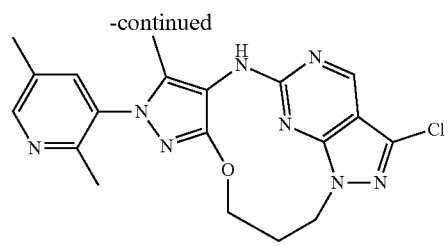

The compound was prepared in a manner similar to Example 2 using 3,6-dichloro-1-(3-((1-(2,5-dimethylpyridin-3-yl)-5-methyl-4-nitro-1H-pyrazol-3-yl)oxy)propyl)-1H-[3,4-d]pyrimidine (500 m, 1.05 mg mm ol), Fe (300, 5.37 mmol), and NH$_4$Cl (300 mg, 5.61 mmol) in EtOH (50 mL) and H$_2$O (5 mL) at 80° C. for 16 h followed by work-up, purification by chromatography on silica gel (eluent: petroleum ether:EtOAc 100:0→0:100), and preparative SFC (Instrument: Thar SFC Prep 80, Column: DAICEL CHIRALCEL OD-H (250 mm×30 mm×5 μm), Mobile phase: supercritical CO$_2$/EtOH (0.1% NH$_3$·H$_2$O, v %)=70/30, Flow Rate: 70 mL/min, Column temperature: 38° C., Nozzle pressure: 100 bar (10 MPa), Nozzle temperature: 60° C., Evaporator temperature: 20° C., Trimmer temperature: 25° C., Wavelength: 220 nm) to afford the title compound (70 mg). $^1$H NMR (CDCl$_3$, 400 MHz) δ 8.70 (s, 1H), 8.44 (s, 1H), 7.44 (s, 1H), 6.75 (br s, 1H), 4.56-4.44 (m, 4H), 2.38 (s, 3H), 2.36 (s, 3H), 2.14 (s, 3H), 2.04-1.94 (m, 2H). LC-MS (Method A) (m/z)=411.2 (MH)$^+$t$_R$ 1.23 minutes.

Example 12: 8-Chloro-2-(2-methoxy-5-methylpyridin-3-yl)-3-methyl-2,4,12,13-tetrahydro-11H-5,7-(azenometheno)dipyrazolo[3,4-b:5',1'-g][1]oxa[4,6,8]triazacycloundecine

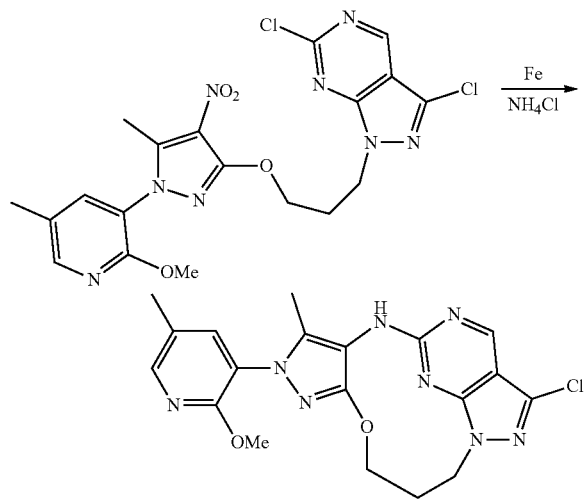

The compound was prepared in a manner similar to Example 2 using 3,6-dichloro-1-(3-((1-(2-methoxy-5-methylpyridin-3-yl)-5-methyl-4-nitro-1H-pyrazol-3-yl)oxy)propyl)-1H-pyrazolo[3,4-d]pyrimidine (500 mg, 1.01 mmol), Fe (283 mg, 5.07 mmol), and NH$_4$Cl (272 mg, 5.09 mmol) in EtOH (30 mL) and H$_2$O (3 mL) at 80° C. for 15 h followed by work-up, purification by chromatography on silica gel (eluent: petroleum ether:EtOAc 100:0→50:50), and preparative SFC (Instrument: SFC150AP, Column: DAICEL CHIRALPAK AD 250×30 mm, 10 μm, Mobile phase: supercritical CO$_2$/ETOH (0.1% NH$_3$·H$_2$O, v %)=50/50, Flow Rate: 110 mL/min, Column Temperature: 38° C., Nozzle Pressure: 100 bar (10 MPa), Nozzle Temperature: 60° C., Evaporator Temperature: 20° C., Trimmer Temperature: 25° C., Wavelength: 220 nm) to afford the title compound (95 mg). $^1$H NMR (DMSO-d$_6$, 400 MHz) δ 9.53 (s, 1H), 8.82 (s, 1H), 8.10 (d, J=1.2 Hz, 1H), 7.65 (d, J=2.0 Hz, 1H), 4.45-4.24 (m, 4H), 3.88 (s, 3H), 2.29 (s, 3H), 2.09 (s, 3H), 1.97-1.60 (m, 2H). LC-MS (Method A) (m/z)=427.2 (MH)$^+$t$_R$=1.55 minutes.

Example 13: 8-Chloro-2-(2-methoxy-6-methylpyridin-3-yl)-3-methyl-2,4,12,13-tetrahydro-11H-5,7-(azenometheno)dipyrazolo[3,4-b:5',1'-g][1]oxa[4,6,8]triazacycloundecine

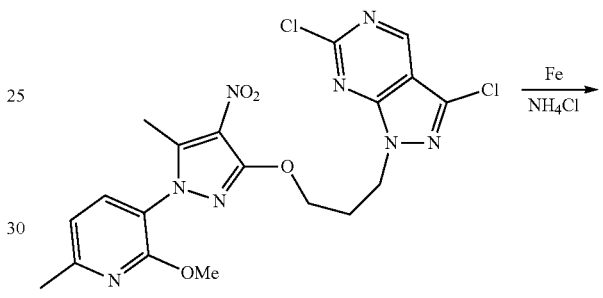

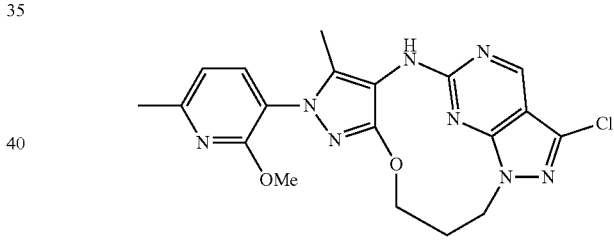

The compound was prepared in a manner similar to Example 2 using 3,6-dichloro-1-(3-((1-(2-methoxy-6-methylpyridin-3-yl)-5-methyl-4-nitro-1H-pyrazol-3-yl)oxy)propyl)-1H-pyrazolo[3,4-d]pyrimidine (1.25 g, 2.53 mmol), Fe (708 mg, 12.7 mmol), and NH$_4$Cl (678 mg, 12.7 mmol) in EtOH (100 mL) and H$_2$O (10 mL) at 80° C. for 12 h followed by work-up, purification by chromatography on silica gel (eluent: petroleum ether:EtOAc 100:0→50:50), and preparative SFC (Instrument: Berger MultiGram II, Column: DAICEL CHIRALCEL OD (250 mm×30 mm, 10 μm), Mobile phase: supercritical CO$_2$/EtOH (0.1% NH$_3$·H$_2$O, v %)=75/25, Flow Rate: 100 mL/min, Column temperature: 38° C., Nozzle pressure: 100 bar (10 MPa), Nozzle temperature: 60° C., Evaporator temperature: 20° C., Trimmer temperature: 25° C., Wavelength: 220 nm) to afford the title compound (160 mg). $^1$H NMR (CDCl$_3$, 400 MHz) δ 8.69 (s, 1H), 7.56 (d, J=7.6 Hz, 1H), 6.85 (d, J=7.2 Hz, 1H), 6.80 (br s, 1H), 4.57-4.43 (m, 4H), 3.97 (s, 3H), 2.52 (s, 3H), 2.16 (s, 3H), 1.99-1.83 (m, 2H). LC-MS (Method A) (m/z)=427.2 (MH)$^+$t$_R$=1.60 minutes.

Example 14: 8-Chloro-2-(2-(1,1-difluoroethyl)pyridin-3-yl)-3-methyl-2,4,12,13-tetrahydro-11H-5,7-(azenometheno)dipyrazolo[3,4-b:5',1'-g][1]oxa[4,6,8]triazacycloundecine

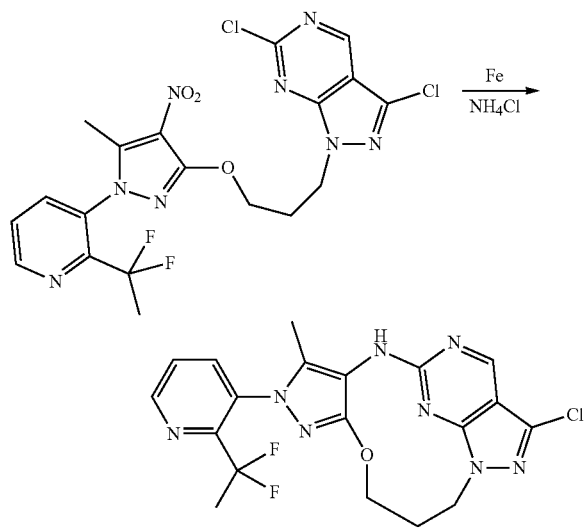

The compound was prepared in a manner similar to Example 2 using 3,6-dichloro-1-(3-((1-(2-(1,1-difluoroethyl)pyridin-3-yl)-5-methyl-4-nitro-1H-pyrazol-3-yl)oxy)propyl)-1H-pyrazolo[3,4-d]pyrimidine (320 mg, 0.623 mmol), Fe (190 mg, 3.40 mmol), and NH$_4$Cl (167 mg, 3.12 mmol) in EtOH (20 mL) and H$_2$O (2 mL) at 80° C. for 15 h followed by work-up, purification by chromatography on silica gel (eluent: petroleum ether:EtOAc 100:0→20:80), and preparative SFC (Instrument: Prep SFC 150 Mgm, Column: DAICEL CHIRALCEL OD 250×30 mm, 10 μm, Mobile phase: supercritical CO$_2$/EtOH (0.1% NH$_3$·H$_2$O, v %)=75/25, Flow Rate: 150 mL/min, Column Temperature: 38° C., Nozzle Pressure: 100 bar (10 MPa), Nozzle Temperature: 60° C., Evaporator Temperature: 20° C., Trimmer Temperature: 25° C., Wavelength: 220 nm) to afford the title compound (110 mg). $^1$H NMR (DMSO-d$_6$, 400 MHz) δ 9.59 (s, 1H), 8.83 (s, 1H), 8.80 (d, J=4.4 Hz, 1H), 8.00 (d, J=7.6 Hz, 1H), 7.74 (dd, J=4.8, 8.4 Hz, 1H), 4.48-4.24 (m, 4H), 2.08 (s, 3H), 2.00 (t, J=19.2 Hz, 3H), 1.94-1.63 (m, 2H). LC-MS (Method A) (m/z)=447.2 (MH)$^+$t$_R$=1.50 minutes.

Example 15: 8-Chloro-2-(5-fluoro-2,6-dimethylpyridin-3-yl)-3-methyl-2,4,12,13-tetrahydro-11H-5,7-(azenometheno)dipyrazolo[3,4-b:5',1'-g][1]oxa[4,6,8]triazacycloundecine

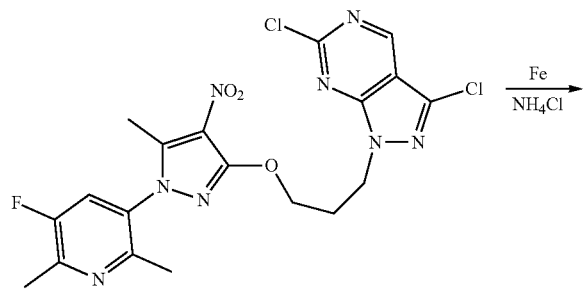

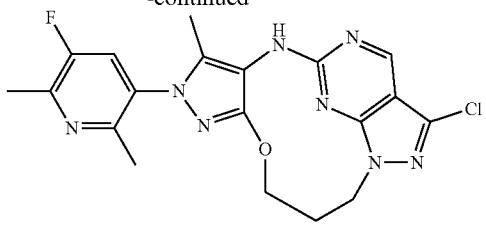

The compound was prepared in a manner similar to Example 2 using 3,6-dichloro-1-(3-((1-(5-fluoro-2,6-dimethylpyridin-3-yl)-5-methyl-4-nitro-1H-pyrazol-3-yl)oxy)propyl)-1H-pyrazolo[3,4-d]pyrimidine (690 mg, 1.40 mmol), Fe (389 mg, 6.97 mmol), and NH$_4$Cl (373 mg, 6.97 mmol) in EtOH (70 mL) and H$_2$O (7 mL) at 80° C. for 16 h followed by work-up, purification by chromatography on silica gel (eluent: petroleum ether:EtOAc 100:0→50:50), and preparative SFC (Instrument: Thar SFC Prep 80, Column: DAICEL CHIRALCEL OD-H (250 mm×30 mm, 5 μm), Mobile phase: supercritical CO$_2$/EtOH (0.1% NH$_3$·H$_2$O, v %)=70/30, Flow Rate: 80 mL/min, Column temperature: 38° C., Nozzle pressure: 100 bar (10 MPa), Nozzle temperature: 60° C., Evaporator temperature: 20° C., Trimmer temperature: 25° C., Wavelength: 220 nm) to afford the title compound (70 mg). $^1$H NMR (DMSO-d$_6$, 400 MHz) δ 9.61 (s, 1H), 8.83 (s, 1H), 7.84 (d, J=9.6 Hz, 1H), 4.44-4.31 (m, 4H), 2.49-2.47 (m, 3H), 2.21 (s, 3H), 2.11 (s, 3H), 2.01-1.61 (m, 2H). LC-MS (Method A) (m/z)=429.2 (MH)$^+$t$_R$=1.51 minutes.

Example 16: 8-Chloro-2-(2-cyclopropoxypyridin-3-yl)-3-methyl-2,4,12,13-tetrahydro-11H-5,7-(azenometheno)dipyrazolo[3,4-b:5',1'-g][1]oxa[4,6,8]triazacycloundecine

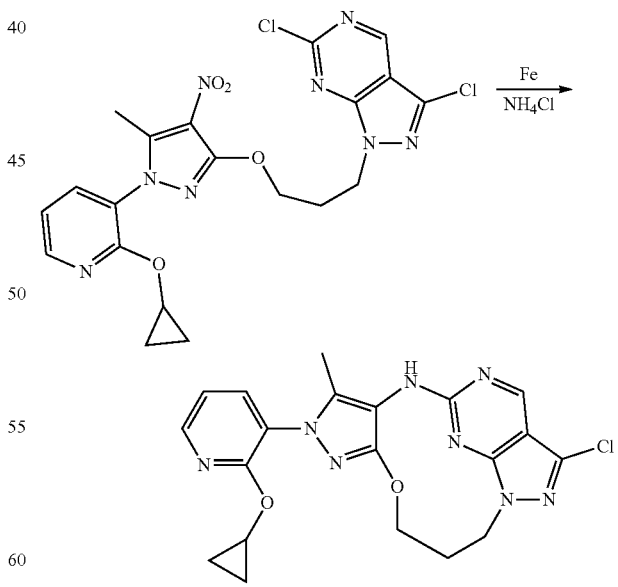

The compound was prepared in a manner similar to Example 2 using 3,6-dichloro-1-(3-((1-(2-cyclopropoxypyridin-3-yl)-5-methyl-4-nitro-1H-pyrazol-3-yl)oxy)propyl)-1H-pyrazolo[3,4-d]pyrimidine (410 mg, 0.811 mmol), Fe (246 mg, 4.40 mmol), and NH$_4$Cl (246 mg, 4.60 mmol)

in EtOH (20 mL) and H₂O (2 mL) at 80° C. for 15 h followed by work-up, purification by chromatography on silica gel (eluent: petroleum ether:EtOAc 100:0→0:100), and preparative SFC (Instrument: SFC-80Q, Column: DAICEL CHIRALPAK AD 250×30 mm, 10 µm, Mobile phase: supercritical CO₂/ETOH (0.1% NH₃·H₂O, v %)=50/50, Flow Rate: 80 mL/min, Column Temperature: 38° C., Nozzle Pressure: 100 bar (10 MPa), Nozzle Temperature: 60° C., Evaporator Temperature: 20° C., Trimmer Temperature: 25° C., Wavelength: 220 nm) to afford the title compound (130 mg). ¹H NMR (CDCl₃, 400 MHz) δ8.69 (s, 1H), 8.29 (dd, J=1.6, 6.4 Hz, 1H), 7.71 (dd, J=2.0, 7.6 Hz, 1H), 7.07 (dd, J=5.2, 7.6 Hz, 1H), 6.95 (br s, 1H), 4.55-4.46 (m, 4H), 4.38-4.32 (m, 1H), 2.15 (s, 3H), 2.03-1.95 (m, 2H), 0.86-0.72 (m, 4H). LC-MS (Method A) (m/z)=439.1 (MH)⁺ t$_R$=1.56 minutes.

Example 17: 8-Chloro-3-methyl-2-(2-(trifluoromethyl)pyridin-3-yl)-2,4,12,13-tetrahydro-11H-5,7-(azenometheno)dipyrazolo[3,4-b:5',1'-g][1]oxa[4,6,8]triazacycloundecine

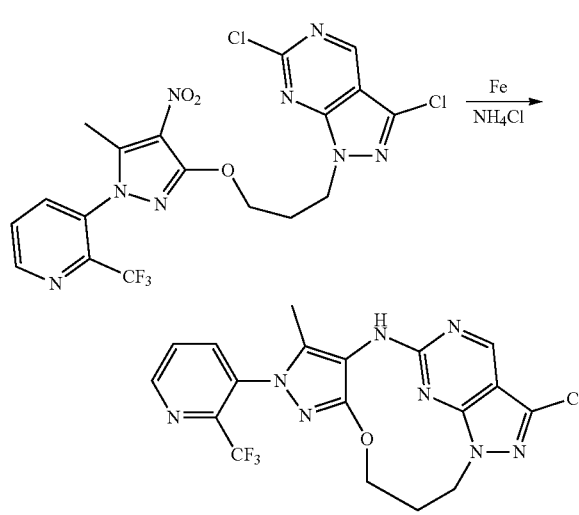

The compound was prepared in a manner similar to Example 2 using 3,6-dichloro-1-(3-((5-methyl-4-nitro-1-(2-(trifluoromethyl)pyridin-3-yl)-1H-pyrazol-3-yl)oxy)propyl)-1H-pyrazolo[3,4-d]pyrimidine (150 mg, 0.290 mmol), Fe (81 mg, 1.45 mmol), and NH₄Cl (78 mg, 1.45 mmol) in EtOH (9 mL) and H₂O (1.5 mL) at 80° C. for 16 h followed by work-up, purification by chromatography on silica gel (eluent: petroleum ether:EtOAc 83:17→0:100), and preparative SFC (Instrument: Thar SFC Prep 80, Column: DAICEL CHIRALCEL OJ (250 mm×30 mm, 10 µm), Mobile phase: supercritical CO₂/EtOH (0.1% NH₃·H₂O, v %)=75/25, Rate: 70 mL/min, Column temperature: 38° C., Nozzle pressure: 100 bar (10 MPa), Nozzle temperature: 60° C., Evaporator temperature: 20° C., Trimmer temperature: 25° C., Wavelength: 220 nm) to afford the title compound (15 mg). ¹H NMR (CDCl₃, 400 MHz) δ8.84 (d, J=3.6 Hz, 1H), 8.71 (s, 1H), 7.85 (d, J=7.2 Hz, 1H), 7.69 (dd, J=8.0, 4.4 Hz, 1H), 6.80 (br s, 1H), 4.56-4.44 (m, 4H), 2.16 (s, 3H), 2.02-1.92 (m, 2H). LC-MS (Method A) (m/z)=451.1 (MH)⁺ t$_R$=1.52 minutes.

Example 18: 8-Chloro-2-(2-(fluoromethoxy)pyridin-3-yl)-3-methyl-2,4,12,13-tetrahydro-11H-5,7-(azenometheno)dipyrazolo[3,4-b:5',1'-g][1]oxa[4,6,8]triazacycloundecine

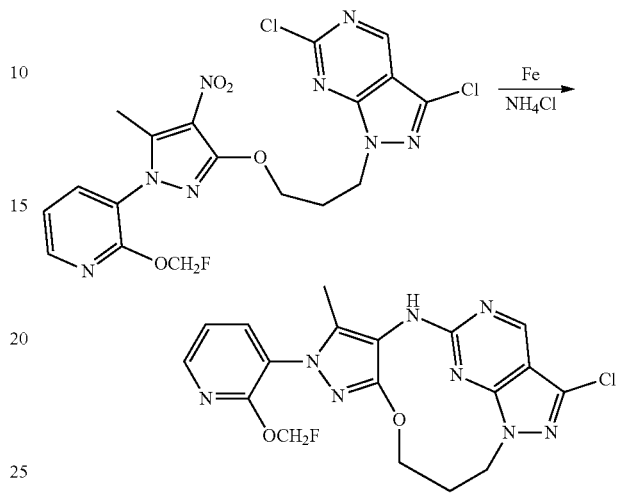

The compound was prepared in a manner similar to Example 2 using 3,6-dichloro-1-(3-((1-(2-(fluoromethoxy)pyridin-3-yl)-5-methyl-4-nitro-1H-pyrazol-3-yl)oxy)propyl)-1H-pyrazolo[3,4-d]pyrimidine (370 mg, 0.744 mmol), Fe (208 mg, 3.72 mmol), and NH₄Cl (199 mg, 3.72 mmol) in EtOH (35 mL) and H₂O (3.5 mL) at 80° C. for 16 h followed by work-up, purification by chromatography on silica gel (eluent: petroleum ether:EtOAc 100:0→50:50), and preparative SFC (Instrument: Thar SFC Prep 80, Column: DAICEL CHIRALPAK AD (250 mm×30 mm, 10 µm, Mobile phase: supercritical CO₂/EtOH (0.1% NH₃·H₂O, v %)=55/45, Flow Rate: 80 mL/min, Column temperature: 38° C., Nozzle pressure: 100 bar (10 MPa), Nozzle temperature: 60° C., Evaporator temperature: 20° C., Trimmer temperature: 25° C., Wavelength: 220 nm) to afford the title compound (70 mg). ¹H NMR (DMSO-d₆, 400 MHz) δ 9.59 (s, 1H), 8.83 (s, 1H), 8.36 (d, J=4.8 Hz, 1H), 7.96 (d, J=7.6 Hz, 1H), 7.39-7.34 (m, 1H), 6.15 (d, J=52.4 Hz, 2H), 4.39-4.36 (m, 4H), 2.12 (s, 3H), 1.87-1.72 (m, 2H). LC-MS (Method A) (m/z)=431.2 (MH)⁺t$_R$=1.50 minutes.

Example 19: 8-Chloro-2-(2-(difluoromethoxy)pyridin-3-yl)-3-methyl-2,4,12,13-tetrahydro-11H-5,7-(azenometheno)dipyrazolo[3,4-b:5',1'-g][1]oxa[4,6,8]triazacycloundecine

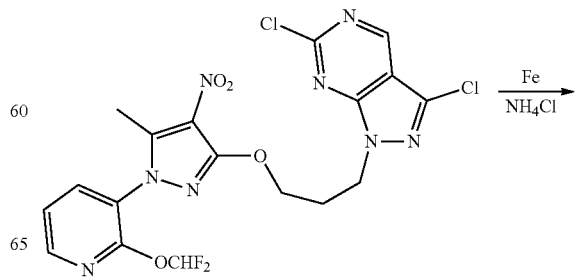

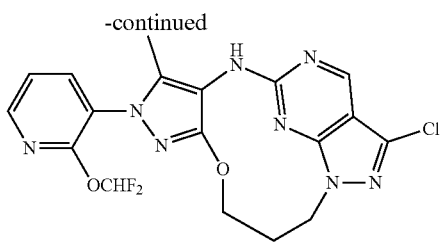

The compound was prepared in a manner similar to Example 2 using 3,6-dichloro-1-(3-((1-(2-(difluoromethoxy)pyridin-3-yl)-5-methyl-4-nitro-1H-pyrazol-3-yl)oxy)propyl)-1H-pyrazolo[3,4-d]pyrimidine (190 mg, 0.369 mmol), Fe (103 mg, 1.84 mmol), and NH$_4$Cl (99 mg, 1.8 mmol) in EtOH (20 mL) and H$_2$O (2 mL) at 80° C. for 16 h followed by work-up, purification by chromatography on silica gel (eluent: petroleum ether:EtOAc 100:0→35:65), and preparative SFC (Instrument: SFC-80Q, Column: DAICEL CHIRALPAK AD (250 mm×30 mm, 10 μm), Mobile phase: supercritical CO$_2$/EtOH (0.1% NH$_3$·H$_2$O, v %)=50/50, Flow Rate: 80 mL/min, Column temperature: 38° C., Nozzle pressure: 100 bar (10 MPa), Nozzle temperature: 60° C., Evaporator temperature: 20° C., Trimmer temperature: 25° C., Wavelength: 220 nm) to afford the title compound (55 mg). $^1$H NMR (DMSO-d$_6$, 400 MHz) δ 9.60 (s, 1H), 8.83 (s, 1H), 8.37 (dd, J=1.6, 4.8 Hz, 1H), 8.05 (dd, J=1.2, 7.6 Hz, 1H), 7.82 (t, J=72.4 Hz, 1H), 7.46 (dd, J=5.2, 8.0 Hz, 1H), 4.39-4.37 (m, 4H), 2.15 (s, 3H), 1.91-1.75 (m, 2H). LC-MS (Method A) (m/z)=449.1 (MH)$^+$ t$_R$=1.59 minutes.

Example 20: 8-Chloro-3-methyl-2-(2-(trifluoromethoxy)pyridin-3-yl)-2,4,12,13-tetrahydro-11H-5,7-(azenometheno)dipyrazolo[3,4-b:5',1'-g][1]oxa[4,6,8]triazacycloundecine

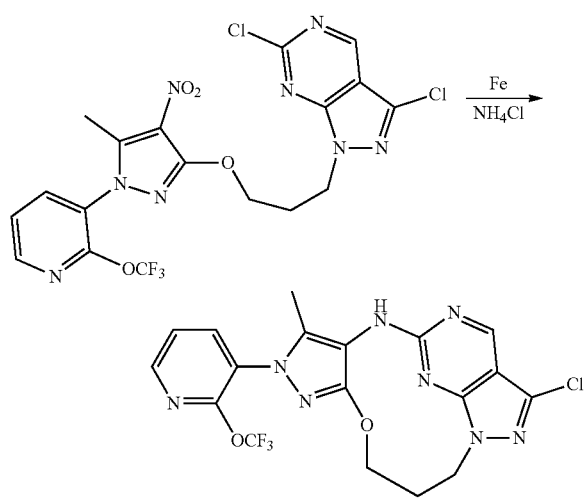

The compound was prepared in a manner similar to Example 2 using 3,6-dichloro-1-(3-((5-methyl-4-nitro-1-(2-(trifluoromethoxy)pyridin-3-yl)-1H-pyrazol-3-yl)oxy)propyl)-1H-pyrazolo[3,4-d]pyrimidine (80 mg, 0.15 mmol), Fe (42 mg, 0.75 mmol), and NH$_4$Cl (40 mg, 0.75 mmol) in EtOH (10 mL) and H$_2$O (1 mL) at 80° C. for 20 h followed by work-up, purification by chromatography on silica gel (eluent: petroleum ether:EtOAc 100:0→30:70), and preparative SFC×2 (Instrument: Prep SFC 150 Mgm, Column: DAICEL CHIRALPAK AD (250 mm×30 mm, 10 μm), Mobile phase: supercritical CO$_2$/EtOH (0.1% NH$_3$·H$_2$O, v %)=70/30, Flow Rate: 150 mL/min, Column temperature: 38° C., Nozzle pressure: 100 bar (10 MPa), Nozzle temperature: 60° C., Evaporator temperature: 20° C., Trimmer temperature: 25° C., Wavelength: 220 nm. SFC method 2: Instrument: Prep SFC 150 Mgm, Column: DAICEL CHIRALPAK OD (250 mm×30 mm, 10 μm), Mobile phase: supercritical CO$_2$/EtOH (0.1% NH$_3$·H$_2$O, v %)=80/20, Flow Rate: 150 mL/min, Column temperature: 38° C., Nozzle pressure: 100 bar (10 MPa), Nozzle temperature: 60° C., Evaporator temperature: 20° C., Trimmer temperature: 25° C., Wavelength: 220 nm) to afford the title compound (18 mg). $^1$H NMR (CDCl$_3$, 400 MHz) δ 8.71 (s, 1H), 8.37 (dd, J=1.6, 4.8 Hz, 1H), 7.92 (dd, J=2.0, 8.0 Hz, 1H), 7.39 (dd, J=4.8, 7.6 Hz, 1H), 6.86 (br s, 1H), 4.55-4.48 (m, 4H), 2.24 (s, 3H), 1.99-1.96 (m, 2H). LC-MS (Method A) (m/z)=467.1 (MH)$^+$ t$_R$=1.64 minutes.

Example 21: 8-Chloro-2-(3-methoxypyridazin-4-yl)-3-methyl-2,4,12,13-tetrahydro-11H-5,7-(azenometheno)dipyrazolo[3,4-b:5',1'-g][1]oxa[4,6,8]triazacycloundecine

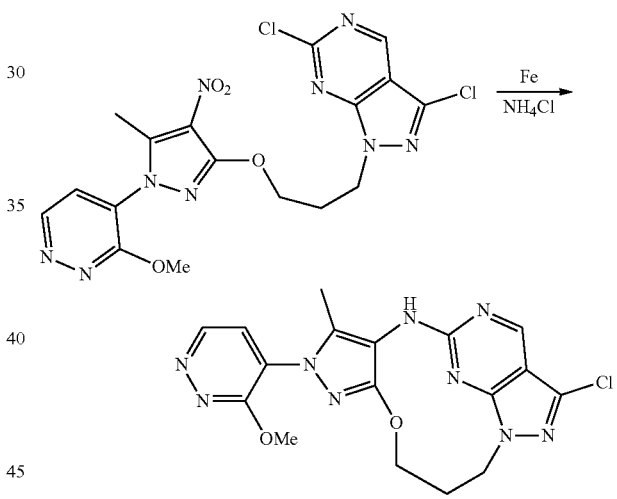

The compound was prepared in a manner similar to Example 2 using 3,6-dichloro-1-(3-((1-(3-methoxypyridazin-4-yl)-5-methyl-4-nitro-1H-pyrazol-3-yl)oxy)propyl)-1H-pyrazolo[3,4-d]pyrimidine (140 mg, 0.292 mmol), Fe (81 mg, 1.5 mmol), and NH$_4$Cl (78 mg, 1.5 mmol) in EtOH (14 mL) and H$_2$O (1.4 mL) at 80° C. for 16 h followed by work-up, purification by chromatography on silica gel (eluent: petroleum ether:EtOAc 100:0→15:85), and preparative SFC×2 (Instrument: Berger MultiGram II, Column: DAICEL CHIRALCEL AD (250 mm×30 mm, 10 μm), Mobile phase: supercritical CO$_2$/EtOH (0.1% NH$_3$·H$_2$O, v %)=40/60, Flow Rate: 80 mL/min, Column temperature: 38° C., Nozzle pressure: 100 bar (10 MPa), Nozzle temperature: 60° C., Evaporator temperature: 20° C., Trimmer temperature: 25° C., Wavelength: 220 nm. Instrument: Berger MultiGram II; Column: DAICEL CHIRALCEL AD (250 mm×30 mm, 10 μm), Mobile phase: supercritical CO$_2$/EtOH (0.1% NH$_3$·H$_2$O, v %)=65/35, Flow Rate: 100 mL/min, Column temperature: 38° C., Nozzle pressure: 100 bar (10 MPa), Nozzle temperature: 60° C., Evaporator temperature:

20° C., Trimmer temperature: 25° C., Wavelength: 220 nm) to afford the title compound (8 mg). $^1$H NMR (CDCl$_3$, 400 MHz) δ 8.99 (br s, 1H), 8.74 (br s, 1H), 7.53 (br s, 1H), 6.88 (br s, 1H), 4.61-4.38 (m, 4H), 4.25 (s, 3H), 2.28 (s, 3H), 1.99-1.94 (m, 2H). LC-MS (Method A) (m/z)=414.1 (MH)$^+$ $t_R$=1.35 minutes.

Example 22: 8-Chloro-2-(4-methoxy-2-methylpyrimidin-5-yl)-3-methyl-2,4,12,13-tetrahydro-11H-5,7-(azenometheno)dipyrazolo[3,4-b:5',1'-g][1]oxa[4,6,8]triazacycloundecine

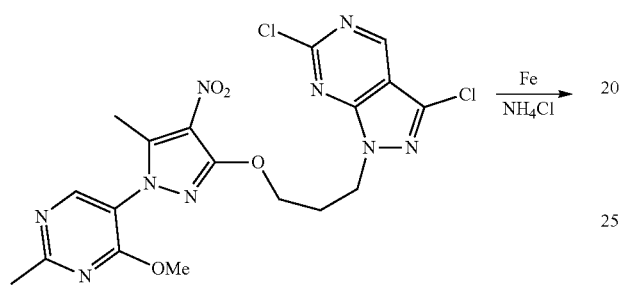

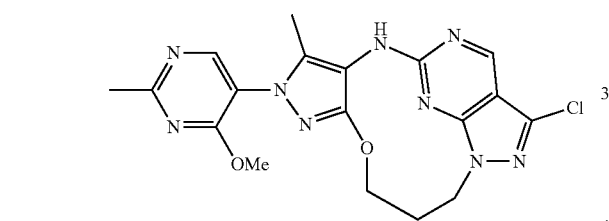

The compound was prepared in a manner similar to Example 2 using 3,6-dichloro-1-[3-[1-(4-methoxy-2-methyl-pyrimidin-5-yl)-5-methyl-4-nitro-pyrazol-3-yl]oxypropyl]pyrazolo[3,4-d]pyrimidine (900 mg, 1.82 mmol), Fe (508 mg, 9.10 mmol), and NH$_4$Cl (487 mg, 9.10 mmol) in EtOH (50 mL) and H$_2$O (5 mL) at 80° C. for 16 h followed by work-up, purification by chromatography on silica gel (eluent: petroleum ether:EtOAc 100:0→0:100), and preparative SFC (Instrument: SFC-80Q, Column: DAICEL CHIRALPAK AD (250 mm×30 mm, 10 μm), Mobile phase: supercritical CO$_2$/EtOH (0.1% NH$_3$·H$_2$O, v %)=45/55, Flow Rate: 80 mL/min, Column temperature: 38° C., Nozzle pressure: 100 bar (10 MPa), Nozzle temperature: 60° C., Evaporator temperature: 20° C., Trimmer temperature: 25° C., Wavelength: 220 nm) to afford the title compound (90 mg). $^1$H NMR (DMSO-d$_6$, 400 MHz) δ 9.58 (s, 1H), 8.83 (s, 1H), 8.51 (s, 1H), 4.44-4.29 (m, 4H), 3.98 (s, 3H), 2.62 (s, 3H), 2.10 (s, 3H), 1.97-1.52 (m, 2H). LC-MS (Method A) (m/z)=428.2 (MH)$^+$ $t_R$ 1.42 minutes.

Example 23: 8-Chloro-2-(5-fluoro-2-(methoxy-d$_3$)pyridin-3-yl)-3-methyl-2,4,12,13-tetrahydro-11H-5,7-(azenometheno)dipyrazolo[3,4-b:5',1'-g][1]oxa[4,6,8]triazacycloundecine

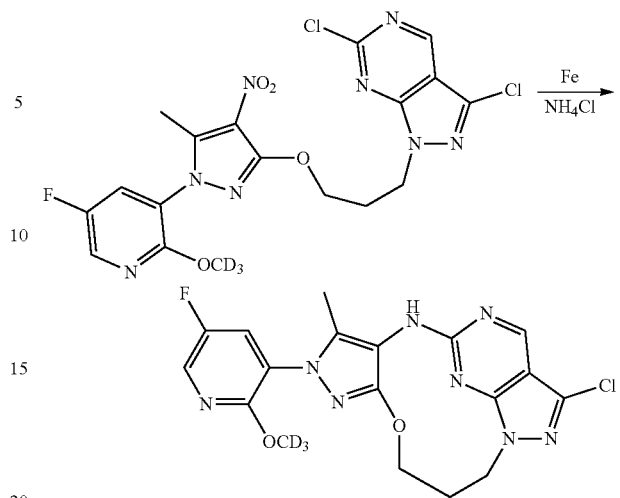

The compound was prepared in a manner similar to Example 2 using 3,6-dichloro-1-(3-((1-(5-fluoro-2-(methoxy-d$_3$)pyridin-3-yl)-5-methyl-4-nitro-1H-pyrazol-3-yl)oxy)propyl)-1H-pyrazolo[3,4-d]pyrimidine (380 mg, 0.760 mmol), Fe (212 mg, 3.80 mmol), and NH$_4$Cl (203 mg, 3.80 mmol) in EtOH (35 mL) and H$_2$O (5 mL) at 80° C. for 16 h followed by work-up, purification by chromatography on silica gel (eluent: petroleum ether:EtOAc 100:0→40:60), and preparative SFC (Instrument: SFC-80Q, Column: DAICEL CHIRALPAK AD (250 mm×30 mm, 10 μm), Mobile phase: supercritical CO$_2$/IPA (0.1% NH$_3$·H$_2$O, v %)=50/50, Flow Rate: 80 mL/min, Column temperature: 38° C., Nozzle pressure: 100 bar (10 MPa), Nozzle temperature: 60° C., Evaporator temperature: 20° C., Trimmer temperature: 25° C., Wavelength: 220 nm) to afford the title compound (60 mg). $^1$H NMR (CDCl$_3$, 400 MHz) δ 8.70 (s, 1H), 8.10 (d, J=2.8 Hz, 1H), 7.55 (dd, J=2.8, 7.8 Hz, 1H), 6.81 (br s, 1H), 4.61-4.48 (m, 4H), 2.21 (s, 3H), 2.09-1.91 (m, 2H). LC-MS (Method A) (m/z)=434.2 (MH)$^+$ $t_R$=1.59 minutes.

Example 24: 8-Chloro-2-(2-(methoxy-d$_3$)pyridin-3-yl)-3-methyl-2,4,12,13-tetrahydro-11H-5,7-(azenometheno)dipyrazolo[3,4-b:5',1'-g][1]oxa[4,6,8]triazacycloundecine

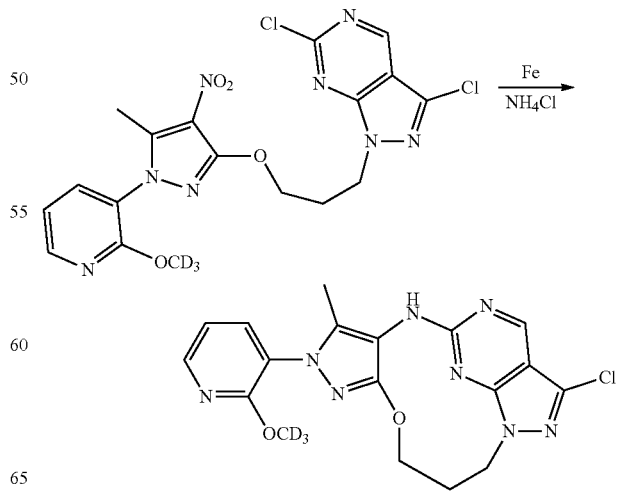

The compound was prepared in a manner similar to Example 2 using 3,6-dichloro-1-(3-((1-(2-(methoxy-d$_3$)pyridin-3-yl)-5-methyl-4-nitro-1H-pyrazol-3-yl)oxy)propyl)-1H-pyrazolo[3,4-d]pyrimidine (310 mg, 0.643 mmol), Fe (185 mg, 3.31 mmol), and NH$_4$Cl (185 mg, 3.46 mmol) in EtOH (40 mL) and H$_2$O (4 mL) at 80° C. for 15 h followed by work-up, purification by chromatography on silica gel (eluent: petroleum ether:EtOAc 100:0→20:80), and preparative SFC (Instrument: SFC-80Q, Column: DAICEL CHIRALPAK AD (250 mm×30 mm, 10 μm), Mobile phase: supercritical CO$_2$/IPA (0.1% NH$_3$·H$_2$O, v %)=50/50, Flow Rate: 80 mL/min, Column temperature: 38° C., Nozzle pressure: 100 bar (10 MPa), Nozzle temperature: 60° C., Evaporator temperature: 20° C., Trimmer temperature: 25° C., Wavelength: 220 nm) to afford the title compound (100 mg). $^1$H NMR (CDCl$_3$, 400 MHz) δ 8.70 (s, 1H), 8.24 (dd, J=1.6, 4.8 Hz, 1H), 7.71 (dd, J=1.6, 7.6 Hz, 1H), 7.04 (dd, J=4.8, 7.6 Hz, 1H), 6.78 (br s, 1H), 4.58-4.45 (m, 4H), 2.18 (s, 3H), 2.04-1.89 (m, 2H). LC-MS (Method F) (m/z)=416.2 (MH)$^+$ t$_R$=1.45 minutes.

Example 25: 8-Chloro-2-(2,6-dimethylpyridin-3-yl)-3-(methyl-d$_3$)-2,4,12,13-tetrahydro-11H-5,7-(azenometheno)dipyrazolo[3,4-b:5',1'-g][1]oxa[4,6,8]triazacycloundecine

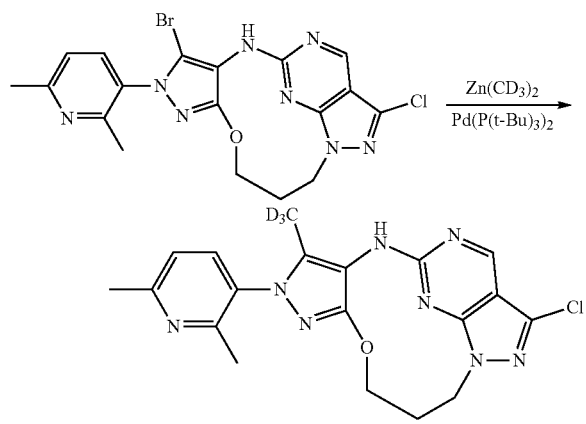

To a mixture of 3-bromo-8-chloro-2-(2,6-dimethylpyridin-3-yl)-2,4,12,13-tetrahydro-11H-5,7-(azenometheno)dipyrazolo[3,4-b:5',1'-g][1]oxa[4,6,8]triazacycloundecine (50 mg, 0.11 mmol) and bis[tris(tert-butyl)phosphine]palladium (5.4 mg, 0.011 mmol) was added THF (2 mL) at room temperature. Then LiHMDS (0.12 mL, 0.12 mmol, 1 M in THF) was added. The mixture was stirred for 20 minutes followed by addition of bis(methyl-d$_3$)zinc in THF-dibutyl ether-PhMe (0.30 mL, 0.18 mmol, 0.6 M). The reaction mixture was heated at 50° C. for 18 h. The mixture was cooled to room temperature and quenched by addition of saturated aqueous NH$_4$Cl solution (5 mL) and water (5 mL). The mixture was stirred for 15 minutes and extracted with EtOAc. The organic phase was washed with brine, dried over Na$_2$SO$_4$, and concentrated under reduced pressure. The residue was purified by chromatography on silica gel (eluent: Heptane:EtOAc) to afford the title compound (11 mg). $^1$H NMR (DMSO-d$_6$, 400 MHz) δ 9.59 (s, 1H), 8.83 (s, 1H), 7.69 (d, J=8.0 Hz, 1H), 7.26 (d, J=8.0 Hz, 1H), 4.30-4.46 (m, 4H), 2.53 (s, 3H), 2.23 (s, 3H), 1.64-2.0 (m, 2H). LC-MS (Method E) (m/z)=414.0 (MH)$^+$t$_R$=0.41 minutes.

Example 26: 8-Chloro-3-(methyl-d$_3$)-2-(2-methylpyridin-3-yl)-2,4,12,13-tetrahydro-11H-5,7-(azenometheno)dipyrazolo[3,4-b:5',1'-g][1]oxa[4,6,8]triazacycloundecine

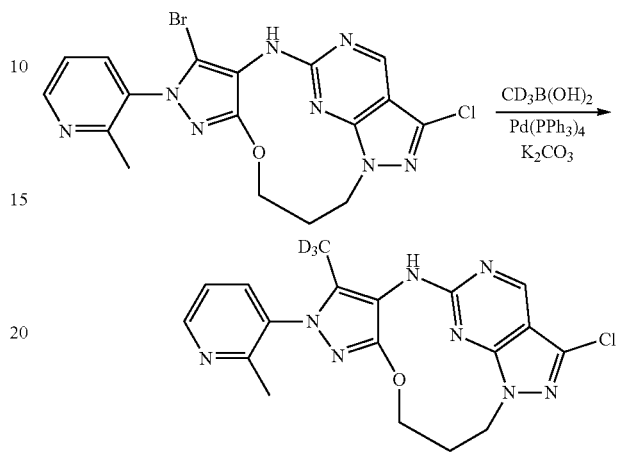

A mixture of 3-bromo-8-chloro-2-(2-methylpyridin-3-yl)-2,4,12,13-tetrahydro-11H-5,7-(azenometheno)dipyrazolo[3,4-b:5',1'-g][1]oxa[4,6,8]triazacycloundecine (150 mg, 0.325 mmol), trideuteri(methyl-d$_3$)boronic acid (102 mg, 1.62 mmol), K$_2$CO$_3$ (135 mg, 0.975 mmol), and Pd(PPh$_3$)$_4$ (38 mg, 0.032 mmol) in 1,4-dioxane (40 mL) and H$_2$O (10 mL) was degassed and purged with N$_2$×3, and then stirred at 90° C. for 15 h. The reaction mixture was concentrated under reduced pressure. The residue was purified by chromatography on silica gel (eluent: petroleum ether:EtOAc 100:0→70:30) followed by preparative SFC (Instrument: Prep SFC 150 Mgm, Column: DAICEL CHIRALCEL OD (250 mm×30 mm, 10 μm), Mobile phase: supercritical CO$_2$/EtOH (0.1% NH$_3$—H$_2$O, v %)=75/25; Rate: 60 mL/min, Column temperature: 38° C.; Nozzle pressure: 100 bar (10 MPa), Nozzle temperature: 60° C., Evaporator temperature: 20° C., Trimmer temperature: 25° C., Wavelength: 220 nm) to afford the title compound (30 mg). $^1$H NMR (DMSO-d$_6$, 400 MHz) δ 9.60 (s, 1H), 8.83 (s, 1H), 8.57 (d, J=3.2 Hz, 1H), 7.80 (dd, J=8.0, 1.6 Hz, 1H), 7.41 (dd, J=8.0, 4.8 Hz, 1H), 4.41-4.31 (m, 4H), 2.28 (s, 3H), 1.95-1.75 (m, 2H). LC-MS (Method F) (m/z)=400.2 (MH)$^+$t$_R$=1.33 minutes.

Example 27: 8-Chloro-2-(2,5-dimethylpyridin-3-yl)-3-(methyl-d$_3$)-2,4,12,13-tetrahydro-11H-5,7-(azenometheno)dipyrazolo[3,4-b:5',1'-g][1]oxa[4,6,8]triazacycloundecine

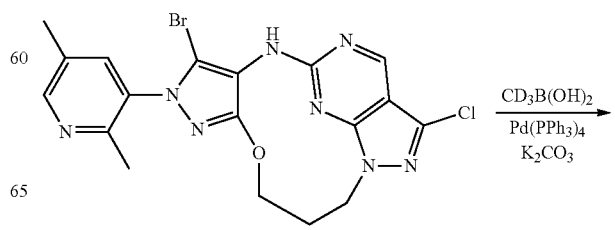

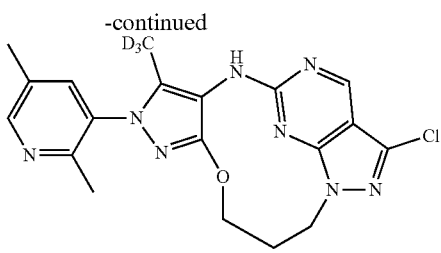

The compound was prepared in a manner similar to Example 26. 3-Bromo-8-chloro-2-(2,5-dimethylpyridin-3-yl)-2,4,12,13-tetrahydro-11H-5,7-(azenometheno)dipyrazolo[3,4-b:5',1'-g][1]oxa[4,6,8]triazacycloundecine (200 mg, 0.42 mmol), (methyl-d$_3$)boronic acid (1 g, 2.4 mmol, ~15 w % containing THF and n-Bu$_2$O), K$_2$CO$_3$ (174 mg, 1.26 mmol), and Pd(PPh$_3$)$_4$(49 mg, 0.042 mmol) in 1,4-dioxane (5 mL) and H$_2$O (1 mL) was stirred at 90° C. for 16 h. Additional (methyl-d$_3$)boronic acid (2.5 g, 6.0 mmol, ~15 w % containing THF and n-Bu$_2$O) and Pd(PPh$_3$)$_4$(40 mg) were added and the mixture was stirred at 90° C. for 16 h. A final portion of (methyl-d$_3$)boronic acid (2 g, 4.7 mmol, ~15 w % containing THF and n-Bu$_2$O), K$_2$CO$_3$ (100 mg), and Pd(PPh$_3$)$_4$(40 mg) was added and the mixture was stirred at 90° C. for another 16 h. This was followed by work-up, purification by chromatography on silica gel (eluent: petroleum ether:EtOAc 100:0→0:100), and preparative SFC (Instrument: Thar SFC Prep 80, Column: DAICEL CHIRALCEL OJ (250 mm×30 mm, 10 μm), Mobile phase: supercritical CO$_2$/EtOH (0.1% NH$_3$—H$_2$O, v %)=70/30, Rate: 70 mL/min, Column temperature: 38° C., Nozzle pressure: 100 bar (10 MPa), Nozzle temperature: 60° C., Evaporator temperature: 20° C., Trimmer temperature: 25° C., Wavelength: 220 nm) to afford the title compound (15 mg). $^1$H NMR (CDCl$_3$, 400 MHz) δ 8.71 (s, 1H), 8.46 (s, 1H), 7.51 (s, 1H), 6.83 (s, 1H), 4.59-4.42 (m, 4H), 2.43-2.39 (m, 6H), 2.02-1.89 (m, 2H). LC-MS (Method A) (m/z)=414.2 (MH)$^+$ t$_R$=1.25 minutes.

Example 28: 8-Chloro-2-(2-methoxypyridin-3-yl)-3-(methyl-d$_3$)-2,4,12,13-tetrahydro-11H-5,7-(azenometheno)dipyrazolo[3,4-b:5',1'-g][1]oxa[4,6,8]triazacycloundecine

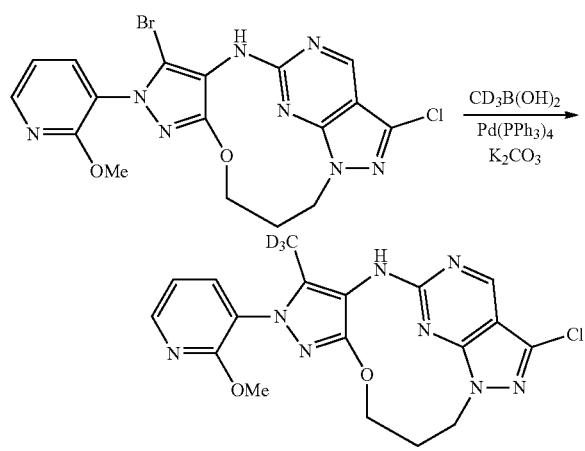

The compound was prepared in a manner similar to Example 26. 3-Bromo-8-chloro-2-(2-methoxypyridin-3-yl)-2,4,12,13-tetrahydro-11H-5,7-(azenometheno)dipyrazolo[3,4-b:5',1'-g][1]oxa[4,6,8]triazacycloundecine (100 mg, 0.21 mmol), (methyl-d$_3$)boronic acid (132 mg, 0.31 mmol, ~15 w %, containing THF and n-Bu$_2$O), K$_2$CO$_3$ (87 mg, 0.63 mmol), and Pd(PPh$_3$)$_4$(24 mg, 0.02 mmol) in 1,4-dioxane (1 mL) and H$_2$O (0.2 mL) was stirred at 90° C. for 16 h. Additional (methyl-d$_3$)boronic acid (2.0 g, 4.7 mmol, ~15 w % containing THF and n-Bu$_2$O), Pd(PPh$_3$)$_4$(25 mg) and K$_2$CO$_3$ (50 mg) were added and the mixture was stirred at 90° C. for 16 h. Additional (methyl-d$_3$)boronic acid (3.0 g, 7.2 mmol, ~15 w %, containing THF and n-Bu$_2$O) and Pd(PPh$_3$)$_4$ (25 mg, 0.02 mmol) were added and the mixture was stirred at 90° C. for another 16 h. A final portion of (methyl-d$_3$)boronic acid (2.0 g, 4.7 mmol, ~15 w % containing THF and n-Bu$_2$O), K$_2$CO$_3$ (50 mg), and Pd(PPh$_3$)$_4$ (25 mg, 0.02 mmol) was added and the mixture was stirred at 90° C. for another 16 h. This was followed by work-up followed and purification by chromatography on silica gel (eluent: petroleum ether:EtOAc 100:0→20:80), and preparative SFC (Instrument: Prep SFC 150 Mgm, Column: DAICEL CHIRALCEL OD (250 mm×30 mm, 10 μm), Mobile phase: supercritical CO$_2$/EtOH (0.1% NH$_3$—H$_2$O, v %)=70/30; Flow Rate: 150 mL/min; Column temperature: 38° C.; Nozzle pressure: 100 bar (10 MPa); Nozzle temperature: 60° C.; Evaporator temperature: 20° C.; Trimmer temperature: 25° C.; Wavelength: 220 nm) to afford the title compound (24 mg). $^1$H NMR (DMSO-d$_6$, 400 MHz) δ 9.56 (s, 1H), 8.82 (s, 1H), 8.29 (dd, J=4.8, 1.6 Hz, 1H), 7.81 (dd, J=7.6, 2.0 Hz, 1H), 7.17 (dd, J=7.6, 5.2 Hz, 1H), 4.44-4.29 (m, 4H), 3.92 (s, 3H), 2.07-1.58 (m, 2H). LC-MS (Method A) (m/z)=416.2 (MH)$^+$ t$_R$=1.48 minutes.

Example 29: 8-Chloro-2-(5-fluoro-2-methoxypyridin-3-yl)-3-(methyl-d$_3$)-2,4,12,13-tetrahydro-11H-5,7-(azenometheno)dipyrazolo[3,4-b:5',1'-g][1]oxa[4,6,8]triazacycloundecine

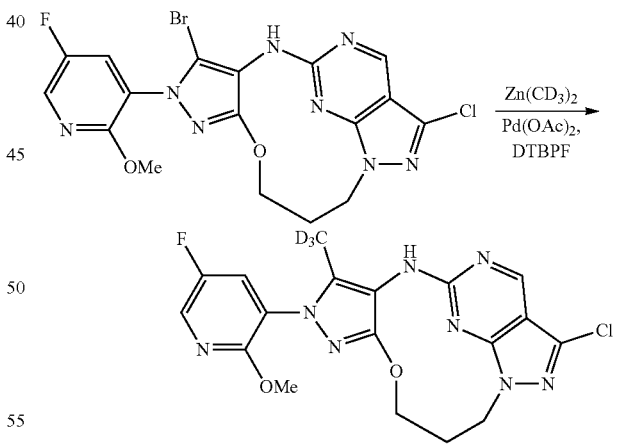

THF (8 mL) was added to 3-bromo-8-chloro-2-(5-fluoro-2-methoxypyridin-3-yl)-2,4,12,13-tetrahydro-11H-5,7-(azenometheno)dipyrazolo[3,4-b:5',1'-g][1]oxa[4,6,8]triazacycloundecine (144 mg, 0.290 mmol), Pd(OAc)$_2$ (7 mg, 0.03 mmol) and 1,1-bis(di-tert-butylphosphino)ferrocene (14 mg, 0.030 mmol). Lithium bis(trimethylsilyl)amide solution (0.330 mL, 0.33 mmol, 1 M in THF) was added dropwise to the solution and stirred for 20 minutes at room temperature, followed by addition of bis(methyl-d$_3$)zinc (1.20 mL, 0.48 mmol, 0.40 M in THF-dibutyl ether-PhMe)

and the reaction was then heated to 50° C. and stirred for 2 h. The mixture was filtered and concentrated under reduced pressure. The residue was purified by chromatography on silica gel (eluent: Heptane.EtOAc) to afford the title compound (79 mg). $^1$H NMR (DMSO-$d_6$, 600 MHz,) δ 9.58 (s, 1H), 8.83 (s, 1H), 8.33 (d, J=2.9 Hz, 1H), 7.94 (dd, J=8.2, 2.9 Hz, 1H), 4.44-4.29 (m, 4H), 3.92 (s, 3H), 1.82 (m, 2H). LC-MS (Method D) (m/z)=436.1 (MH)$^+$ $t_R$=0.67 minutes.

Example 30: 8-Chloro-2-(5-fluoro-2-methylpyridin-3-yl)-3-(methyl-$d_3$)-2,4,12,13-tetrahydro-11H-5,7-(azenometheno)dipyrazolo[3,4-b:5',1'-g][1]oxa[4,6,8]triazacycloundecine

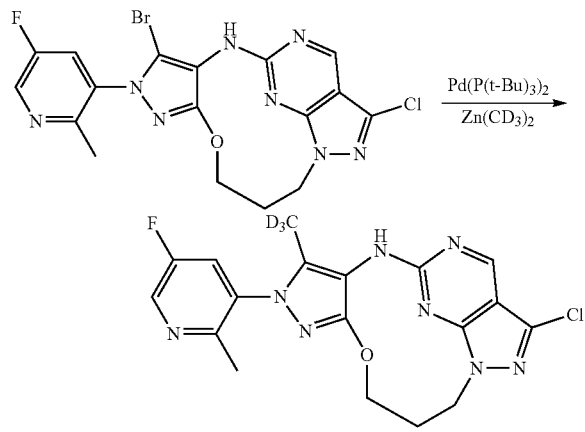

The compound was prepared in a manner similar to Example 25 using 3-bromo-8-chloro-2-(5-fluoro-2-methylpyridin-3-yl)-2,4,12,13-tetrahydro-11H-5,7-(azenometheno)dipyrazolo[3,4-b:5',1'-g][1]oxa[4,6,8]triazacycloundecine (381 mg, 0.794 mmol), bis[tris(tert-butyl)phosphine]palladium (40 mg, 0.078 mmol), LiHMDS (0.80 mL, 0.80 mmol, 1 M in THF), and bis(methyl-$d_3$)zinc in (1.82 mL, 1.27 mmol, 0.70 M in THF-dibutyl ether-PhMe) in THF (8.5 mL) at 50° C. for 3 h and additional bis(methyl-$d_3$)zinc (0.3 mL, 0.2 mmol, 0.70 M in THF-dibutyl ether-PhMe) at 50° C. for 2 h followed by work-up, purification by chromatography on silica gel (eluent: Heptane:EtOAc), and preparative SFC (Instrument: Shimadzu Nexera Prep SFC; Column: 2-Ethylpyridine (21.2 mm×150 mm, 5 μm); Mobile phase: supercritical $CO_2$/iPrOH (EtOH)=15%; Flow Rate: 60 mL/min; Column temperature: 40° C.; Nozzle pressure: 100 bar (10 MPa); Nozzle temperature: 60° C.; Evaporator temperature: 20° C.; Trimmer temperature: 25° C.; Wavelength: 254 nm) to afford the title compound (133 mg). 1H NMR (CDCl$_3$, 600 MHz) δ8.71 (s, 1H), 8.50 (d, J=2.8 Hz, 1H), 7.38 (dd, J=8.1, 2.7 Hz, 1H), 6.61 (s, 1H), 4.50 (m, 4H), 2.39 (d, J=1.3 Hz, 3H), 2.00-1.92 (m, 2H). LC-MS (Method E) (m/z)=418.1 (MH)$^+$ $t_R$=0.69 minutes.

Example I—LRRK2 Wild-Type and G2019S Kinase Activity Assay

LRRK2 kinase activity was measured using a LanthaScreen kinase activity assay available from Invitrogen (Life Technologies Corporation). The assay is a homogeneous time resolved-fluorescence resonance energy transfer (TR-FRET) assay that measures phosphorylation of a fluorescein-labelled peptide substrate (Fluorescein-ERM LRRKtide obtainable from Life Technologies Corporation) as a result of LRRK2 kinase activity. The phosphorylated peptide is recognized by a terbium-labelled phospho-specific anti-LRRKtide antibody (pLRRKtide antibody), obtainable from Life Technologies Corporation) and, subsequently, the phosphorylated LRRKtide can be quantified by the extent of TR-FRET between the terbium donor and fluorescein acceptor.

The LRRK2 kinase was obtained from Invitrogen (Life Technologies Corporation) and comprises residue 970 to 2527 of the full length human wild-type LRRK2 kinase, or a similar sequence with the G2019S mutation. As discussed above, this mutation increases the kinase activity relative to the wild type. The kinase reactions were performed in a 20 μL volume in 384-well plates. The kinase reaction buffer consisted of 50 mM Tris pH 8.5, 0.01% BRIJ-35, 10 mM $MgCl_2$, 1 mM EGTA, and 2 mM DTT.

In the assay, 1 nM LRRK2 WT or 250 pM LRRK2 G2019S kinase in kinase reaction buffer was incubated with the test compound (typically at 0 to 30 μM) for 30 minutes before the kinase reaction was initiated by addition of 1.3 mM ATP and 0.4 μM fluorescein-LRRKtide. The reaction mixture (20 μl total volume) was incubated for 3.5 h (for LRRK2 WT) and 3 h (for LRRK2 G2019S) at 30° C., before the reaction was terminated by addition of 10 mM EDTA and 1 nM terbium-labelled anti-phospho-LRRKtide antibody (final volume 20 l). The mixture was further incubated for 30 minutes at RT. TR-FRET was measured by excitation of the terbium-donor with 340 nm light and subsequent (delay time 100 s) measurement of terbium and fluorescein emission at 495 nm and 520 nm, respectively, over a time window of 1000 s. The measurement was repeated 30 times for fluorescein and 30 times for terbium emission with a 1000 s time window between repeats. TR-FRET measurements were performed on a Biotek Synergy plate. The TR-FRET signal was calculated as the emission-ratio at 520 nm over 495 nm.

The TR-FRET ratio readout for test compounds was normalized to 0% inhibition corresponding to TR-FRET ratio measured in control wells with no inhibition of the kinase activity and 100% inhibition corresponding to TR-FRET ratio measured in control wells with inhibitor. Test compound potency (IC$_{50}$) was estimated by nonlinear regression using the sigmoidal dose-response (variable slope) using Xlfit 4 (IDBS, Guildford, Surrey, UK, model 205). Were the IC$_{50}$ could not be determined the % inhibition at the highest tested concentration is given by equation 1.

Equation (1):

$$y=(A+((B-A)/(1+((C/x)^\wedge D)))) \tag{1}$$

where y is the normalized TR-TRET ratio measurement for a given concentration of test compound, x is the concentration of test compound, A is the estimated efficacy (% inhibition) at infinite compound dilution, and B is the maximal efficacy (% inhibition). C is the IC$_{50}$ value and D is the Hill slope coefficient. IC$_{50}$ estimates were obtained from independent experiment and the logarithmic average was calculated.

LRRK2 Wild-Type ADP-Glo Protocol

LRRK2 kinase activity was measured using an ADP-Glo kinase assay from Promega Corporation. The assay is a homogeneous luminescence-based assay that measures ADP formed from a kinase reaction. The ADP is converted into ATP, which is used to generate light in a luciferase reaction. The luminescence generated correlates with kinase activity.

The LRRK2 kinase was obtained from Invitrogen (Life Technologies Corporation) and comprises residue 970 to 2527 of the full length human wild-type LRRK2 kinase. The kinase reactions were performed in a 10 µL volume in 384-well plates. The kinase reaction buffer consisted of 50 mM Tris pH 8.5, 0.01% BRIJ-35, 10 mM MgCl$_2$, 1 mM EGTA, and 2 mM DTT.

In the assay, 0.5 nM LRRK2 WT kinase in kinase reaction buffer was incubated with the test compound (typically at 0 to 2 µM) for 30 minutes before the kinase reaction was initiated by addition of 1.0 mM ATP and 260 µM LRRKtide. The reaction mixture (10 µl total volume) was incubated for 3 hours at room temperature (RT, ca. 25° C.), before the reaction was terminated by addition of 10 µl ADP-Glo reagent. The mixture was further incubated for 60 minutes at RT before addition of 20 µl Kinase detection reagent from the ADP-Glo assay kit. Luminescence signal was measure on a BMG Labtech Pherastar FSX multimode microplate reader. The signal integration time was 0.5 s.

The luminescence readout for test compounds was normalized to 0% inhibition corresponding to luminescence measured in control wells with no inhibition of the kinase activity and 100% inhibition corresponding to luminescence measured in control wells with inhibitor. Test compound potency ($K_{i,app}$) was estimated by nonlinear regression using the tight-binding fit model in GeneData Screener (GeneData AG). In cases where the $K_{i,app}$ could not be determined, the % inhibition at the highest tested concentration is reported. The tight-binding fit model is given by euquation (2).

Equation (2):

$$S_S = S_0 - (S_{inf} - S_0)*(([E]+[I]+K_{i,app} - ([E]+[1]+K_{i,app})^2 - 4*[E]*[I])^{0.5})/(2*[E]))$$ (2)

Where $S_0$ is the estimated efficacy (% inhibition) at infinite compound dilution, and $S_{inf}$ is the maximal efficacy (% inhibition), [E] is the enzyme concentration (active enzyme concentration) and [I] is the concentration of test compound. $K_{i,app}$ is the apparent dissociation constant of the inhibitor. The IC$_{50}$ can be calculated as given by equation (3).

Equation (3):

$$IC_{50} = K_{i,app} + [E]/2$$ (3)

IC$_{50}$ estimates were obtained from independent experiment and the logarithmic average was calculated.

Table 2 below shows the IC$_{50}$ values in nM obtained as described above for the exemplified compounds, data is based on n≥2 tests.

TABLE 2

LRRK2 wild-type and G2019S kinase activity

| Example Number | LRRK2 G2019S IC$_{50}$ (nM) | LRRK2 WT IC$_{50}$ (nM) | LRRK2 WT ADPGlo IC$_{50}$ (nM) |
|---|---|---|---|
| 1 | 0.45 | 1.1 | 0.46 |
| 2 | 0.35 | 0.98 | 0.28 |
| 3 | 1.9 | 7.6 | 1.2 |
| 4 | 1.8 | 7.0 | 0.82 |
| 5 | 1.4 | 4.0 | 0.41 |
| 6 | 0.2 | 0.53 | 0.40 |
| 7 | 2.3 | 6.9 | 0.78 |
| 8 | 12 | 35 | 2.5 |
| 9 | 2.4 | 6.3 | 1.0 |
| 10 | 2.7 | 8.8 | 1.0 |
| 11 | 0.59 | 2.0 | 0.39 |
| 12 | 0.13 | 0.4 | 0.63 |
| 13 | 0.22 | 0.57 | 0.33 |
| 14 | 4.2 | 14 | 1.5 |
| 15 | 1.4 | 4.0 | 0.66 |
| 16 | 0.93 | 2.1 | 0.57 |
| 17 | 5.5 | 20 | 3.1 |
| 18 | 0.49 | 0.67 | 0.44 |
| 19 | 0.35 | 1.1 | 0.32 |
| 20 | 1.1 | 3.4 | 0.48 |
| 21 | 0.24 | 0.94 | 0.45 |
| 22 | 0.59 | 2.1 | 0.60 |
| 23 | 0.32 | 0.61 | 0.34 |
| 24 | 0.35 | 0.95 | 0.49 |
| 25 | 1.4 | 4.8 | 0.83 |
| 26 | 1.7 | 4.9 | 0.96 |
| 27 | 0.65 | 2.1 | 0.56 |
| 28 | 0.23 | 0.76 | 0.63 |
| 29 | 0.79 | 2.4 | 0.53 |
| 30 | 7.7 | 16 | 1.4 |

Example II—Broad Kinase Selectivity

Protein kinase profiling of the inhibitors (Fabian, M. A. et al. A small molecule-kinase interaction map for clinical kinase inhibitors. Nat. Biotechnol. 23, 329-336 (2005)) were undertaken at a concentration of 0.010 µM and carried out in Eurofins DiscoverX KINOMEscan scanMAX panel of 403 wild type kinases (primarily of human origin) covering AGC (PKA, PKG, PKC family kinases), CAMK (Calcium/calmodulin-dependent protein kinases), CK1 (Casein kinase 1 kinases), CMGC (CDK, MAPK, GSK3, CLK families), STE (homologs of yeast Sterile 7, Sterile 11, Sterile 20 kinases), TK (Tyrosine kinases), TKL (Tyrosine kinase-like kinases), lipid and atypical kinase families.

Selectivity Score or S-score is a quantitative measure of compound selectivity. It was calculated by dividing the number of kinases that a compound binds to by the total number of distinct kinases tested, excluding mutant variants. S=Number of hits/Number of assays. This value can be calculated using % Ctrl as a potency threshold (below) and provides a quantitative method of describing compound selectivity to facilitate comparison of different compounds.

TABLE 3

Kinase selectivity

| Compound | Selectivity Score Type | Number of Hits | Number of Non-Mutant Kinases | Screening Concentration (nM) | Selectivity Score |
|---|---|---|---|---|---|
| Example 1 | S(35) | 12 | 403 | 10 | 0.03 |
| | S(10) | 4 | 403 | 10 | 0.01 |
| | S(1)* | 2 | 403 | 10 | 0.005 |

*LRRK2 WT; S(35) = (number of non-mutant kinases with % Ctrl <35)/(number of non-mutant kinases tested); S(10) = (number of non-mutant kinases with % Ctrl <10)/(number of non-mutant kinases tested); S(1) = (number of non-mutant kinases with % Ctrl <1)/(number of non-mutant kinases tested)

Example III—Rat Brain Disposition

Brain disposition was evaluated in male Sprague-Dawley rats (n=3, standard body weight). Briefly, test compound was formulated as a simple suspension (0.5% HPMC in water) then administered by oral gavage (10 mg/kg, 10 mL/kg or 5 mg/kg, 10 mL/kg). At the designated time point (0.5 or 1 h post dose) rats were sacrificed and terminal blood and brain samples taken. Isolated plasma and brain homogenates were extracted by standard protein precipitation in acetonitrile, containing internal standard. Diluted extracts were analyzed by liquid-chromatography coupled with tandem mass spectrometry detection (LC-MS/MS) using a bioanalytical method. Concentrations of test compound in plasma and brain were quantified against matrix matched calibration standards. The total plasma and brain concentration time data are presented in Table 4 alongside the calculated brain $K_p$ (total brain concentration:total plasma concentration ratio).

The fraction of unbound compound in male Sprague-Dawley rat plasma ($fu_{plasma}$) and brain homogenate ($fu_{brain}$) were determined by equilibrium dialysis using 96-well HTD-dialysis plates with dialysis membranes (molecular weight cut off 12-14 KDa). One side of the HTD-dialysis plate was loaded with matrix (plasma or brain homogenate) and the other side with buffer (100 mM sodium phosphate buffer, pH 7.4). Test compounds were dissolved in DMSO then spiked (5 µL of 0.2 mM) into blank (995 µL) plasma or diluted brain homogenate (1:4 ratio in phosphate buffer) giving a final nominal concentration 1 µM (≤0.5% DMSO). The matrices were loaded into respective chambers and equilibrated against phosphate buffer for 5 h at 37° C. (in a humidified air incubator with 5% $CO_2$ with shaking). Samples from both chambers (buffer and plasma or brain homogenate) were aliquoted to fresh 96-well polypropylene plates then matrix matched using an equal volume of opposite blank matrix before extraction with cold solvent (3 volumes acetonitrile) containing an appropriate bioanalytical internal standard. After centrifugation (20 min, 3200 g, 4° C.) the supernatants were diluted with appropriate volumes of water and compound concentrations were quantified by LC/MS-MS against matrix matched calibration standards. The $fu_{plasma}$ and $fu_{brain}$ were calculated according to equation 4 below.

Equation (4)

$$\text{Percent of unbound compound} = 100 \times \left( \frac{\frac{1}{D}}{\frac{1}{\frac{[F]}{[T]}} - 1 + \frac{1}{D}} \right) \quad (4)$$

Where [F] is the compound concentration on the buffer (receiver) side of the membrane; [T] is the compound concentration on the plasma or brain (donor) side of the membrane; D is the matrix dilution factor which is determined as D=4 for brain matrix and D=1 for plasma matrix in these assays.

TABLE 4

Total concentrations, brain $K_p$ and brain $K_{p,uu}$ are presented (mean ± stdev from n = 3 rats)

| Example Number | Oral dose (mg/kg) | Time point (h) | Total plasma concentration (ng/ml) | Total brain concentration (ng/g) | Brain $K_p$ | $fu_{brain}/fu_{plasma}$ (% free) | Brain $K_{p,uu}$ |
|---|---|---|---|---|---|---|---|
| 1 | 10 | 1 | 245 ± 121 | 620 ± 280 | 2.6 ± 0.2 | 4.7/14.7 | 0.83 ± 0.07 |
| 2 | 10 | 0.5 | 32 ± 18 | 31 ± 11 | 1.2 ± 0.7 | 2.7/9.7 | 0.35 ± 0.18 |
| 3 | 5 | 0.5 | 362 ± 38 | 414 ± 97 | 1.1 ± 0.1 | 10.4/22.6 | 0.52 ± 0.06 |
| 5 | 5 | 1 | 4 ± 0.8 | 7 ± 3 | 1.9 ± 0.3 | 5.2/12.3 | 0.80 ± 0.13 |
| 6 | 5 | 1 | 69 ± 7 | 205 ± 21 | 3 ± 0.06 | 3.7/8.9 | 1.22 ± 0.03 |
| 7 | 5 | 1 | 6 ± 2 | 10 ± 2 | 1.9 ± 0.3 | 7.5/21.0 | 0.68 ± 0.12 |
| 8 | 5 | 1 | 297 ± 29 | 279 ± 10 | 0.9 ± 0.1 | 7.5/19.3 | 0.37 ± 0.03 |
| 9 | 5 | 1 | 664 ± 47 | 906 ± 87 | 1.4 ± 0.2 | 7.4/10.2 | 1.00 ± 0.12 |
| 10 | 5 | 1 | 246 ± 61 | 524 ± 79 | 2.2 ± 0.3 | 9.3/22.7 | 0.89 ± 0.14 |
| 11 | 5 | 1 | 586 ± 82 | 649 ± 99 | 1.1 ± 0.2 | 5.3/11.7 | 0.51 ± 0.07 |
| 12 | 5 | 1 | 76 ± 23 | 146 ± 56 | 1.9 ± 0.3 | 3.0/6.7 | 0.85 ± 0.15 |
| 13 | 5 | 1 | 199 ± 52 | 496 ± 128 | 2.5 ± 0.1 | 1.9/7.4 | 0.74 ± 0.01 |
| 14 | 5 | 1 | 283 ± 57 | 347 ± 53 | 1.2 ± 0.1 | 5.8/14.6 | 0.49 ± 0.04 |
| 15 | 5 | 1 | 143 ± 8 | 254 ± 32 | 1.8 ± 0.2 | 5.0/11.0 | 0.81 ± 0.07 |
| 16 | 5 | 1 | 112 ± 18 | 141 ± 30 | 1.3 ± 0.2 | 3.5/13.9 | 0.32 ± 0.06 |
| 18 | 5 | 1 | 122 ± 11 | 343 ± 54 | 2.8 ± 0.6 | 4.7/12.8 | 1.04 ± 0.21 |
| 19 | 5 | 1 | 19 ± 8 | 48 ± 11 | 2.8 ± 0.5 | 2.7/8.6 | 0.87 ± 0.17 |
| 22 | 5 | 1 | 86 ± 8 | 216 ± 42 | 2.5 ± 0.4 | 6.8/16.8 | 1.02 ± 0.17 |

The total brain-to-plasma partition coefficient (brain $K_p$) is given by the ratio of the total brain concentration and total plasma concentration of the compound according to the equation below:

$$\text{Brain } K_p = \frac{\text{total brain concentration}}{\text{total plasma concentration}}$$

Based on the measured rat $fu_{plasma}$ and $fu_{brain}$ values and the brain $K_p$ the unbound brain-to-plasma partition coefficient (brain $K_{p,uu}$ for each compound was calculated. The $K_{p,uu}$ parameter describes the extent of brain penetration for each compound, i.e. the parameter gives a direct quantitative description of how the blood-brain barrier (BBB) handles the compounds regarding passive transport and active influx/efflux. The brain $K_{p,uu}$ is given by the equation below:

$$\text{Brain } K_{p,uu} = \text{brain } K_p \times \frac{fu_{brain}}{fu_{plasma}}$$

The Compounds reported in Table 4 are classified as being moderately or highly brain penetrant.

Example IV—Hepatocyte Intrinsic Clearance Assay

Test compounds (final concentration 0.05 µM, 0.05% organic) were incubated for 2 h at 37° C., with shaking, in supplemented Leibovitz L-15 media (pH 7.4) containing commercially sourced, pooled donor, cryopreserved hepatocytes (final concentration 1×10⁶ hepatocytes/mL). The $CL_{int}$ reactions (350 µL) were initiated by addition of test compound. Aliquots (25 µL) were taken at 1, 5, 10, 15, 30, 60, 90 and 120 minutes and then protein crashed with ice-cold acetonitrile containing internal standard (150 µL) then centrifuged (1960 g for 20 minutes at 4° C.). Supernatant was diluted (1:4) with deionized water then analyzed by liquid chromatography (LC)-tandem mass spectrometry (MS/MS). The intrinsic clearances ($CL_{int}$) were calculated from the slope (k) of the linear regressions of percentages of compound remaining in incubation against incubation time, according to equations 5 and 6:

Equation (5):

$$t_{1/2}=ln(2)/k \qquad (5)$$

Equation (6):

$$CL_{int}(L/h/kg \text{ body weight})=Ln(2)\times V(L/10^6 \text{ hepatocytes})/t_{1/2}(h)\times \text{hepatocellularity}(10^6 \text{ hepatocytes}/g \text{ liver})\times \text{liver weight}(g \text{ liver}/kg \text{ body weight}) \qquad (6)$$

V=incubation volume=0.001 L/10⁶ hepatocytes, Human hepatocellularity=120×10⁶ hepatocytes/g, Human liver weight=20 g/kg body weight.

TABLE 5

Hepatocyte intrinsic clearance for compounds of the invention

| Example Number | $CL_{int}$ (L/h/kg) |
|---|---|
| 1 | 0.64* |
| 3 | 0.36* |
| 6 | 0.86* |
| 7 | 0.47 |
| 9 | 0.97* |
| 10 | 0.33* |
| 11 | <0.24 ** |
| 12 | 0.48 |
| 13 | 1.88 |
| 14 | 0.47 |
| 15 | 0.72 |
| 22 | <0.24 *** |
| 23 | 0.97* |
| 24 | 1.06 |
| 25 | 1.19* |
| 29 | 0.93* |

*CLint measured on a single occasion
**Below the assay lower limit of quantification Based on the hepatocyte $CL_{int}$ values reported in Table 5 the tested compounds are classified as having low rates of metabolism, excepting compound 13 which shows a moderate to high rate of metabolism.

Example V—Hepatic Microsomal Intrinsic Clearance Assay

Compounds (final concentration 1 µM, 1% organic) of the invention were incubated for 1 hour at 37° C., with shaking, in phosphate buffer (pH 7.4) containing commercially sourced pooled liver microsomes (final concentration 0.5 mg/mL). The intrinsic clearance ($CL_{int}$) reactions were initiated by addition of cofactor solution (final concentration 1 mM NADPH and 1 mM MgCl₂, final incubation volume 100 µL). At designated time points (0, 5, 10, 20, 30 and 60 minutes) ice-cold acetonitrile containing internal standard (300 µL) was added to an incubation well to stop the reaction then mixed and centrifuged (3220 g for 20 minutes at 4° C.). Supernatant was diluted (1:4) with deionized water then analyzed by LC-MS/MS. The intrinsic clearances were calculated from the slope (k) of the linear regressions of percentages of compound remaining in incubation against incubation time, according to equations 7 and 8.

Equation (7):

$$t_{1/2}=ln(2)k \qquad (7)$$

Equation (8):

$$CL_{int}(L/h/kg \text{ body weight})=ln(2)\times V(L/mg)/t_{1/2}(h)\times \text{microsomal protein concentration}(mg \text{ protein}/g \text{ liver})\times \text{liver weight}(g \text{ liver}/kg \text{ body weight}) \qquad (8)$$

V=incubation volume=0.002 L/mg (0.5 mg/mL protein concentration)
Microsomal protein concentration=45 mg/g liver
Rat liver weight=45 g/kg body weight
Human liver weight=25 g/kg body weight

TABLE 6

Hepatic microsomal intrinsic clearance for compounds of the invention

| Example Number | $CL_{int}$ (L/h/kg) |
|---|---|
| 1 | 0.58 |
| 2 | 1.25 |
| 3 | 0.43 |
| 4 | 1.43 |
| 5 | 1.39 |
| 6 | 1.26 |
| 7 | 0.97 |
| 8 | 1.01 |
| 9 | BQL** |
| 10 | 1.20 |
| 11 | 0.74 |
| 12 | 1.01 |
| 13 | 1.82 |
| 14 | 1.03 |
| 15 | 0.72 |
| 16 | 1.12 |
| 17 | 0.92 |
| 18 | 0.67 |
| 19 | 2.03 |
| 20 | 1.10 |
| 21 | 1.54 |
| 22 | <0.36** |
| 23 | 1.43 |
| 24 | 0.75 |
| 25 | <0.36* |
| 26 | 0.70 |
| 27 | 0.49 |
| 28 | 0.61 |
| 29 | 1.28 |
| 30 | 0.84 |

*CLint measured on a single occasion
**below the assay lower limit of quantification, 0.36 L/h/kg Based on the liver microsomal $CL_{int}$ values reported in Table 6 the tested compounds are classified as having either low or low to moderate rates of metabolism, excepting compounds 13 and 19 which show a moderate to high rate of metabolism.

The invention claimed is:

1. A compound of formula IIa, or a pharmaceutically acceptable salt thereof, wherein:

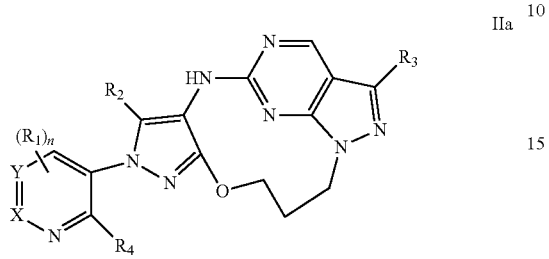

IIa

X is CH, $CR_1$ or N;
Y is CH, $CR_1$ or N;
$R_1$ is independently selected from the group consisting of a $C_1$-$C_3$ alkyl, a $C_1$-$C_3$ haloalkyl, and a halogen;
$R_2$ is selected from a $C_1$-$C_3$ alkyl and an isotopically labelled $C_1$-$C_3$ alkyl;
$R_3$ is selected from the group consisting of a halogen, a cyano, and a $C_1$-$C_3$ haloalkyl;
$R_4$ is selected from the group consisting of a $C_1$-$C_3$ alkyl, an isotopically labelled $C_1$-$C_3$ alkyl, a $C_1$-$C_3$ haloalkyl, a O—$C_1$-$C_3$ alkyl, an isotopically labelled O—$C_1$-$C_3$ alkyl, a O—$C_1$-$C_3$ haloalkyl, and a O—$C_3$-$C_6$ cycloalkyl;
n is 0, 1 or 2.

2. The compound of claim 1, or a pharmaceutically salt thereof, wherein X is CH and Y is CH; X is $CR_1$ and Y is $CR_1$; X is CH and Y is $CR_1$; X is $CR_1$ and Y is CH; X is CH and Y is N; X is $CR_1$ and Y is N; X is N and Y is CH; or X is N and Y is $CR_1$.

3. The compound of claim 1, or a pharmaceutically salt thereof, wherein $R_1$ is a $C_1$-$C_3$ alkyl or a halogen.

4. The compound of claim 1, or a pharmaceutically salt thereof, wherein $R_1$ is —$CH_3$; —$CH_2CH_3$; or fluoro.

5. The compound of claim 1, or a pharmaceutically salt thereof, wherein $R_2$ is selected from the group consisting of —$CH_3$, —$CH_2CH_3$, and —$CD_3$.

6. The compound of claim 1, or a pharmaceutically salt thereof, wherein $R_3$ is chloro.

7. The compound of claim 1, or a pharmaceutically salt thereof, wherein $R_4$ is selected from the group consisting of —$CH_3$, —$CH_2CH_3$, —$OCH_3$, —$OCH_2CH_3$, —$CHF_2$, —$CF_3$, —$CF_2CH_3$, O-cyclopropane, —$OCH_2F$, —$OCHF_2$, —$OCF_3$, and —$OCD_3$.

8. The compound of claim 1, or a pharmaceutically salt thereof, wherein n is 0 or 1.

9. The compound of claim 1, wherein the compound is selected from the list consisting of:

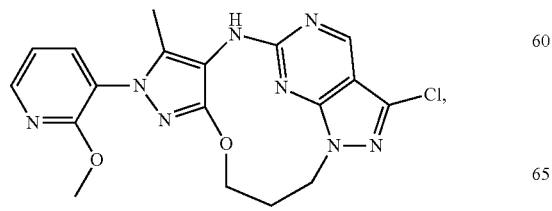

-continued

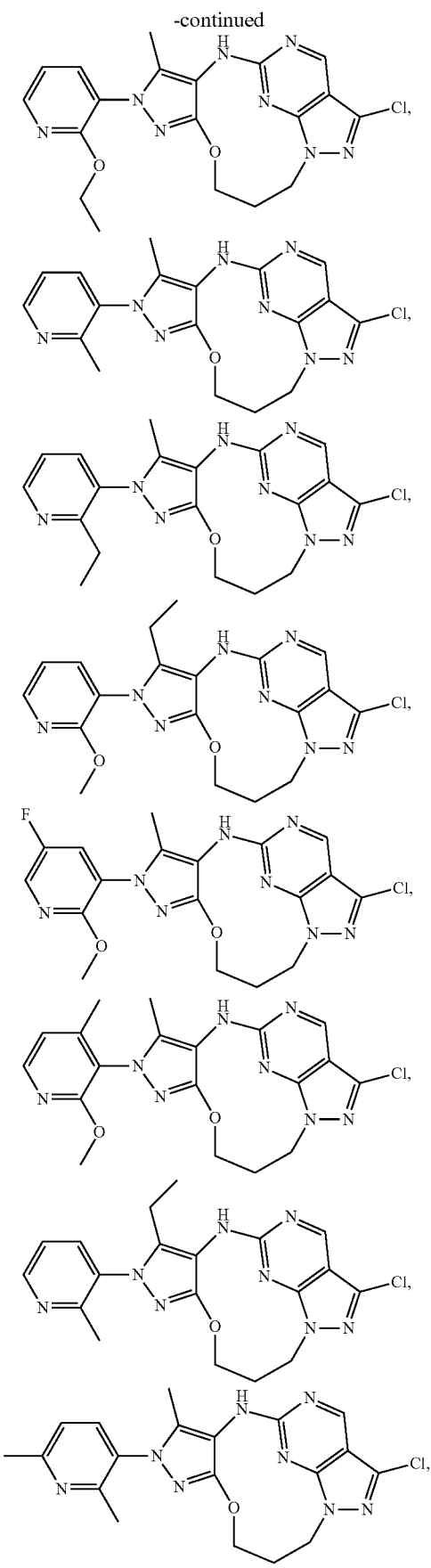

-continued
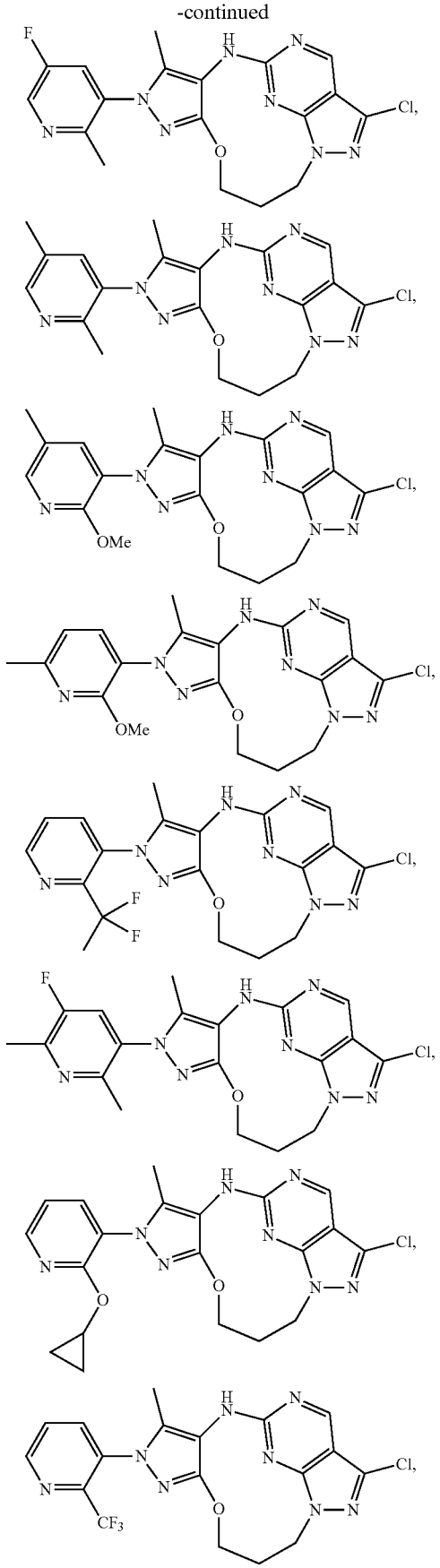
-continued
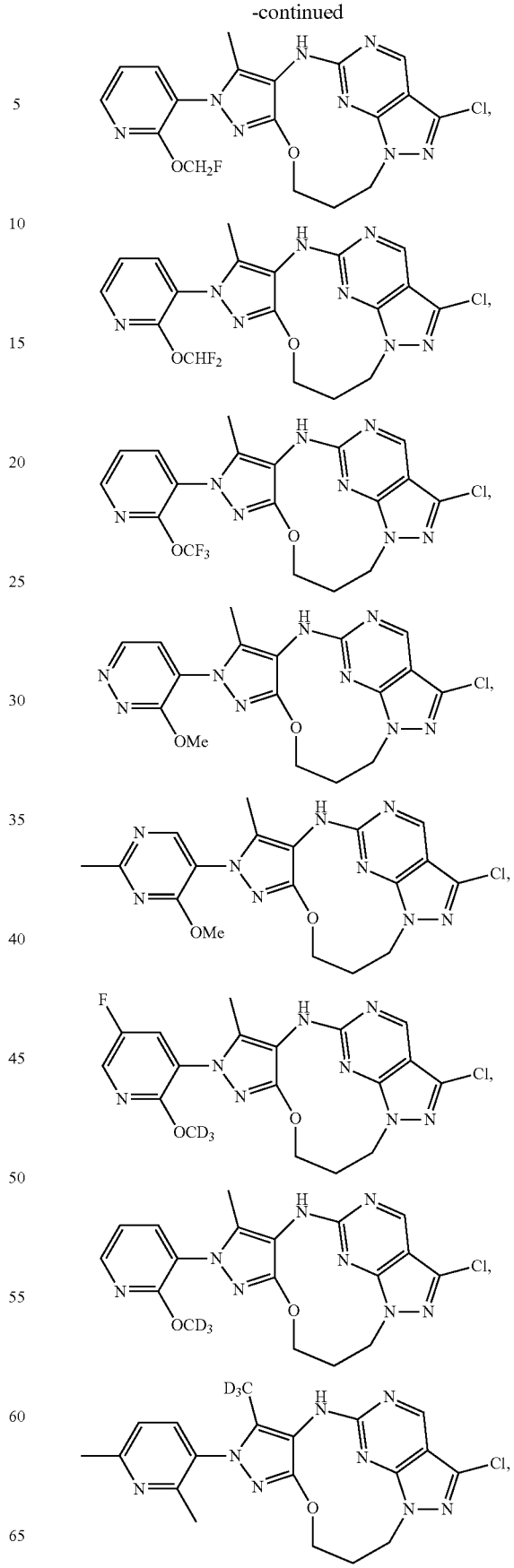

-continued

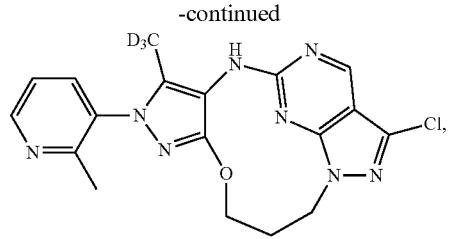

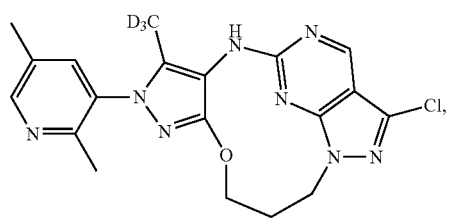

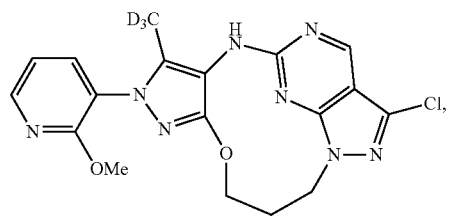

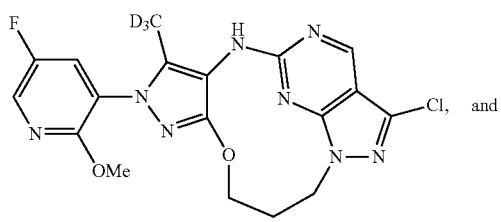

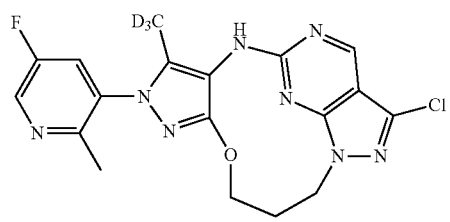

or a pharmaceutically acceptable salt thereof.

10. The compound of claim 1, wherein the compound is

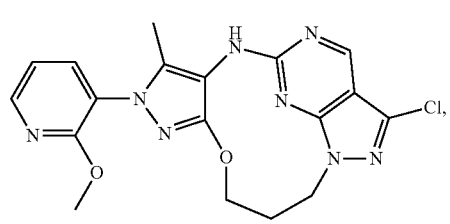

11. The compound of claim 1, wherein the compound is

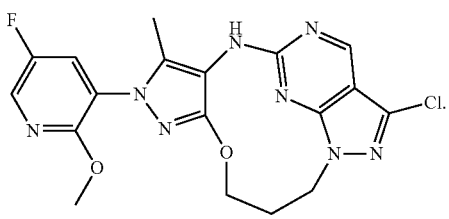 [SMILES: COc1ncc(F)cc1-n1nc2c(c1C)Nc1ncc3c(Cl)nn(c3n1)CCCO2]

12. The compound of claim 1, wherein the compound is

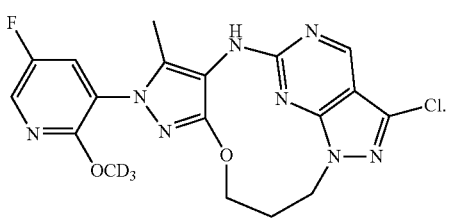

13. The compound of claim 1, wherein the compound is

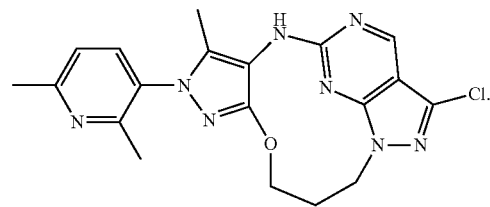 [SMILES: Cc1ccc(-n2nc3c(c2C)Nc2ncc4c(Cl)nn(c4n2)CCCO3)c(C)n1]

14. The compound of claim 1, wherein the compound is

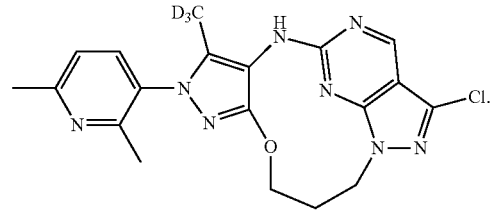 [SMILES: [2H]C([2H])([2H])c1c2c(nn1-c1ccc(C)nc1C)OCCCn1nc(Cl)c3cnc(nc31)N2]

15. The compound of claim 1, wherein the compound is

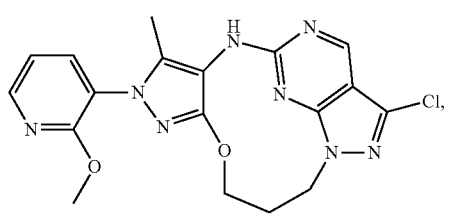

or a pharmaceutically acceptable salt thereof.

16. The compound of claim 1, wherein the compound is

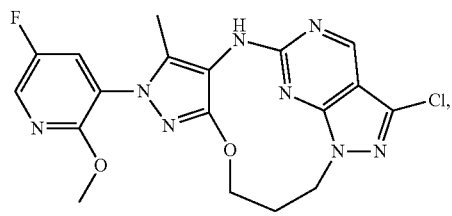 [SMILES: COc1ncc(F)cc1-n1nc2c(c1C)Nc1ncc3c(Cl)nn(c3n1)CCCO2]

or a pharmaceutically acceptable salt thereof.

17. The compound of claim 1, wherein the compound is

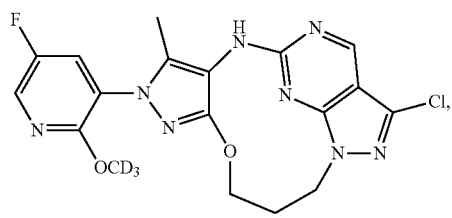

or a pharmaceutically acceptable salt thereof.

18. The compound of claim 1, wherein the compound is

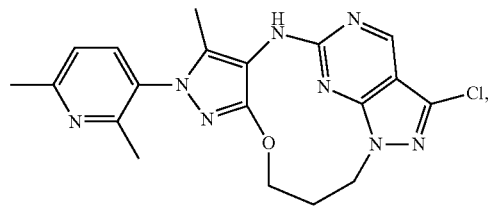 [SMILES: Cc1ccc(-n2nc3c(c2C)Nc2ncc4c(Cl)nn(c4n2)CCCO3)c(C)n1]

or a pharmaceutically acceptable salt thereof.

19. The compound of claim 1, wherein the compound is

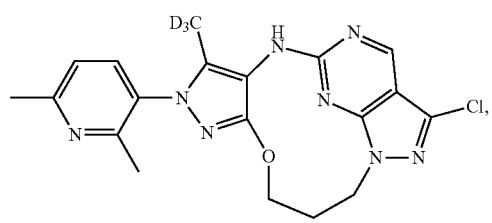 [SMILES: [2H]C([2H])([2H])c1c2c(nn1-c1ccc(C)nc1C)OCCCn1nc(Cl)c3cnc(nc31)N2]

or a pharmaceutically acceptable salt thereof.

* * * * *